US009428452B2

(12) United States Patent
Birault et al.

(10) Patent No.: US 9,428,452 B2
(45) Date of Patent: Aug. 30, 2016

(54) COMPOUNDS

(71) Applicant: Glaxo Group Limited, Brentford, Middlesex (GB)

(72) Inventors: Veronique Birault, Stevenage (GB); Amanda Jennifer Campbell, Stevenage (GB); Stephen Harrison, Stevenage (GB); Joelle Le, Stevenage (GB); Lena Shukla, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 14/394,105

(22) PCT Filed: Apr. 25, 2013

(86) PCT No.: PCT/EP2013/058666
§ 371 (c)(1),
(2) Date: Oct. 13, 2014

(87) PCT Pub. No.: WO2013/160418
PCT Pub. Date: Oct. 31, 2013

(65) Prior Publication Data

US 2015/0080369 A1 Mar. 19, 2015

(30) Foreign Application Priority Data

Apr. 27, 2012 (GB) .................................. 1207403.5
Mar. 14, 2013 (GB) .................................. 1304596.8

(51) Int. Cl.

| | |
|---|---|
| ***C07C 317/22*** | (2006.01) |
| ***C07D 309/04*** | (2006.01) |
| ***C07D 309/06*** | (2006.01) |
| ***C07D 309/10*** | (2006.01) |
| ***C07D 319/12*** | (2006.01) |
| ***C07C 311/29*** | (2006.01) |
| ***C07D 239/54*** | (2006.01) |
| ***C07D 205/04*** | (2006.01) |
| ***C07D 265/30*** | (2006.01) |
| ***C07D 207/08*** | (2006.01) |
| ***C07D 265/32*** | (2006.01) |
| ***C07D 491/107*** | (2006.01) |
| ***C07D 207/10*** | (2006.01) |
| ***C07D 207/26*** | (2006.01) |
| ***C07D 211/22*** | (2006.01) |
| ***C07D 295/088*** | (2006.01) |
| ***C07D 211/38*** | (2006.01) |
| ***C07D 295/096*** | (2006.01) |
| ***C07D 211/76*** | (2006.01) |
| ***C07D 305/06*** | (2006.01) |
| ***C07D 305/08*** | (2006.01) |
| ***C07D 307/12*** | (2006.01) |
| ***C07C 311/37*** | (2006.01) |
| ***C07D 207/09*** | (2006.01) |
| ***C07D 211/28*** | (2006.01) |
| ***C07D 295/135*** | (2006.01) |
| ***C07D 307/14*** | (2006.01) |
| ***C07D 491/044*** | (2006.01) |

(52) U.S. Cl.

CPC ........... *C07C 317/22* (2013.01); *C07C 311/29* (2013.01); *C07C 311/37* (2013.01); *C07D 205/04* (2013.01); *C07D 207/08* (2013.01); *C07D 207/09* (2013.01); *C07D 207/10* (2013.01); *C07D 207/26* (2013.01); *C07D 211/22* (2013.01); *C07D 211/28* (2013.01); *C07D 211/38* (2013.01); *C07D 211/76* (2013.01); *C07D 239/54* (2013.01); *C07D 265/30* (2013.01); *C07D 265/32* (2013.01); *C07D 295/088* (2013.01); *C07D 295/096* (2013.01); *C07D 295/135* (2013.01); *C07D 305/06* (2013.01); *C07D 305/08* (2013.01); *C07D 307/12* (2013.01); *C07D 307/14* (2013.01); *C07D 309/04* (2013.01); *C07D 309/06* (2013.01); *C07D 309/10* (2013.01); *C07D 319/12* (2013.01); *C07D 491/044* (2013.01); *C07D 491/107* (2013.01); *C07C 2101/02* (2013.01)

(58) Field of Classification Search

CPC . C07D 309/04; C07D 309/06; C07D 309/10
See application file for complete search history.

(56) References Cited

U.S. PATENT DOCUMENTS 9,150,508 B2 10/2015 Birault et al.
2015/0065507 A1 3/2015 Birault et al.

FOREIGN PATENT DOCUMENTS

WO WO 2013/045431 A1 4/2013

OTHER PUBLICATIONS

Kumar, et al. Probe Reports from the NIH Molecular Libraries Program, pp. 1-22 (2010). http://www.ncbi.nlm.nih.gov/books/NBK56239/.

*Primary Examiner* — Shawquia Jackson

(74) *Attorney, Agent, or Firm* — Fang Qian; Kathryn A. Lutomski; Edward R. Gimmi

(57) ABSTRACT

The present invention is directed to novel retinoid-related orphan receptor gamma (RORγ) modulators, processes for their preparation, pharmaceutical compositions containing these modulators, and their use in the treatment of inflammatory, metabolic and autoimmune diseases mediated by RORγ.

39 Claims, No Drawings

COMPOUNDS

This application is a §371 national stage entry of International Application No. PCT/EP2013/058666, filed 25 Apr. 2013, which claims priority of GB Application Nos. 1304596.8, filed 14 Mar. 2013, and 1207403.5, filed 27 Apr. 2012, which are incorporated herein in their entireties.

FIELD OF THE INVENTION

The present invention is directed to novel retinoid-related orphan receptor gamma (RORγ) modulators, processes for their preparation, pharmaceutical compositions containing these modulators, and their use in the treatment of inflammatory, metabolic and autoimmune diseases mediated by RORγ.

BACKGROUND OF THE INVENTION

Retinoid-related orphan receptors (RORs) are transcription factors that form a subgroup of the nuclear receptor superfamily (*Adv. Dev. Biol.* 2006, 16, 313-355). This subgroup consists of three members: ROR alpha (RORα), ROR beta (RORβ) and ROR gamma (RORγ). RORα and RORβ have approximately 55% homology in the ligand binding domains to RORγ. RORs contain four principal domains shared by the majority of nuclear receptors: an N-terminal A/B domain, a DNA-binding domain, a hinge domain and a ligand binding domain.

The RORα, RORβ and RORγ genes have been mapped to human chromosomes 15q22.2, 9q21.13 and 1q21.3, respectively. Each ROR gene generates several isoforms, which differ only in their N-terminal A/B domain. To date, five splice variants have been recorded for RORγ and two isoforms of this member of the ROR family have been identified: RORγ1 and RORγ2 (also known as RORγt). RORγ is a term used to describe RORγ1 and/or RORγt.

While RORγ1 is expressed in a variety of tissues including thymus, muscle, kidney and liver, RORγt is exclusively expressed in the cells of the immune system and has a critical role in thymopoiesis, development of several secondary lymphoid tissues and Th17 lineage specification.

RORγt has been identified as a key regulator of Th17 cell differentiation (A. Jetten, *Nuclear Receptor Signalling* 2009, 7, 1-32). Th17 cells are a recently discovered subset of T helper cells which preferentially produce cytokines IL-17A, IL-17F, IL-21 and IL-22. RORγt also induces transcription of the gene encoding IL-17A and IL-17F in naïve $CD4^+$ T helper cells, iNKT and NKT (*Mucosal Immunol.* 2009, 2(5), 383-392; *J. Immunol.* 2008, 180, 5167-5171), γδT cells (*Am. J. Respir. Crit. Care Med.* 2010, 182, 464-476), $CD8^+$ T cells (*J. Leukocyte Biol.* 2007, 82, 354-360) and finally $CD4^-$ $CD8^-TCR\alpha\beta^+$ T cells (*J. Immunol.* 2008, 181, 8761-8766). Additional immune cells such as eosinophils, neutrophils and macrophages can also be a source of IL-17A in allergic inflammation related to asthma (*J. Allergy Clin. Immunol.* 2001, 108, 430-438; *J. Immunol.* 2008, 181, 6117-6124; *Immunity* 2004, 21, 467-476).

Th17 cells and their products have been shown to be associated with the pathology of a number of human inflammatory and autoimmune disorders. IL-17A and IL-17F are implicated in numerous immune and inflammatory responses primarily as pro-inflammatory regulators inducing the expression of cytokines, chemokines, adhesion molecules, mucin genes and growth factors. There is emerging evidence that an increase in IL-17A level is closely associated with a range of chronic inflammatory diseases such as rheumatoid arthritis (*Curr. Opin. Investig. Drugs* 2009, 10, 452-462), multiple sclerosis (*Allergol. Int.* 2008, 57(2), 115-120), inflammatory bowel diseases (*J. Inflamm. Res.* 2010, 3, 33-44), uveitis, psoriasis (*Sci. Transl. Med.* 2010, 2(52)) and lung diseases (*Prog. Respir. Res. Basel* 2010, 39, 141-149; *Resp. Research* 2010, 11 (78), 1-11).

There is considerable evidence suggesting that Th17 cells/IL-17 play a key role in the pathogenesis of asthma. In asthmatic patients, both RORγt and IL-17A expression levels have been shown to be increased in sputum (*Chin. Med. J.* 2005, 118, 953-956; *Resp. Res.* 2006, 7(135), 1-9), lung (*J. Allergy Clin. Immuno.* 2003, 111(6), 1293-1298), bronchoalveolar lavage (BAL) fluids and peripheral blood (*Immunol. Invest.* 2009, 38, 652-664; *Int. Arch. Allergy Immunol.* 2005, 137(suppl. 1), 51-54) and levels directly correlate with disease severity (*Int. Arch. Allergy Immunol.* 2010, 151, 297-307). In addition to IL-17A, a recent study has shown that a further cytokine of the IL-17 family, IL-17F, may have a crucial role in allergic airway inflammation and hence have key implications in airway diseases, such as asthma. The overexpression of the IL-17F gene in mice airways was associated with airway neutrophilia, cytokine induction, an increase in airway hyperreactivity and mucus hypersecretion (*Inflamm. Allergy Drug Targets* 2009, 8, 383-389). Evidence of role of Th17 cells in allergens has been discussed in *Int. Immunopharmacol.* 2010, 10, 226-229.

The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (*J. Exp. Med.* 2008, 205, 1517-1522; *Cell. Mol. Immunol.* 2010, 7, 182-189). There is also evidence that Th17 cells are activated during the disease process and are responsible for recruiting other inflammatory cells types, especially neutrophils, to mediate pathology in the target tissues (*Annu. Rev. Immunol.* 2009, 27, 485-517). RORγt plays a critical role in the pathogenic responses of Th17 cells (*Cell* 2006, 126, 1121-1133). RORγt deficient mice show very few Th17 cells. Further support for the role of RORγt in the pathogensis of autoimmune or inflammatory diseases can be found in the following references: *Immunity* 2007, 26, 643-654; *Nat. Rev. Immunol.* 2006, 6, 205-217; *J. Immunol.* 2009, 183, 7169-7177; *Brain Pathol.* 2004, 14, 164-174; *Brain* 2007, 130, 1089-1104; *Nat. Rev. Immunol* 2008, 8, 183-192.

In light of the role RORγ plays in the pathogenesis of diseases, it is desirable to prepare compounds that modulate RORγ activity and hence have utility in the treatment of inflammatory, metabolic and autoimmune diseases mediated by RORγ, such as the respiratory diseases asthma, chronic obstructive pulmonary disease (COPD) and bronchitis, allergic diseases including allergic rhinitis and atopic dermatitis, cystic fibrosis and lung allograph rejection.

SUMMARY OF THE INVENTION

According to the invention, there is provided novel retinoid-related orphan receptor gamma (RORγ) modulators, processes for their preparation, pharmaceutical compositions comprising these modulators, and their use in the treatment of inflammatory, metabolic and autoimmune diseases mediated by RORγ. More specifically, the present invention is directed to compounds of formula (I), and to pharmaceutically acceptable salts thereof:

(I)

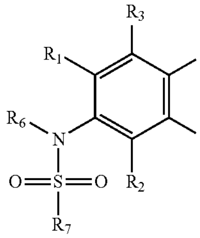

wherein $R_1$, $R_2$, and $R_5$ are each independently selected from the group consisting of H, $C_{1-3}$alkyl, $C_{1-3}$alkoxy, $CF_3$, and halo;

$R_3$ and $R_4$ are each independently selected from the group consisting of H, $CH_3$, $OCH_3$, $CF_3$ and halo;

$R_6$ is $C_{3-5}$alkyl or —$CH_2C_{3-4}$cycloalkyl;

$R_7$ is selected from the group consisting of:

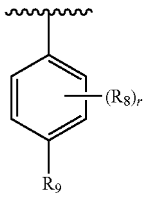

and

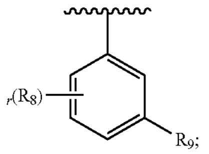

each $R_8$ is independently selected from the group consisting of halo, $C_{1-6}$alkyl, $C_{1-6}$alkoxy, $C_{3-6}$cycloalkyl, CN, OH, C(O)OH, C(O)O$C_{1-3}$alkyl and $CH_2OH$;

$R_9$ is the group —$(CHR_{10})_s$—$(X)_t$—$(CHR_{10})_u$—$R_{11}$;

each $R_{10}$ is independently selected from H, $CH_3$, OH and $CH_2OH$;

X is $CH_2$, NH or O;

$R_{11}$ is a heterocycloalkyl or $C_{3-6}$cycloalkyl group which may be unsubstituted or substituted with one or more substituents independently selected from the group consisting of $CH_3$, OMe, OH, $CH_2OH$ and halo;

r is 0, 1 or 2;

s is 0, 1 or 2;

t is 0 or 1;

u is 0, 1 or 2;

with the proviso that no more than two $R_{10}$ groups represent $CH_3$, OH or $CH_2OH$.

In one aspect, the present invention provides a pharmaceutical composition comprising a) a compound of formula (I), or a pharmaceutically acceptable salt thereof, and b) one or more pharmaceutically acceptable excipients.

In a further aspect, the present invention provides a compound of formula (I), or a pharmaceutically acceptable salt thereof, for use in therapy.

Compounds of formula (I), and pharmaceutically acceptable salts thereof, are modulators of RORγ and can be useful in the treatment of inflammatory, metabolic and autoimmune diseases mediated by RORγ, such as asthma, chronic obstructive pulmonary disease (COPD) and bronchitis, allergic diseases including allergic rhinitis and atopic dermatitis, cystic fibrosis, lung allograph rejection, multiple sclerosis, rheumatoid arthritis, juvenile rheumatoid arthritis, Osteoarthritis, ankylosing spondylitis, systemic lupus erythematosus, psoriasis, Hashimoto's disease, pancreatisis, autoimmune diabetes, autoimmune ocular disease, ulcerative colitis, Crohn's disease, inflammatory bowel disease (IBS), inflammatory bowel syndrome (IBD), Sjorgen's syndrome, optic neuritis, type I diabetes, neuromyelitis optica, Myasthenia Gravis, uveitis, Guillain-Barre syndrome, psoriatic arthritis, Graves' disease, and scleritis.

In a further aspect, the present invention provides a compound of formula (I), or a pharmaceutically acceptable salt thereof, for use in the treatment of asthma or chronic obstructive pulmonary disease.

In a further aspect, the present invention provides a compound of formula (I), or a pharmaceutically acceptable salt thereof, for use in the treatment of psoriasis.

In a further aspect, the present invention is directed to a method of treatment of an inflammatory, metabolic or autoimmune disease mediated by RORγ, which comprises administering to a subject in need thereof, a safe and therapeutically effective amount of a compound of formula (I), or a pharmaceutically acceptable salt thereof.

In yet a further aspect, the present invention is directed to a method of treating chronic obstructive pulmonary disease or asthma, which comprises administering to a subject in need thereof, a safe and therapeutically effective amount of a compound of formula (I), or a pharmaceutically acceptable salt thereof.

In yet a further aspect, the present invention is directed to a method of treating psoriasis, which comprises administering to a subject in need thereof, a safe and therapeutically effective amount of a compound of formula (I), or a pharmaceutically acceptable salt thereof.

In a further aspect, the present invention is directed to the use of a compound of formula (I), or a pharmaceutically acceptable salt thereof, in the manufacture of a medicament for use in the treatment of an inflammatory, metabolic or autoimmune disease mediated by RORγ.

DETAILED DESCRIPTION OF THE INVENTION

In a first aspect, the present invention is directed to a compound of formula (I), or a pharmaceutically acceptable salt thereof:

(I)

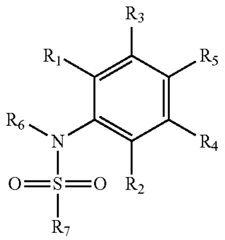

wherein $R_1$, $R_2$, and $R_5$ are each independently selected from the group consisting of H, $C_{1-3}$alkyl, $C_{1-3}$alkoxy, $CF_3$, and halo;

$R_3$ and $R_4$ are each independently selected from the group consisting of H, $CH_3$, $OCH_3$, $CF_3$ and halo;

$R_6$ is $C_{3-5}$alkyl or —$CH_2C_{3-4}$cycloalkyl;

$R_7$ is selected from the group consisting of:

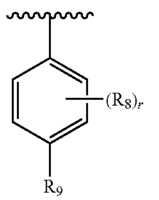

and

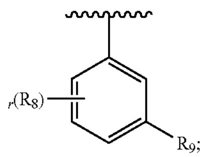

each $R_8$ is independently selected from the group consisting of halo, $C_{1-6}$alkyl, $C_{1-6}$alkoxy, $C_{3-6}$cycloalkyl, CN, OH, C(O)OH, C(O)O$C_{1-3}$alkyl and $CH_2OH$;

$R_9$ is the group $—(CHR_{10})_s—(X)_t—(CHR_{10})_u—R_{11}$;

each $R_{10}$ is independently selected from H, $CH_3$, OH and $CH_2OH$;

X is $CH_2$, NH or O;

$R_{11}$ is a heterocycloalkyl or $C_{3-6}$cycloalkyl group which may be unsubstituted or substituted with one or more substituents independently selected from the group consisting of $CH_3$, OMe, OH, $CH_2OH$ and halo;

r is 0, 1 or 2;

s is 0, 1 or 2;

t is 0 or 1;

u is 0, 1 or 2;

with the proviso that no more than two $R_{10}$ groups represent $CH_3$, OH or $CH_2OH$.

In a further aspect, the present invention is directed to a compound of formula (I), or a pharmaceutically acceptable salt thereof:

(I)

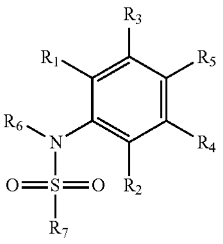

wherein $R_1$, $R_2$, and $R_5$ are each independently selected from the group consisting of H, $C_{1-3}$alkyl, $C_{1-3}$alkoxy, $CF_3$, and halo;

$R_3$ and $R_4$ are each independently selected from the group consisting of H, $CH_3$, $OCH_3$, $CF_3$ and halo;

$R_6$ is $C_{3-5}$alkyl or $—CH_2C_{3-4}$cycloalkyl;

$R_7$ is selected from the group consisting of:

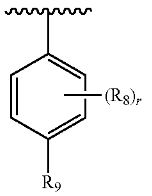

and

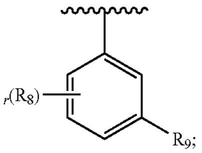

each $R_8$ is independently selected from the group consisting of halo, $C_{1-6}$alkyl, $C_{1-6}$alkoxy, $C_{3-6}$cycloalkyl, CN, OH, C(O)OH, C(O)O$C_{1-3}$alkyl and $CH_2OH$;

$R_9$ is the group $—(CHR_{10})_s—(X)_t—(CHR_{10})_u—R_{11}$;

each $R_{10}$ is independently selected from H, $CH_3$, OH and $CH_2OH$;

X is $CH_2$, NH or O;

$R_{11}$ is a heterocycloalkyl or $C_{3-6}$cycloalkyl group which may be unsubstituted or substituted with one or more substituents independently selected from the group consisting of $CH_3$, OMe, OH, $CH_2OH$ and halo;

r is 0, 1 or 2;

s is 0, 1 or 2;

t is 0 or 1;

u is 0, 1 or 2;

with the proviso that no more than two $R_{10}$ groups represent $CH_3$, OH or $CH_2OH$, and with the further proviso that $R_1$, $R_2$, $R_3$, $R_4$ and $R_5$ are not all H.

In a further aspect, the present invention provides subsets of the compounds of formula (I), of formula (Ia-Ig), or a pharmaceutically acceptable salt thereof:

(Ia)

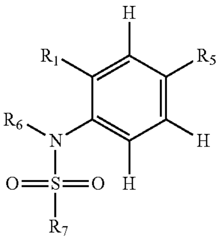

(Ib)

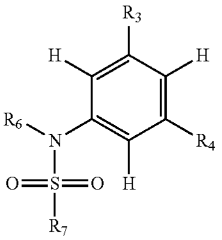

(Ic)

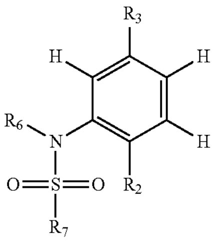

(Id)

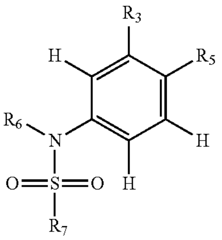

(Ie)

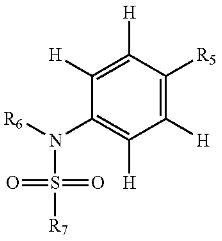

-continued (If)

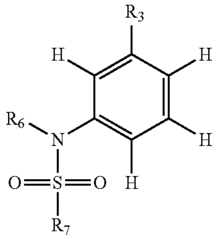

(Ig)

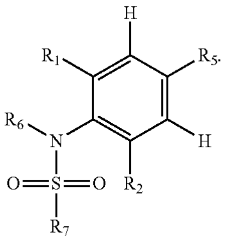

In a further aspect, the present invention provides subsets of the compounds of formula (I), of formula (Ia-Ic), or a pharmaceutically acceptable salt thereof:

(Ia)

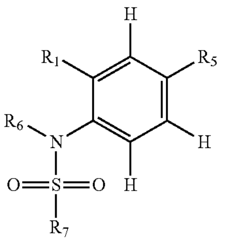

(Ib)

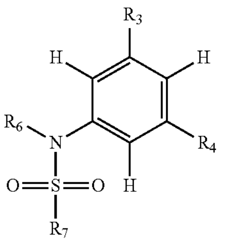

(Ic)

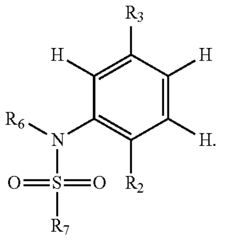

In a further aspect, the present invention provides a subset of compounds of formula (I), of formula (Ia), or a pharmaceutically acceptable salt thereof:

(Ia)

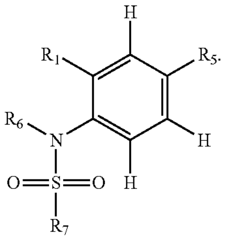

In a further aspect, the present invention provides a subset of compounds of formula (I), of formula (Ia) above, or a pharmaceutically acceptable salt thereof, wherein $R_5$ is $C_{1-3}$alkyl.

In a further aspect, the present invention is directed to a compound of formula (Ia), or a pharmaceutically acceptable salt thereof:

(Ia)

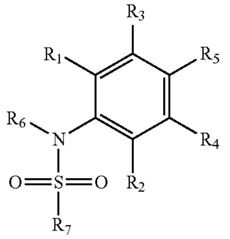

wherein $R_1$ is selected from the group consisting of H, $C_{1-3}$alkyl, $C_{1-3}$alkoxy, $CF_3$, and halo;

$R_2$, $R_3$ and $R_4$ are H;

$R_5$ is $C_{1-3}$alkyl;

$R_6$ is $C_{3-5}$alkyl or —$CH_2C_{3-4}$cycloalkyl;

$R_7$ is selected from the group consisting of:

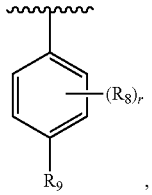

, and

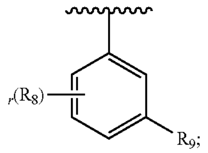

each $R_8$ is independently selected from the group consisting of halo, $C_{1-6}$alkyl, $C_{1-6}$alkoxy, $C_{3-6}$cycloalkyl, CN, OH, C(O)OH, C(O)O$C_{1-3}$alkyl and $CH_2OH$;

$R_9$ is the group $-(CHR_{10})_s-(X)_t-(CHR_{10})_u-R_{11}$;

each $R_{10}$ is independently selected from H, $CH_3$, OH and $CH_2OH$;

X is $CH_2$, NH or O;

$R_{11}$ is a heterocycloalkyl or $C_{3-6}$cycloalkyl group which may be unsubstituted or substituted with one or more substituents independently selected from the group consisting of $CH_3$, OMe, OH, $CH_2OH$ and halo;

r is 0, 1 or 2;

s is 0, 1 or 2;

t is 0 or 1;

u is 0, 1 or 2;

with the proviso that no more than two $R_{10}$ groups represent $CH_3$, OH or $CH_2OH$.

In a further aspect, the present invention provides a subset of compounds of formula (I), of formula (Ia) above, or a pharmaceutically acceptable salt thereof, wherein $R_1$ is H.

In a further aspect, the present invention provides a subset of compounds of formula (I), of formula (Ia) above, or a pharmaceutically acceptable salt thereof, wherein $R_1$ and $R_5$ are each independently $CH_3$ or halo.

In a further aspect, the present invention provides a subset of compounds of formula (I), of formula (Ia) above, or a pharmaceutically acceptable salt thereof, wherein $R_1$ and $R_5$ are $CH_3$.

In a further aspect of the present invention, $R_6$ is selected from the group consisting of propyl, isobutyl, and —$CH_2$cyclopropyl.

In a further aspect of the present invention, $R_6$ is isobutyl.

In a further aspect of the present invention, $R_7$ is:

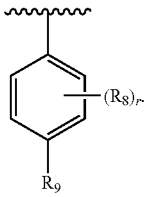

In a further aspect of the present invention, $R_7$ is:

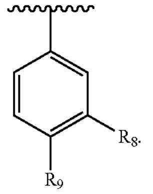

In a further aspect of the present invention, r is 1.

In a further aspect of the present invention, r is 2.

In a further aspect of the present invention, each $R_8$ is independently selected from the group consisting of $CH_3$, $OCH_3$, $CH_2OH$, cyclopropyl, fluoro and chloro.

In a further aspect of the present invention, $R_8$ is $CH_2OH$.

In a further aspect of the present invention, r is 0.

In a further aspect of the present invention, s is 0.

In a further aspect of the present invention, s is 1.

In a further aspect of the present invention, u is 2.

In a further aspect of the present invention, u is 1.

In a further aspect of the present invention, u is 0.

In a further aspect of the present invention, t is 1 and X is O.

In a further aspect of the present invention, t is 0.

In a further aspect of the present invention, each $R_{10}$ is H.

In a further aspect of the present invention, s is 0, t is 1, X is O, and u is 1 in which $R_{10}$ is H.

In a further aspect of the present invention, s is 1 in which $R_{10}$ is OH, t is 0 and u is 1 in which $R_{10}$ is H.

In a further aspect of the present invention, $R_{11}$ is a heterocycloalkyl group selected from oxirane, oxetane, tetrahydrofuran, tetrahydro-2H-pyran, pyrrolidine, piperidine, morpholine, morpholin-3-one, and thiomorpholine 1,1-dioxide.

In a further aspect of the present invention, $R_{11}$ is a heterocycloalkyl selected from tetrahydro-2H-pyran and morpholine.

In a further aspect of the present invention, $R_{11}$ is cyclohexane.

In a further aspect of the present invention, $R_{11}$ is unsubstituted.

It is understood that the present invention covers all combinations of substituent groups referred to herein above.

Specific examples of compounds of formula (I) are:

N-(2,4-dimethylphenyl)-N-(2-methylpropyl)-3-[(oxan-4-ylmethoxy)methyl]benzene-1-sulfonamide;

N-(2,4-dimethylphenyl)-N-(2-methylpropyl)-4-[2-(morpholin-4-yl)ethoxy]benzene-1-sulfonamide;

2-[(2,4-dimethylphenyl)(2-methylpropyl)sulfamoyl]-5-(oxan-4-ylmethoxy)benzoic acid;

N-(2,4-dimethylphenyl)-2-methoxy-N-(2-methylpropyl)-4-(oxan-4-ylmethoxy)benzene-1-sulfonamide;

N-(2,4-dimethylphenyl)-2-(hydroxymethyl)-N-(2-methylpropyl)-4-(oxan-4-ylmethoxy)benzene-1-sulfonamide;

N-(2,4-dimethylphenyl)-N-(2-methylpropyl)-4-{[(oxan-4-ylmethyl)amino]methyl}benzene-1-sulfonamide;

N-(2,4-dimethylphenyl)-4-[(cis-3-fluoropiperidin-4-yl)methoxy]-N-(2-methylpropyl)benzene-1-sulfonamide;

N-(2,4-dimethylphenyl)-N-(2-methylpropyl)-4-(piperidin-4-ylmethoxy)benzene-1-sulfonamide;

N-(2,4-dimethylphenyl)-N-(2-methylpropyl)-4-[(1-methylpyrrolidin-3-yl)methoxy]benzene-1-sulfonamide;

N-(2,4-dimethylphenyl)-N-(2-methylpropyl)-4-[(5-oxomorpholin-2-yl)methoxy]benzene-1-sulfonamide;

N-(2,4-dimethylphenyl)-4-[(3-methyl-5-oxomorpholin-3-yl)methoxy]-N-(2-methylpropyl)benzene-1-sulfonamide;

N-(2,4-dimethylphenyl)-N-(2-methylpropyl)-4-(oxan-4-ylmethoxy)benzene-1-sulfonamide;

N-(2,4-dimethylphenyl)-N-(2-methylpropyl)-4-{[1-(2,2,2-trifluoroethyl)piperidin-4-yl]methoxy}benzene-1-sulfonamide;

N-(2,4-dimethylphenyl)-4-((cis-5-(hydroxymethyl)tetrahydrofuran-2-yl)methoxy)-N-isobutylbenzenesulfonamide;

4-[(3,5-dihydroxycyclohexyl)oxy]-N-(2,4-dimethylphenyl)-N-(2-methylpropyl)benzene-1-sulfonamide;

4-(((1S,3R,5S)-3,5-dihydroxycyclohexyl)oxy)-N-(2,4-dimethylphenyl)-N-isobutylbenzenesulfonamide;

4-[2-(3,5-dimethylmorpholin-4-yl)ethoxy]-N-(2,4-dimethylphenyl)-N-(2-methylpropyl)benzene-1-sulfonamide;

N-(2,4-dimethylphenyl)-N-(2-methylpropyl)-4-[(oxan-4-ylmethoxy)methyl]benzene-1-sulfonamide;

N-(2,4-dimethylphenyl)-N-(2-methylpropyl)-4-[(oxetan-3-ylmethoxy)methyl]benzene-1-sulfonamide;

3-chloro-N-(2,4-dimethylphenyl)-N-(2-methylpropyl)-4-(oxan-4-ylmethoxy)benzene-1-sulfonamide;

3-cyclopropyl-N-(2,4-dimethylphenyl)-N-(2-methylpropyl)-4-(oxan-4-ylmethoxy)benzene-1-sulfonamide;

N-(2,4-dimethylphenyl)-4-[1-hydroxy-2-(morpholin-4-yl)ethyl]-N-(2-methylpropyl)benzene-1-sulfonamide;

N-(2,4-dimethylphenyl)-3,5-difluoro-N-(2-methylpropyl)-4-(oxan-4-ylmethoxy)benzene-1-sulfonamide;

N-(2,4-dimethylphenyl)-3-methyl-N-(2-methylpropyl)-4-(oxan-4-ylmethoxy)benzene-1-sulfonamide;

N-(2,4-dimethylphenyl)-2-methyl-N-(2-methylpropyl)-4-(oxan-4-ylmethoxy)benzene-1-sulfonamide;

N-(2,4-dimethylphenyl)-2-hydroxy-N-(2-methylpropyl)-4-(oxan-4-ylmethoxy)benzene-1-sulfonamide;

2-chloro-N-(2,4-dimethylphenyl)-N-(2-methylpropyl)-4-(oxan-4-ylmethoxy)benzene-1-sulfonamide;

N-(2,4-dimethylphenyl)-2-fluoro-N-(2-methylpropyl)-4-(oxan-4-ylmethoxy)benzene-1-sulfonamide;

N-(2,4-dimethylphenyl)-3-fluoro-N-(2-methylpropyl)-4-(oxan-4-ylmethoxy)benzene-1-sulfonamide;

N-(2,4-dimethylphenyl)-3-methoxy-N-(2-methylpropyl)-4-(oxan-4-ylmethoxy)benzene-1-sulfonamide;
N-(2,4-dimethylphenyl)-N-(2-methylpropyl)-4-(oxolan-3-ylmethoxy)benzene-1-sulfonamide;
N-(2,4-dimethylphenyl)-3-hydroxy-N-(2-methylpropyl)-4-(oxan-4-ylmethoxy)benzene-1-sulfonamide;
N-(2,4-dimethylphenyl)-N-(2-methylpropyl)-4-(morpholin-4-yl)benzene-1-sulfonamide;
N-(2,4-dimethylphenyl)-N-(2-methylpropyl)-4-(oxan-4-yloxy)benzene-1-sulfonamide;
N-(2,4-dimethylphenyl)-2-ethoxy-N-(2-methylpropyl)-4-(oxan-4-ylmethoxy)benzene-1-sulfonamide;
N-(2,4-dimethylphenyl)-N-isobutyl-4-(((2R,3R)-2-methylmorpholin-3-yl)methoxy)benzenesulfonamide;
3-cyano-N-(2,4-dimethylphenyl)-N-(2-methylpropyl)-4-(oxan-4-ylmethoxy)benzene-1-sulfonamide;
2-cyano-N-(2,4-dimethylphenyl)-N-(2-methylpropyl)-4-(oxan-4-ylmethoxy)benzene-1-sulfonamide;
N-(2,4-dimethylphenyl)-4-[(cis-3-fluoropiperidin-4-yl)methoxy]-N-(2-methylpropyl)benzene-1-sulfonamide;
4-(cyclohexylmethoxy)-N-(2,4-dimethylphenyl)-N-(2-methylpropyl)benzene-1-sulfonamide;
4-[(2,6-dimethylcyclohexyl)methoxy]-N-(2,4-dimethylphenyl)-N-(2-methylpropyl)benzene-1-sulfonamide;
N-(2,4-dimethylphenyl)-4-[(3-hydroxycyclohexyl)oxy]-N-(2-methylpropyl)benzene-1-sulfonamide;
4-{[(2S)-4,4-difluoropyrrolidin-2-yl]methoxy}-N-(2,4-dimethylphenyl)-N-(2-methylpropyl)benzene-1-sulfonamide;
N-(2,4-dimethylphenyl)-N-(2-methylpropyl)-4-(oxan-3-ylmethoxy)benzene-1-sulfonamide;
N-(2,4-dimethylphenyl)-N-(2-methylpropyl)-4-[(6-oxopiperidin-3-yl)oxy]benzene-1-sulfonamide;
N-(2,4-dimethylphenyl)-4-(1,4-dioxan-2-ylmethoxy)-N-(2-methylpropyl)benzene-1-sulfonamide;
N-(2,4-dimethylphenyl)-4-[(4-methylcyclohexyl)methoxy]-N-(2-methylpropyl)benzene-1-sulfonamide;
N-(2,4-dimethylphenyl)-N-(2-methylpropyl)-4-{[1-(morpholin-4-yl)propan-2-yl]oxy}benzene-1-sulfonamide;
N-(2,4-dimethylphenyl)-N-(2-methylpropyl)-4-(morpholin-2-ylmethoxy)benzene-1-sulfonamide;
N-(2,4-dimethylphenyl)-N-(2-methylpropyl)-4-(morpholin-3-ylmethoxy)benzene-1-sulfonamide;
N-(2,4-dimethylphenyl)-N-(2-methylpropyl)-4-(oxan-2-ylmethoxy)benzene-1-sulfonamide;
4-[(6,6-dimethylmorpholin-3-yl)methoxy]-N-(2,4-dimethylphenyl)-N-(2-methylpropyl)benzene-1-sulfonamide;
N-(2,4-dimethylphenyl)-N-(2-methylpropyl)-3-[2-(morpholin-4-yl)ethoxy]benzene-1-sulfonamide;
N-(2,4-dimethylphenyl)-4-{[(2R,3S)-3-hydroxyoxan-2-yl]methoxy}-N-(2-methylpropyl)benzene-1-sulfonamide;
N-(2,4-dimethylphenyl)-4-[(4-fluoropiperidin-4-yl)methoxy]-N-(2-methylpropyl)benzene-1-sulfonamide;
N-(2,4-dimethylphenyl)-4-[(2,6-dioxo-1,2,3,6-tetrahydropyrimidin-4-yl)methoxy]-N-(2-methylpropyl)benzene-1-sulfonamide;
N-(2,4-dimethylphenyl)-N-(2-methylpropyl)-3-(oxan-4-ylmethoxy)benzene-1-sulfonamide;
N-(2,4-dimethylphenyl)-N-(2-methylpropyl)-4-{[(2R,3S,4R,5S)-3,4,5-trihydroxyoxan-2-yl]methoxy}benzene-1-sulfonamide;
N-(2,4-dimethylphenyl)-4-[(1-methylpiperidin-4-yl)oxy]-N-(2-methylpropyl)benzene-1-sulfonamide;
N-(2,4-dimethylphenyl)-4-{[(cis-3-fluoropiperidin-4-yl)methoxy]methyl}-N-(2-methylpropyl)benzene-1-sulfonamide;
4-[2-(2,6-dimethylmorpholin-4-yl)ethoxy]-N-(2,4-dimethylphenyl)-N-(2-methylpropyl)benzene-1-sulfonamide;
N-(2,4-dimethylphenyl)-2,3-difluoro-N-(2-methylpropyl)-4-(oxan-4-ylmethoxy)benzene-1-sulfonamide;
N-(2,4-dimethylphenyl)-4-{[1-(2-methoxyethyl)pyrrolidin-3-yl]methoxy}-N-(2-methylpropyl)benzene-1-sulfonamide;
N-(2,4-dimethylphenyl)-4-[(1-ethylpyrrolidin-3-yl)methoxy]-N-(2-methylpropyl)benzene-1-sulfonamide;
N-(2,4-dimethylphenyl)-4-[(1-methylpiperidin-4-yl)methoxy]-N-(2-methylpropyl)benzene-1-sulfonamide;
N-(2,4-dimethylphenyl)-N-(2-methylpropyl)-4-(pyrrolidin-3-ylmethoxy)benzene-1-sulfonamide;
N-(2,4-dimethylphenyl)-N-(2-methylpropyl)-4-(piperidin-4-yloxy)benzene-1-sulfonamide;
N-(2,4-dimethylphenyl)-N-(2-methylpropyl)-3-(piperidin-4-yloxy)benzene-1-sulfonamide;
4-(azetidin-3-ylmethoxy)-N-(2,4-dimethylphenyl)-N-(2-methylpropyl)benzene-1-sulfonamide;
N-(2,4-dimethylphenyl)-N-(2-methylpropyl)-4-{[(6-oxopiperidin-3-yl)oxy]methyl}benzene-1-sulfonamide;
N-(2,4-dimethylphenyl)-N-(2-methylpropyl)-4-(oxan-4-ylmethoxy)-2-(propan-2-yloxy)benzene-1-sulfonamide;
N-(2,4-dimethylphenyl)-4-{1-hydroxy-2-[(3-methyloxetan-3-yl)amino]ethyl}-N-(2-methylpropyl)benzene-1-sulfonamide;
N-(2,4-dimethylphenyl)-4-[1-hydroxy-2-(piperidin-1-yl)ethyl]-N-(2-methylpropyl)benzene-1-sulfonamide;
N-(2,4-dimethylphenyl)-4-(2-(1,1-dioxidothiomorpholino)-1-hydroxyethyl)-N-isobutylbenzenesulfonamide;
N-(2,4-dimethylphenyl)-4-[2-(3-fluoropiperidin-1-yl)-1-hydroxyethyl]-N-(2-methylpropyl)benzene-1-sulfonamide;
N-(2,4-dimethylphenyl)-4-{1-hydroxy-2-[2-(hydroxymethyl)morpholin-4-yl]ethyl}-N-(2-methylpropyl)benzene-1-sulfonamide;
N-(2,4-dimethylphenyl)-4-[2-(4-fluoropiperidin-1-yl)-1-hydroxyethyl]-N-(2-methylpropyl)benzene-1-sulfonamide;
N-(2,4-dimethylphenyl)-4-[2-hydroxy-1-(piperidin-1-yl)ethyl]-N-(2-methylpropyl)benzene-1-sulfonamide;
N-(2,4-dimethylphenyl)-4-[3-(hydroxymethyl)morpholin-4-yl]-N-(2-methylpropyl)benzene-1-sulfonamide;
N-(2,4-dimethylphenyl)-N-(2-methylpropyl)-4-{[(3S,4R)-3,4,5-trihydroxyoxolan-2-yl]methoxy}benzene-1-sulfonamide;
N-(2,4-dimethylphenyl)-N-(2-methylpropyl)-4-{[(3R,4S,5S)-3,4,5-trihydroxyoxolan-2-yl]methoxy}benzene-1-sulfonamide;
3-chloro-4-[2-(4,4-difluoropiperidin-1-yl)-1-hydroxyethyl]-N-(2,4-dimethylphenyl)-N-(2-methylpropyl)benzene-1-sulfonamide;
3-chloro-N-(2,4-dimethylphenyl)-4-[2-hydroxy-1-(morpholin-4-yl)ethyl]-N-(2-methylpropyl)benzene-1-sulfonamide;
3-chloro-N-(2,4-dimethylphenyl)-4-[1-hydroxy-2-(morpholin-4-yl)ethyl]-N-(2-methylpropyl)benzene-1-sulfonamide;
3-chloro-N-(2,4-dimethylphenyl)-4-(1-hydroxy-2-{2-oxa-6-azaspiro[3.3]heptan-6-yl}ethyl)-N-(2-methylpropyl)benzene-1-sulfonamide;
3-chloro-N-(2,4-dimethylphenyl)-4-{1-hydroxy-2-[trans-(3-hydroxycyclobutyl)amino]ethyl}-N-(2-methylpropyl)benzene-1-sulfonamide;
N-(2,4-dimethylphenyl)-3-fluoro-4-[1-hydroxy-2-(morpholin-4-yl)ethyl]-N-(2-methylpropyl)benzene-1-sulfonamide;
N-(2,4-dimethylphenyl)-4-[1-hydroxy-2-(morpholin-4-yl)ethyl]-2-methyl-N-(2-methylpropyl)benzene-1-sulfonamide;

N-(2,4-dimethylphenyl)-4-[2-hydroxy-1-(morpholin-4-yl)ethyl]-3-methyl-N-(2-methylpropyl)benzene-1-sulfonamide;

N-(2,4-dimethylphenyl)-4-[1-hydroxy-2-(morpholin-4-yl)ethyl]-3-methyl-N-(2-methylpropyl)benzene-1-sulfonamide;

5-[(2,4-dimethylphenyl)(2-methylpropyl)sulfamoyl]-2-(oxan-4-ylmethoxy)benzoic acid;

2-bromo-N-(2,4-dimethylphenyl)-N-(2-methylpropyl)-4-(oxan-4-ylmethoxy)benzene-1-sulfonamide;

2-cyclopropyl-N-(2,4-dimethylphenyl)-N-(2-methylpropyl)-4-(oxan-4-ylmethoxy)benzene-1-sulfonamide;

N-(2,4-dimethylphenyl)-4-{1-hydroxy-2-[(oxan-4-yl)amino]ethyl}-N-(2-methylpropyl)benzene-1-sulfonamide;

N-(2,4-dimethylphenyl)-4-[1-hydroxy-2-(4-methoxypiperidin-1-yl)ethyl]-N-(2-methylpropyl)benzene-1-sulfonamide;

N-(2,4-dimethylphenyl)-4-[1-hydroxy-2-(4-hydroxypiperidin-1-yl)ethyl]-N-(2-methylpropyl)benzene-1-sulfonamide;

3-cyano-N-(2,4-dimethylphenyl)-N-(2-methylpropyl)-4-(oxan-4-ylmethoxy)benzene-1-sulfonamide;

3-chloro-N-(2,4-dimethylphenyl)-N-(2-methylpropyl)-4-(oxan-4-ylmethoxy)benzene-1-sulfonamide;

N-(2,4-dimethylphenyl)-4-[2-hydroxy-1-(4-hydroxypiperidin-1-yl)ethyl]-N-(2-methylpropyl)benzene-1-sulfonamide;

N-(2,4-dimethylphenyl)-4-{1-hydroxy-2-[(oxan-3-yl)amino]ethyl}-N-(2-methylpropyl)benzene-1-sulfonamide;

N-(2,4-dimethylphenyl)-4-[2-hydroxy-1-(morpholin-4-yl)ethyl]-N-(2-methylpropyl)benzene-1-sulfonamide;

N-(2,4-dimethylphenyl)-N-(2-methylpropyl)-4-(5-oxopyrrolidin-2-yl)benzene-1-sulfonamide;

N-(2,4-dimethylphenyl)-4-[2-(hydroxymethyl)morpholin-4-yl]-N-(2-methylpropyl)benzene-1-sulfonamide;

N-(2,4-dimethylphenyl)-3,5-difluoro-4-[1-hydroxy-2-(morpholin-4-yl)ethyl]-N-(2-methylpropyl)benzene-1-sulfonamide;

N-(5-chloro-2-fluorophenyl)-4-[1-hydroxy-2-(morpholin-4-yl)ethyl]-N-(2-methylpropyl)benzene-1-sulfonamide;

N-(2,4-dimethylphenyl)-3-fluoro-4-{1-hydroxy-2-[(3-methyloxetan-3-yl)amino]ethyl}-N-(2-methylpropyl)benzene-1-sulfonamide;

N-(2,4-dimethylphenyl)-4-{1-hydroxy-2-[(3-methyloxetan-3-yl)amino]ethyl}-2-methyl-N-(2-methylpropyl)benzene-1-sulfonamide;

N-(2,4-dimethylphenyl)-4-{1-hydroxy-2-[(3-methyloxetan-3-yl)amino]ethyl}-3-methyl-N-(2-methylpropyl)benzene-1-sulfonamide;

N-(2,4-dimethylphenyl)-3-hydroxy-4-[2-hydroxy-1-(morpholin-4-yl)ethyl]-N-(2-methylpropyl)benzene-1-sulfonamide;

methyl 5-[(2,4-dimethylphenyl)(2-methylpropyl)sulfamoyl]-2-(oxan-4-ylmethoxy)benzoate;

N-(2,4-dimethylphenyl)-3-(hydroxymethyl)-N-(2-methylpropyl)-4-(oxan-4-ylmethoxy)benzene-1-sulfonamide;

N-(4-ethylphenyl)-4-{1-hydroxy-2-[(3-methyloxetan-3-yl)amino]ethyl}-N-(2-methylpropyl)benzene-1-sulfonamide;

N-(4-ethylphenyl)-4-[1-hydroxy-2-(morpholin-4-yl)ethyl]-N-(2-methylpropyl)benzene-1-sulfonamide;

N-(2-ethylphenyl)-4-[1-hydroxy-2-(morpholin-4-yl)ethyl]-N-(2-methylpropyl)benzene-1-sulfonamide;

4-[1,2-dihydroxy-3-(morpholin-4-yl)propyl]-N-(2,4-dimethylphenyl)-N-(2-methylpropyl)benzene-1-sulfonamide;

4-[1,2-dihydroxy-3-(morpholin-4-yl)propyl]-N-(2,4-dimethylphenyl)-N-(2-methylpropyl)benzene-1-sulfonamide;

N-(2,4-dimethylphenyl)-4-{1-hydroxy-2-[(oxetan-3-yl)amino]ethyl}-N-(2-methylpropyl)benzene-1-sulfonamide;

4-[1,3-dihydroxy-2-(morpholin-4-yl)propyl]-N-(2,4-dimethylphenyl)-N-(2-methylpropyl)benzene-1-sulfonamide;

4-[1,3-dihydroxy-2-(morpholin-4-yl)propyl]-N-(2,4-dimethylphenyl)-N-(2-methylpropyl)benzene-1-sulfonamide;

N-(2,4-dimethylphenyl)-4-[1-hydroxy-2-(morpholin-4-yl)ethyl]-N-(2-methylpropyl)benzene-1-sulfonamide;

N-(2,4-dimethylphenyl)-4-[1-hydroxy-2-(morpholin-4-yl)ethyl]-N-(2-methylpropyl)benzene-1-sulfonamide;

N-(2,4-dimethylphenyl)-4-[1-hydroxy-2-(morpholin-4-yl)ethyl]-N-(2-methylpropyl)benzene-1-sulfonamide;

N-(4-ethylphenyl)-4-(1-hydroxy-2-morpholinoethyl)-3-(hydroxymethyl)-N-isobutylbenzenesulfonamide;

N-(4-ethylphenyl)-3-(hydroxymethyl)-N-isobutyl-4-((tetrahydro-2H-pyran-4-yl)methoxy)benzenesulfonamide;

(S)—N-(4-ethylphenyl)-4-(1-hydroxy-2-morpholinoethyl)-3-(hydroxymethyl)-N-isobutylbenzenesulfonamide; and (R)—N-(4-ethylphenyl)-4-(1-hydroxy-2-morpholinoethyl)-3-(hydroxymethyl)-N-isobutylbenzenesulfonamide.

In a further aspect, the present invention provides a compound, or a pharmaceutically acceptable salt thereof, which is selected from the group consisting of:

N-(4-ethylphenyl)-4-(1-hydroxy-2-morpholinoethyl)-3-(hydroxymethyl)-N-isobutylbenzenesulfonamide;

N-(4-ethylphenyl)-3-(hydroxymethyl)-N-isobutyl-4-((tetrahydro-2H-pyran-4-yl)methoxy)benzenesulfonamide;

(S)—N-(4-ethylphenyl)-4-(1-hydroxy-2-morpholinoethyl)-3-(hydroxymethyl)-N-isobutylbenzenesulfonamide; and (R)—N-(4-ethylphenyl)-4-(1-hydroxy-2-morpholinoethyl)-3-(hydroxymethyl)-N-isobutylbenzenesulfonamide.

In a further aspect, the present invention provides a compound, or a pharmaceutically acceptable salt thereof, which is (S)—N-(4-ethylphenyl)-4-(1-hydroxy-2-morpholinoethyl)-3-(hydroxymethyl)-N-isobutylbenzenesulfonamide.

In a further aspect, the present invention provides a compound, or a pharmaceutically acceptable salt thereof, which is N-(4-ethylphenyl)-3-(hydroxymethyl)-N-isobutyl-4-((tetrahydro-2H-pyran-4-yl)methoxy)benzenesulfonamide.

As used herein, the term "alkyl" refers to a saturated hydrocarbon chain having the specified number of carbon atoms. For example, $C_{1-6}$alkyl refers to an alkyl group having from 1 to 6 member atoms. Unless otherwise stated, alkyl groups are unsubstituted. Alkyl groups may be straight chain or branched. The term "alkyl" includes, but is not limited to, methyl, ethyl, propyl (n-propyl and isopropyl), butyl (n-butyl, sec-butyl, isobutyl and tert-butyl), pentyl, and hexyl.

As used herein, the term "alkoxy" refers to an —O-alkyl group wherein "alkyl" is defined above.

As used herein, the term "heterocycloalkyl" refers to a saturated or unsaturated 3 to 7 membered monocyclic or bicyclic ring, which must contain 1, 2 or 3 non-carbon atoms, which are selected from nitrogen, oxygen, and sulfur. Heterocycloalkyl groups may contain one or more C(O), S(O) or $SO_2$ groups. Bicyclic heterocycloalkyl groups include spiro compounds, wherein rings are connected through just one atom. However, heterocycloalkyl groups are not aromatic. Heterocycloalkyl groups containing more than one heteroatom may contain different heteroatoms. Heterocycloalkyl includes, but is not limited to, pyrrolidine, piperidine, oxetane, tetrahydrofuran, tetrahydro-2H-pyran, morpholine, morpholine-3-one, piperidin-2-one, pyrimidine-2,4(1H,3H)-dione, thiomorpholine, thiomorpholine 1,1-dioxide.

As used herein, the term "cycloalkyl" refers to a saturated hydrocarbon ring having the specified number of carbon atoms. Cycloalkyl groups are monocyclic ring systems. For example, $C_{3-6}$cycloalkyl refers to a cycloalkyl group having from 3 to 6 carbon atoms. Cycloalkyl includes cyclopropyl, cyclobutyl, cyclopentyl and cyclohexyl.

As used herein, the term "halo" refers to the halogen radicals fluoro, chloro, bromo and iodo.

As used herein, the term "RORγ" refers to all isoforms of this member of the ROR family, including RORγ1 and RORγt.

As used herein, the term "RORγ modulator" refers to a chemical compound of formula (I) that inhibits, either directly or indirectly, the activity of RORγ. RORγ modulators include antagonists and inverse agonists of RORγ.

The compounds of formula (I) and pharmaceutically acceptable salts thereof may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in a compound of formula (I), or in any chemical structure illustrated herein, is not specified the structure is intended to encompass all individual stereoisomers and all mixtures thereof. Thus, compounds of formula (I) and pharmaceutically acceptable salts thereof containing one or more chiral center may be used as racemic mixtures, enantiomerically enriched mixtures, or as enantiomerically pure individual stereoisomers.

Individual stereoisomers of a compound of formula (I), or a pharmaceutically acceptable salt thereof, which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

In certain aspects, compounds of formula (I) may contain an acidic functional group. In certain other embodiments, compounds of formula (I) may contain a basic functional group. Thus, the skilled artisan will appreciate that pharmaceutically-acceptable salts of the compounds of formula (I) may be prepared. Indeed, in certain embodiments of the invention, pharmaceutically-acceptable salts of the compounds of formula (I) may be preferred over the respective free base or free acid because such salts may impart greater stability or solubility to the molecule thereby facilitating formulation into a dosage form.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopaedia of Pharmaceutical Technology, Marcel Dekker Inc, New York 1996, Volume 13, page 453-497. Other salts that are not deemed pharmaceutically acceptable may be useful in the preparation of compounds of formula (I) and are included within the scope of the invention, such as those formed with ammonia and trifluoroacetic acid. The present invention encompasses all possible stoichiometric and non-stoichiometric forms of the salts of the compounds of formula (I).

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

The invention also includes all suitable isotopic variations of a compound of formula (I) or a pharmaceutically acceptable salt thereof. An isotopic variation of a compound of formula (I), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^{2}H$, $^{3}H$, $^{13}C$, $^{14}C$, $^{15}N$, $^{17}O$, $^{18}O$ $^{18}F$ and $^{36}Cl$, respectively. Certain isotopic variations of a compound of formula (I) or a salt or solvate thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of a compound of formula (I), or a pharmaceutically salt thereof, can generally be prepared by conventional procedures such as by the illustrative methods or by the preparations described in the Examples hereafter using appropriate isotopic variations of suitable reagents.

A compound of formula (I), or a pharmaceutically acceptable salt thereof, may be in amorphous or crystalline form. Moreover, a compound of formula (I), or a pharmaceutically acceptable salt thereof, may exist in one or more crystalline forms. Consequently, the present invention includes within its scope all forms of a compound of formula (I), or a pharmaceutically acceptable salt thereof.

The person skilled in the art will appreciate that many organic compounds can form complexes with solvents in which they are reacted or from which they are precipitated or crystallised. These complexes are known as “solvates”. Where the solvent is water the complex is known as a “hydrate”. The present invention encompasses all solvates of the compounds of formula (I).

In addition, prodrugs are also included within the context of this invention. As used herein, the term “prodrug” means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra “Improved oral drug delivery: solubility limitations overcome by the use of prodrugs”, Advanced Drug Delivery Reviews (1996) 19(2) 115-130, each of which are incorporated herein by reference.

Prodrugs are any covalently bonded carriers that release a compound of formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of formula (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Experimental

Compounds of the invention may be prepared by methods known in the art of organic synthesis as set forth in part by the following synthesis schemes. In the following reaction schemes and hereafter, unless otherwise stated, all the groups are defined in the first aspect. It is also recognised that in all of the schemes described below, it is well understood that protecting groups for sensitive or reactive groups are employed where necessary in accordance with general principles of organic synthesis (T. W. Greene and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of the invention.

General Reaction Schemes

Scheme 1a and 1b

1a

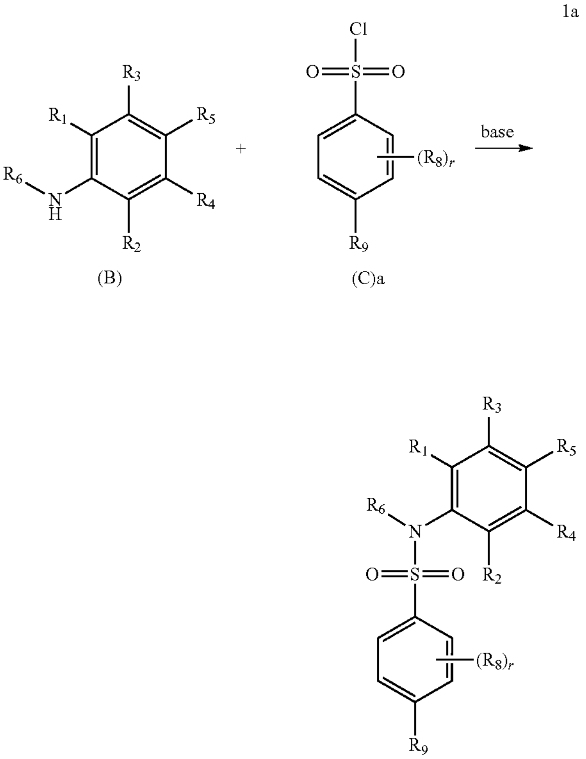

(B) (C)a (A)a

1b

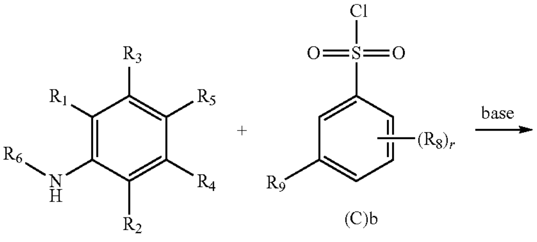

(B) (C)b

-continued

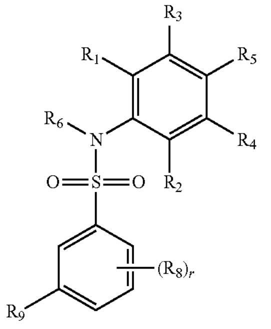

(A)b

Compounds of formula (A)a and (A)b may be prepared from sulfonyl chlorides of formula (C)a and (C)b respectively, by reaction with an aniline of formula (B), according to Scheme 1a and 1b. Typical reaction conditions comprise mixing together a sulfonyl chloride of formula (C)a or (C)b with the appropriate aniline (B), in a basic solvent such as pyridine, for a suitable time, such as 16 hours, at a suitable temperature, such as ambient.

Scheme 2a and 2b

2a

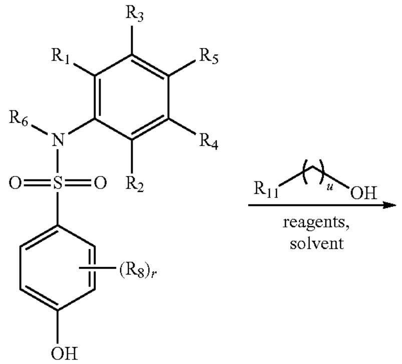

(D)a

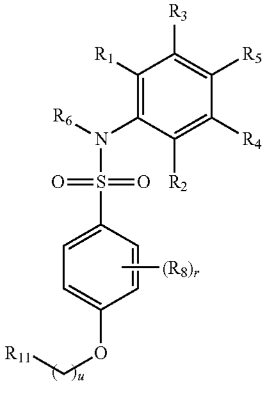

(A)c $u = 1, 2$

-continued

2b

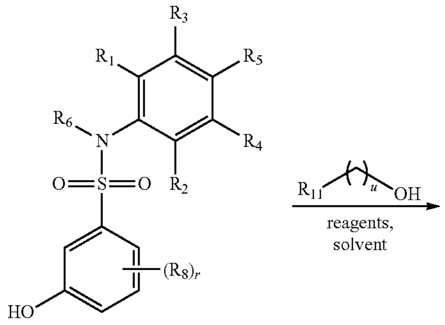

(D)b

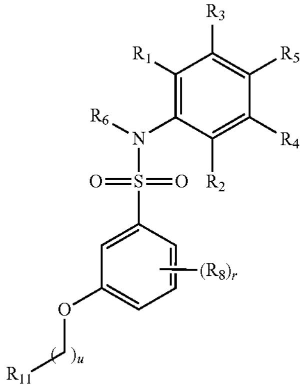

(A)d $u = 1, 2$

Compounds of formula (A)c and (A)d may be prepared from intermediate compounds of formula (D)a and (D)b respectively, by coupling with an appropriately substituted alcohol according to Scheme 2a and 2b. Typical coupling conditions would include the ‘Mitsunobu reaction’ and comprise mixing the alcohol together with an intermediate compound of formula (D)a or (D)b and triphenylphosphine, in a suitable solvent, such as tetrahydrofuran. The mixture is then treated with a suitable coupling reagent, such as diisopropyl azodicarboxylate, and the reaction stirred for a suitable time, such as 16 hours, at a suitable temperature, such as ambient.

Scheme 3a and 3b

3a

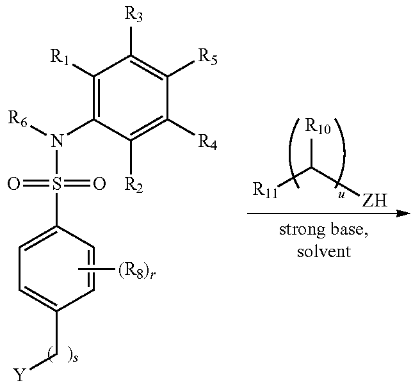

(D)c

-continued

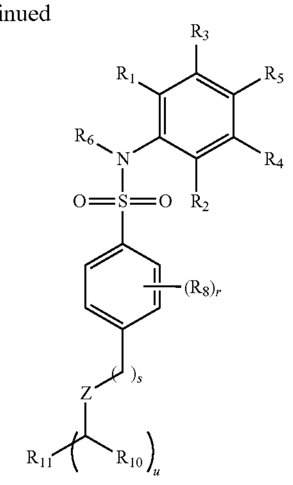

(A)e

Y = suitable leaving group eg. Br, I, Cl, F, OTs, OMs
Z = O, NH
$s$ = 0, 1, 2
$u$ = 0, 1, 2

3b

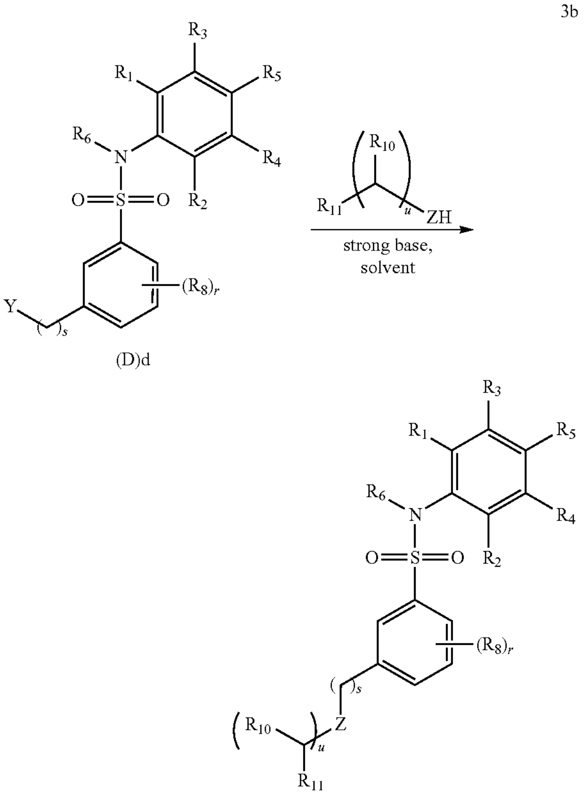

(D)d (A)f

Y = suitable leaving group eg. Br, I, Cl, F, OTs, OMs
Z = O, NH
$s$ = 1, 2
$u$ = 0, 1, 2

Compounds of formula (A)e and (A)f may be prepared from intermediate compounds of formula (D)c and (D)d respectively, by reaction with an appropriately substituted alkyl or heterocycloalkyl alcohol or amine according to Scheme 3a and 3b. Typical reaction conditions comprise mixing the alcohol or amine together with an intermediate compound of formula (D)c or (D)d, with a strong base such as sodium hydride, in a suitable solvent such as 2-methyltetrahydrofuran, under nitrogen at a suitable temperature, such as ambient for a suitable time, such as 3 hours.

Scheme 4a and 4b

4a

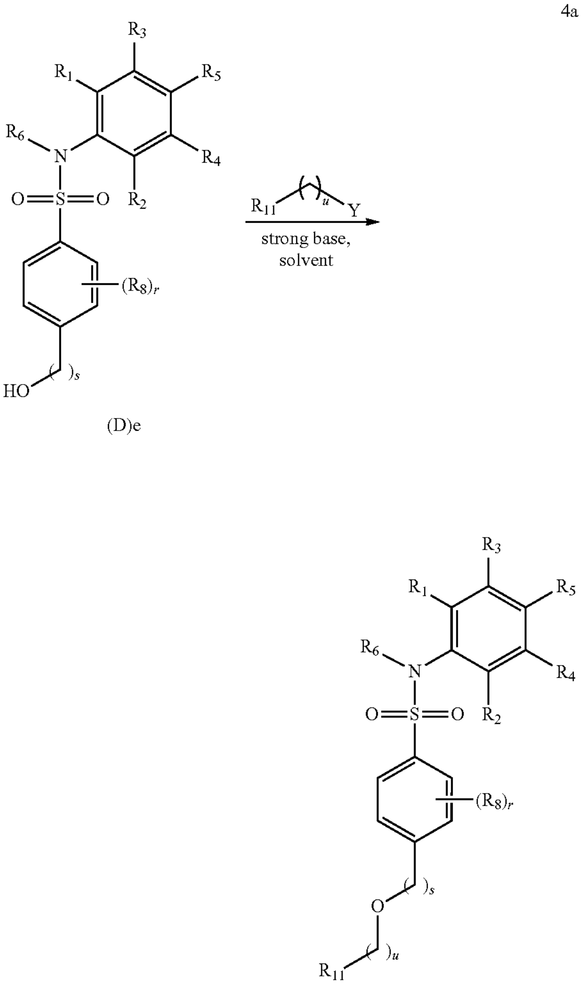

(D)e (A)g

Y = suitable leaving group eg. Br, I, Cl, F, OTs, OMs
$s$ = 0, 1, 2
$u$ = 1, 2

4b

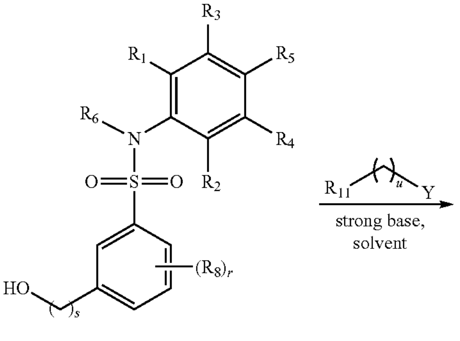

(D)f

-continued

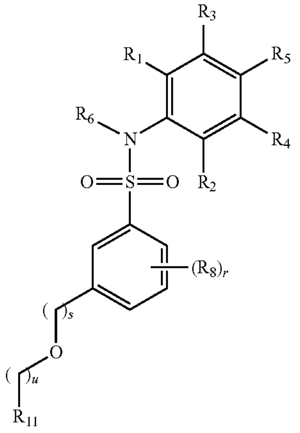

(A)h

Y = suitable leaving group eg. Br, I, Cl, F, OTs, OMs
$s$ = 0, 1, 2
$u$ = 1, 2

Compounds of formula (A)g and (A)h may be prepared from intermediate compounds of formula (D)e and (D)f respectively, by reaction with an appropriate alkylating agent according to Scheme 4a and 4b. Typical reaction conditions comprise mixing an intermediate compound of formula (D)e or (D)f, with a strong base such as sodium hydride in a suitable solvent, such as dimethyl sulfoxide, for a suitable time, such as 5 minutes, under nitrogen. The mixture is then treated with the alkylating agent and stirred at a suitable temperature such as ambient for a suitable time, such as 18 hours.

Scheme 5a and 5b

5a

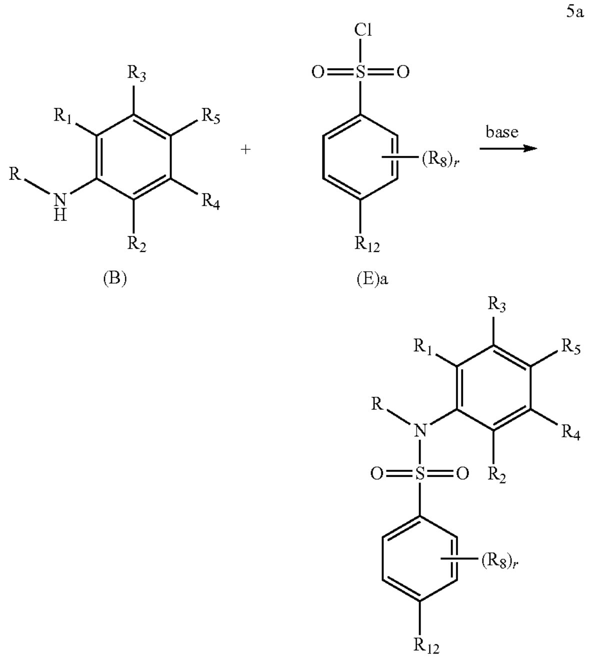

(B) (E)a (D)

$R_{12}$ = -halo, —$(CHR_{10})_s$-halo, -vinyl, —OMe/—OBn, —$CO_2Me$/—$CO_2Et$, —CN, —NHAc
R = $R_6$ or H -continued 5b

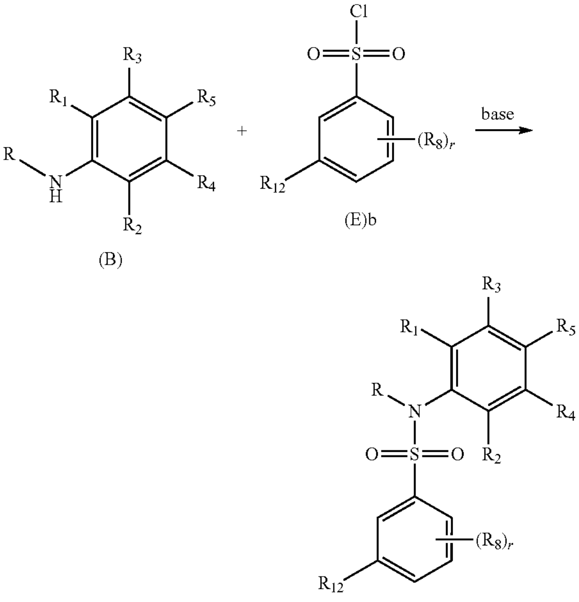

(B) (E)b (D)

$R_{12}$ = -halo, —$(CHR_{10})_s$-halo, -vinyl, —OMe/—OBn, —$CO_2Me$/—$CO_2Et$, —CN, —NHAc
R = $R_6$ or H Key intermediate compounds of formula (D), where $R_{12}$ is a suitable functional group for later transformation into $R_9$; may be prepared from sulfonyl chlorides of formula (E)a and (E)b, by reaction with an aniline of formula (B) according to Scheme 5a and 5b. Typical reaction conditions comprise mixing together a sulfonyl chloride of formula (E)a or (E)b with the appropriate aniline (B) in a basic solvent such as pyridine, for a suitable time, such as 16 hours, at a suitable temperature such as ambient.

$R_{12}$ may include functionality (which can be protected/masked) that is inert to reaction under the above conditions and may then be converted to $R_9$ in subsequent step(s). Suitable examples for $R_{12}$ can include -halo, —$(CHR_{10})_s$-halo, -vinyl, —OMe/—OBn, —$CO_2Me$/—$CO_2Et$, —CN, —NHAc (the latter four which may then be deprotected or transformed to —OH, —$CH_2OH$, —$CH_2NH_2$ and —$NH_2$ respectively using methods known to those skilled in the art of organic synthesis).

Scheme 6a and 6b

6a

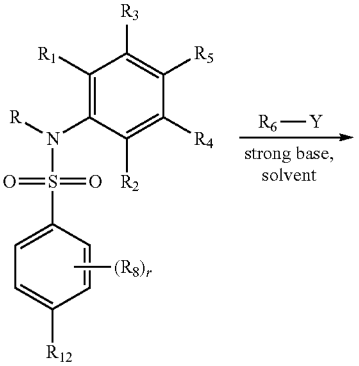

(D), R = H

-continued

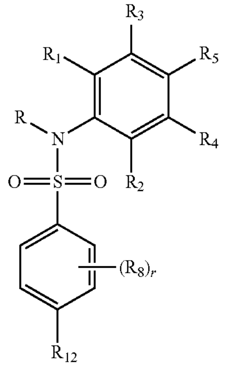

(D), R = $R_6$

Y = suitable leaving group eg. Br, I, Cl, OTs
$R_{12}$ = -halo, —$(CHR_{10})_s$-halo, -vinyl, —OMe/—OBn, —$CO_2Me$/—$CO_2Et$, —CN, —NHAc 6b

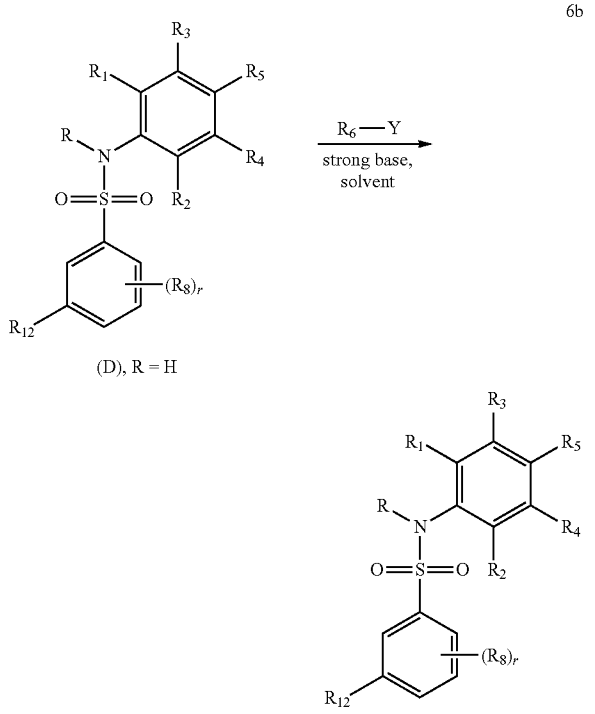

(D), R = H (D), R = $R_6$

Y = suitable leaving group eg. Br, I, Cl, OTs
$R_{12}$ = -halo, —$(CHR_{10})_s$-halo, -vinyl, —OMe/—OBn, —$CO_2Me$/—$CO_2Et$, —CN, —NHAc Compounds of formula (D) where R═$R_6$, may be prepared from intermediate compounds of formula (D), where R═H, by reaction with a suitable alkylating agent according to Scheme 6a and 6b. Typical reaction conditions comprise mixing together a compound of formula (D), where R═H, with a strong base, such as Barton's base, in a suitable solvent such as acetonitrile, for a suitable time, such as 1 hour, at a suitable temperature such as ambient. The mixture is then treated with the appropriate alkylating agent and heated in a sealed vessel to a suitable temperature, for example 150° C., by microwaves, for a suitable time, such as 25 minutes.

Scheme 7a and 7b

7a

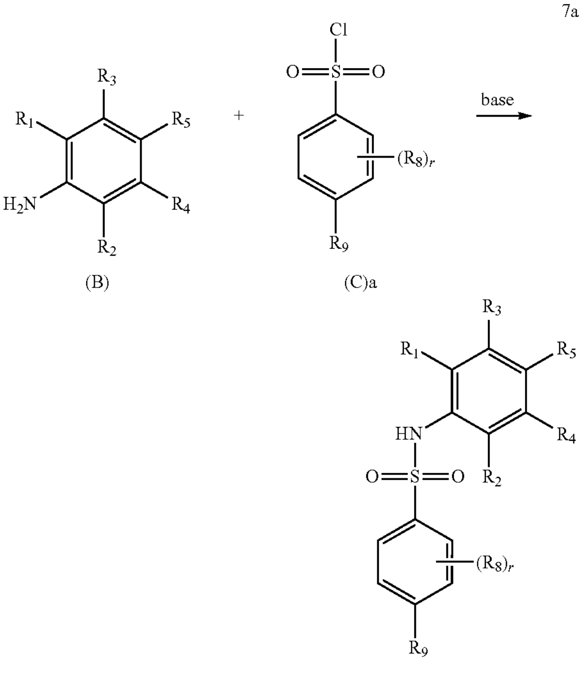

(B) (C)a (F)a

7b

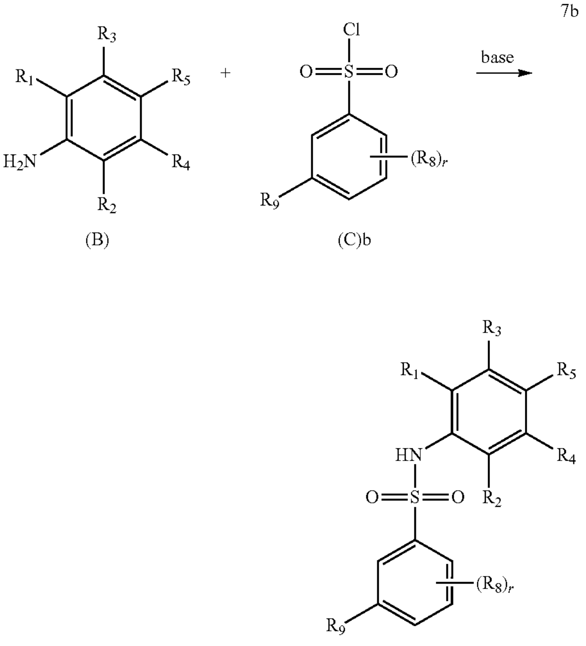

(B) (C)b (F)b

Secondary sulfonamide compounds of formula (F)a and (F)b may be prepared from sulfonyl chlorides of formula (C)a and (C)b respectively, by reaction with a primary aniline of formula (B), R═H, according to Scheme 7a and 7b. Typical reaction conditions comprise mixing together a sulfonyl chloride of formula (C)a or (C)b with the appropriate aniline (B), R═H, in a basic solvent such as pyridine, for a suitable time, such as 16 hours, at a suitable temperature such as ambient.

Scheme 8a and 8b

8a

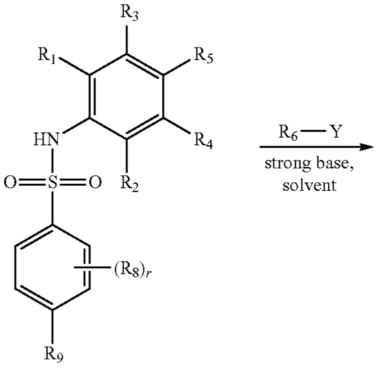

(F)a

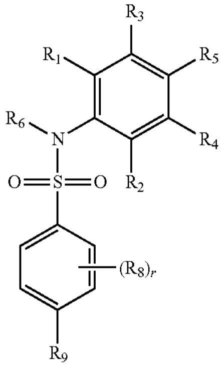

(A)i

Y = suitable leaving group eg. Br, I, Cl, OTs

8b

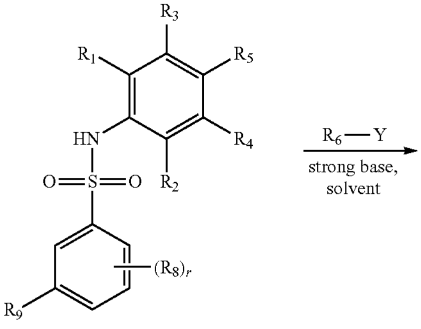

(F)b

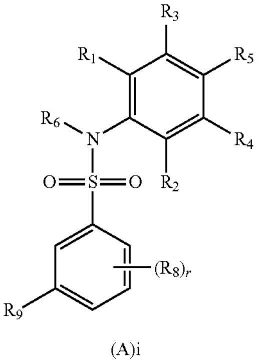

(A)i

Y = suitable leaving group eg. Br, I, Cl, OTs

Compounds of formula (A)i and (A)j, may be prepared from intermediate compounds of formula (F)a and (F)b, by reaction with a suitable alkylating agent according to Scheme 8a and 8b. Typical reaction conditions comprise mixing together a compound of formula (F)a or (F)b, with a strong base, such as Barton's base, in a suitable solvent such as acetonitrile, for a suitable time, such as 1 hour, at a suitable temperature such as ambient. The mixture is then treated with the appropriate alkylating agent and heated in a sealed vessel to a suitable temperature, for example 150° C., by microwaves, for a suitable time, such as 25 minutes.

Scheme 9

9

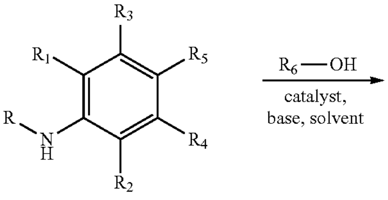

(B), R = H

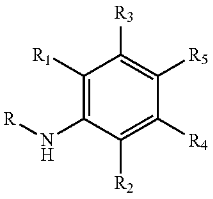

(B), R = $R_6$

Secondary anilines of formula (B), R=$R_6$ may be prepared from primary anilines of formula (B), R=H, by reaction with an appropriate primary alcohol according to Scheme 9. Typical reaction conditions comprise mixing together a primary aniline (B), R=H, with the appropriate alcohol, a suitable base such as potassium iodide and a suitable catalyst such as pentamethylcyclopentadienyliridium(III) chloride in a suitable solvent, such as water. The mixture is then heated in a sealed vessel to a suitable temperature, for example 170° C., by microwaves, for a suitable time, such as 1 hour.

Scheme 10

10

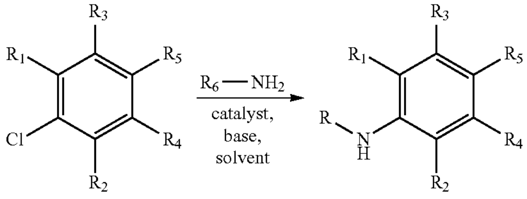

(G) (B), R = $R_6$

Where $R_1$-$R_5$ should not be reactive towards palladium cross-coupling

Secondary anilines of formula (B), R=$R_6$ may be prepared from aryl chlorides of formula (G), by reaction with an appropriate primary alkylamine according to Scheme 10. Typical reaction conditions comprise mixing together an aryl chloride (G), with the appropriate primary alkyl amine, a suitable catalyst such as {1,3-bis[2,6-bis(1-methylethyl) phenyl]-2-imidazolidinyl}(chloro)(2-methyl-2-propen-1-yl) palladium and a suitable base such as lithium hexamethyldisilizide, in a suitable solvent, such as tetrahydrofuran. The mixture is then heated in a sealed vessel to a suitable temperature, for example 70° C., by microwaves, for a suitable time, such as 45 minutes.

Scheme 11

11

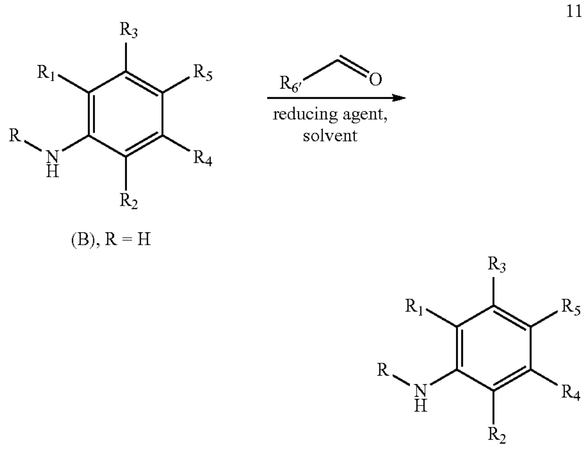

(B), R = H (B), R = $R_6$ $R_{6'}$ = $C_{2\text{-}4}$ alkyl or $C_{3\text{-}4}$ cycloalkyl A secondary aniline of formula (B), R=$R_6$ may be prepared from a primary aniline of formula (B), R=H, by reaction with an appropriate aldehyde according to Scheme 11. Typical reaction conditions comprise mixing together a primary aniline (B), R=H, with the appropriate aldehyde, in a suitable solvent such as tetrahydrofuran, for a suitable time, such as 20 minutes. The mixture is then treated with a suitable reducing agent, such as sodium triacetoxyborohydride and stirred for a suitable time, such as 18 hours, at a suitable temperature, such as ambient.

Scheme 12

12

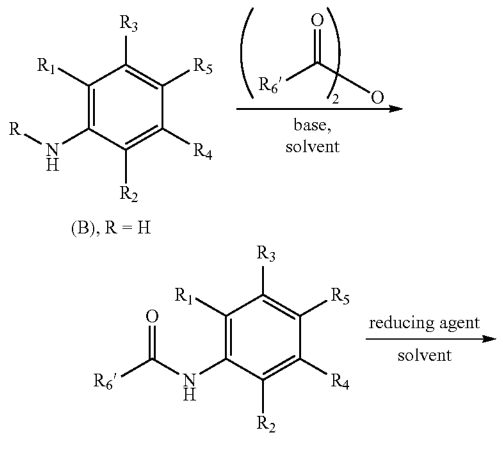

(B), R = H (H)

-continued

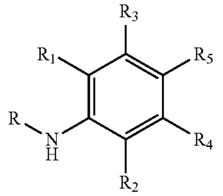

(B), R = $R_6$ $R_{6'}$ = $C_{2\text{-}4}$ alkyl or $C_{3\text{-}4}$ cycloalkyl

A secondary aniline of formula (B), R=$R_6$ may be prepared from a primary aniline (B), in a two step process, via an intermediate primary amide of formula (H), according to Scheme 12. Intermediate (H) may be prepared from a primary aniline (B) by reaction with a suitable anhydride. Typical reaction conditions comprise mixing together a primary aniline of formula (B) with the appropriate anhydride in a suitable solvent, such as dichloromethane, with a suitable base such as triethylamine, under nitrogen, for a suitable time, such as 20 hours, at a suitable temperature, such as ambient.

Secondary aniline (B), R=$R_6$ may then be prepared from intermediate (H), by reduction of the amide. Typical reaction conditions comprise mixing together an intermediate primary amide (H), with a suitable reducing agent, such as a solution of borane-tetrahydrofuran complex in tetrahydrofuran, in a suitable solvent such as tetrahydrofuran, under nitrogen. The mixture is then warmed to a suitable temperature, such as 60° C., and stirred for a suitable time, such as 2 hours.

Scheme 13

13

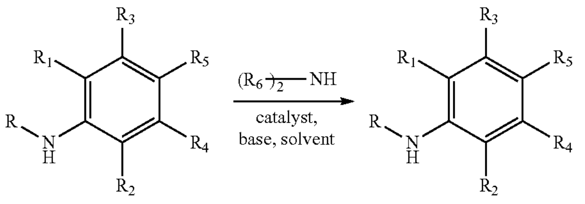

(B), R = H (B), R = $R_6$

Secondary anilines of formula (B), R=$R_6$ may be prepared from primary anilines of formula (B), R=H, by reaction with an appropriate dialkylamine according to Scheme 13. Typical reaction conditions comprise mixing together a primary aniline (B), R=H, with the appropriate dialkylamine, a suitable base such as potassium iodide and a suitable catalyst such as pentamethylcyclopentadienyliridium(III) chloride in a suitable solvent such as xylene. The mixture is then heated in a sealed vessel to a suitable temperature, for example 190° C., by microwaves, for a suitable time, such as 2 hours.

Scheme 14

14a

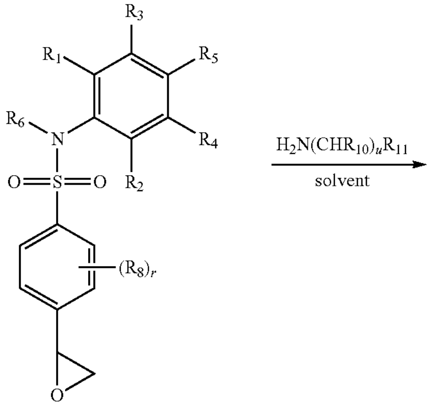

(K)a

-continued

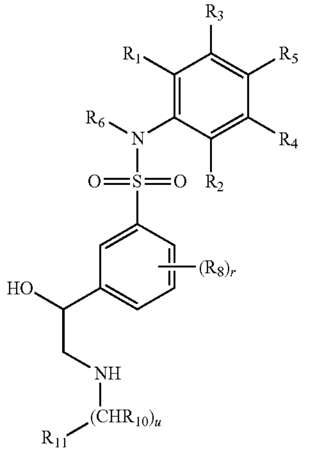

(A)m

+

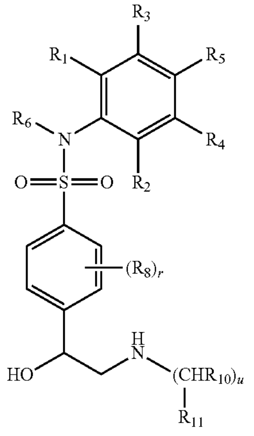

(A)k

+

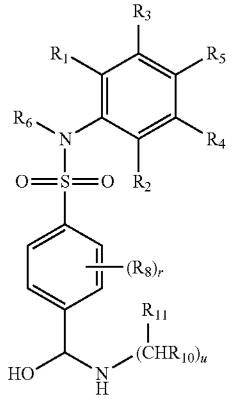

(A)l

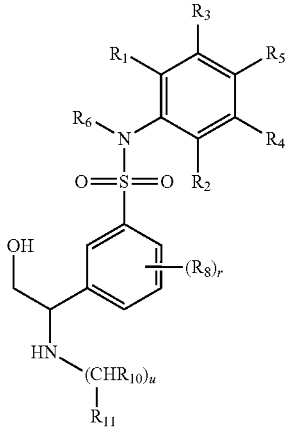

(A)n

14b

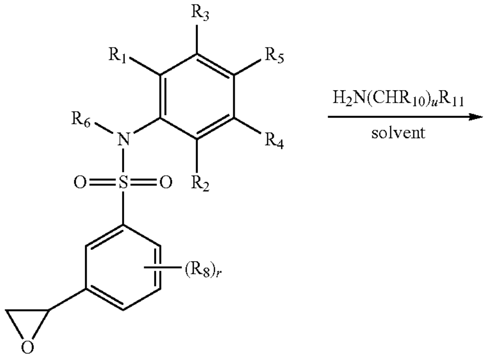

(K)b

Compounds of formula (A)k/(A)l and (A)m/(A)n may be prepared from epoxide-containing intermediate compounds of formula (K)a and (K)b respectively, by reaction with an appropriate amine, according to Scheme 14a and 14b. Typical reaction conditions comprise mixing together epoxide-containing intermediate compound (K)a or (K)b with an excess of an appropriate amine, in a suitable solvent, such as ethanol, at a suitable temperature, such as 50° C., for a suitable time, such as overnight. The ratio of regioisomeric products (A)k to (A)l or (A)m to (A)n may vary with selection of amine, and where a mixture of products results, separation may be achieved using a suitable purification system, such as preparative HPLC.

Scheme 15

15a

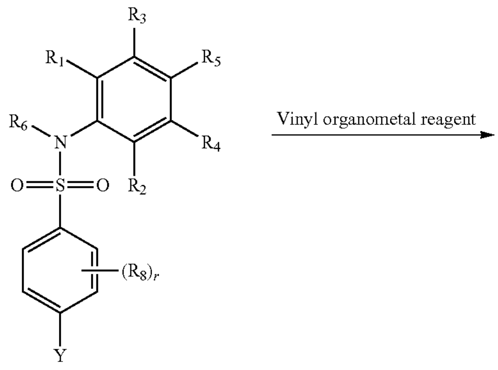

(D)g

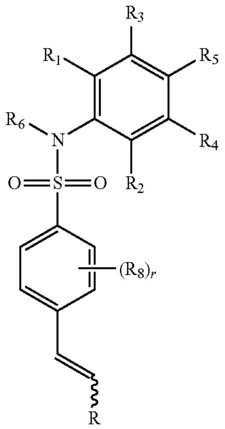

(L)a

Y = suitable cross-coupling group, eg. halogen, OTf
R = H, alkyl or substituted alkyl 15b

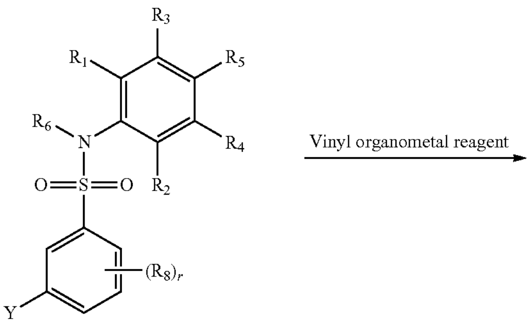

(D)h

-continued

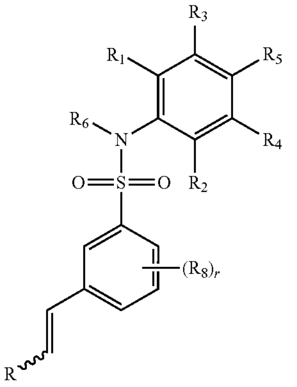

(L)b

Y = suitable cross-coupling group, eg. halogen, OTf
R = H, alkyl or substituted alkyl Vinyl containing intermediate compounds of formula (L)a and (L)b, may be prepared from intermediate compounds of formula (D)g and (D)h respectively, by reaction with a vinyl organometal reagent, according to Scheme 15. Typical reaction conditions comprise mixing together intermediate compound (D)g or (D)h with a suitable vinyl organometal reagent, such as potassium trifluoro(vinyl)borate, an appropriate base such as cesium carbonate and a suitable catalyst such as palladium(II)chloride with a suitable ligand, such as triphenylphosphine. A suitable solvent, such as tetrahydrofuran/water mixture is then added and the reaction heated in a sealed vessel to a suitable temperature, for example 140° C., by microwaves, for a suitable time, such as 1 hour.

Scheme 16

16a

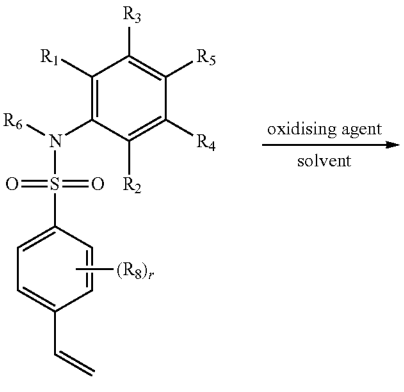

(L)a

-continued

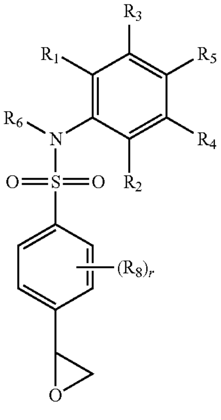

(K)a

16b

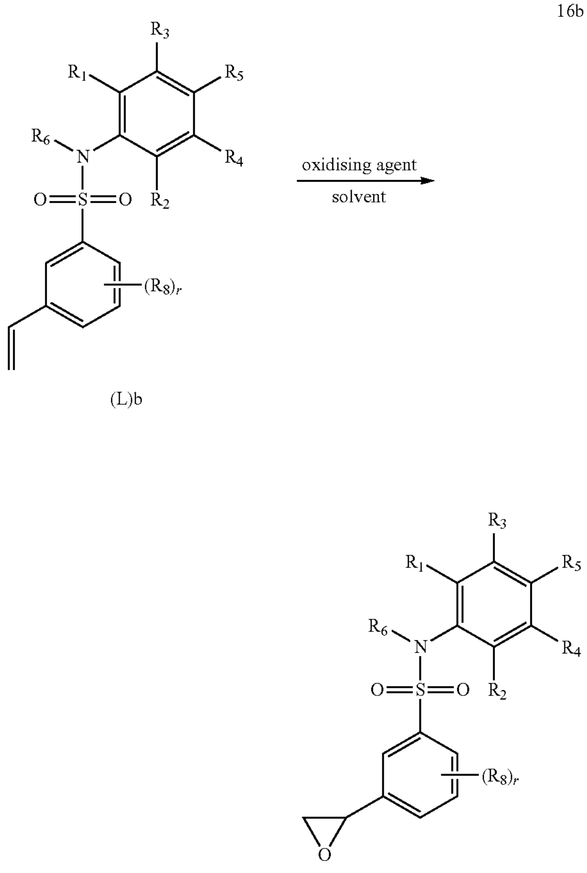

(L)b (K)b

Epoxide-containing intermediate compounds of formula (K)a and (K)b, may be prepared from intermediate compounds of formula (L)a and (L)b respectively, by oxidation of the vinyl group, according to Scheme 16. Typical reaction conditions comprise mixing together intermediate vinyl compound (L)a or (L)b with a suitable oxidising agent, such as m-chloroperbenzoic acid in an appropriate solvent such as dichloromethane, for a suitable time, such as 16 hours, at a suitable temperature, such as 0° C. to ambient.

Scheme 17a and 17b

17a

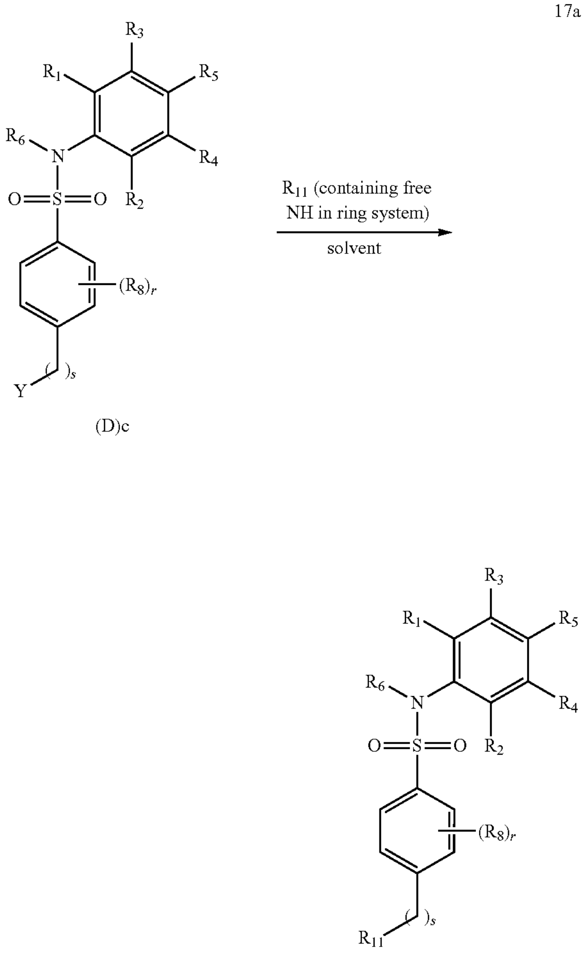

(D)c (A)p

Y = suitable leaving group eg. halo, OTs, OMs
*s* = 0, 1, 2

17b

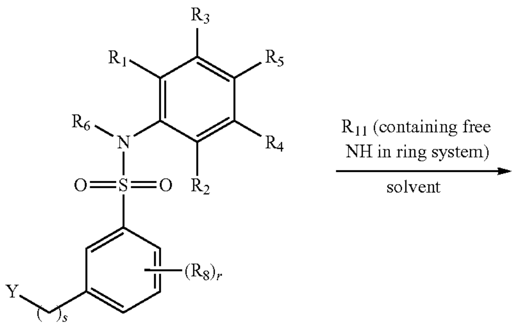

(D)d

-continued

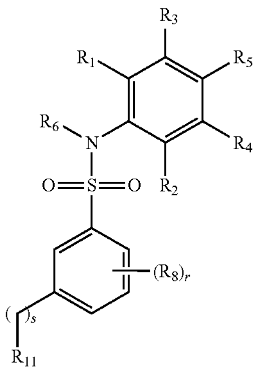

(A)q

Y = suitable leaving group eg. halo, OTs, OMs
$s$ = 1, 2

Compounds of formula (A)p and (A)q may be prepared from intermediate compounds of formula (D)c and (D)d respectively, by reaction with an appropriate heterocycloalkyl compound containing a free NH group within the heterocycloalkyl ring system, according to Scheme 17a and 17b. Typical reaction conditions comprise mixing the amine together with an intermediate compound of formula (D)c or (D)d, with a strong base such as sodium hydride, in a suitable solvent such as 2-methyltetrahydrofuran, under nitrogen at a suitable temperature, such as ambient for a suitable time, such as 3 hours.

Scheme 18a and 18b

18a

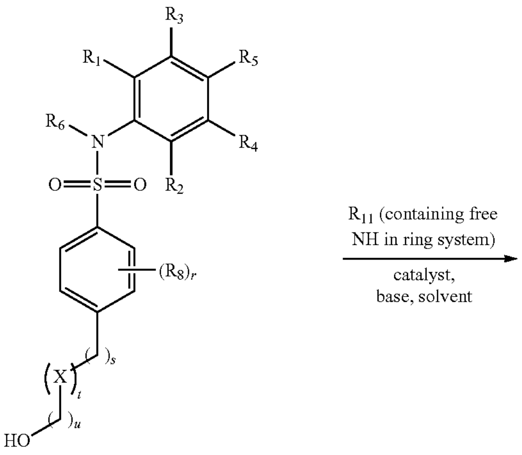

(D)i

-continued

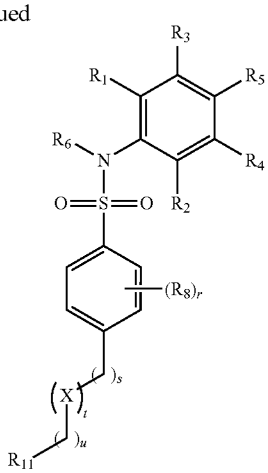

(A)r

X = $CH_2$ or O
$s$ = 0, 1, 2
$t$ = 0, 1
$u$ = 1, 2

18b

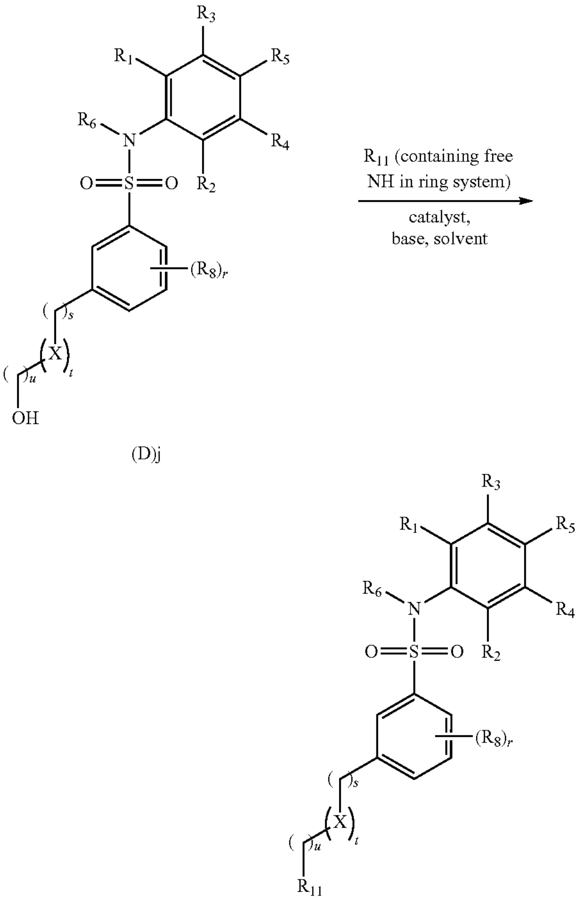

(D)j (A)s

X = $CH_2$ or O
$s$ = 0, 1, 2
$t$ = 0, 1
$u$ = 1, 2

Compounds of formula (A)r and (A)s may be prepared from intermediate compounds of formula (D)i and (D)j respectively, by reaction with an appropriate heterocycloalkyl compound containing a free NH within the heterocycloalkyl ring system, according to Scheme 18a and 18b. Typical reaction conditions comprise mixing together an intermediate compound of formula (D)i or (D)j, with the appropriate heterocycloalkyl compound, a suitable base such as potassium iodide and a suitable catalyst such as pentamethylcyclopentadienyliridium(III) chloride in a suitable solvent such as water. The mixture is then heated in a sealed vessel to a suitable temperature, for example 150° C., by microwaves, for a suitable time, such as 3 hours.

Scheme 19

19a

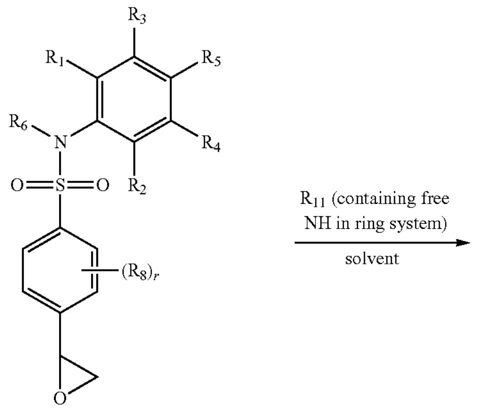

(K)a

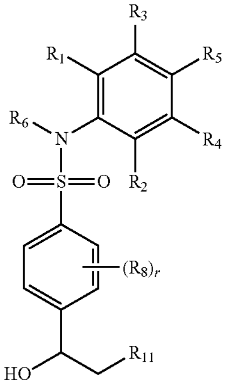

(A)t

+

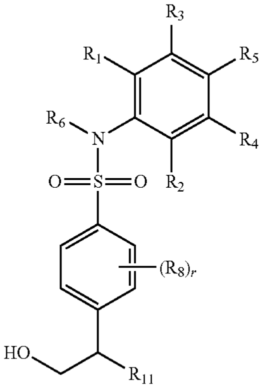

(A)u

19b

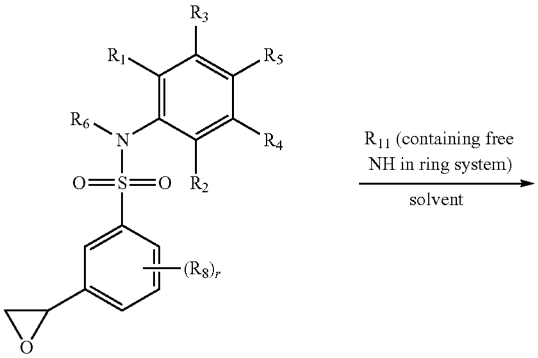

(K)b

-continued

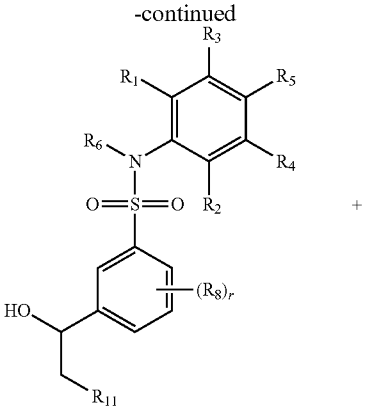

(A)v

+

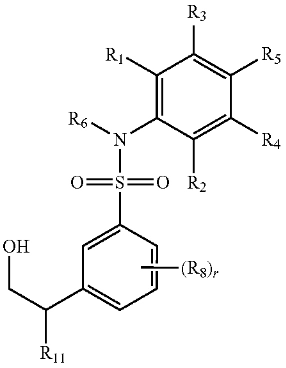

(A)w

Compounds of formula (A)t/(A)u and (A)v/(A)w may be prepared from epoxide-containing intermediate compounds of formula (K)a and (K)b respectively, by reaction with an appropriate heterocycloalkyl compound containing a free NH within the heterocycloalkyl ring system, according to Scheme 19a and 19b. Typical reaction conditions comprise mixing together epoxide-containing intermediate compound (K)a or (K)b with an excess of an appropriate amine, in a suitable solvent, such as ethanol, at a suitable temperature, such as 50° C., for a suitable time, such as overnight. The ratio of products (A)t to (A)u or (A)v to (A)w may vary with selection of amine, and where a mixture of products results, separation may be achieved using a suitable purification system, such as preparative HPLC.

Example RORγ Modulators

The present invention is further illustrated by the following non-limiting examples of RORγ modulators, which have been prepared by a number of different methods.

Intermediate Preparation

Intermediate 1

(2,4-dimethylphenyl)(2-methylpropyl)amine (2,4-dimethylphenyl)(2-methylpropyl)amine was prepared by one of four different routes as shown below:

a) Intermediate 1a (I1a)

An aqueous solution of ammonium formate (3.15 g, 50.0 mmol, 10 mL) was diluted with isopropanol (80 mL) and added to palladium on carbon 10% wet (1.064 g, 10.00 mmol) under nitrogen. A solution of 2,4-dimethylaniline (1.212 g, 10 mmol) and isobutyraldehyde (1.004 mL, 11.00 mmol) in isopropanol (3 mL) was added and the mixture was stirred for 1 h. The mixture was filtered through celite, the celite cake washed with isopropanol and combined liquid phases concentrated in vacuo. The residue (1.8 g) was purified using a pre-conditioned aminopropyl solid phase extraction cartridge ($NH_2$ SPE) (20 g) using methanol as an eluent. The methanolic organic phase was concentrated under vacuum to give a second residue which was further purified on a Biotage Flashmaster II using silica (Si) 10 g/mmol using a 0-100% dichloromethane-cyclohexane gradient over 40 mins. The fractions containing the expected product were combined and concentrated in vacuo to give the desired product, 1.5 g, as a yellow oil. LCMS [LCMS1] Rt 1.04 min, m/z (ES+) 178 (M+H).

b) Intermediate 1b (I1b)

Isobutylaldehyde (5 mL, 55.1 mmol) was added to (2,4-dimethylphenyl)amine (7.01 g, 57.8 mmol) in tetrahydrofuran (50 mL) to give a brown solution. The solution was stirred for 20 mins at room temperature before sodium triacetoxy borohydride (16.34 g, 77 mmol) was added. The reaction mixture was stirred at room temperature for 18 hours and the reaction was analysed by LCMS to confirm conversion to the desired product. The solution was diluted with ethyl acetate (100 mL) and the organic phase washed with water (100 mL). The organic phase was separated from the aqueous phase. The organic phase was concentrated in vacuo to give the product as a brown oil. LCMS [LCMS3] Rt 1.34 min, m/z (ES+) 178 (M+H).

c) Intermediate 1c (I1c)

A mixture of 1-chloro-2,4-dimethylbenzene (1687 mg, 12 mmol), isobutylamine (1755 mg, 24.00 mmol), and Caddick catalyst (140 mg, 0.238 mmol) was treated with lithium hexamethyl disilizide in tetrahydrofuran (1 M LHMDS in THF, 15 mL, 15.00 mmol) under nitrogen. The reaction mixture was heated to 70° C. for 45 minutes in a septum-sealed vessel. The cooled mixture was concentrated in vacuo and the residue was partitioned between aqueous citric acid (50 mL) and tert butyl methyl ether (TBME) (2×50 mL). The organic phase was treated with dried $MgSO_4$, the solid removed by filtration and the organic phase was concentrated in vacuo to give (2,4-dimethylphenyl)(2-methylpropyl)amine (2.05 g, 11.56 mmol) as an orange oil. LCMS [LCMS1] Rt 1.03 min, m/z (ES+) 178 (M+H).

d) Intermediate 1d (I1d)

2-methyl-1-propanol (3.12 mL, 33.8 mmol), 2,4-dimethylaniline (2.093 ml, 16.92 mmol), potassium iodide (5.62 g, 33.8 mmol) and $[Cp^*IrCl_2]_2$ (0.108 g, 0.135 mmol) were dissolved in water (10 mL). The resulting mixture was irradiated under microwaves (CEM microwave) at 150° C. for 1 hour. Reaction was analysed, vessel resealed and heated at 150° C. for an additional 30 minutes. To the reaction mixture was added dichloromethane (25 mL) and water (25 mL). The organic phase was passed through a hydrophobic frit and concentrated in vacuo. The crude product was then dissolved in the minimum of dichloromethane, loaded on a silica column and purified by normal phase chromatography. The relevant fractions were combined and condensed, leaving the purified product (1.89 g, 10.67 mmol) as an orange oil. LCMS [LCMS1] Rt 1.02 min, m/z (ES+) 178 (M+H).

Intermediate 2

N-(2,4-dimethylphenyl)-4-[(2-hydroxyethyl)oxy]-N-(2-methylpropyl)benzenesulfonamide To a solution of (2,4-dimethylphenyl)(2-methylpropyl)amine (0.2 g, 1.128 mmol) in pyridine (10 mL) stirred in air at room temperature, was added 2-{[4-(chlorosulfonyl)phenyl]oxy}-ethyl 2-propenoate (0.656 g, 1.128 mmol). The reaction mixture was stirred at 20° C. for 30 minutes to ensure dissolution and then left to stand overnight. The pyridine was evaporated in vacuo (biotage V10) to give a residue. This was partially dissolved in methanol and applied to a pre-conditioned aminopropyl ($NH_2$) solid phase extraction (SPE) cartridge eluting with additional methanol. The methanol fraction was then passed down a sulfonic acid (SCX) SPE cartridge again eluting with methanol. Solvent was evaporated in vacuo and the sample loaded in methanol and purified by reverse phase (C18) chromatography. The appropriate fractions were combined and dried under a stream of nitrogen to give the intermediate product. This was then taken up in tetrahydrofuran (THF) (1 mL) and lithium hydroxide (0.027 g, 1.128 mmol) in water (1 mL) was added. The mixture was stirred for 2 hours and then evaporated under a stream of nitrogen to give a residue. This was partitioned between water and dichloromethane and separated with a hydrophobic frit. The organic solvent was evaporated in vacuo (Biotage v10) to give the deprotected product as a colourless oil, 44.8 mg. LCMS [LCMS1] Rt 1.23 min, m/z (ES+) 378 (M+H).

Intermediates 3 to 24 were prepared according to Route 1 outlined below. Specific reaction conditions and characterisation data for Intermediates 3 to 24 are provided in Table 1 below.

Route 1

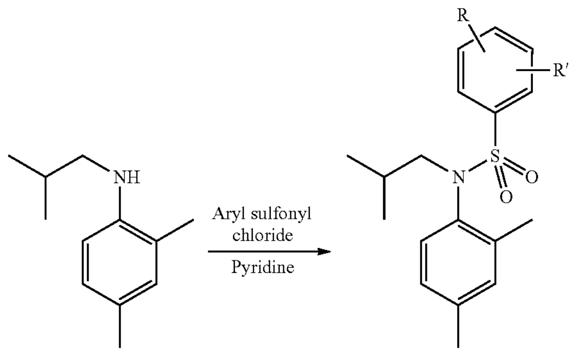

To a solution of secondary aniline (1 equivalent) in pyridine (4 mL/mmol) was added a sulfonyl chloride (1 equivalent, see Table 1 for specific sulfonyl chloride used) in one charge at room temperature. The reaction mixture was left to stand at 20° C. for 16 hours. In some cases, the reaction solution was heated (80 or 95° C.) for 1 hour before being left at room temperature overnight. Workup was then carried out according to the workup procedure listed in Table 1 and the crude material purified if necessary, according to the purification procedure listed in Table 1.

Specific Example of Route 1

Preparation of N-(2,4-dimethylphenyl)-N-(2-methylpropyl)-4-[(phenylmethyl)oxy]benzenesulfonamide (Intermediate 3)

To (2,4-dimethylphenyl)(2-methylpropyl)amine (1.00 g, 5.64 mmol) in pyridine (20 mL) was added 4-[(phenylmethyl)oxy]benzenesulfonyl chloride (1.754 g, 6.20 mmol). The reaction mixture was stirred overnight at room temperature. The reaction mixture was concentrated in vacuo then redissolved in ethyl acetate and washed with a 10% solution of citric acid. At this stage a white precipitate formed and was isolated by filtration, LCMS analysis confirmed the precipitate was the desired product. The organic phase was then washed with 2 M NaOH and further precipitate was collected, again confirmed as the desired product by LCMS analysis. The organic phase was dried with magnesium sulfate, concentrated in vacuo and treated with dichloromethane to give a cloudy suspension, which was filtered to provide more of the desired product. Finally the filtrate was concentrated in vacuo and treated with methanol, whereupon additional product crystallised from the solution. The collected batches of product were combined (974 mg, 2.300 mmol) and used without further purification in the next step. LCMS [LCMS1] Rt 1.54 min, m/z (ES+) 424 (M+H).

in an ice-water bath and a solution of Fmoc chloride (2.93 g, 11.33 mmol) in 1,4-dioxane (30 mL) was added. The mixture was stirred at ambient temperature for 2 hours. The mixture was partitioned between ethyl acetate (150 mL) and water (150 mL). The phases were separated and the organic extract washed with 1 M aqueous HCl (150 mL) and brine (50 mL). The organic extract was dried ($MgSO_4$), filtered and the solvent removed in vacuo to leave a colourless gum, 4.2 g. LCMS [LCMS4] Rt 3.10 min, m/z (ES+) 368 (M+H).

Intermediate 27

9H-fluoren-9-ylmethyl 3-formyl-4-morpholinecarboxylate

To a stirred solution of 4-(9H-fluoren-9-ylmethyl) 3-methyl 3,4-morpholinedicarboxylate (0.6 g, 1.633 mmol) in anhydrous toluene (80 mL) cooled to −78° C. in a dry-ice acetone bath under nitrogen was added dropwise 1.0 M diisobutylaluminium hydride in hexanes (6.53 mL, 6.53 mmol) over 4 minutes. The solution was stirred at −78° C. for 1.5 hours. The reaction was quenched at −78° C. with methanol (1.5 mL) and then aqueous HCl (1 M, 50 mL). The mixture was allowed to warm to ambient temperature and the phases separated. The aqueous was washed with ethyl acetate (2×50 mL). The combined organic extracts were dried ($MgSO_4$), filtered and the solvent removed in vacuo to leave an oil. The residue was loaded in dichloromethane and purified by flash chromatography (Si) using 0-100% ethyl acetate-cyclohexane over 30 minutes. The appropriate fractions were combined and evaporated in vacuo to give the required product as a white foam, 329 mg. LCMS [LCMS4] Rt 2.43 min, m/z (ES+) 338 (M+H).

TABLE 1

Preparation Details for Intermediates 3 to 24 (I3 to I24)
Intermediates 3 to 24 (I3 to I24) were prepared using Intermediate 1 (as SM1), prepared following one of the four methods outlined above (1a-d).

| Product ID | Route | SM1 ID | SM2 ID | Source | Scale (mmol) | Yield (%) | Work up | Purification | RT | Base ion (M + 1) | LCMS Method |
|---|---|---|---|---|---|---|---|---|---|---|---|
| I3 | R1 | I1 | S1 | Enamine Ltd | 5.6 | 41 | A&F | R | 1.54 | 424 | LCMS1 |
| I4 | R1 | I1 | S2 | Sigma Aldrich | 5.64 | 92 | A | N/A | 1.42 | 336 | LCMS1 |
| I5 | R1 | I1 | S4 | Sigma Aldrich | 0.564 | 58 | A | E1 | 1.47 | 366 | LCMS1 |
| I6 | R1 | I1 | S5 | Apollo Scientific Ltd | 1.918 | 61 | A | D3 | 1.41 | 179 | LCMS1 |
| I7 | R1 | I1 | S6 | Apollo Scientific Ltd | 0.919 | 62 | E | N/A | 1.53 | 370 | LCMS2 |
| I8 | R1 | I1 | S7 | Fluorochem | 1.128 | 99 | E | E2 | 1.57 | 414/416 | LCMS2 |
| I9 | R1 | I1 | S8 | Sigma Aldrich | 1.128 | 97 | E | E2 | 1.62 | 410/412 | LCMS2 |
| I10 | R1 | I1 | S9 | Asdi Chemicals | 1.128 | 87 | E | E2 | 1.63 | 410/412 | LCMS2 |
| I11 | R1 | I1 | S10 | Acros Organics | 2.82 | 100 | E | N/A | 1.56 | 370 | LCMS2 |
| I12 | R1 | I1 | S11 | Apollo Scientific Ltd | 2.54 | 70 | S | N/A | 1.47 | 414/416 | LCMS1 |
| I13 | R1 | I1 | S12 | Sigma Aldrich | 11.28 | 99 | A | N/A | 1.49 | 396/398 | LCMS1 |
| I14 | R1 | I1 | S13 | Sigma Aldrich | 0.1 | 100 | A&S | N/A | 1.5 | 372 | LCMS2 |
| I15 | R1 | I1 | S14 | Enamine Ltd | 0.2 | 100 | E | N/A | 1.59 | 350 | LCMS2 |
| I16 | R1 | I1 | S15 | Sigma Aldrich | 0.2 | 100 | E | N/A | 1.5 | 350 | LCMS2 |
| I17 | R1 | I1 | S16 | Sigma Aldrich | 0.1 | 100 | A&S | N/A | 1.4 | 361 | LCMS2 |
| I18 | R1 | I1 | S17 | Sigma Aldrich | 0.2 | 100 | E | N/A | 1.44 | NO | LCMS2 |
| I19 | R1 | I1 | S18 | Sigma Aldrich | 0.2 | 100 | E | N/A | 1.45 | 354 | LCMS2 |
| I20 | R1 | I1 | S19 | ChemCollect GmbH | 0.6 | 46 | E | E3 | 1.26 | 364 | LCMS1 |
| I21 | R1 | I1 | S20 | Alfa Aesar | 2.096 | 59 | A | E3 | 1.44 | 348 | LCMS1 |
| I22 | R1 | I1 | S21 | Sigma Aldrich | 0.1 | 100 | A&S | N/A | 1.47 | 372 | LCMS2 |
| I23 | R1 | I1 | S22 | Activate Scientific | 1.777 | 42 | A | D2 | 1.4 | 376 | LCMS1 |
| I24 | R1 | I1 | S3 | Activate Scientific | 2.82 | 98 | A | E3 | 1.56 | 430 | LCMS1 |

Intermediate 25

(Tetrahydro-2H-pyran-4-yl)methyl methanesulfonate (Tetrahydro-2H-pyran-4-yl)methanol (29.9 mg, 0.257 mmol) was dissolved in dichloromethane (DCM) (4 mL). To this solution was added triethylamine (0.108 mL, 0.772 mmol). The reaction was cooled to 0° C., methanesulfonyl chloride (0.03 mL, 0.386 mmol) added and the reaction left to stir overnight, allowing the reaction to warm to 20° C. The reaction was concentrated in vacuo. The product was partitioned between ethyl acetate (20 mL) and aqueous saturated sodium bicarbonate (20 mL). The organic phase was dried and concentrated in vacuo, before being used in the next reaction with no further purification or characterisation, 49 mg.

Intermediate 26

4-(9H-fluoren-9-ylmethyl) 3-methyl 3,4-morpholinedicarboxylate

To a stirred solution of methyl morpholine-3-carboxylate hydrochloride (2.0 g, 11.01 mmol) in a mixture of 1,4-dioxane (10 mL) and water (20 mL) was added sodium bicarbonate (2.79 g, 33.2 mmol). The suspension was cooled Intermediate 28

9H-fluoren-9-ylmethyl 3-(hydroxymethyl)-4-morpholinecarboxylate

To a solution of 9H-fluoren-9-ylmethyl 3-formyl-4-morpholinecarboxylate (610 mg, 1.808 mmol) in dichloromethane (DCM) (6 mL) cooled in an ice-water bath, was added trimethylsilyl trifluoromethanesulphonate (0.470 mL, 2.60 mmol). To the solution was added dropwise a solution of methyl 5-bromo-1H-indole-7-carboxylate (333 mg, 1.311 mmol) in DCM (18 mL). The resulting orange solution was stirred at 0° C. for 1 hour, under nitrogen. To the dark orange solution was added triethylsilane (1 mL, 6.26 mmol) and the mixture stirred between 5-10° C. for 1.5 hours. The solution was allowed to warm to ambient temperature over 6 hours, then stored overnight at 5° C. The reaction was quenched with saturated aqueous sodium hydrogen carbonate (75 mL) and DCM (50 mL). The phases were separated and the aqueous phase washed with DCM (2×40 mL). The combined organic extracts were concentrated in vacuo to leave a yellow foam. The residue was loaded in dichloromethane and purified on silica (Si) using 0-100% ethyl acetate-cyclohexane over 40 minutes. The appropriate fractions were combined and evaporated in vacuo to give the product, 142 mg, as a yellow gum. LCMS [LCMS4] Rt 2.61 min, m/z (ES+) 340 (M+H).

Intermediate 29

2-{[4-(chlorosulfonyl)phenyl]oxy}ethyl 2-propenoate

A solution of 2-(phenyloxy)ethyl 2-propenoate (5 g, 26.0 mmol) in dichloromethane (50 mL), was cooled to 0° C. Chlorosulfonic acid (5.21 mL, 78 mmol) was added dropwise over 15 minutes at 0° C. then the mixture was allowed to warm to room temperate over 30 minutes. The reaction mixture was stirred overnight (16 hours) at room temperature. The solution was then poured onto ice and extracted with dichloromethane (3×50 mL). Resulting emulsion was diluted with ethyl acetate (200 mL) and brine (50 mL) in order to achieve separation of phases. The aqueous layer was further extracted with ethyl acetate (100 mL). The combined organic fractions were dried with magnesium sulphate then evaporated in vacuo to give an oily solid, which was dried under high vacuum overnight. After drying, a sticky solid was isolated (3.2 g) and this was taken on to the next step without further purification. LCMS [LCMS1] Rt 0.47 min, m/z (ES−) 272 (M−Cl+OH).

Intermediate 30

N-(2,4-dimethylphenyl)-3-hydroxy-N-isobutylbenzenesulfonamide

N-(2,4-dimethylphenyl)-N-isobutyl-3-methoxybenzenesulfonamide (431.4 mg, 1.242 mmol) was dissolved in dichloromethane (DCM) (10 mL) and cooled to −78° C. $BBr_3$ in DCM (1M) (6.21 mL, 6.21 mmol) was added dropwise and the reaction put under nitrogen. The reaction was allowed to reach room temperature and left to stir overnight. Water (20 mL) was added dropwise into the reaction mixture, until no more fumes were released. The crude product was then extracted to the organic phase of an aqueous work up between DCM (30 mL) and water (20 mL). The aqueous phase was washed with DCM (2×20 mL). The organic phase was then dried and concentrated in vacuo. The crude product was then dissolved in a minimum of DCM, and loaded onto a silica column before being purified by silica (Si) column chromatography (20 minutes, 0-25% EtOAc in cyclohexane). The relevant fractions were then combined and condensed, to give the desired product, 384.4 mg. LCMS [LCMS1] Rt 1.26 min, m/z (ES+) 334 (M+H).

Intermediate 31

N-(2,4-dimethylphenyl)-4-hydroxy-N-(2-methylpropyl)benzenesulfonamide

To N-(2,4-dimethylphenyl)-N-(2-methylpropyl)-4-[(phenylmethyl)oxy]benzenesulfonamide (974 mg, 2.300 mmol) was added ammonium formate (725 mg, 11.50 mmol) palladium(II) hydroxide (20% on carbon) (164 mg, 0.230 mmol) and ethanol (65 mL). The reaction mixture was heated to reflux with stirring overnight. A product peak was observed by LCMS, but only partial conversion had occurred. A further 5 equivalents of ammonium formate (725 mg, 11.50 mmol) were added to the reaction mixture. The reaction mixture was reheated to boiling point. After a further 30 minutes of heating, LCMS showed no change in the ratio of starting material to product. The reaction was cooled for 5 minutes then additional palladium(II) hydroxide (20% on carbon) (164 mg, 0.230 mmol) was added. The reaction mixture was then reheated to reflux for another 30 minutes after which full conversion to the product was observed. The reaction mixture was cooled, filtered through a celite cartridge, then concentrated in vacuo to give 727 mg of crude product. The crude mixture was diluted with ethyl acetate and washed with water, then brine. The organic phase was then concentrated in vacuo to give 663 mg of the title compound. LCMS [LCMS1] Rt 1.25 min, m/z (ES+) 334 (M+H).

Intermediate 32

N-(2,4-dimethylphenyl)-3-(hydroxymethyl)-N-isobutylbenzenesulfonamide

Methyl 3-(N-(2,4-dimethylphenyl)-N-isobutylsulfamoyl)benzoate (400 mg, 1.065 mmol) was dissolved in tetrahydrofuran (THF) (10 mL). To this solution was added lithium borohydride (2 M in THF) (0.932 mL, 1.864 mmol). The reaction was left to stir overnight, at room temperature. The reaction was quenched by the addition of 5% citric acid (10 mL), and the reaction allowed to stir under nitrogen, for 1 hour. The reaction mixture was then diluted with ethyl acetate (25 mL), and the product extracted to the organic phase. The organic phase was dried by passing it through a hydrophobic frit and then concentrated in vacuo to give the desired product, 378.7 mg. LCMS [LCMS1] Rt 1.23 min, m/z (ES+) 348 (M+H).

Intermediate 33

N-(5-chloro-2-fluorophenyl)-4-vinylbenzenesulfonamide

To a stirred solution of 4-vinylbenzene-1-sulfonyl chloride (950 mg, 4.69 mmol) in pyridine (8 mL) at 20° C. was added 5-chloro-2-fluoroaniline (682 mg, 4.69 mmol). The reaction mixture was stirred at 20° C. for 2 hours then evaporated in vacuo and redissolved in ethyl acetate. The organic phase was washed with saturated aqueous sodium carbonate (25 mL), dried using a hydrophobic frit and evaporated in vacuo to give the crude product as a yellow oil. The crude was purified by silica (Si) chromatography using a 0-25% ethyl acetate-cyclohexane gradient. The appropriate fractions were combined and evaporated in vacuo to give the required product, 822.7 mg as a white solid. LCMS [LCMS2] Rt 0.86 min, m/z (ES+) 312 (M+H).

Intermediate 34

N-(5-chloro-2-fluorophenyl)-N-isobutyl-4-vinylbenzenesulfonamide

To a solution of N-(5-chloro-2-fluorophenyl)-4-vinylbenzenesulfonamide (822 mg, 2.64 mmol) in acetonitrile (10 mL) stirred in air at 20° C., was added 2-(tert-butyl)-1,1,3,3-tetramethylguanidine (903 mg, 5.27 mmol). The reaction mixture was stirred at 20° C. for 2 hours. 1-bromo-2-methylpropane (0.573 mL, 5.27 mmol) was then added and the reaction vessel sealed and heated by microwaves (Emrys Optimiser) to 150° C. for 30 minutes. After cooling, the reaction mixture was concentrated in vacuo and redissolved in ethyl acetate. The organic phase was washed with water (10 mL), dried using a hydrophobic frit and evaporated in vacuo to give the crude product as a yellow oil which solidified. The crude was purified by silica (Si) chromatography using a 0-50% ethyl acetate-cyclohexane gradient. The appropriate fractions were combined and evaporated in vacuo to give the required product, 824 mg as a colourless oil. LCMS [LCMS2] Rt 1.46 min, m/z (ES+) 368 (M+H).

Intermediate 35

4-(N-(2,4-dimethylphenyl)-N-isobutylsulfamoyl)benzamide

Methyl 4-(N-(2,4-dimethylphenyl)-N-isobutylsulfamoyl)benzoate (280 mg, 0.746 mmol) was dissolved in tetrahydrofuran (THF) (5 mL) and to this solution was added ammonia in dioxane (0.5 M) (4.47 mL, 2.237 mmol), followed by LiHMDS in THF (1 M, 0.895 mL, 0.895 mmol). The reaction was left to stir overnight at room temperature, under nitrogen. The reaction was quenched with water (1 mL) then combined with a previous identical trial reaction on a smaller (0.075 mmol) scale, for workup. The crude was concentrated in vacuo, then the product was extracted to the organic phase of an aqueous work up between ethyl acetate (15 mL) and brine (10 mL). The organic phase was passed through a hydrophobic frit and concentrated in vacuo to give the crude product, 263 mg. No further purification was undertaken. LCMS [LCMS1] Rt 1.14 min, m/z (ES+) 361 (M+H).

Intermediate 36

4-(aminomethyl)-N-(2,4-dimethylphenyl)-N-isobutylbenzenesulfonamide 4-(N-(2,4-dimethylphenyl)-N-isobutylsulfamoyl)benzamide (263.6 mg, 0.731 mmol) was dissolved in tetrahydrofuran (THF) (10 mL) and to this solution was added borane-tetrahydrofuran complex (1 M) (2.194 mL, 2.194 mmol). The reaction was then heated to 75° C. and refluxed overnight under nitrogen. The reaction was cooled and quenched by the addition of 2 M HCl. The reaction mixture was then neutralised by the slow addition of 10 M sodium hydroxide and the product extracted to the organic phase of an aqueous work up between ethyl acetate and water. The organic phase was passed through a hydrophobic frit and concentrated in vacuo. The crude was purified by mass directed autoprep (formic acid modifier), over 3 injections. The relevant fractions were evaporated in vacuo to give the required product, 152 mg. LCMS [LCMS1] Rt 0.87 min, m/z (ES+) 347 (M+H).

Route 2

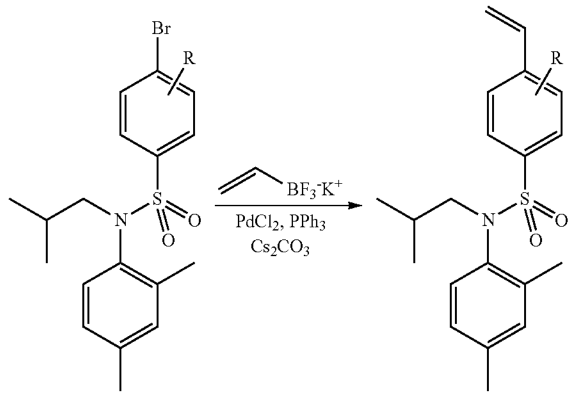

To a microwave vial was added bromobenzenesulfonamide (1 equivalent), potassium trifluoro(vinyl)borate (1.2 equivalents), triphenylphosphine (0.06 equivalents), cesium carbonate (3 equivalents) and palladium(II) chloride (0.02 equivalents). Tetrahydrofuran (THF) (3.6 mL/mmol) and water (0.4 mL/mmol) were added. The vessel was sealed and heated by microwaves (Biotage Initiator) to 140° C. for 30 minutes, then cooled to room temperature. Workup and purification were then carried out according to the relevant procedure(s) listed in Table 2.

Specific Example

Preparation of N-(2,4-dimethylphenyl)-N-isobutyl-4-vinylbenzenesulfonamide (Intermediate 45)

To a microwave vial was added 4-bromo-N-(2,4-dimethylphenyl)-N-isobutylbenzenesulfonamide (4.44 g, 11.20 mmol), potassium trifluoro(vinyl)borate (4.50 g, 33.6 mmol), triphenylphosphine (0.176 g, 0.672 mmol), cesium carbonate (10.95 g, 33.6 mmol) and palladium(II) chloride (0.040 g, 0.224 mmol). Tetrahydrofuran (THF) (12 mL) and water (1.333 mL) were then added, ensuring all particles were below the solvent level. The reaction vessel was sealed and heated in a microwave (Biotage Initiator) to 140° C. for 60 minutes, cooled to room temperature and ethyl acetate (40 mL) added to the mixture. The organic phase was washed with water (50 mL), dried using a hydrophobic frit and evaporated in vacuo to give the crude product as a orange oil. The sample was loaded in dichloromethane and purified by silica (Si) chromatography using a 0-25% ethyl acetate-cyclohexane gradient. The appropriate fractions were combined and evaporated in vacuo to give the required product, 1.8 g, as an off-white solid. LCMS [LCMS1] Rt 1.47 min, m/z (ES+) 344 (M+H).

Route 3

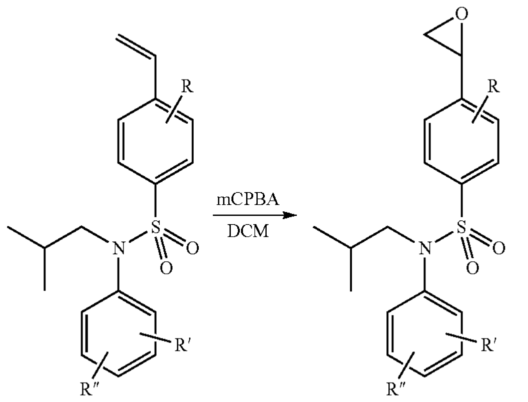

To a solution of vinylbenzenesulfonamide (1 equivalent) in dichloromethane (DCM) (8.1 mL/mmol) stirred under nitrogen at 0° C., was added meta-chloroperoxybenzoic acid (mCPBA) (4 equivalents), portionwise. The reaction mixture was stirred at 0° C. for 30 minutes. The reaction was then stirred for 16 hours at 20° C. Workup and purification were then carried out according to the relevant procedure(s) listed in Table 2.

Specific Example

Preparation of N-(2,4-dimethylphenyl)-N-isobutyl-4-(oxiran-2-yl)benzenesulfonamide (Intermediate 46)

To a solution of N-(2,4-dimethylphenyl)-N-isobutyl-4-vinylbenzenesulfonamide (1.27 g, 3.70 mmol) in dichloromethane (DCM) (30 mL) stirred under nitrogen at 0° C., was added meta-chloroperoxybenzoic acid (mCPBA) (2.55 g, 14.79 mmol), portionwise. The reaction mixture was stirred at 0° C. for 30 minutes. The reaction was then stirred for 16 hours at 20° C. DCM (20 mL) was added to the mixture. The organic phase was washed with 0.1M sodium hydroxide solution (2×50 mL), dried using a hydrophobic frit and evaporated in vacuo to give the crude product. The sample was loaded in dichloromethane and purified on silica (Si) using a 0-50% ethyl acetate-cyclohexane gradient. The appropriate fractions were combined and evaporated in vacuo to give the required product, 935 mg, as an off-white oil which solidified on standing. LCMS [LCMS1] Rt 1.35 min, m/z (ES+) 360 (M+H).

Intermediates 37 to 51 were prepared according to either Route 2, 3, 4, 5 or 8. Specific reaction conditions and characterisation data for Intermediates 37 to 51 are provided in Table 2 below.

Routes 4, 5 and 8 are outlined in the Example Preparation section.

TABLE 2

Preparation Details for Intermediates 37 to 51 (I37 to I51)

| Product ID | Route | SM1 ID | SM2 ID | SM2 Source | Scale (mmol) | Yield (%) | Work up | Purification | RT | Base ion (M + H unless specified) | LCMS |
|---|---|---|---|---|---|---|---|---|---|---|---|
| I37 | R4* | I31 | S23 | *Bioorg. Med. Chem. Lett.*, 2006, 16(6), 1749-1752 | 0.15 | 42 | A | N/A | 1.54 | 549 | LCMS1 |
| I38 | R5* | I4 | S24 | Astech | 0.075 | 17 | Q&E | F | 1.57 | 561 | LCMS1 |
| I39 | R8* | I5 | S23 | *Bioorg. Med. Chem. Lett.*, 2006, 16(6), 1749-1752 | 0.122 | 17 | A | F | 1.54 | 580 (M + 18) | LCMS1 |
| I40 | R2 | I8 | S25 | Aldrich | 1.115 | 64 | A | E3 | 1.57 | 362 | LCMS2 |
| I41 | R2 | I9 | S25 | Aldrich | 1.165 | 54 | A | E3 | 1.59 | 358 | LCMS2 |
| I42 | R2 | I10 | S25 | Aldrich | 1.045 | 77 | A | E3 | 1.6 | 358 | LCMS2 |
| I43 | R3 | I40 | N/A | N/A | 1.098 | 30 | A | E2 | 1.48 | 378 | LCMS2 |
| I44 | R3 | I42 | N/A | N/A | 1.021 | 40 | A | E2 | 1.48 | 374 | LCMS2 |
| I45 | R2 | I13 | S25 | Aldrich | 11.2 | 48 | A | E3 | 1.47 | 344 | LCMS1 |
| I46 | R3 | I45 | N/A | N/A | 3.70 | 70 | A | E2 | 1.35 | 360 | LCMS1 |
| I47 | R3 | I41 | N/A | N/A | 0.906 | 24 | A | E2 | 1.47 | 374 | LCMS2 |
| I48 | R4* | I31 | S26 | Acros | 0.75 | 59 | A | E3 | 1.57 | 517 | LCMS1 |
| I49 | R4* | I30 | S26 | Acros | 0.883 | 24 (55% pure) | A | E3 | 1.58 | 517 | LCMS1 |
| I50 | R3 | I51 | N/A | N/A | 1.191 | 42 | A | E3 | 1.5 | 394 | LCMS1 |
| I51 | R2 | I24 | S25 | Aldrich | 1.5 | 83 | A | E3 | 1.58 | 378 | LCMS1 |

*procedure carried out as an individual reactions, not in an array format

Example Preparation

Example 1

N-(2,4-dimethylphenyl)-N-isobutyl-3-(((tetrahydro-2H-pyran-4-yl)methoxy)methyl)benzenesulfonamide N-(2,4-dimethylphenyl)-3-(hydroxymethyl)-N-isobutyl-benzenesulfonamide (40 mg, 0.115 mmol) and sodium hydride (4.14 mg, 0.173 mmol) were dissolved in anhydrous N,N-dimethylformamide (DMF) (3 mL). The solution was stirred for 10 minutes under nitrogen at 20° C. (Tetrahydro-2H-pyran-4-yl)methyl methanesulfonate (49 mg, 0.252 mmol) was added to the solution, which was stirred overnight at 20° C. under nitrogen. The reaction was concentrated under vacuum (Biotage V10) to give the crude product. This was then partitioned between ethyl acetate (10 mL) and water (10 mL). The organic layer was washed with water (5×5 mL), passed through a hydrophobic frit and concentrated in vacuo. The crude product was then dissolved in a minimum of DCM and purified by silica (Si) chromatography using a 0-25% ethyl acetate-cyclohexane gradient. The relevant fractions were combined and condensed to provide the required product, 28 mg. LCMS [LCMS1] Rt 1.46 min, m/z (ES+) 446 (M+H).

Example 2

N-(2,4-dimethylphenyl)-N-(2-methylpropyl)-4-{[2-(4-morpholinyl)ethyl]oxy}benzenesulfonamide To a microwave vial was added morpholine (5.10 µL, 0.058 mmol), potassium iodide (19.26 mg, 0.116 mmol), $[Cp^*IrCl_2]_2$ (0.639 mg, 0.580 µmol), N-(2,4-dimethylphenyl)-4-[(2-hydroxyethyl)oxy]-N-(2-methylpropyl)benzenesulfonamide (43.8 mg, 0.116 mmol), a stirrer bar and water (0.1 mL). The vial was then sealed and the mixture was heated to 150° C. by microwaves (Biotage Initiator) for 3 hours. Reaction mixture was then diluted with methanol (1 mL) and passed down a pre-conditioned sulfonic acid (SCX) solid phase extraction (SPE) cartridge, eluting with methanol and then 2N methanolic ammonia. The fractions from the methanolic ammonia wash were concentrated in vacuo and the residue purified by mass-directed autoprep, using a formic acid modifier. Product containing fractions were evaporated under a stream of nitrogen to provide product, 2.6 mg. LCMS [LCMS1] Rt 1.01 min, m/z (ES+) 447 (M+H).

Example 3

2-(N-(2,4-dimethylphenyl)-N-isobutylsulfamoyl)-5-((tetrahydro-2H-pyran-4-yl)methoxy)benzoic acid To a stirred solution of 2-bromo-N-(2,4-dimethylphenyl)-N-isobutyl-4-((tetrahydro-2H-pyran-4-yl)methoxy)benzenesulfonamide (50 mg, 0.098 mmol) in tetrahydrofuran (THF) at −78° C. was added nBuLi 1.6 M in hexanes (92 µL, 0.147 mmol) and the reaction stirred for 1 hour. After this time carbon dioxide (small pellet) was added and the reaction mixture stirred at −78° C. for 30 minutes, then warmed to 20° C. and stirred for a further 1 hour. The reaction was quenched with saturated ammonium chloride solution and the mixture concentrated in vacuo. The residue was then taken up in ethyl acetate (20 mL) and the organic phase was washed with saturated ammonium chloride solution (2×25 mL), the organics were dried using a hydrophobic frit and evaporated in vacuo to give the crude product as a colourless gum, 40 mg. LCMS [LCMS2] Rt 0.97 min, m/z (ES+) 476 (M+H).

Example 4

N-(2,4-dimethylphenyl)-N-isobutyl-2-methoxy-4-((tetrahydro-2H-pyran-4-yl)methoxy)benzenesulfonamide To a stirred solution of N-(2,4-dimethylphenyl)-2-fluoro-N-isobutyl-4-((tetrahydro-2H-pyran-4-yl)methoxy)benzenesulfonamide (358 mg, 0.478 mmol) in methanol (1 mL) at room temperature was added 25% sodium methoxide in methanol (109 uL, 0.478 mmol). The reaction mixture was stirred at room temperature for 2 hours, then heated to reflux for 1 hour. The reaction was quenched with water (1 mL) and the solvents removed in vacuo to give a yellow solid. The crude residue was dissolved in dichloromethane (DCM) (10 mL) and the organics washed with water (3×10 mL). The organics were passed through a hydrophobic frit and the filtrate evaporated to dryness to give a yellow oil. The crude was purified by mass directed autoprep (ammonium carbonate modifier). The solvent was evaporated under a stream of nitrogen to give the required product, 129 mg. LCMS [LCMS2] Rt 1.47 min, m/z (ES+) 462 (M+H).

Example 5

N-(2,4-dimethylphenyl)-2-(hydroxymethyl)-N-isobutyl-4-((tetrahydro-2H-pyran-4-yl)methoxy)benzenesulfonamide To a stirred solution of 2-(N-(2,4-dimethylphenyl)-N-isobutylsulfamoyl)-5-((tetrahydro-2H-pyran-4-yl)methoxy)benzoic acid (40 mg, 0.084 mmol) in tetrahydrofuran (THF) (1 mL) at 0° C. was added lithium aluminium hydride (1.0M in diethyl ether) (0.084 mL, 0.084 mmol) and the reaction mixture was stirred at 0° C. for 30 minutes then warmed to 25° C. for 1 hour. The reaction mixture was quenched carefully with water. The organic solvent was removed in vacuo and the remaining aqueous layer was extracted with ethyl acetate (20 mL×3). The organics were combined and concentrated in vacuo to give a yellow oil. The crude was then purified by mass directed autoprep (ammonium carbonate modifier). The appropriate fractions were concentrated under a stream of nitrogen in a Radleys blowdown apparatus to give the required product, 25.2 mg. LCMS [LCMS2] Rt 1.40 min, m/z (ES+) 462 (M+H).

Example 6

N-(2,4-dimethylphenyl)-N-isobutyl-4-((((tetrahydro-2H-pyran-4-yl)methyl)amino)methyl)benzenesulfonamide 4-(aminomethyl)-N-(2,4-dimethylphenyl)-N-isobutyl-benzenesulfonamide (25 mg, 0.072 mmol), (tetrahydro-2H-pyran-4-yl)methanol (16.76 mg, 0.144 mmol), potassium iodide (23.95 mg, 0.144 mmol) and $[Cp^*IrCl_2]_2$ (1.150 mg, 1.443 µmol) were dissolved in water (2 mL) in a microwave vial. The reaction vessel was sealed and heated by microwaves (Biotage Initiator) to 150° C. for 1 hour. After analysis the reaction vessel was resealed and heated again by microwaves (Biotage Initiator) to 150° C. for a further 1 hour. After further analysis an additional 1 eq of $[Cp^*IrCl_2]_2$ and 1 eq of (tetrahydro-2H-pyran-4-yl)methanol were added and the reaction heated for a third time by microwaves (Biotage Initiator) to 150° C. for 1 hour. The reaction was cooled and the mixture concentrated in vacuo (Biotage V10). The crude product was extracted to the organic phase of an aqueous workup between ethyl acetate (5 mL) and water (5 mL). The organic phase was passed through a hydrophobic frit and concentrated in vacuo. The crude was purified by mass directed autoprep (formic acid modifier). The appropriate fractions were evaporated in vacuo (Biotage V10) to give the required product, 1.2 mg. LCMS [LCMS1] Rt 0.97 min, m/z (ES+) 445 (M+H).

Examples 7 to 101 were prepared according to one of the following routes (4 to 14). Specific reaction conditions and characterisation data for Examples 7 to 112 are provided in Table 3 below.

Route 4

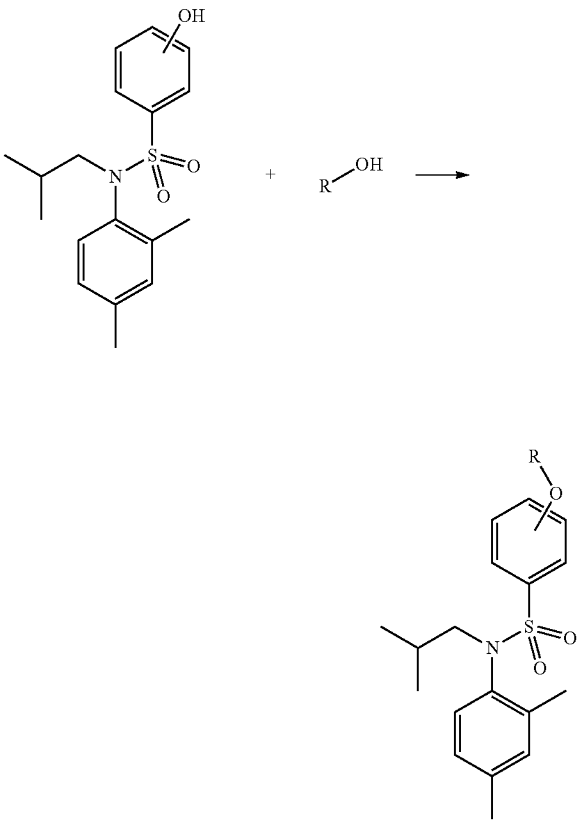

Array Format

A mixture of phenol sulfonamide (1 equivalent, see Tables 2 and 3 for specific phenol used), an alcohol (1.2 equivalents, see Tables 2 and 3 for specific alcohol used in each reaction) and triphenylphosphine (1 equivalent) was dissolved in tetrahydrofuran (THF) (6 mL/mmol) and treated with diisopropyl diazene-1,2-dicarboxylate (DIAD) (1.3 equivalents). The vessel was capped and stirred at 20° C. for 2 days. If LCMS analysis showed incomplete reaction, additional alcohol (1.2 equivalents) and diisopropyl diazene-1,2-dicarboxylate (DIAD) (1.6 equivalents) were added and reaction stirred for further 18 hours. Workup and purification were then carried out according to the relevant procedure(s) listed in Tables 2 or 3.

Specific Example

Preparation of N-(2,4-dimethylphenyl)-4-((2,6-dioxo-1,2,3,6-tetrahydropyrimidin-4-yl)methoxy)-N-isobutylbenzenesulfonamide (Example 56)

A mixture of N-(2,4-dimethylphenyl)-4-hydroxy-N-isobutylbenzenesulfonamide (33 mg, 0.099 mmol), 6-(hydroxymethyl)pyrimidine-2,4(1H,3H)-dione (17.1 mg, 0.12 mmol) and triphenylphosphine (26 mg, 0.099 mmol) was dissolved in tetrahydrofuran (THF) (0.6 mL) and treated with diisopropyl diazene-1,2-dicarboxylate (DIAD) (25 uL, 0.13 mmol). The vessel was capped and stirred at 20° C. for 2 days. Additional 6-(hydroxymethyl)pyrimidine-2,4(1H,3H)-dione (17.1 mg, 0.12 mmol) and diisopropyl diazene-1,2-dicarboxylate (DIAD) (30 uL, 0.156 mmol) were added and reaction stirred for further 18 hours. The reaction was then filtered and purification attempted by mass directed autoprep (ammonium carbonate modifier), but this failed to isolate clean material. Purification successfully achieved by mass directed autoprep (formic acid modifier), to provide the required product, 1.1 mg. LCMS [LCMS1] Rt 1.13 min, m/z (ES+) 458 (M+H).

Single Reaction Format

A phenol sulfonamide (1 equivalent, see Tables 2 and 3 for specific phenol used), an alcohol (1.2-1.5 equivalents, see Tables 2 and 3 for specific alcohol used in each reaction) and triphenylphosphine (1-1.5 equivalents) were pre-weighed into a vessel. Tetrahydrofuran (THF) (4 mL/mmol) was added followed by diisopropyl diazene-1,2-dicarboxylate (DIAD) (1.2-1.5 equivalents). The vessel was capped and in some instances back-filled with nitrogen 3 times before being stirred at 20° C. for up to 2 days. Workup and purification were then carried out according to the relevant procedure(s) listed in Tables 2 or 3.

Specific Example

Preparation of tert-butyl 4-(3-(N-(2,4-dimethylphenyl)-N-isobutylsulfamoyl)phenoxy)piperidine-1-carboxylate (Intermediate 49)

Tert-butyl 4-hydroxypiperidine-1-carboxylate (213.0 mg, 1.061 mmol), N-(2,4-dimethylphenyl)-4-hydroxy-N-isobutyl benzenesulfonamide (294.5 mg, 0.883 mmol) and triphenylphosphine (232 mg, 0.883 mmol) were dissolved in tetrahydrofuran (THF) (4 mL). The solution was left to stir for 20 minutes, then DIAD (0.206 mL, 1.060 mmol) was added, the vial sealed and back filled with nitrogen 3 times, before being stirred overnight at 20° C. The reaction solution was concentrated under vacuum (Biotage V10) to give the crude product. This was partitioned between ethyl acetate (20 mL) and brine (20 mL). The organic phase was passed through a hydrophobic frit then concentrated in vacuo to give the crude product 200 mg, which was carried on to the next step, with no further purification. LCMS [LCMS1] Rt 1.58 min, m/z (ES+) 517 (M+H).

Route 5

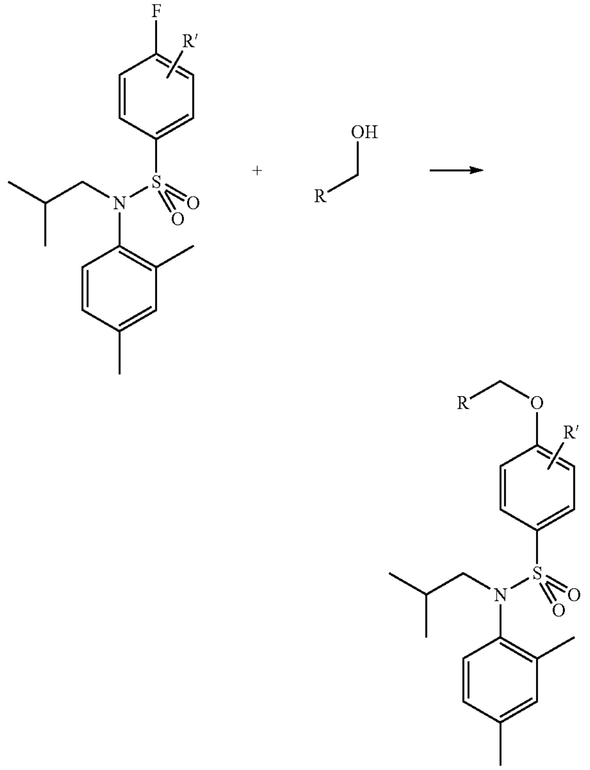

Array Format

Each para-fluoro-sulphonamide intermediate (8 equivalents, see Tables 2 or 3 for specific para-fluoro-sulphonamide intermediate used) was dissolved in dimethyl sulfoxide (DMSO) (8 reactions×0.75 mL/mmol) and an aliquot representing 1 equivalent was added to each of eight alcohols (1 equivalent, see Tables 2 or 3 for specific alcohol used). 60% sodium hydride dispersed in oil (1 equivalent) was then added to each reaction. The reactions were capped and sonicated to aid dispersion and then left to stand at 20° C. for 18 hours. Workup and purification were then carried out according to the relevant procedure(s) listed in Tables 2 or 3.

Note: Where Fmoc protected amino-alcohols were used, the Fmoc group was found to be removed under the above coupling reaction conditions, although an additional second purification (by mass directed autoprep) was often required. Where Boc protected amino-alcohols or isopropilidine-protected polyhydroxy compounds were used, deprotection was carried out on the products as follows: Following purification, the protected product was dissolved in a mixture of trifluoroacetic acid (TFA) (0.7 mL/mmol) and dichloromethane (DCM) (0.7 mL/mmol), then stood for 18 hours at room temperature and evaporated to dryness to give the deprotected product (as its TFA salt in the case of basic compounds). Where Benzyl protected amino-alcohols were used, deprotection was carried out on the products as follows: Following purification, the Benzyl-protected products were redissolved in methanol (1 mL) and hydrogenated using a flow hydrogenator (H-cube automated system) with settings: room temperature, 1 bar hydrogen, 1 mL/min flow rate and fitted with a 10% Pd/C CatCart 30 as the catalyst. Purification (by mass directed autoprep) was then carried out if required.

Specific Example

Preparation of N-(2,4-dimethylphenyl)-N-isobutyl-4-(piperidin-4-ylmethoxy)benzenesulfonamide, Trifluoroacetic acid salt (Example 8)

A stock solution of N-(2,4-dimethylphenyl)-4-fluoro-N-isobutylbenzenesulfonamide (8 equivalents, 0.808 g, 2.4 mmol) was prepared in dimethyl sulfoxide (DMSO) (3.2 mL) and an aliquot representing 1 equivalent (0.4 mL) added to each of eight alcohols (0.3 mmol each), including in this example tert-butyl 4-(hydroxymethyl)piperidine-1-carboxylate (64.6 mg, 0.3 mmol). 60% sodium hydride dispersed in oil (0.012 g, 0.300 mmol) was then added to each reaction. The reactions were capped and sonicated to aid dispersion, then left to stand at 20° C. for 18 hours. The reactions were then quenched with methanol (0.5 mL) and sonicated to aid dispersion. All the samples were purified by mass directed autoprep (ammonium carbonate modifier). The relevant fractions were concentrated under a stream of nitrogen to give the required products (as ammonium salts where appropriate). To remove the Boc protection group, the purified samples were each dissolved in dichloromethane (DCM) (0.2 mL) and trifluoroacetic acid (TFA) (0.2 mL) added. The samples were capped and stood at 20° C. for 18 hours. The solvent was then removed under a stream of nitrogen to give desired product, in this case 54 mg. LCMS [LCMS1] Rt 1.59 min, m/z (ES+) 431 (M+H).

Single Reaction Format

To a solution of a para-fluoro-sulphonamide intermediate (0.075 mmol, see Tables 2 or 3 for specific para-fluoro-sulphonamide intermediate used) and an alcohol (1 equivalent see Tables 2 or 3 for specific alcohol used) in dimethyl sulfoxide (DMSO) (6.6 mL/mmol) stirred in air at 20° C., was added solid sodium hydride (1 equivalent, 60% dispersed in oil) in one charge. The reaction mixture was stirred at 20° C. for 16 hours. Workup and purification were then carried out according to the relevant procedure(s) listed in Tables 2 or 3.

Specific Example

Preparation of N-(2,4-dimethylphenyl)-N-isobutyl-4-((1-(2,2,2-trifluoroethyl)piperidin-4-yl)methoxy)benzenesulfonamide (Example 13)

To a solution of N-(2,4-dimethylphenyl)-4-fluoro-N-isobutylbenzenesulfonamide (25 mg, 0.075 mmol) and (1-(2,2,2-trifluoroethyl)piperidin-4-yl)methanol (14.70 mg, 0.075 mmol) in dimethyl sulfoxide (DMSO) (0.5 mL) stirred in air at 20° C., was added sodium hydride (approximately 2.98 mg, 0.075 mmol, 60% dispersed in oil) in one charge. The reaction mixture was stirred at 20° C. for 16 hours. The reaction was carefully quenched with methanol (0.5 mL) and water (0.5 mL). The solvent was concentrated in vacuo (Biotage V10) to give the crude product in DMSO (0.5 mL). The residue was taken up in additional DMSO (0.5 mL) and methanol (1 mL) then purified by mass directed autoprep (formic acid modifier). The appropriate fractions were evaporated under a stream of nitrogen to give the required product, 11.5 mg. LCMS [LCMS1] Rt 1.51 min, m/z (ES+) 513 (M+H).

Route 6

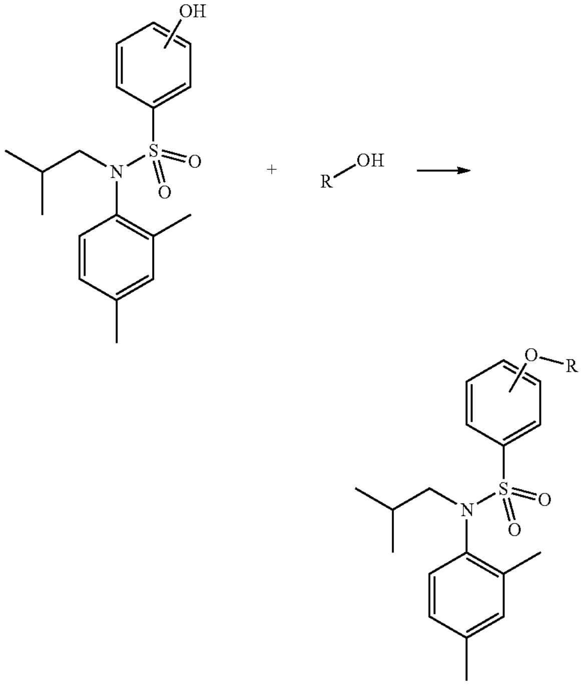

A phenol intermediate (1 equivalent, see Table 3 for specific phenol used), an alcohol (1.25 equivalents, see Table 3 for specific alcohol used) and (4-(3,3,4,4,5,5,6,6,7,7,8,8,9,9,10,10,10-heptadecafluorodecyl)phenyl)diphenylphosphine (Fluoroflash, 1.5 equivalents) were added to a vessel. Tetrahydrofuran (THF) (14 mL/mmol) was added followed by diisopropyl diazene-1,2-dicarboxylate (DIAD) (1.25 equivalents). The vials were capped and stirred at room temperature overnight. Workup and purification were then carried out according to the relevant procedure(s) listed in Table 3.

Specific Example

Preparation of N-(2,4-dimethylphenyl)-N-isobutyl-3-(2-morpholinoethoxy)benzenesulfonamide (Example 53)

N-(2,4-dimethylphenyl)-3-hydroxy-N-isobutylbenzenesulfonamide (76.9 mg, 0.231 mmol), 2-morpholinoethanol (0.035 mL, 0.288 mmol) and (4-(3,3,4,4,5,5,6,6,7,7,8,8,9,9,10,10,10-heptadecafluorodecyl)phenyl)diphenylphosphine (204 mg, 0.288 mmol) were added to a vessel. Tetrahydrofuran (THF) (4 mL) was added followed by diisopropyl diazene-1,2-dicarboxylate (DIAD) (0.056 ml, 58.3 mg 0.288 mmol). The reaction vial was sealed and left to stir overnight at 20° C. The reaction mixture was concentrated in vacuo and then diluted with ethyl acetate (25 mL) and water (25 mL). The organic fraction was separated, dried and concentrated in vacuo to give the crude product. The crude product was dissolved in DMF:$H_2O$ (9:1) (1 mL) and loaded onto a fluorous column (pre-conditioned with 1 mL DMF, followed by 6 mL MeOH:$H_2O$ (5:1)). The semi-purified material was eluted with 6 mL MeOH:$H_2O$ (5:1). This was concentrated and dissolved in 1:1 MeOH:DMSO (1 mL) then further purified by mass directed autoprep (formic acid modifier). The relevant fractions were concentrated under a stream of nitrogen to give the required product, 17 mg. LCMS [LCMS1] Rt 1.03 min, m/z (ES+) 447 (M+H).

Route 7

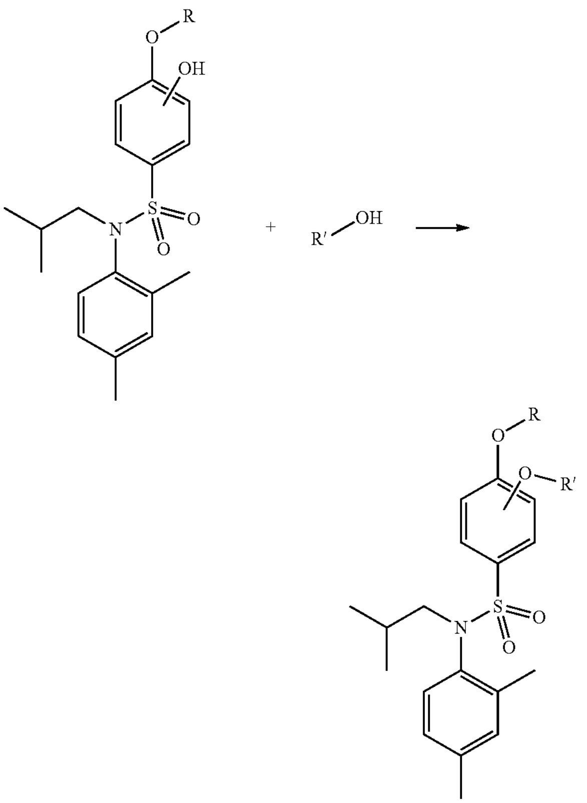

To a solution of phenol sulphonamide intermediate (1 equivalent) and alcohol (3 equivalents) in toluene (42 mL/mmol) stirred in air at 20° C., was added a solution of 2-(tributylphosphoranylidene)acetonitrile (1 equivalent) in toluene (14 mL/mmol) over 1 minute. The reaction mixture was stirred at 20° C. for 24 hours. If necessary additional 2-(tributylphosphoranylidene)acetonitrile (1 equivalent) was added and the reaction stirred for a further 2 hours. Workup and purification were then carried out according to the relevant procedure(s) listed in Table 3.

Specific Example

Preparation of N-(2,4-dimethylphenyl)-2-ethoxy-N-isobutyl-4-((tetrahydro-2H-pyran-4-yl)methoxy)benzenesulfonamide (Example 35)

To a solution of N-(2,4-dimethylphenyl)-2-hydroxy-N-isobutyl-4-((tetrahydro-2H-pyran-4-yl)methoxy)benzenesulfonamide (15.7 mg, 0.035 mmol) and ethanol (4.8 mg, 0.105 mmol) in toluene (1.5 mL) stirred in air at 20° C., was added a solution of 2-(tributylphosphoranylidene)acetonitrile (8.47 mg, 0.035 mmol) in toluene (0.5 mL) over 1 minute. The reaction mixture was stirred at 20° C. for 24 hours. Additional 2-(tributylphosphoranylidene)acetonitrile (8.47 mg, 0.035 mmol) was then added and the reaction stirred for a further 2 hours. The solvent was evaporated in vacuo and the residue purified by pre-packed silica cartridge eluting with ethyl acetate-cyclohexane (0-50%). The relevant fractions were evaporated to give the title product, 8.7 mg. LCMS [LCMS1] Rt 1.48 min, m/z (ES+) 476 (M+H).

Route 8

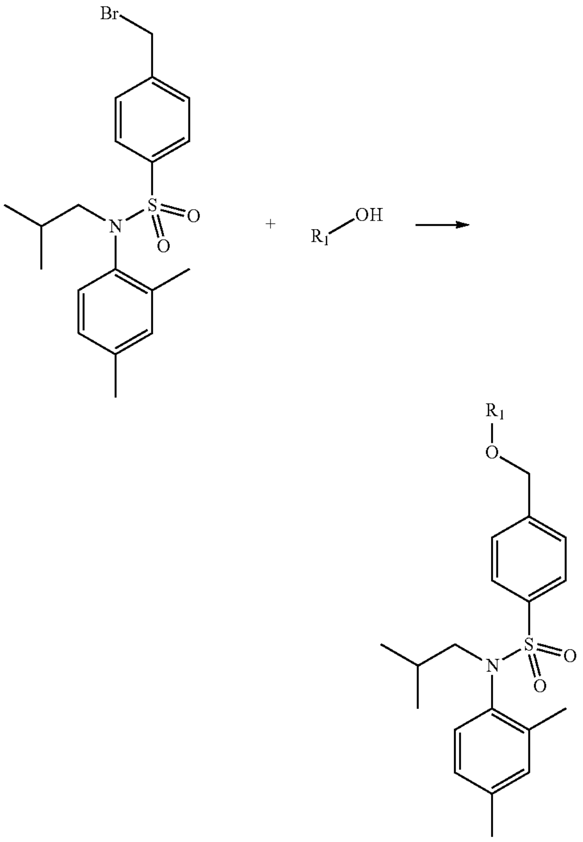

Array Format

To a solution of an alcohol (1 equivalent, see Table 2 or 3 for specific alcohol used) and 4-(bromomethyl)-N-(2,4-dimethylphenyl)-N-isobutylbenzenesulfonamide (1 equivalent) in 2-methyltetrahydrofuran (2-MeTHF) (13 mL/mmol) stirred under nitrogen at room temperature was added sodium hydride (60% dispersed in oil, 1 equivalent). The reaction mixture was stirred at 20° C. for 3 hours. Workup and purification were then carried out according to the relevant procedure(s) listed in Tables 2 or 3.

Specific Example

Preparation of N-(2,4-dimethylphenyl)-N-isobutyl-4-((oxetan-3-ylmethoxy)methyl)benzenesulfonamide (Example 19)

To a solution of oxetan-3-ylmethanol (7 mg, 0.075 mmol) and 4-(bromomethyl)-N-(2,4-dimethylphenyl)-N-isobutylbenzenesulfonamide (31 mg, 0.075 mmol) in 2-methyltetrahydrofuran (2-MeTHF) (1 mL) stirred under nitrogen at room temperature was added sodium hydride (60% dispersed in oil, approximately 2 mg, 0.075 mmol). The reaction mixture was stirred at 20° C. for 3 hours then quenched with water (75 uL). The solvent was removed under a stream of nitrogen to give the crude product. The crude was then purified by mass directed autoprep (ammonium carbonate modifier). The appropriate fractions were concentrated under a stream of nitrogen to give the required product, 2.4 mg. LCMS [LCMS1] Rt 1.34 min, m/z (ES+) 418 (M+H).

Single Reaction Format

To a solution of crude 4-(bromomethyl)-N-(2,4-dimethylphenyl)-N-isobutylbenzenesulfonamide (1 equivalent) and alcohol (1 equivalent) in 2-methyltetrahydrofuran (2-MeTHF) (8.2 mL/mmol) and dimethyl sulfoxide (DMSO) (4.1 mL/mmol) was added sodium hydride (approximately 1 equivalent, 60% dispersed in oil) in one charge. The reaction mixture was stirred at 20° C. for 16 hours. Workup and purification were then carried out according to the relevant procedure(s) listed in Tables 2 or 3.

Specific Example

Preparation of N-(2,4-dimethylphenyl)-N-isobutyl-4-(((tetrahydro-2H-pyran-4-yl)methoxy)methyl)benzenesulfonamide (Example 18)

To a solution of crude 4-(bromomethyl)-N-(2,4-dimethylphenyl)-N-isobutylbenzenesulfonamide (100 mg, 0.122 mmol) and (tetrahydro-2H-pyran-4-yl)methanol (14.15 mg, 0.122 mmol) in 2-methyltetrahydrofuran (2-MeTHF) (1 mL) and dimethyl sulfoxide (DMSO) (0.5 mL) was added sodium hydride (approximately 4.87 mg, 0.122 mmol, 60% dispersed in oil) in one charge. The reaction mixture was stirred at 20° C. for 16 hours. The reaction was then quenched with methanol (0.5 mL) and water (0.5 mL) and concentrated in vacuo to give a residue in DMSO. This was diluted with dichloromethane (10 mL) and water (10 mL) and stirred vigorously for 10 minutes. The layers were separated by hydrophobic frit and the organic fraction evaporated to give the crude product. The sample was then purified by mass directed autoprep (formic acid modifier). The appropriate fractions were concentrated under a stream of nitrogen to give the required product, 4.2 mg. LCMS [LCMS1] Rt 1.44 min, m/z (ES+) 446 (M+H).

Route 9

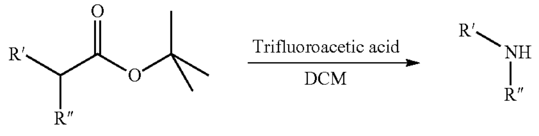

Boc-deprotection of final products was achieved as follows: The Boc-protected compound was dissolved in a mixture of dichloromethane (DCM) (1.0 mL/0.1 mmol) and trifluoroacetic acid (TFA) (1.0 mL/0.1 mmol). The solution was left to stir for 30 minutes at 20° C., under nitrogen. Workup and purification were then carried out according to the relevant procedure(s) listed in Table 3.

Specific Example

Preparation of N-(2,4-dimethylphenyl)-4-[(cis-3-fluoropiperidin-4-yl)methoxy]-N-(2-methylpropyl)benzene-1-sulfonamide (Example 39)

Tert-butyl cis-4-((4-(N-(2,4-dimethylphenyl)-N-isobutylsulfamoyl)phenoxy)methyl)-3-fluoropiperidine-1-carboxylate was dissolved in dichloromethane (DCM) (1.0 mL) and trifluoroacetic acid (TFA) (1.0 mL). The solution was left to stir for 30 minutes at 20° C., under nitrogen. The reaction was concentrated under a stream of nitrogen. The crude deprotected product was then purified by mass directed autoprep (ammonium carbonate modifier). The appropriate fractions were evaporated in vacuo to give the deprotected product, 15 mg. LCMS [LCMS2] Rt 1.38 min, m/z (ES+) 449 (M+H).

Route 10

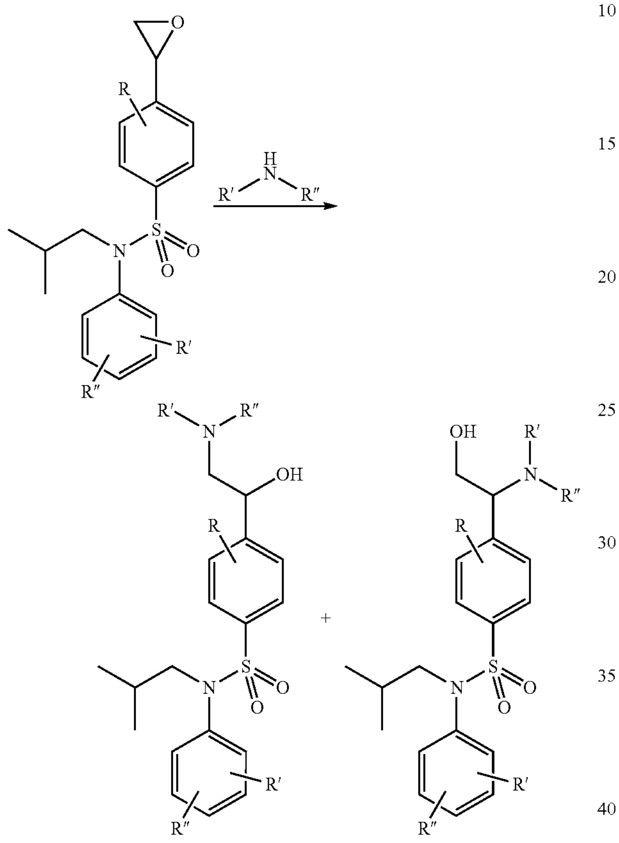

Array Format

A solution of epoxide-sulphonamide intermediate (7 equivalents) was prepared in ethanol (0.5 mL/mmol×7) and an aliquot (representing 1 equivalent) dispensed for each individual reaction. To each reaction was added one of the amines (1.1 equivalents) as a solution in ethanol (0.5 mL/mmol), followed by triethylamine (2 equivalents). The reactions were then heated at 50° C. for up to 2 days. Workup and purification were then carried out according to the relevant procedure(s) listed in Table 3. Note: In some cases both regioisomers were isolated.

Specific Example

Preparation of N-(2,4-dimethylphenyl)-4-(1-hydroxy-2-((3-methyloxetan-3-yl)amino)ethyl)-N-isobutylbenzenesulfonamide (Example 72)

A solution of N-(2,4-dimethylphenyl)-N-isobutyl-4-(oxiran-2-yl)benzenesulfonamide (173 mg, 0.481 mmol) was prepared in ethanol (1.75 mL) and dispensed at 0.25 mL/vial into 7 vials for each individual reaction. To one vial was added 3-methyloxetan-3-amine (0.076 mmol) as a solution in ethanol (0.25 mL), followed by triethylamine (0.023 mL, 0.165 mmol). The reaction was then heated at 50° C. over the weekend. Solvent was concentrated under stream of nitrogen and sample purified by mass directed autoprep (ammonium carbonate modifier). Relevant fractions were evaporated under a stream of nitrogen to give the product, 7.3 mg (only one regioisomer isolated). LCMS [LCMS2] Rt 1.23 min, m/z (ES+) 447 (M+H).

Single Reaction Format

To a stirred solution of epoxide-sulphonamide intermediate (1 equivalent) in ethanol (1.5 mL/mmol) at 25° C. was added either an amine (1.1 equivalents) and triethylamine (2.4 equivalents) or an amine (2 equivalents) and the reaction mixture heated to 50° C. for up to 2 days. Workup and purification were then carried out according to the relevant procedure(s) listed in Table 3. Note: In some cases both regioisomers were isolated.

Specific Example

Preparation of N-(2,4-dimethylphenyl)-4-(2-hydroxy-1-morpholinoethyl)-N-isobutyl-3-methylbenzenesulfonamide (Example 89) and N-(2,4-dimethylphenyl)-4-(1-hydroxy-2-morpholinoethyl)-N-isobutyl-3-methylbenzenesulfonamide (Example 90)

To a stirred solution of N-(2,4-dimethylphenyl)-N-isobutyl-3-methyl-4-(oxiran-2-yl)benzenesulfonamide (50 mg, 0.134 mmol) in ethanol (200 uL) at 25° C., was added morpholine (12.83 mg, 0.147 mmol) and triethylamine (44.8 µL, 0.321 mmol) and the reaction mixture heated to 50° C. for 12 hours. The reaction mixture was concentrated in vacuo and purified by mass directed autoprep (ammonium carbonate modifier). The solvent was dried under a stream of nitrogen to give the required regioisomeric products: N-(2,4-dimethylphenyl)-4-(2-hydroxy-1-morpholinoethyl)-N-isobutyl-3-methylbenzenesulfonamide (12 mg) and N-(2,4-dimethylphenyl)-4-(1-hydroxy-2-morpholinoethyl)-N-isobutyl-3-methylbenzenesulfonamide (16 mg). LCMS [LCMS2] Rt 1.30 min, m/z (ES+) 461 (M+H).

Route 11

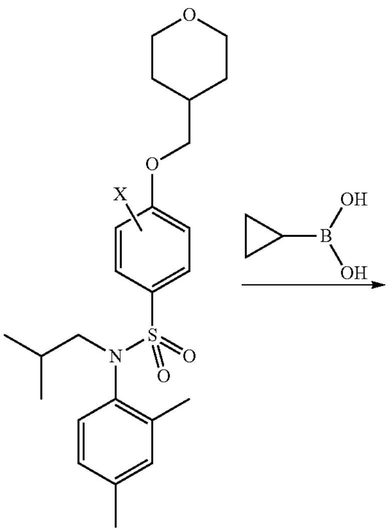

X = halo

-continued

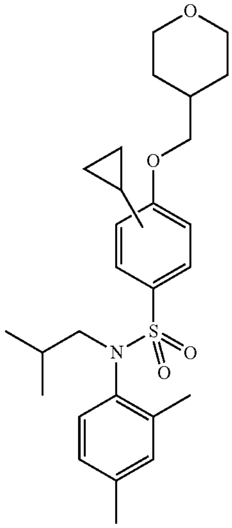

To a suspension of halo-sulfonamide intermediate (1 equivalent), cyclopropylboronic acid (2.5 equivalents), tricyclohexylphosphine (0.2 equivalents) and tripotassium phosphate (3 equivalents) in toluene (18.6 mL/mmol) and water (0.9 mL/mmol), was added palladium(II) acetate (0.1 equivalents). The reaction vessel was sealed and heated by microwaves to 120° C. for 30 minutes. The reaction mixture was then passed through a silica column to remove palladium residues, eluting with methanol. Workup and purification were then carried out according to the relevant procedure(s) listed in Table 3.

Specific Example

Preparation of 3-cyclopropyl-N-(2,4-dimethylphenyl)-N-isobutyl-4-((tetrahydro-2H-pyran-4-yl)methoxy)benzenesulfonamide (Example 21)

To a suspension of 3-chloro-N-(2,4-dimethylphenyl)-N-isobutyl-4-((tetrahydro-2H-pyran-4-yl)methoxy)benzenesulfonamide (100 mg, 0.215 mmol), cyclopropylboronic acid (46.1 mg, 0.536 mmol), tricyclohexylphosphine (12.03 mg, 0.043 mmol) and tripotassium phosphate (137 mg, 0.644 mmol) in toluene (4 mL) and water (0.2 mL), was added palladium(II) acetate (approximately 4.82 mg, 0.021 mmol) ensuring all particles were below solvent level. The reaction vessel was sealed and heated by microwaves (Emrys Optimiser) to 120° C. for 30 minutes. After cooling, the reaction mixture was passed through a pre-packed silica column (500 mg) to remove palladium residues, eluting with methanol. The reaction solution was evaporated in vacuo to and purified by mass directed autoprep (formic acid modifier). The appropriate fractions were concentrated under a stream of nitrogen to give the required product, 34 mg. LCMS [LCMS1] Rt 1.55 min, m/z (ES+) 472 (M+H).

Route 12

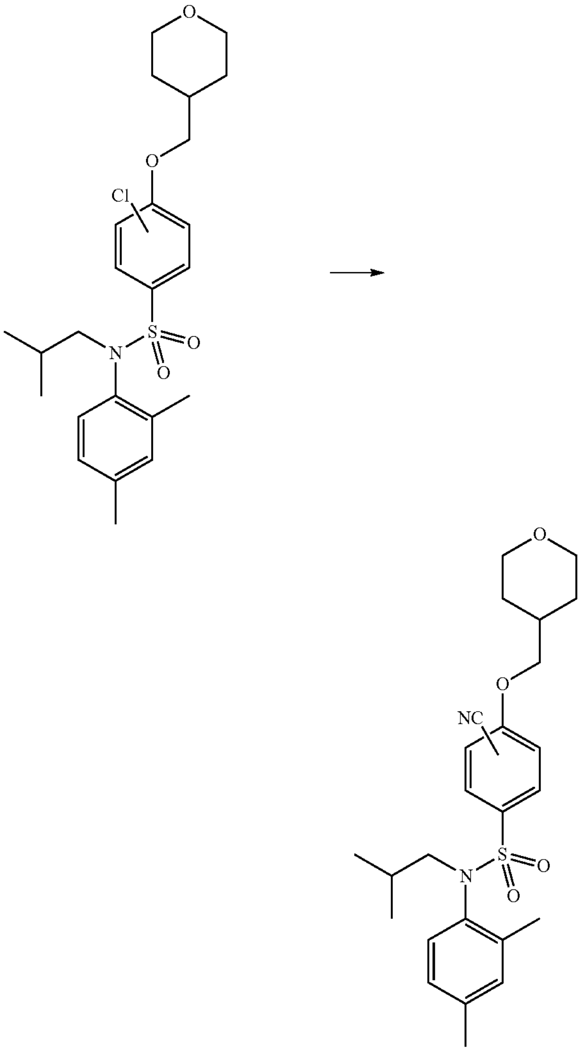

To a solution of chloro-sulfonamide intermediate (1 equivalent) in N-methyl-2-pyrrolidone (NMP) (4.6 mL/mmol) was added copper(I) cyanide (2 equivalents). The reaction vessel was sealed and heated by microwaves (Biotage Initiator) to 220° C. for 2 hours. If required, the reaction was further heated at 220° C. for an additional 6 hours. Workup and purification were then carried out according to the relevant procedure(s) listed in Table 3.

Specific Example

Preparation of 2-cyano-N-(2,4-dimethylphenyl)-N-isobutyl-4-((tetrahydro-2H-pyran-4-yl)methoxy)benzenesulfonamide (Example 38)

To a solution of 2-chloro-N-(2,4-dimethylphenyl)-N-isobutyl-4-((tetrahydro-2H-pyran-4-yl)methoxy)benzenesulfonamide (200 mg, 0.429 mmol) in N-methyl-2-pyrrolidone (NMP) (2 mL) was added copper(I) cyanide (77 mg, 0.858 mmol). The reaction vessel was sealed and heated by microwaves (Biotage Initiator) to 220° C. for 2 hours. After cooling the reaction LCMS analysis showed some evidence of the desired product. The reaction was reheated by microwaves to 220° C. for an additional 6 hours. The reaction was slowly and carefully quenched with dilute HCl (5 mL) and DCM (5 mL). The mixture was passed through a hydrophobic frit and the organic layer collected and concentrated in vacuo to give a brown oil. The crude was purified by mass directed autoprep (ammonium carbonate modifier). The appropriate fractions were evaporated in vacuo to give the required product, 56 mg. LCMS [LCMS2] Rt 1.47 min, m/z (ES+) 457 (M+H).

Route 13

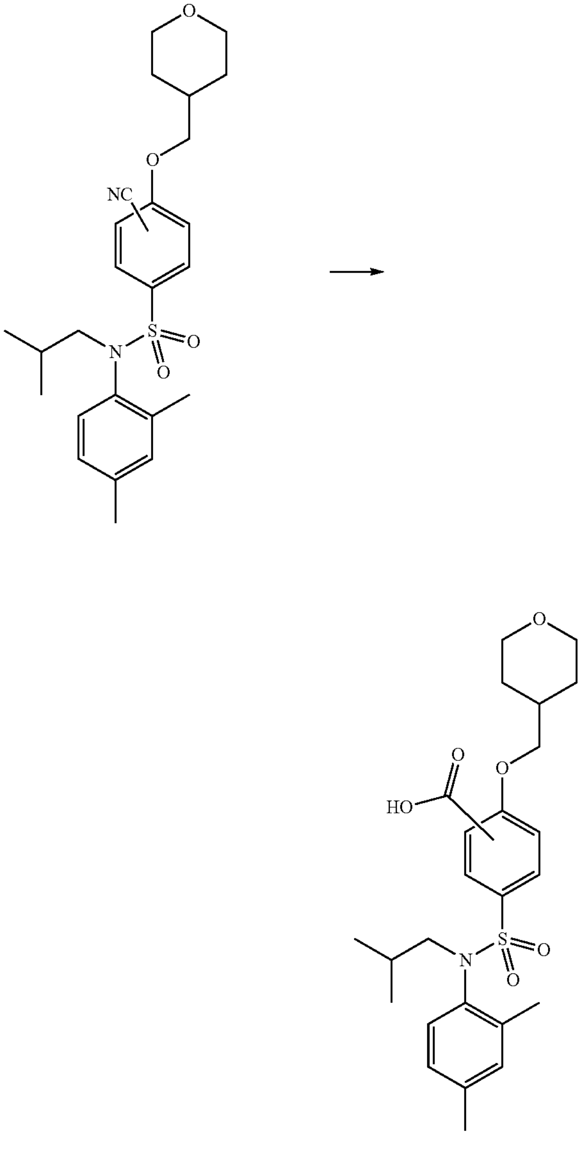

To a stirred solution of cyano-sulfonamide intermediate (1 equivalent) in ethanol (2.5 mL/mmol) was added 4N sodium hydroxide solution (20 equivalents). The reaction mixture was stirred at 80° C. for 15 hours, then cooled and ethanol removed in vacuo. Workup and purification were then carried out according to the relevant procedure(s) listed in Table 3.

Specific Example

Preparation of 5-[(2,4-dimethylphenyl)(2-methylpropyl)sulfamoyl]-2-(oxan-4-ylmethoxy)benzoic acid (Example 91)

To a stirred solution of 3-cyano-N-(2,4-dimethylphenyl)-N-isobutyl-4-((tetrahydro-2H-pyran-4-yl)methoxy)benzenesulfonamide (50 mg, 0.110 mmol) in ethanol (1 mL) at 25° C. was added sodium hydroxide (0.548 mL, 2.190 mmol). After which the reaction mixture was stirred at 80° C. for 15 hours, then cooled, ethanol removed and crude partitioned between ethyl acetate (20 mL) and HCl (2N, 15 mL). The organic layer was separated, dried over $MgSO_4$ and the solvent removed in vacuo to give a yellow oil. The crude was purified by mass directed autoprep (ammonium carbonate modifier). The relevant fractions were evaporated in vacuo to give the required product, 16.1 mg. LCMS [LCMS2] Rt 0.91 mins, m/z (ES+) 476 (M+H).

Route 14

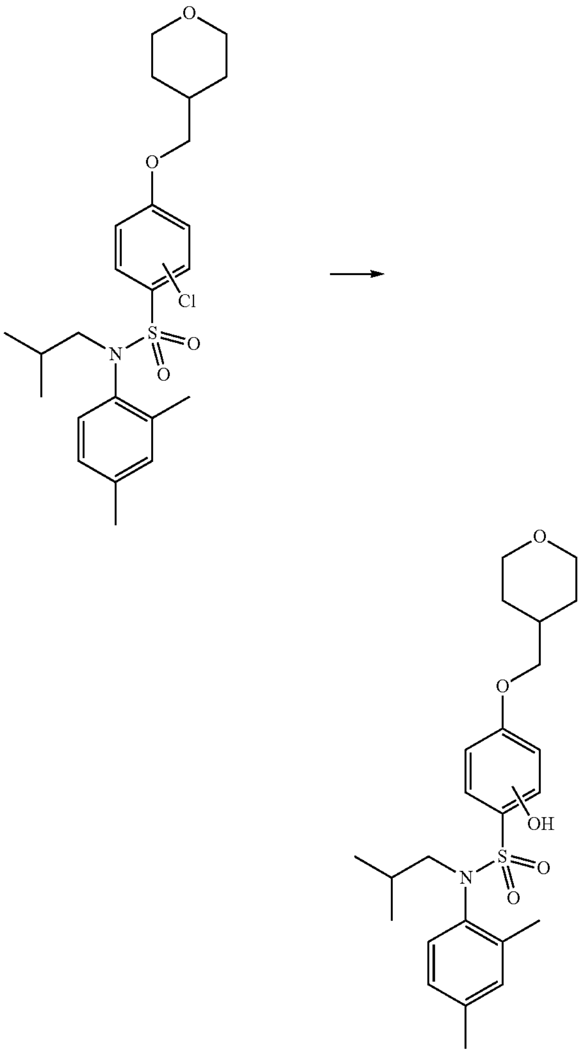

Chloro-benzenesulfonamide intermediate (1 equivalent), tris(dibenzylideneacetone)dipalladium(0) (catalytic, 1 mol %), 2-di-tert-butylphosphino-2',4',6'-triisopropylbiphenyl (catalytic, 1 mol %), and potassium hydroxide (3 equivalents) were added to a microwave vial. The reactants where dissolved in 1,4-dioxane (2.8 mL/mmol) and water (2.8 mL/mmol). The reaction vessel was sealed and heated by microwaves to 150° C. for 2 hours. Workup and purification were then carried out according to the relevant procedure(s) listed in Table 3.

Specific Example

Preparation of N-(2,4-dimethylphenyl)-2-hydroxy-N-isobutyl-4-((tetrahydro-2H-pyran-4-yl)methoxy)benzenesulfonamide (Example 26)

2-chloro-N-(2,4-dimethylphenyl)-N-isobutyl-4-((tetrahydro-2H-pyran-4-yl)methoxy)benzenesulfonamide (200 mg, 0.429 mmol), tris(dibenzylideneacetone)dipalladium(0) (3.93 mg, 4.29 μmol), 2-di-tert-butylphosphino-2',4',6'-triisopropylbiphenyl (1.822 mg, 4.29 μmol) and potassium hydroxide (72.2 mg, 1.287 mmol) were added to a microwave vial. The reactants where dissolved in 1,4-dioxane (1.2 mL) and water (1.2 mL). The reaction vessel was sealed and heated by microwaves (Biotage Initiator) to 150° C. for 2 hours. The reaction mixture was concentrated in vacuo, 2N NaOH was added and the reaction was diluted with ethyl acetate. The organic phase was separated and was washed with 2N HCl. The organic phase was separated, dried using a hydrophobic frit and evaporated in vacuo to give the crude product as a yellow oil. The crude was purified by mass directed autoprep (ammonium carbonate modifier). The relevant fractions were then concentrated under a stream of nitrogen to give the required product, 32 mg. LCMS [LCMS2] Rt 1.51 min, m/z (ES+) 448 (M+H).

TABLE 3

Preparation Details for Examples 7 to 101

| Example No. | Route | SM1 ID | SM2 ID | SM2 Source | Array | Scale (mmol) | Yield (%) | Work up | Purification | RT | base ion (M + 1) | LCMS |
|---|---|---|---|---|---|---|---|---|---|---|---|---|
| E7 | R5 | I4 | S23 | *Bioorg. Med. Chem. Lett.*, 2006, 16 (6), 1749-1752 | yes | 0.3 | 33 | Q&F | F | 1.56 | 449 | LCMS1 |
| E8 | R5 | I4 | S28 | Tokyo Chemical Industry UK Ltd | yes | 0.3 | 30 | Q&F | F | 1.59 | 431 | LCMS1 |
| E9 | R5 | I4 | S29 | Chembridge Corporation | yes | 0.15 | 12 | Q&F | A | 1.00 | 431 | LCMS1 |
| E10 | R5 | I4 | S30 | *Org. Lett.*, 2005, 7(5), 937-940 | yes | 0.15 | 54 | Q&F | A | 1.18 | 447 | LCMS1 |
| E11 | R5 | I4 | S31 | *Arch. Pharm. Ber. Dtsch. Pharm. Ges.*, 1964, (297), 632-638 | yes | 0.15 | 36 | Q&F | A | 1.24 | 461 | LCMS1 |
| E12 | R5 | I4 | S32 | Apollo Scientific | yes | 0.15 | 30 | Q&F | A | 1.48 | 432 | LCMS1 |
| E13 | R5 | I4 | S33 | UKOrgSynthesis | no | 0.075 | 30 | Q&F | F | 1.51 | 513 | LCMS1 |
| E14 | R5 | I4 | S35 | Fluorochem | yes | 0.15 | 3 | Q&F | A | 1.28 | 448 | LCMS1 |
| E15 | R5 | I4 | S36 | Tokyo Chemical Industry UK Ltd | yes | 0.15 | 9 | Q&F | A | 1.14 | 448 | LCMS1 |
| E16 | R5 | I4 | S37 | Tokyo Chemical Industry UK Ltd | yes | 0.15 | 9 | Q&F | A | 1.15 | 448 | LCMS1 |
| E17 | R5 | I4 | S38 | Czech. 1983, CS 203705 B1 19810331 | no | 0.198 | 9 | Q&F | F | 1.05 | 475 | LCMS1 |
| E18 | R8 | I5 | S32 | Apollo Scientific | no | 0.122 | 8 | Q&A | F | 1.44 | 446 | LCMS1 |
| E19 | R8 | I5 | S34 | Pharmablock | yes | 0.075 | 8 | Q | A | 1.34 | 418 | LCMS1 |
| E20 | R5 | I11 | S32 | Apollo Scientific | yes | 0.034 | 46 | Q&F | A | 1.52 | 466 | LCMS1 |
| E21 | R11 | E20 | S39 | Fluorochem | no | 0.215 | 33 | E | F | 1.55 | 472 | LCMS1 |
| E22 | R10 | I46 | S40 | Aldrich | no | 0.556 | 77 | E | E2 | 1.30 | 447 | LCMS2 |
| E23 | R5 | I14 | S32 | Apollo Scientific | yes | 0.05 | 33 | Q | A | 1.53 | 408 | LCMS1 |
| E24 | R5 | I15 | S32 | Apollo Scientific | yes | 0.1 | 37 | Q&F | A | 1.51 | 446 | LCMS1 |
| E25 | R5 | I16 | S32 | Apollo Scientific | yes | 0.1 | 36 | Q&F | A | 1.51 | 446 | LCMS1 |
| E26 | R14 | E27 | N/A | N/A | no | 0.429 | 16 | A | A | 1.51 | 448 | LCMS2 |
| E27 | R5 | I7 | S32 | Apollo Scientific | no | 4.97 | 50 | Q&F | E3 | 1.57 | 486 | LCMS2 |
| E28 | R5 | I18 | S32 | Apollo Scientific | yes | 0.1 | 31 | Q&F | A | 1.46 | 450 | LCMS1 |
| E29 | R5 | I19 | S32 | Apollo Scientific | yes | 0.1 | 21 | Q&F | A | 1.46 | 450 | LCMS1 |
| E30 | R7 | I20 | S32 | Apollo Scientific | no | 0.091 | 42 | E | F | 1.40 | 462 | LCMS1 |
| E31 | R5 | I4 | S41 | Sigma Aldrich | yes | 0.15 | 50 | Q&F | A | 1.41 | 418 | LCMS1 |
| E32 | R14 | E20 | N/A | N/A | no | 0.429 | 28 | A | A | 1.37 | 448 | LCMS2 |
| E33 | R5 | I4 | S40 | Alfa Aesar | no | 0.089 | 6 | A | F | 1.38 | 403 | LCMS1 |
| E34 | R5 | I4 | S42 | Sigma Aldrich | yes | 0.15 | 43 | Q&F | A | 1.42 | 418 | LCMS1 |
| E35 | R7 | E26 | S43 | Sigma Aldrich | no | 0.035 | 52 | E | E2 | 1.48 | 476 | LCMS1 |
| E36 | R5 | I4 | S44 | *Helv. Chim. Acta.* 2004, 87(1), 90-105 | yes | 0.3 | 6 | Q&F | A | 1.03 | 447 | LCMS1 |
| E37 | R5 | I17 | S32 | Apollo Scientific | yes | 0.1 | 11 | Q | A | 1.41 | 457 | LCMS1 |
| E38 | R12 | E27 | N/A | N/A | no | 0.429 | 28 | Q&A | A | 1.47 | 457 | LCMS2 |
| E39 | R9 | I37 | N/A | N/A | no | 0.063 | 53 | E | A | 1.38 | 449 | LCMS2 |
| E40 | R5 | I4 | S45 | Sigma Aldrich | yes | 0.1 | 40 | Q&F | A | 1.70 | 430 | LCMS1 |
| E41 | R5 | I4 | S46 | Asdi Incorporated | yes | 0.1 | 22 | Q&F | A | 1.76 | 458 | LCMS1 |
| E42 | R5 | I4 | S47 | Sigma Aldrich | yes | 0.1 | 12 | Q&F | A | 1.35 | 432 | LCMS1 |
| E43 | R5 | I4 | S48 | *Tet. Lett.*, 2003, 44 (42), 7809-7812 | yes | 0.1 | 18 | Q&F | A | 1.00 | 453 | LCMS1 |
| E44 | R5 | I4 | S49 | Milestone PharmTech LLC | yes | 0.1 | 50 | Q&F | A | 1.47 | 432 | LCMS1 |
| E45 | R5 | I4 | S50 | Fluorochem | yes | 0.1 | 51 | Q&F | A | 1.18 | 431 | LCMS1 |
| E46 | R5 | I4 | S51 | www.hit2lead.com | yes | 0.149 | 50 | Q&F | A | 1.35 | 434 | LCMS1 |
| E47 | R5 | I4 | S52 | TCI Europe NV | yes | 0.149 | 53 | Q&F | A | 1.72 | 444 | LCMS1 |
| E48 | R5 | I4 | S53 | TCI Europe NV | yes | 0.149 | 45 | Q&F | A | 0.98 | 461 | LCMS1 |
| E49 | R5 | I4 | S54 | *J. Org. Chem.*, 2008, 73 (9), 3662-3665 | yes | 0.3 | 3 | Q&F | A | 1.01 | 433 | LCMS1 |
| E50 | R5 | I4 | I28 | See text | yes | 0.3 | 7 | Q&F | A | 0.89 | 433 | LCMS1 |
| E51 | R5 | I4 | S55 | Sigma Aldrich | yes | 0.149 | 36 | Q&F | A | 1.49 | 432 | LCMS1 |
| E52 | R9 | I38 | N/A | N/A | no | 0.024 | 84 | E | N/A | 0.97 | 461 | LCMS1 |
| E53 | R6 | I30 | S56 | Aldrich | no | 0.288 | 16 | A&FL | F | 1.03 | 447 | LCMS1 |
| E54 | R5 | I4 | S57 | *Tet. Lett.*, 1996, 37(16), 2865-2868 | yes | 0.115 | 15 | Q&F | A | 1.29 | 448 | LCMS1 |
| E55 | R5 | I4 | S58 | Activate Scientific | yes | 0.15 | 37 | Q&F | A | 1.01 | 449 | LCMS1 |
| E56 | R4 | I31 | S59 | ABCR GmbH & CO. KG | yes | 0.099 | 2 | E | F | 1.13 | 458 | LCMS1 |
| E57 | R6 | I30 | S32 | Apollo Scientific | No | 0.288 | 35 | A&FL | F | 1.47 | 432 | LCMS1 |

TABLE 3-continued

Preparation Details for Examples 7 to 101

| Example No. | Route | SM1 ID | SM2 ID | SM2 Source | Array | Scale (mmol) | Yield (%) | Work up | Purification | RT | base ion (M + 1) | LCMS |
|---|---|---|---|---|---|---|---|---|---|---|---|---|
| E58 | R5 | I4 | S60 | Sigma Aldrich | yes | 0.115 | 12 | Q&F | A | 1.09 | 480 | LCMS1 |
| E59 | R5 | I4 | S61 | UkrOrgSynthesis Ltd. | yes | 0.149 | 41 | Q&F | A | 1.04 | 431 | LCMS1 |
| E60 | R9 | I39 | N/A | N/A | No | 0.021 | 96 | E &S | N/A | 1.03 | 463 | LCMS1 |
| E61 | R5 | I4 | S62 | Asdi Incorporated | yes | 0.149 | 45 | Q&F | A | 1.01 | 475 | LCMS1 |
| E62 | R5 | I22 | S32 | Apollo Scientific | yes | 0.05 | 3 | Q | A | 1.53 | 468 | LCMS1 |
| E63 | R5 | I4 | S63 | Aldrich | yes | 0.15 | 38 | Q&F | A | 1.00 | 475 | LCMS1 |
| E64 | R5 | I4 | S64 | *J. Org. Chem.*, 1961, 26, 1519 | yes | 0.15 | 15 | Q&F | A | 1.04 | 445 | LCMS1 |
| E65 | R5 | I4 | S65 | SynChen Inc | No | 0.095 | 22 | Q&F | F | 0.98 | 445 | LCMS1 |
| E66 | R5 | I4 | S66 | Tyger Scientific Inc. | yes | 0.3 | 36 | Q&F | A | 1.03 | 417 | LCMS1 |
| E67 | R9 | I48 | N/A | N/A | No | 0.446 | 99 | E | N/A | 1.00 | 417 | LCMS1 |
| E68 | R9 | I49 | N/A | N/A | no | 0.214 | 77 | E | A | 1.03 | 417 | LCMS1 |
| E69 | R5 | I4 | S67 | Manchester Organics Limited | yes | 0.149 | 52 | Q&F | A | 0.96 | 403 | LCMS1 |
| E70 | R8 | I5 | S50 | Fluorochem Ltd | yes | 0.075 | 2 | Q&F | A | 1.18 | 445 | LCMS1 |
| E71 | R7 | E26 | S68 | Sigma Aldrich | no | 0.076 | 26 | E | F | 1.50 | 490 | LCMS1 |
| E72 | R10 | I46 | S69 | Fluorochem Limited | yes | 0.069 | 24 | E | A | 1.23 | 447 | LCMS2 |
| E73 | R10 | I46 | S70 | Sigma Aldrich | yes | 0.069 | 75 | E | A | 1.56 | 445 | LCMS2 |
| E74 | R10 | I46 | S71 | Syntech Development Company | yes | 0.069 | 25 | E | A | 1.24 | 495 | LCMS2 |
| E75 | R10 | I46 | S72 | Aldrich | yes | 0.069 | 70 | E | A | 1.46 | 463 | LCMS2 |
| E76 | R10 | I46 | S73 | Tyger Scientific Inc. | yes | 0.069 | 56 | E | A | 1.20 | 477 | LCMS2 |
| E77 | R10 | I46 | S74 | Sigma Aldrich | yes | 0.069 | 63 | E | A | 1.44 | 463 | LCMS2 |
| E78 | R10 | I46 | S70 | Sigma Aldrich | yes | 1.069 | 13 | E | A | 1.47 | 445 | LCMS2 |
| E79 | R5 | I4 | S76 | Activate Scientific | yes | 0.1 | 7 | E | F | 1.23 | 433 | LCMS1 |
| E80 | R5 | I4 | S77 | emolecules | yes | 0.15 | 1 | E | A | 1.11 | 466 | LCMS1 |
| E81 | R5 | I4 | S78 | emolecules | yes | 0.15 | 2 | E | A | 1.10 | 466 | LCMS1 |
| E82 | R10 | I50 | S79 | Milestone PharmTech LLC | yes | 0.075 | 61 | E | A | 1.50 | 515 | LCMS2 |
| E83 | R10 | I50 | S40 | Sigma Aldrich | yes | 0.075 | 10 | E | A | 1.37 | 481 | LCMS2 |
| E84 | R10 | I50 | S40 | Sigma Aldrich | yes | 0.075 | 62 | E | A | 1.42 | 481 | LCMS2 |
| E85 | R10 | I50 | S80 | Enamine | yes | 0.075 | 9 | A | A | 1.32 | 493 | LCMS2 |
| E86 | R10 | I50 | S81 | Chembridge corporation | yes | 1.075 | 14 | A | A | 1.22 | 481 | LCMS2 |
| E87 | R10 | I43 | S40 | Sigma Aldrich | no | 0.106 | 45 | E | A | 1.36 | 465 | LCMS2 |
| E88 | R10 | I44 | S40 | Sigma Aldrich | no | 0.054 | 50 | E | A | 1.39 | 461 | LCMS2 |
| E89 | R10 | I47 | S40 | Sigma Aldrich | no | 0.134 | 19 | E | A | 1.23 | 461 | LCMS2 |
| E90 | R10 | I47 | S40 | Sigma Aldrich | no | 0.134 | 26 | E | A | 1.30 | 461 | LCMS2 |
| E91 | R13 | E97 | N/A | N/A | no | 0.11 | 28 | A | A | 1.27 | 476 | LCMS2 |
| E92 | R5 | I12 | S32 | Apollo Scientific | no | 1.791 | 74 | A | E1 | 1.52 | 510/512 | LCMS1 |
| E93 | R11 | E92 | S39 | Sigma Aldrich | no | 0.098 | 22 | F&E | F | 1.53 | 472 | LCMS1 |
| E94 | R10 | I46 | S82 | 3BScientific corporation | yes | 0.08 | 32 | E | A | 1.25 | 461 | LCMS2 |
| E95 | R10 | I46 | S83 | Enamine | yes | 0.08 | 16 | E | A | 1.42 | 475 | LCMS2 |
| E96 | R10 | I46 | S84 | Aldrich | yes | 0.08 | 69 | E | A | 1.24 | 461 | LCMS2 |
| E97 | R12 | E98 | N/A | N/A | no | 0.751 | 74 | A | A | 1.46 | 457 | LCMS2 |
| E98 | R5 | I11 | S32 | Apollo Scientific | no | 2.82 | 49 | A | N/A | 1.56 | 466 | LCMS2 |
| E99 | R10 | I46 | S84 | Aldrich | yes | 0.08 | 12 | E | A | 1.12 | 461 | LCMS2 |
| E100 | R10 | I46 | S85 | Fluorochem Ltd | yes | 0.08 | 25 | E | M | 1.27 | 461 | LCMS2 |
| E101 | R10 | I46 | S40 | Aldrich | no | 0.55 | 610 | E | E2 | 1.25 | 447 | LCMS2 |

Example 102

N-(2,4-dimethylphenyl)-N-isobutyl-4-(5-oxopyrrolidin-2-yl)benzenesulfonamide a) Intermediate 52 methyl 4-(4-(N-(2,4-dimethylphenyl)-N-isobutylsulfamoyl)phenyl)-4-nitrobutanoate To a solution of methyl 4-nitrobutanoate (0.094 mL, 0.757 mmol), 4-bromo-N-(2,4-dimethylphenyl)-N-isobutylbenzenesulfonamide (200 mg, 0.505 mmol), di-tert-butyl(2'-methyl-[1,1'-biphenyl]-2-yl)phosphine (15.77 mg, 0.050 mmol) and cesium carbonate (197 mg, 0.606 mmol) in 1,2-dimethoxyethane (DME) (3 mL) at room temperature was added bis(dibenzylideneacetone)palladium(0) (14.51 mg, 0.025 mmol). The vial was flushed with nitrogen for 2 minutes then sealed and heated by microwaves (Emrys Optimiser) to 120° C. for 60 minutes. The reaction mixture was cooled then passed through a pre-packed silica (Si) cartridge, eluting with methanol (15 mL). The resulting filtrate was evaporated in vacuo then purified by mass directed autoprep (formic acid modifier). The relevant fractions were concentrated under a stream of nitrogen to give the required product (N70% pure), 96 mg, used directly in next step without further purification. LCMS [LCMS1] Rt 1.41 min, m/z (ES+) 463 (M+H).

b) Example 102

N-(2,4-dimethylphenyl)-N-isobutyl-4-(5-oxopyrrolidin-2-yl)benzenesulfonamide To a suspension of palladium on carbon (22.09 mg, 0.208 mmol) in ethanol (5 mL) stirred under nitrogen at room temperature was added a solution of methyl 4-(4-(N-(2,4-dimethylphenyl)-N-isobutylsulfamoyl)phenyl)-4-nitrobutanoate (96 mg, 0.208 mmol) in ethanol (5 mL) dropwise. The flask was carefully filled with hydrogen and the reaction mixture was stirred at 20° C. for 2 hours. LCMS analysis showed disappearance of starting material. The reaction mixture was filtered through celite under an atmosphere of nitrogen and the filtrate evaporated in vacuo to give a yellow gum. The crude was purified by mass directed autoprep (formic acid modifier). The relevant fractions were concentrated under a stream of nitrogen to give the required product, 1.01 mg. LCMS [LCMS1] Rt 1.17 min, m/z (ES+) 400 (M+H, weak) 442 (M+MeCN+H)

Example 103

N-(2,4-dimethylphenyl)-4-(2-(hydroxymethyl)morpholino)-N-isobutylbenzenesulfonamide To a solution of morpholin-2-ylmethanol (30 mg, 0.256 mmol) in tetrahydrofuran (THF) (3 mL) stirred under nitrogen at room temperature was added triethylamine (0.071 mL, 0.512 mmol) dropwise. The reaction mixture was stirred at room temperature for 10 minutes then N-(2,4-dimethylphenyl)-4-fluoro-N-isobutylbenzenesulfonamide (86 mg, 0.256 mmol) was added. The reaction mixture was stirred at room temperature overnight. LCMS analysis showed no product, so the solvent was removed under a stream of nitrogen and the crude treated with LiHMDS (1M in THF, 0.768 mL, 0.768 mmol) and THF (2 mL). The reaction vessel was sealed and heated by microwaves (Biotage Initiator) to 150° C. for 30 minutes. After cooling, LCMS analysis showed some conversion, so the reaction vessel was resealed and reheated by microwaves (Biotage Initiator) to 150° C. for a further 30 minutes. No further conversion was seen by LCMS, so ethyl acetate (10 mL) was added to the mixture and the organic phase washed with water (10 mL) then dried using a hydrophobic frit. Solvent was removed under a stream of nitrogen to give the crude product. The crude was purified by mass directed autoprep (ammonium carbonate modifier). The relevant fractions were concentrated under a stream of nitrogen to give the required product, 4 mg. LCMS [LCMS2] Rt 1.29 min, m/z (ES+) 433 (M+H).

Example 104

N-(2,4-dimethylphenyl)-3,5-difluoro-4-(1-hydroxy-2-morpholinoethyl)-N-isobutylbenzenesulfonamide a) Intermediate 53

4-bromo-N-(2,4-dimethylphenyl)-3,5-difluoro-N-isobutylbenzenesulfonamide

To a solution of 4-bromo-3,5-difluorobenzene-1-sulfonyl chloride (1462 mg, 5.02 mmol) in pyridine (10 mL) at 20° C. was added N-isobutyl-2,4-dimethylaniline (889 mg, 5.01 mmol) and the reaction mixture was stirred at 20° C. for 2 hours. The reaction mixture was then evaporated in vacuo and redissolved in ethyl acetate. The organic phase was washed with saturated sodium carbonate (25 mL), dried using a hydrophobic frit and evaporated in vacuo to give the required product as a yellow oil, 2.06 g. LCMS [LCMS2] Rt 1.57 min, m/z (ES+) 432/434 (M+H).

b) Intermediate 54

N-(2,4-dimethylphenyl)-3,5-difluoro-N-isobutyl-4-vinylbenzenesulfonamide

To a vial was added potassium trifluoro(vinyl)borate (0.744 g, 5.55 mmol), triphenylphosphine (0.073 g, 0.278 mmol), 4-bromo-N-(2,4-dimethylphenyl)-3,5-difluoro-N-isobutylbenzenesulfonamide (2 g, 4.63 mmol) suspension in tetrahydrofuran (THF) (22 mL), cesium carbonate (4.52 g, 13.88 mmol), water (2.200 mL) and palladium(II) chloride (0.016 g, 0.093 mmol). The mixture was divided evenly between two microwave vials and the vessels then sealed and heated by microwaves (Biotage Initiator) to 140° C. for 30 minutes. LCMS analysis showed some conversion, so additional 0.5 equivalent of potassium trifluoro(vinyl)borate was added to each reaction, along with extra water (2 mL) and THF (2 mL). The reactions were reheated by microwaves for a further 1 hour at 140° C. The reactions were then diluted with dichloromethane (5 mL) and water (2 mL), filtered through celite and dried using a hydrophobic frit. The organics were concentrated and purified by flash silica (Si) chromatography (0-25% ethyl acetate-cyclohexane gradient). The appropriate fractions were combined and evaporated in vacuo to give two batches of the required product, 769 mg and 856 mg, as yellow oils. LCMS [LCMS2] Rt 1.60 min, m/z (ES+) 380 (M+H).

c) Intermediate 55

N-(2,4-dimethylphenyl)-3,5-difluoro-N-isobutyl-4-(oxiran-2-yl)benzenesulfonamide To a solution of N-(2,4-dimethylphenyl)-3,5-difluoro-N-isobutyl-4-vinylbenzenesulfonamide (1.5 g, 3.95 mmol) in dichloromethane (DCM) at 0° C. was added meta-chloroperoxybenzoic acid (mCPBA) (2.73 g, 15.81 mmol) and the reaction mixture stirred for 24 hours from 0° C. to 25° C. Additional mCPBA (1.364 g, 7.91 mmol) was then added and the reaction stirred for a further 6 hours. The reaction was then washed with water (2 mL), sodium hydroxide solution (2M, 2 mL) and brine (2 mL), then evaporated in vacuo. The crude was purified by flash silica (Si) chromatography (0-100% dichloromethane-cyclohexane gradient). The appropriate fractions were combined and evaporated in vacuo to give the required product, 926 mg, as a yellow oil. LCMS [LCMS2] Rt. 1.45, m/z (ES+) 396 (M+H).

d) Example 104

N-(2,4-dimethylphenyl)-3,5-difluoro-4-(1-hydroxy-2-morpholinoethyl)-N-isobutylbenzenesulfonamide To a solution of N-(2,4-dimethylphenyl)-3,5-difluoro-N-isobutyl-4-(oxiran-2-yl)benzenesulfonamide (150 mg, 0.379 mmol) in ethanol (1.5 mL) at 25° C. was added morpholine (0.033 ml, 0.379 mmol) and the reaction mixture stirred at 50° C. for 6 hours. The mixture was concentrated in vacuo and purified by mass directed autoprep (ammonium carbonate modifier). The appropriate fractions were combined and evaporated in vacuo to give the required product, 9 mg, as a colourless oil. LCMS [LCMS2] Rt 1.33 min, m/z (ES+) 483 (M+H).

Example 105

N-(5-chloro-2-fluorophenyl)-4-(1-hydroxy-2-morpholinoethyl)-N-isobutylbenzenesulfonamide a) Intermediate 56

N-(5-chloro-2-fluorophenyl)-N-isobutyl-4-(oxiran-2-yl)benzenesulfonamide

To a stirred solution of N-(5-chloro-2-fluorophenyl)-N-isobutyl-4-vinylbenzenesulfonamide (824 mg, 2.240 mmol) in dichloromethane (DCM) at 0° C. was added meta-chloroperoxybenzoic acid (mCPBA) (1546 mg, 8.96 mmol) and the reaction mixture stirred for 6 hours from 0° C. to 25° C. The reaction was then washed with water (5 mL), sodium hydroxide solution (2M, 5 mL) and brine (5 mL), then evaporated in vacuo to give the required product (503 mg). LCMS [LCMS2] Rt 1.34 min, m/z (ES+) 384 (M+H).

b) Example 105

N-(5-chloro-2-fluorophenyl)-4-(1-hydroxy-2-morpholinoethyl)-N-isobutylbenzenesulfonamide To a stirred solution of N-(5-chloro-2-fluorophenyl)-N-isobutyl-4-(oxiran-2-yl)benzenesulfonamide (200 mg, 0.521 mmol) in ethanol (2 mL) at 25° C. was added morpholine (0.045 ml, 0.521 mmol) and the reaction mixture stirred at 50° C. for 24 hours. The mixture was then purified by mass directed autoprep (ammonium carbonate modifier). The appropriate fractions were combined and evaporated in vacuo to give the required product, 51.4 mg. LCMS [LCMS2] Rt 1.25 min, m/z (ES+) 471 (M+H).

Example 106

N-(2,4-dimethylphenyl)-3-fluoro-4-(1-hydroxy-2-((3-methyloxetan-3-yl)amino)ethyl)-N-isobutylbenzenesulfonamide To a stirred solution of N-(2,4-dimethylphenyl)-3-fluoro-N-isobutyl-4-(oxiran-2-yl)benzenesulfonamide (20 mg, 0.053 mmol) in ethanol at 25° C. was added 3-methyloxetan-3-amine (5.08 mg, 0.058 mmol). The reaction mixture was then stirred at 50° C. for 18 hours. Another portion of 3-methyloxetan-3-amine (5.08 mg, 0.058 mmol) was then added and the reaction stirred for a further 8 hours at 50° C. The reaction mixture was concentrated in vacuo and purified by mass directed autoprep (ammonium carbonate modifier). The relevant fractions were concentrated under a stream of nitrogen to give the required product, 11.2 mg. LCMS [LCMS2] Rt 1.25 min, m/z (ES+) 465 (M+H).

Example 107

N-(2,4-dimethylphenyl)-4-(1-hydroxy-2-((3-methyloxetan-3-yl)amino)ethyl)-N-isobutyl-3-methylbenzenesulfonamide To a stirred solution of N-(2,4-dimethylphenyl)-N-isobutyl-3-methyl-4-(oxiran-2-yl)benzenesulfonamide (20 mg, 0.054 mmol) in ethanol at 25° C. was added 3-methyloxetan-3-amine (5.08 mg, 0.058 mmol). The reaction mixture was then stirred at 50° C. for 18 hours. Another portion of 3-methyloxetan-3-amine (5.08 mg, 0.058 mmol) was then added and the reaction stirred for a further 8 hours at 50° C. The reaction mixture was concentrated in vacuo and purified by mass directed autoprep (ammonium carbonate modifier). The relevant fractions were concentrated under a stream of nitrogen to give the required product, 9.3 mg. LCMS [LCMS2] Rt 1.25 min, m/z (ES+) 461 (M+H).

Example 108

N-(2,4-dimethylphenyl)-4-(1-hydroxy-2-((3-methyloxetan-3-yl)amino)ethyl)-N-isobutyl-2-methylbenzenesulfonamide To a stirred solution of N-(2,4-dimethylphenyl)-N-isobutyl-2-methyl-4-(oxiran-2-yl)benzenesulfonamide (20 mg, 0.054 mmol) in ethanol at 25° C. was added 3-methyloxetan-3-amine (5.08 mg, 0.058 mmol). The reaction mixture was then stirred at 50° C. for 18 hours. Another portion of 3-methyloxetan-3-amine (5.08 mg, 0.058 mmol) was then added and the reaction stirred for a further 8 hours at 50° C. The reaction mixture was concentrated in vacuo and purified by mass directed autoprep (ammonium carbonate modifier). The relevant fractions were concentrated under a stream of nitrogen to give the required product, 5.2 mg. LCMS [LCMS2] Rt 1.23 min, m/z (ES+) 461 (M+H).

Example 109

N-(2,4-dimethylphenyl)-3-hydroxy-4-(2-hydroxy-1-morpholinoethyl)-N-isobutylbenzenesulfonamide a) Intermediate 57

N-(2,4-dimethylphenyl)-3-hydroxy-N-isobutyl-4-vinylbenzenesulfonamide 3-chloro-N-(2,4-dimethylphenyl)-N-isobutyl-4-vinylbenzenesulfonamide (250 mg, 0.662 mmol), tris(dibenzylideneacetone)dipalladium(0) (6.06 mg, 6.62 μmol), 2-di-tert-butylphosphino-2',4',6'-triisopropylbiphenyl (2.81 mg, 6.62 μmol) and potassium hydroxide (111 mg, 1.985 mmol) were added to a microwave vial. 1,4-dioxane (1 mL) and water (1.000 mL) were then added. The reaction vessel was sealed and heated by microwaves (Biotage Initiator) to 150° C. for 2 hours. LCMS analysis showed the desired product and several side-products. The crude material was purified by silica (Si) chromatography (0-100% ethyl acetate-cyclohexane gradient). The appropriate fractions were combined and evaporated in vacuo to give the required product, 100.8 mg, as a yellow gum. LCMS [LCMS2] Rt 1.42 min, m/z (ES+) 360 (M+H).

b) Intermediate 58

N-(2,4-dimethylphenyl)-3-hydroxy-N-isobutyl-4-(oxiran-2-yl)benzenesulfonamide

To a solution of N-(2,4-dimethylphenyl)-3-hydroxy-N-isobutyl-4-vinylbenzenesulfonamide (100.8 mg, 0.280 mmol) in dichloromethane (DCM) (20 mL) stirred under nitrogen at 0° C. was added meta-chloroperoxybenzoic acid (mCPBA) (194 mg, 1.122 mmol) portionwise. The reaction mixture was stirred at 0° C. for 30 minutes, then for 72 hours at room temperature. DCM (20 mL) was added to the mixture and the organic phase washed with water (20 mL), dried using a hydrophobic frit and concentrated under a stream of nitrogen to give the crude product, 60 mg, which was used directly in the next step with no further purification. LCMS [LCMS2] Rt 1.42 min, m/z (ES−) 374 (M−H).

c) Example 109

N-(2,4-dimethylphenyl)-3-hydroxy-4-(2-hydroxy-1-morpholinoethyl)-N-isobutylbenzenesulfonamide To a stirred solution of N-(2,4-dimethylphenyl)-3-hydroxy-N-isobutyl-4-(oxiran-2-yl)benzenesulfonamide (60 mg, 0.160 mmol) in ethanol (1 mL) at 25° C. was added morpholine (30.6 mg, 0.352 mmol) and the reaction mixture stirring at 50° C. for 12 hours. The reaction mixture was then concentrated in vacuo and purified by mass directed autoprep (ammonium carbonate modifier). The relevant fractions were concentrated under a stream of nitrogen to give a single regioisomer of the desired product, 11.2 mg. LCMS [LCMS2] Rt 1.25 min, m/z (ES+) 463 (M+H).

Example 110

Methyl 5-(N-(2,4-dimethylphenyl)-N-isobutylsulfamoyl)-2-((tetrahydro-2H-pyran-4-yl)methoxy)benzoate a) Intermediate 59 methyl 5-(N-(2,4-dimethylphenyl)-N-isobutylsulfamoyl)-2-methoxybenzoate

To a stirred solution of methyl 5-(chlorosulfonyl)-2-methoxybenzoate (1 g, 3.78 mmol) in pyridine (3 mL) at 25° C. was added N-isobutyl-2,4-dimethylaniline (0.670 g, 3.78 mmol) and the reaction mixture stirred at 25° C. for 2 hours, then stood for 12 hours. The pyridine was evaporated in vacuo to give a yellow oil which was purified by silica (Si) chromatography (0-50% ethyl acetate-cyclohexane). The appropriate fractions were combined and evaporated in vacuo to give the required product, 1.485 g, as a colourless oil. LCMS [LCMS2] Rt 1.37 min, m/z (ES+) 406 (M+H).

b) Intermediate 60 methyl 5-(N-(2,4-dimethylphenyl)-N-isobutylsulfamoyl)-2-hydroxybenzoate

Methyl 5-(N-(2,4-dimethylphenyl)-N-isobutylsulfamoyl)-2-methoxybenzoate (1.485 g, 3.66 mmol) was dissolved in dichloromethane (DCM) (10 mL) and this was cooled to −78° C. A solution of boron tribromide in DCM (1M, 18.31 mL, 18.31 mmol) was then added dropwise and the reaction stirred under nitrogen. The reaction was then allowed to warm to room temperature and stirred overnight. Water (20 mL) was added dropwise to the reaction mixture and the crude product extracted to the organic phase of an aqueous work up between DCM and water. The aqueous phase was washed twice with DCM. The organic phase was then dried and concentrated in vacuo to give the crude product. LCMS [LCMS2] Rt 1.42 min, m/z (ES+) 392 (M+H).

c) Example 110 methyl 5-(N-(2,4-dimethylphenyl)-N-isobutylsulfamoyl)-2-((tetrahydro-2H-pyran-4-yl)methoxy)benzoate To a solution of methyl 5-(N-(2,4-dimethylphenyl)-N-isobutylsulfamoyl)-2-hydroxybenzoate (100 mg, 0.255 mmol) and (tetrahydro-2H-pyran-4-yl)methanol (29.7 mg, 0.255 mmol) in toluene (1.5 mL) stirred in air at room temperature was added a solution of 2-(tributylphosphoranylidene)acetonitrile (61.7 mg, 0.255 mmol) in toluene (0.5 mL). The reaction mixture was then stirred at 20° C. for 24 hours. After this time, additional 2-(tributylphosphoranylidene)acetonitrile (61.7 mg, 0.255 mmol) was added and the reaction stirred for a further 2 hours. The solvent was evaporated and the purification attempted by mass directed autoprep (ammonium carbonate modifier). The relevant fractions were concentrated under a stream of nitrogen to give a mixture of two products. Further purification was carried out by mass directed autoprep (Method O), to provide the desired product, 25 mg. LCMS [LCMS2] Rt 1.44 min, m/z (ES+) 490 (M+H).

Example 111

N-(2,4-dimethylphenyl)-3-(hydroxymethyl)-N-isobutyl-4-((tetrahydro-2H-pyran-4-yl)methoxy)benzenesulfonamide To a stirred solution of methyl 5-(N-(2,4-dimethylphenyl)-N-isobutylsulfamoyl)-2-((tetrahydro-2H-pyran-4-yl)methoxy)benzoate (20 mg, 0.041 mmol) in tetrahydrofuran (THF) at 25° C. was added lithium triethylborohydride in THF (Superhydride®, 1.1 M, 0.037 mL, 0.041 mmol) and the reaction mixture stirring at 25° C. for 15 hours. Dilute HCl was added to reaction mixture and stirred for 10 minutes. The reaction mixture was then neutralised with base and the product was extracted into ethyl acetate (3×10 mL). The organics were combined and dried using a hydrophobic frit, then concentrated under a stream of nitrogen to give the crude product. This was purified by silica (Si) chromatography (0-50% ethyl acetate-cyclohexane gradient). The appropriate fractions were combined and concentrated under a stream of nitrogen to give the required product, 16.2 mg, as a colourless oil. LCMS [LCMS2] Rt 1.33 min, m/z (ES+) 462 (M+H).

Example 112

N-(4-ethylphenyl)-4-(1-hydroxy-2-((3-methyloxetan-3-yl)amino)ethyl-N-isobutylbenzenesulfonamide a) Intermediate 61

4-ethyl-N-isobutylaniline

To potassium iodide (5342 mg, 32.2 mmol), $[Cp^*IrCl_2]_2$ (128 mg, 0.161 mmol) and 4-ethylaniline (2 mL, 16.09 mmol) at room temperature, was added 2-methylpropan-1-ol (5.94 mL, 64.4 mmol), followed by water (10 mL). The reaction vessel was sealed and heated by microwaves (Biotage Initiator) to 150° C. for 90 minutes. After cooling the reaction mixture was diluted with water (10 mL) and dichloromethane (20 mL) then stirred vigorously for 3 minutes. The organic phase was separated by hydrophobic frit. The aqueous phase was diluted with further dichloromethane (10 mL) and again stirred vigorously for 2 minutes, then the organics separated by hydrophobic frit. The combined organic fractions were evaporated in vacuo to give the crude product as a brown oil. The crude was purified by silica (Si) chromatography (0-50% dichloromethane-cyclohexane gradient). The appropriate fractions were combined and evaporated in vacuo to give the required product, 2.612 g, as a pale yellow oil. LCMS [LCMS1] Rt 0.96 min, m/z (ES+) 178 (M+H).

b) Intermediate 62

N-(4-ethylphenyl)-N-isobutyl-4-vinylbenzenesulfonamide

To a solution of 4-ethyl-N-isobutylaniline (400 mg, 2.256 mmol) in pyridine (5 mL) stirred in air at room temperature was added 4-vinylbenzene-1-sulfonyl chloride (760 mg, 3.75 mmol) in one charge. The reaction mixture was stirred at 20° C. for 30 minutes then stood for 16 hours. The solvent was evaporated in vacuo (Vaportec V10) to give the crude product, which was then purified by silica (Si) chromatography (0-50% ethyl acetate-cyclohexane gradient). The appropriate fractions were combined and evaporated in vacuo to give the required product, 940 mg, as a colourless gum. LCMS [LCMS1] Rt 1.44 min, m/z (ES+) 344 (M+H).

c) Intermediate 63

N-(4-ethylphenyl)-N-isobutyl-4-(oxiran-2-yl)benzenesulfonamide

A solution of N-(4-ethylphenyl)-N-isobutyl-4-vinylbenzenesulfonamide (775 mg, 2.256 mmol) was prepared in dichloromethane (DCM) (60 mL) and meta-chloroperoxybenzoic acid (mCPBA) (1557 mg, 9.02 mmol) added at 0° C. The stirred reaction was allowed to warm to room temperature and stirred over the weekend at 20° C. The reaction was then washed with water (30 mL), sodium hydroxide solution (2 M, 30 mL) and brine (30 mL). The organic layer was dried with hydrophobic frit and concentrated under vacuum to give the required product, 868 mg. LCMS [LCMS1] Rt 1.33 min, m/z (ES+) 360 (M+H).

d) Example 112

N-(4-ethylphenyl)-4-(1-hydroxy-2-((3-methyloxetan-3-yl)amino)ethyl-N-isobutylbenzenesulfonamide A solution of N-(4-ethylphenyl)-N-isobutyl-4-(oxiran-2-yl)benzenesulfonamide (400 mg, 1.113 mmol) was prepared in ethanol (6 mL) and 3-methyloxetan-3-amine (388 mg, 4.45 mmol) added. The reaction mixture was heated at 50° C. and stirred 16 hours. The solvent was evaporated in vacuo to give the crude product which was then purified by silica (Si) chromatography (0-100% ethyl acetate-cyclohexane+0-20% methanol). The appropriate fractions were combined and evaporated in vacuo to give the required product, 170.7 mg, as a white solid. LCMS [LCMS2] Rt 1.21 min, m/z (ES+) 447 (M+H).

Example 113

N-(4-ethylphenyl)-4-(1-hydroxy-2-morpholinoethyl)-N-isobutylbenzenesulfonamide

A solution of N-(4-ethylphenyl)-N-isobutyl-4-(oxiran-2-yl)benzenesulfonamide (400 mg, 1.113 mmol) was prepared in ethanol (3 mL) and morpholine (0.389 mL, 4.45 mmol) added. The reaction mixture was stirred at 50° C. for 18 hours. The solvent was evaporated in vacuo (Vaportec V10) to give the crude product, which was then purified by silica (Si) chromatography (0-100% ethyl acetate-cyclohexane+0-20% methanol gradient). The appropriate fractions were combined and evaporated in vacuo to give the required product as a colourless oil which solidified on standing, 294.9 mg. LCMS [LCMS2] Rt 1.30 min, m/z (ES+) 447 (M+H).

Example 114

N-(2-ethylphenyl)-4-(1-hydroxy-2-morpholinoethyl)-N-isobutylbenzenesulfonamide a) Intermediate 64

2-ethyl-N-isobutylaniline 2-ethylaniline (0.102 mL, 0.825 mmol), 2-methylpropan-1-ol (0.305 mL, 3.30 mmol), potassium iodide (274 mg, 1.650 mmol) and $[Cp^*IrCl_2]_2$ (10.52 mg, 0.013 mmol) were added to a microwave vial with water (1.5 mL). This was heated, by microwaves, for 90 minutes at 150° C. Dichloromethane (10 mL) and water (10 mL) were added and the phases separated using a hydrophobic frit. The aqueous layer was further extracted with dichloromethane (15 mL). The combined organic layers were concentrated under vacuum and purified by silica (Si) chromatography (0-50% dichloromethane-cyclohexane gradient). The relevant fractions were concentrated to provide the product as a clear oil, 0.83 mg. LCMS [LCMS1] Rt 1.26 min, m/z (ES+) 178 (M+H).

b) Intermediate 65

N-(2-ethylphenyl)-N-isobutyl-4-vinylbenzenesulfonamide 2-ethyl-N-isobutylaniline (83 mg, 0.468 mmol) was dissolved in pyridine (3 mL) add 4-vinylbenzene-1-sulfonyl chloride (114 mg, 0.562 mmol) added. Reaction stirred for over the weekend. Ethyl acetate (10 mL) was added to the solution and the organic phase was washed with water (10 mL), sodium hydroxide solution (2M, 2×10 mL) and brine (10 mL), then dried and concentrated under vacuum to provide the product, 129 mg. LCMS [LCMS1] Rt 1.43 min, m/z (ES+) 344 (M+H).

c) Intermediate 66

N-(2-ethylphenyl)-N-isobutyl-4-(oxiran-2-yl)benzenesulfonamide

A solution of N-(2-ethylphenyl)-N-isobutyl-4-vinylbenzenesulfonamide (129 mg, 0.376 mmol) was prepared in dichloromethane (DCM) (2 mL) and meta-chloroperoxybenzoic acid (mCPBA) (259 mg, 1.502 mmol) added at 0° C. The reaction was stirred overnight from 0° C. to 25° C. Dichloromethane (10 mL) was then added and the organics washed with water (10 mL), sodium hydroxide solution (2 M, 2×10 mL) and brine (10 mL). The combined organics were dried with a hydrophobic frit and concentrated under vacuum to provide the product as a yellow oil, 106 mg. LCMS [LCMS1] Rt 1.31 min, m/z (ES+) 360 (M+H).

d) Example 114

N-(2-ethylphenyl)-4-(1-hydroxy-2-morpholinoethyl)-N-isobutylbenzenesulfonamide

A solution of N-(2-ethylphenyl)-N-isobutyl-4-(oxiran-2-yl)benzenesulfonamide (106 mg, 0.295 mmol) was prepared in ethanol (2.5 mL) and morpholine (103 mg, 1.179 mmol) added. The reaction was heated at 50° C. and stirred for 24 hours. Solvents were evaporated and the crude material purified by flash silica (Si) chromatography (0-50% ethyl-acetate-cyclohexane gradient). The relevant fractions were concentrated to provide the desired product as a clear solid, 62 mg. LCMS [LCMS2] Rt 1.29 min, m/z (ES+) 447 (M+H).

Example 115

4-(1,2-dihydroxy-3-morpholinopropyl)-N-(2,4-dimethylphenyl)-N-isobutylbenzenesulfonamide α-enantiomer)

a) Intermediate 67

(E)-N-(2,4-dimethylphenyl)-N-isobutyl-4-(3-morpholinoprop-1-en-1-yl)benzenesulfonamide A suspension of 4-bromo-N-(2,4-dimethylphenyl)-N-isobutylbenzenesulfonamide (200 mg, 0.505 mmol), potassium trans-3-bromo-1-propenyltrifluoroborate (126 mg, 0.555 mmol), morpholine (0.088 mL, 1.009 mmol), bis (triphenylphosphine)palladium(II) chloride (10.63 mg, 0.015 mmol) and cesium carbonate (493 mg, 1.514 mmol) was prepared in dimethyl sulfoxide (DMSO) (1 mL). The reaction was then heated by microwaves, to 140° C. for 30 minutes. The reaction was then passed through a sulfonic acid (SCX) solid phase extraction (SPE) cartridge, eluting with methanol followed by ammonia in methanol, then concentrated under a stream of nitrogen. Purification was carried out by mass directed autoprep (ammonium carbonate modifier). The relevant fractions were concentrated and combined to give the desired product, 23.2 mg. LCMS [LCMS2] Rt 1.41 min, m/z (ES+) 443 (M+H).

b) Example 115

4-(1,2-dihydroxy-3-morpholinopropyl)-N-(2,4-dimethylphenyl)-N-isobutylbenzenesulfonamide α-enantiomer)

AD-Mix-alpha (73.4 mg, 0.052 mmol) was stirred at room temperature in tert-butanol (2 mL) and water (2.000 mL) until two clear phases seen. Methanesulfonamide (4.99 mg, 0.052 mmol) was added to the solution and the mixture cooled to 0° C. (E)-N-(2,4-dimethylphenyl)-N-isobutyl-4-(3-morpholinoprop-1-en-1-yl)benzenesulfonamide (23.2 mg, 0.052 mmol) was added and the mixture stirred vigorously at 0° C. to room temperature over 2 days. The reaction was cooled again to 0° C. and further AD-Mix-alpha (73.4 mg, 0.052 mmol) was added, then the reaction stirred at 0° C. for 4 hours, after which time a third portion of AD-Mix-alpha (73.4 mg, 0.052 mmol) was added. Stirring was continued from 0° C. to room temperature over the weekend. The reaction was again cooled to 0° C. and a final portion of AD-Mix-alpha (73.4 mg, 0.052 mmol) was added along with additional methanesulfonamide (4.99 mg, 0.052 mmol). Reaction was stirred overnight from 0° C. to room temperature. After this time, the reaction was cooled at 0° C. and stirred for 1 hour, then sodium sulfite (70 mg, 0.555 mmol) was added to the solution and the mixture was stirred at room temperature for 40 minutes. Ethyl acetate (10 mL) was added and the organics separated, the aqueous phase was extracted with further ethyl acetate (3×5 mL). The combined organic layers were washed with sodium hydroxide solution (2 M, 10 mL), dried and concentrated under vacuum. Purification was carried out by mass directed autoprep (Method N) to provide the desired product, 4 mg, of unknown enantiomeric excess (referred to herein as α-enantiomer). LCMS [LCMS2] Rt 1.18 min, m/z (ES+) 477 (M+H).

Example 116

4-(1,2-dihydroxy-3-morpholinopropyl)-N-(2,4-dimethylphenyl)-N-isobutylbenzenesulfonamide β-enantiomer)

AD-Mix-beta (249 mg, 0.178 mmol) was stirred at room temperature in tert-butanol (1.000 mL) and water (1.000 mL) until two clear phases seen. Methanesulfonamide (16.93 mg, 0.178 mmol) was added to the solution and the mixture was cooled to 0° C. (E)-N-(2,4-dimethylphenyl)-N-isobutyl-4-(3-morpholinoprop-1-en-1-yl)benzenesulfonamide (39.4 mg, 0.089 mmol) was added and the mixture was stirred vigorously at 0° C. for 60 hours, maintaining temperature throughout. After this time, additional AD-Mix-beta (249 mg, 0.178 mmol) and methanesulfonamide (16.93 mg, 0.178 mmol) were added. The reaction was stirred overnight at a maintained 0° C. A final portion of AD-Mix-beta (498 mg, 0.356 mmol) was then added and the solution was stirred overnight at a maintained 0° C. Sodium sulfite (2×11.22 mg, 0.089 mmol) was added to the solution and the mixture was stirred at room temperature for 40 minutes. Ethyl acetate (5 mL) was added to the solution and the aqueous phase extracted with further ethyl acetate (3×15 mL). The combined organic layers were washed with sodium hydroxide solution (2 M, 15 mL), dried and concentrated under vacuum. The crude material was purified by mass directed autoprep (ammonium carbonate modifier). The relevant fractions were concentrated and combined to give the desired product, 17.9 mg, of unknown enantiomeric excess (referred to herein as 3-enantiomer). LCMS [LCMS2] Rt 1.18 min, m/z (ES+) 477 (M+H).

Example 117

N-(2,4-dimethylphenyl)-4-(1-hydroxy-2-(oxetan-3-ylamino)ethyl-N-isobutylbenzenesulfonamide To a stirred solution of N-(2,4-dimethylphenyl)-N-isobutyl-4-(oxiran-2-yl)benzenesulfonamide (50 mg, 0.139 mmol) in ethanol (1 mL) at 25° C. was added oxetan-3-amine hydrochloride (15.24 mg, 0.139 mmol) and the reaction mixture stirred at 50° C. for 12 hours. The reaction mixture was then concentrated in vacuo and purification attempted by mass directed autoprep (ammonium carbonate modifier). The relevant fractions were evaporated in vacuo but give a mixture of the desired product, its regioisomer and unreacted starting material. Further attempts to separate the two regioisomers by preparative achiral HPLC failed. Separation of regioisomers was achieved successfully only by using a chiral preparative HPLC column (conditions HPLC2p) but no resolution of enantiomers was seen. 1 mg of the (presumed racemic) title product was isolated. HPLC [HPLC2a] Rt 8.5 min. LCMS [LCMS2] Rt 1.16 min, m/z (ES+) 433 (M+H).

Example 118 diastereoisomer 1-4-(1,3-dihydroxy-2-morpholinopropyl)-N-(2,4-dimethylphenyl)-N-isobutylbenzenesulfonamide and Example 119: diastereoisomer 2-4-(1,3-dihydroxy-2-morpholinopropyl)-N-(2,4-dimethylphenyl)-N-isobutylbenzenesulfonamide a) Intermediate 68

N-(2,4-dimethylphenyl)-4-formyl-N-isobutylbenzenesulfonamide

To a solution of (2,4-dimethylphenyl)(2-methylpropyl) amine (400 mg, 2.256 mmol) in pyridine (5 mL) stirred in air at room temperature was added 4-formylbenzene-1-sulfonyl chloride (760 mg, 3.71 mmol) in one charge. The reaction mixture was stirred at 20° C. for 30 minutes and then stood for 6 hours. The solvent was evaporated in vacuo (Vaportec V10) to give the crude product. The crude was purified by silica (Si) chromatography (0-25% ethyl acetate-cyclohexane). The appropriate fractions were combined and evaporated in vacuo to give the required product, 794 mg as a colourless gum. LCMS [LCMS1] Rt 1.33 min, m/z (ES+) 346 (M+H).

b) Intermediate 69 diastereoisomer 1-methyl 3-(4-(N-(2,4-dimethylphenyl)-N-isobutylsulfamoyl)phenyl)-3-hydroxy-2-morpholinopropanoate trifluoroacetic acid salt and Intermediate 70 diastereoisomer 2-methyl 3-(4-(N-(2,4-dimethylphenyl)-N-isobutylsulfamoyl)phenyl)-3-hydroxy-2-morpholinopropanoate trifluoroacetic acid salt A solution of methyl 2-morpholinoacetate (0.022 g, 0.139 mmol) was prepared in tetrahydrofuran (THF) (1 mL) and added to a solution of N-(2,4-dimethylphenyl)-4-formyl-N-isobutylbenzenesulfonamide (0.040 g, 0.116 mmol) in tetrahydrofuran (THF) (1 mL). The mixture was cooled to approximately −90° C. (dry ice/diethylether bath), under nitrogen and treated with lithium diisopropylamide solution in THF/hexanes (2 M, 0.232 mL, 0.463 mmol). The reaction was stirred for 2 hours at −90° C., then warmed slowly to room temperature over the weekend. Reaction quenched with water (4 mL) and ethyl acetate added (4 mL). Organic phase separated, dried by hydrophobic frit and concentrated under stream of nitrogen. Isolation of the two product diastereoisomers carried out by mass directed autoprep (Method R) to provide diastereoisomer 1-methyl 3-(4-(N-(2,4-dimethylphenyl)-N-isobutylsulfamoyl)phenyl)-3-hydroxy-2-morpholinopropanoate trifluoroacetic acid salt (8.2 mg) LCMS [LCMS2] Rt 1.31 min, m/z (ES+) 505 (M+H) and diastereoisomer 2-methyl 3-(4-(N-(2,4-dimethylphenyl)-N-isobutylsulfamoyl)phenyl)-3-hydroxy-2-morpholinopropanoate trifluoroacetic acid salt (8.1 mg) LCMS [LCMS2] Rt 1.34 min, m/z (ES+) 505 (M+H).

c) Example 118 diastereoisomer 1-4-(1,3-dihydroxy-2-morpholinopropyl)-N-(2,4-dimethylphenyl)-N-isobutylbenzenesulfonamide A solution of diastereoisomer 1-methyl 3-(4-(N-(2,4-dimethylphenyl)-N-isobutylsulfamoyl)phenyl)-3-hydroxy-2-morpholinopropanoate (6 mg, 0.012 mmol) was prepared in tetrahydrofuran (THF) (0.5 mL) and a solution of lithium aluminium hydride in diethylether (1 M, 0.024 mL, 0.024 mmol) was added at 0° C. After addition, reaction stirred for 1 hour from 0° C. to room temperature. Water (0.5 mL) was added, followed by ethylacetate (0.5 mL). Organic layer was separated, dried (hydrophobic frit) and concentrated under stream of nitrogen. Analysis by LCMS showed only ~50% conversion to product, so crude material redissolved in THF (0.5 mL) and cooled to 0° C. This was then treated with a second portion of lithium aluminium hydride in diethylether (1 M, 0.024 mL, 0.024 mmol). The reaction was stirred from 0° C. to room temperature over 5 hours. Analysis by LCMS now showed complete conversion. Water (0.5 mL) was added, followed by ethylacetate (0.5 mL). Organic layer was separated, dried (hydrophobic frit) and concentrated under stream of nitrogen, then purification carried out by mass directed autoprep (Method M) to provide the desired product, 1.7 mg. LCMS [LCMS2] Rt 1.19 min, m/z (ES+) 477 (M+H).

d) Example 119 diastereoisomer 2-4-(1,3-dihydroxy-2-morpholinopropyl)-N-(2,4-dimethylphenyl)-N-isobutylbenzenesulfonamide A solution of diastereoisomer 2-methyl 3-(4-(N-(2,4-dimethylphenyl)-N-isobutylsulfamoyl)phenyl)-3-hydroxy-2-morpholinopropanoate (6 mg, 0.012 mmol) was prepared in tetrahydrofuran (THF) (0.5 mL) and a solution of lithium aluminium hydride in diethylether (1 M, 0.024 mL, 0.024 mmol) was added at 0° C. After addition, reaction stirred for 1 hour from 0° C. to room temperature. Water (0.5 mL) was added followed by ethylacetate (0.5 mL). Analysis by LCMS showed complete conversion to product. Organic layer was separated, dried (hydrophobic frit) and concentrated under stream of nitrogen, then purification carried out by mass directed autoprep (Method M) to provide the desired product, 1.8 mg. LCMS [LCMS2] Rt 1.22 min, m/z (ES+) 477 (M+H).

Example 120

N-(2,4-dimethylphenyl)-4-(1-hydroxy-2-morpholinoethyl-N-isobutylbenzenesulfonamide hydrochloride HCl salt was prepared by dissolving N-(2,4-dimethylphenyl)-4-(1-hydroxy-2-morpholinoethyl)-N-isobutylbenzenesulfonamide (180 mg) in diethylether (2 mL) and treating with solution of HCl in dioxane (4 M, excess). Mixture concentrated then recrystallised from ethanol (minimum) with slow diffusion of diethylether to give required product (146 mg) as white crystals. LCMS [LCMS2] Rt 1.30 min, m/z (ES+) 447 (M+H).

Example 121 enantiomer 1-N-(2,4-dimethylphenyl)-4-(1-hydroxy-2-morpholinoethyl-N-isobutylbenzenesulfonamide and Example 122: enantiomer2-N-(2,4-dimethylphenyl)-4-(1-hydroxy-2-morpholinoethyl)-N-isobutylbenzenesulfonamide by chiral separation of rac-Example 22

Enantiomers of rac-N-(2,4-dimethylphenyl)-4-(1-hydroxy-2-morpholinoethyl)-N-isobutylbenzenesulfonamide (26 mg) were separated by chiral preparative HPLC (conditions HPLC1p) to provide enantiomer 1-N-(2,4-dimethylphenyl)-4-(1-hydroxy-2-morpholinoethyl)-N-isobutylbenzenesulfonamide (10 mg) HPLC [HPLC1a] Rt 17.5 min. LCMS [LCMS2] Rt 1.32 min, m/z (ES+) 447 (M+H) and enantiomer2-N-(2,4-dimethylphenyl)-4-(1-hydroxy-2-morpholinoethyl)-N-isobutylbenzenesulfonamide (10 mg) HPLC [HPLC1a] Rt 23.5 min. LCMS [LCMS2] Rt 1.32 min, m/z (ES+) 447 (M+H).

Example 123

N-(4-ethylphenyl)-4-(1-hydroxy-2-morpholinoethyl)-3-(hydroxymethyl)-N-isobutylbenzenesulfonamide a) Intermediate 71

Methyl 2-bromo-5-(N-(4-ethylphenyl)-N-isobutylsulfamoyl)benzoate

To a solution of 4-ethyl-N-isobutylaniline (400 mg, 2.256 mmol) in pyridine (2 mL) stirred in air at 20° C. was added methyl 2-bromo-5-(chlorosulfonyl)benzoate (707 mg, 2.256 mmol) portionwise, over 30 minutes. The reaction mixture was stirred at 20° C. for 30 minutes, then left to stand overnight. The solvent was evaporated in vacuo to give the crude product as a sticky yellow solid. This was triturated with methanol and filtered and dried to give the desired product as a white solid, 600 mg. LCMS [LCMS1] Rt 1.41 min, m/z (ES+) 454/456 (M+H).

b) Intermediate 72

Methyl 5-(N-(4-ethylphenyl)-N-isobutylsulfamoyl-2-((trimethylsilyl)ethynyl)benzoate A mixture of methyl 2-bromo-5-(N-(4-ethylphenyl)-N-isobutylsulfamoyl)benzoate (325 mg, 0.715 mmol), bis(triphenylphosphine)palladium(II) chloride (15.06 mg, 0.021 mmol), copper(I) iodide (5.45 mg, 0.029 mmol), dicyclohexylamine (0.157 ml, 0.787 mmol) and acetonitrile (2 mL) was degassed under a gentle stream of nitrogen then ethynyltrimethylsilane (211 mg, 2.146 mmol) was added. The mixture was sealed and heated by microwaves to 80° C. for 3 hours. After cooling, the mixture was partitioned between sodium bicarbonate solution (10 mL) and dichloromethane (DCM) (20 mL), then the organic phase washed with water (5 mL) and HCl (2N, 10 mL). The organics were dried and evaporated to give the desired product as a yellow gum, 320 mg. LCMS [LCMS1] Rt 1.58 min, m/z (ES+) 472 (M+H).

c) Intermediate 73

Methyl 2-acetyl-5-(N-(4-ethylphenyl)-N-isobutylsulfamoyl)benzoate

A mixture of methyl 5-(N-(4-ethylphenyl)-N-isobutylsulfamoyl)-2-((trimethylsilyl)ethynyl)benzoate (320 mg, 0.678 mmol), mercuric sulphate (201 mg, 0.678 mmol), $H_2SO_4$ (1.357 mL, 1.357 mmol) and acetone (6 mL) was heated at reflux for 4 hours. The mixture was partitioned between ammonium chloride solution (10%, 20 mL) and dichloromethane (DCM) (2×25 mL) then organics separated, dried ($MgSO_4$) and evaporated onto florisil. The crude material was purified by silica (Si) chromatography (0-100% dichloromethane-cyclohexane gradient) to give the title compound as a colourless gum, 110 mg. LCMS [LCMS1] Rt 1.33 min, m/z (ES+) 418 (M+H).

d) Intermediate 74

Methyl 5-(N-(4-ethylphenyl)-N-isobutylsulfamoyl)-2-(2-morpholinoacetyl)benzoate

A solution of phenyltrimethylaminotribromide (100 mg, 0.266 mmol) in tetrahydrofuran (THF) (0.5 mL) was added dropwise over 5 minutes, to a solution of methyl 2-acetyl-5-(N-(4-ethylphenyl)-N-isobutylsulfamoyl)benzoate (105 mg, 0.251 mmol) in THF (1.5 mL) at room temperature, under nitrogen. The orange solution was stirred for 1 hour to give a yellow solution containing a white precipitate. Analysis showed major product to be the desired intermediate bromoketone. The precipitate was filtered off and the solution was treated with morpholine (0.066 mL, 0.754 mmol). The resulting suspension was stirred for 30 minutes and partitioned between ammonium chloride solution (10 mL) and ethyl acetate (2×5 mL). The dried ($MgSO_4$) extract was evaporated to give the desired product (65 mg), as an orange gum, which was used directly in the next step. LCMS [LCMS1] Rt 1.06 min, m/z (ES+) 503 (M+H).

e) Example 123

N-(4-ethylphenyl)-4-(1-hydroxy-2-morpholinoethyl)-3-(hydroxymethyl)-N-isobutylbenzenesulfonamide A solution of Super-Hydride® (1 M in tetrahydrofuran, 0.388 mL, 0.388 mmol) was added slowly to a solution of methyl 5-(N-(4-ethylphenyl)-N-isobutylsulfamoyl)-2-(2-morpholinoacetyl)benzoate (65 mg, 0.129 mmol) in tetrahydrofuran (THF) (0.5 mL) at room temperature, under nitrogen. The solution was stirred for 16 hours, then treated with HCl (2 N, 2 mL) and stirred for 10 minutes. The mixture was basified with sodium bicarbonate solution and extracted with ethyl acetate (2×5 mL). The organics were dried ($MgSO_4$) then evaporated and purification of the crude attempted on a silica (Si) cartridge eluting with 5% methanol-dichloromethane+0.5% ammonia, although this gave poor separation. Purification was successfully achieved using a silica (Si) cartridge eluting with 1-3% methanol-dichloromethane+0.1-0.3% ammonia to give the desired product as a cream solid, 31 mg. LCMS [LCMS1] Rt 0.90 min, m/z (ES+) 477 (M+H).

Example 124

N-(4-ethylphenyl)-3-(hydroxymethyl)-N-isobutyl-4-((tetrahydro-2H-pyran-4-yl)methoxy)benzenesulfonamide a) Intermediate 75 methyl 5-(N-(4-ethylphenyl)-N-isobutylsulfamoyl)-2-hydroxybenzoate

To a solution of 4-ethyl-N-isobutylaniline (598 mg, 3.37 mmol) in pyridine (10 mL) stirred in air at 20° C., was added methyl 5-(chlorosulfonyl)-2-hydroxybenzoate (845 mg, 3.37 mmol) portionwise, over 1 hour. The reaction mixture was then stirred at 20° C. for 30 minutes. The solvent was evaporated in vacuo to give the crude product as a yellow sticky solid. This was triturated with methanol then filtered and dried to give the title product as a white solid, 907 mg. LCMS [LCMS1] Rt 1.38 min, m/z (ES+) 392 (M+H).

b) Intermediate 76 methyl 5-(N-(4-ethylphenyl)-N-isobutylsulfamoyl)-2-((tetrahydro-2H-pyran-4-yl)methoxy)benzoate To a solution of (tetrahydro-2H-pyran-4-yl)methanol (74.2 mg, 0.639 mmol) and methyl 5-(N-(4-ethylphenyl)-

N-isobutylsulfamoyl)-2-hydroxybenzoate (500 mg, 1.277 mmol) in toluene (0.5 mL) at room temperature, was added a solution of 2-(tributylphosphoranylidene)acetonitrile (339 mg, 1.405 mmol) in toluene (0.5 mL) in one charge. The reaction mixture was stirred vigorously for 1 hour, then left to stand overnight. Additional 2-(tributylphosphoranylidene)acetonitrile (339 mg, 1.405 mmol) and (tetrahydro-2H-pyran-4-yl)methanol (74.2 mg, 0.639 mmol) were added and the reaction mixture stirred for an additional 8 hours. The solvent was evaporated in vacuo to give the crude product, which was purified by silica (Si) chromatography (0-100% ethyl acetate-cyclohexane) to give the title compound as an orange gum, 109.6 mg. LCMS [LCMS1] Rt 1.37 min, m/z (ES+) 490 (M+H).

c) Example 124

N-(4-ethylphenyl)-3-(hydroxymethyl)-N-isobutyl-4-((tetrahydro-2H-pyran-4-yl)methoxy)benzenesulfonamide A solution of Super-Hydride® (1 M in tetrahydrofuran, 0.449 mL, 0.449 mmol) was added over 5 minutes, to a solution of methyl 5-(N-(4-ethylphenyl)-N-isobutylsulfamoyl)-2-((tetrahydro-2H-pyran-4-yl)methoxy)benzoate (100 mg, 0.204 mmol) in tetrahydrofuran (THF) (2 mL) under nitrogen. The solution was stirred for 1 hour then was added to a 1:1 mixture of ammonium chloride solution and HCl (2 N, 10 mL). The mixture was extracted with tert-butyl methyl ether (TBME) (2×5 mL), then organics dried and evaporated. The residue was purified by silica (Si) chromatography (0-50% ethyl acetate-cyclohexane) to give the title compound as a white foam (75 mg). LCMS [LCMS1] Rt 1.28 min, m/z (ES+) 462 (M+H).

Chiral Separation of N-(4-ethylphenyl)-4-(1-hydroxy-2-morpholinoethyl)-3-(hydroxymethyl)-N-isobutylbenzenesulfonamide N-(4-ethylphenyl)-4-(1-hydroxy-2-morpholinoethyl)-3-(hydroxymethyl)-N-isobutylbenzenesulfonamide (racemic compound, which may be prepared, for example, according to Example 123; 4.5 g, 9.44 mmol, LCMS: 97.39%) was dissolved in 54 ml of co-solvent (0.5% DEA in Isopropanol).

Chiral Separation—Instrument Parameters

System: Thar SFC-80 Auto purification system

Solubility: Methanol

Loading/injection: 25 mg/inj

Column: Chiralcel-OX—H

Total Flow: 70 g/min

% Co Solvent: 30% (0.5% DEA in Isopropanol)

Stacked injection Time: 7.5 min

UV: 222 nm

Peak of Enantiomer 1 (Example 125):

Fractions 5.0 lit collected and concentrated under reduced pressure to afford N-(4-ethylphenyl)-4-(1-hydroxy-2-morpholinoethyl)-3-(hydroxymethyl)-N-isobutylbenzenesulfonamide (peak-1) (730 mg, 1.523 mmol, 16.14% yield) as a white solid.

$^1H$ NMR (400 MHz, $CD_3OD$) δ: 7.715-7.694 (1H, d), 7.648-7.643 (1H, d), 7.469-7.444 (1H, dd), 7.153-7.132 (2H, d), 6.957-6.936 (2H, dd), 5.226-5.194 (1H, dd), 4.748-4.657 (2H, m), 3.728-3.694 (4H, m), 3.354-3.336 (2H, d), 2.723-2.566 (8H, m), 1.54-1.506 (1H, m), 1.286 (2H, s), 1.238-1.201 (3H, t), 0.909-0.892 (6H, d).

SOR: $[\alpha]^{25}_{589}$ +23.4$^0$ (C-1.0 in Methanol)

Peak of Enantiomer 2 (Example 126)

Fractions 8.0 lit collected and concentrated under reduced pressure to afford N-(4-ethylphenyl)-4-(1-hydroxy-2-morpholinoethyl)-3-(hydroxymethyl)-N-isobutylbenzenesulfonamide (peak-2) (820 mg, 1.709 mmol, 18.10% yield) as a yellow solid.

$^1H$ NMR (400 MHz, $CD_3OD$) δ: 7.708-7.688 (1H, d), 7.649-7.644 (1H, d), 7.464-7.439 (1H, dd), 7.153-7.132 (2H, d), 6.957-6.936 (2H, dd), 5.209-5.177 (1H, m), 4.745-4.656 (2H, m), 3.715-3.682 (4H, m), 3.354-3.335 (2H, d), 2.689-2.521 (8H, m), 1.542-1.506 (1H, m), 1.286 (2H, s), 1.238-1.201 (3H, t), 0.909-0.802 (6H, d).

SOR: $[\alpha]^{25}_{589}$ −21.2$^0$ (C-1.0 in Methanol)

LC-MS Analysis Conditions

LCMS analysis was conducted on an X-Bridge C18 column (4.6 mm×75 mm i.d. 3.5 μm packing diameter) at 25° C.

The solvents employed were:

A=0.05 mM solution of ammonium acetate in water

B=100% Acetonitrile

The gradient employed was:

| Time (min) | Flow (mL/min) | % A |
|---|---|---|
| 0.0 | 0.8 | 95 |
| 2.5 | 0.8 | 2 |
| 8.0 | 0.8 | 2 |
| 8.1 | 0.8 | 95 |

The UV detection was an averaged signal from wavelength of 190 nm to 400 nm (extracted at compound UV) and mass spectra were recorded on a mass spectrometer using alternate scan positive and negative mode electrospray ionization.

Example 125: LC-MS m/z 477.4 $[M+H]^+$ 99.47% purity at 4.2 RT (Minutes)

Example 126: LC-MS m/z 477.4 $[M+H]^+$ 99.33% purity at 4.17 RT (Minutes)

CHIRAL-HPLC Analysis Conditions (Purity Check)

Column: Chiralpak 1A (4.6×250 mm) 5μ

Mobile phase: D: 0.1% DEA in hexane: C=Ethanol

Isocratic: 90:10

Flow rate: 0.8 ml/min

Temperature: Ambient ° C.

Diluent: Ethanol

Example 125: Chiral HPLC 99.53% purity at 14.11 RT (Minutes)

Example 126: Chiral HPLC 98.46% purity at 12.68 RT (Minutes)

HPLC Analysis Conditions

Column: X-Bridge C18 (4.6×150 mm) 3.5 μm

Mobile phase: A: 0.01 Ammonium acetate B: ACN

T/% B: 0/30, 2/30, 4/70, 6/95, 15/95, 15.1/30

Flow rate: 1.0 ml/min

Temperature: Ambient ° C.

Diluent: ACN+H2O

Example 125: HPLC 99.51% purity at 6.68 RT (Minutes)

Example 126: HPLC 99.51% purity at 6.69 RT (Minutes)

Vibrational Circular Dichronism (VCD)

The absolute configurations of Example 125 and Example 126 were determined by ab initio vibrational circular dichroism (VCD), a form of differential vibrational spectroscopy that combines experimental and computational VCD data to determine absolute stereochemistry (Appl. Spectrosc. 65 (7), 699 (2011)).

Experimental

Concentrations: equimolar solutions (0.15-M) in DCM

Cell: sealed transmission/$BaF_2$ windows/100 um path-length

Spectrometer: ChiralIR-2X™ FT-VCD spectrometer (BioTools, Inc.)

Scan Parameters: 2200-800 $cm^{-1}$ at 4 $cm^{-1}$ resolution

Computation

Conformational Search: stochastic with MMFF94x

Model Chemistry (vibrational properties): B3LYP/dgdzvp

Spectral Synthesis Boltzmann statistics

Quantitative Analysis CompareVOA™ (BioTools, Inc.)

Assigned Configurations and Confidence Limit

Example 125 was assigned with S absolute configuration.

Example 126 was assigned with R absolute configuration.

The confidence limit for these assignments was estimated to be >98%.

TABLE 4

| Intermediate Structures (I3-I24 and I37 to I51) | |
|---|---|
| I3 | 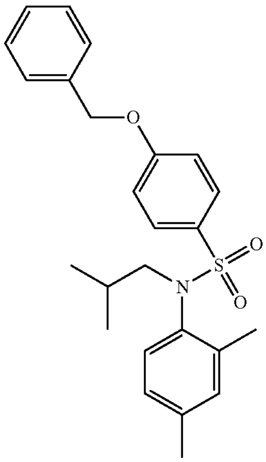 [SMILES: Cc1ccc(N(CC(C)C)S(=O)(=O)c2ccc(OCc3ccccc3)cc2)c(C)c1] |
| I4 | 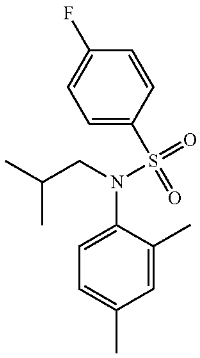 [SMILES: Cc1ccc(N(CC(C)C)S(=O)(=O)c2ccc(F)cc2)c(C)c1] |

TABLE 4-continued

| Intermediate Structures (I3-I24 and I37 to I51) | |
|---|---|
| I5 | 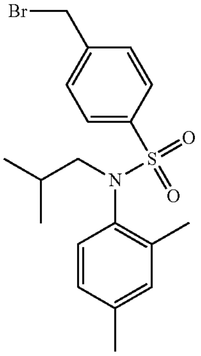 [SMILES: Cc1ccc(N(CC(C)C)S(=O)(=O)c2ccc(CBr)cc2)c(C)c1] |
| I6 | 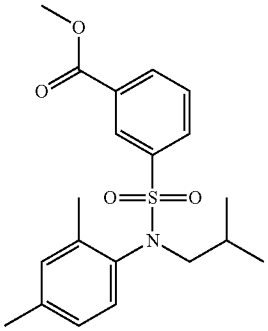 [SMILES: COC(=O)c1cccc(S(=O)(=O)N(CC(C)C)c2ccc(C)cc2C)c1] |
| I7 | 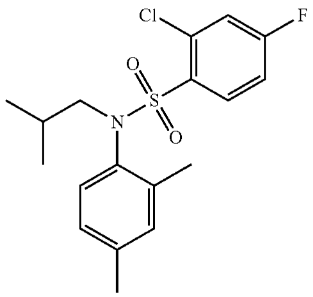 [SMILES: Cc1ccc(N(CC(C)C)S(=O)(=O)c2ccc(F)cc2Cl)c(C)c1] |
| I8 | 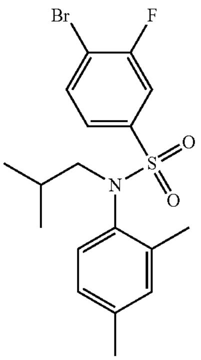 |

TABLE 4-continued
| Intermediate Structures (I3-I24 and I37 to I51) | |
|---|---|
| I9 | 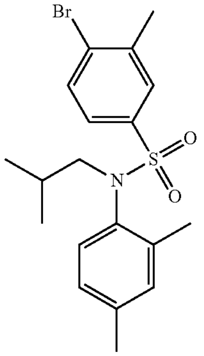 [SMILES: Cc1ccc(N(CC(C)C)S(=O)(=O)c2ccc(Br)c(C)c2)c(C)c1] |
| I10 | 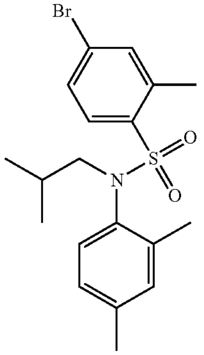 [SMILES: Cc1ccc(N(CC(C)C)S(=O)(=O)c2ccc(Br)cc2C)c(C)c1] |
| I11 | 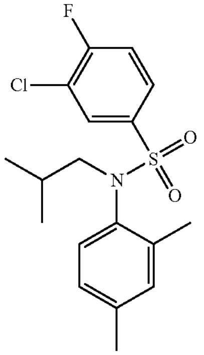 [SMILES: Cc1ccc(N(CC(C)C)S(=O)(=O)c2ccc(F)c(Cl)c2)c(C)c1] |
| I12 | 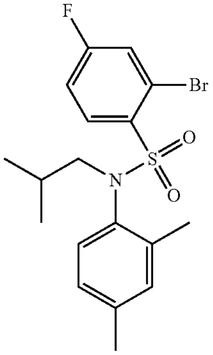 [SMILES: Cc1ccc(N(CC(C)C)S(=O)(=O)c2ccc(F)cc2Br)c(C)c1] |
TABLE 4-continued
| Intermediate Structures (I3-I24 and I37 to I51) | |
|---|---|
| I13 | 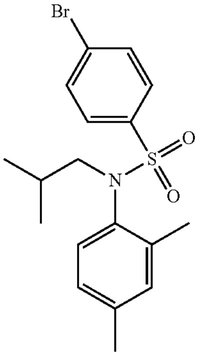 |
| I14 | 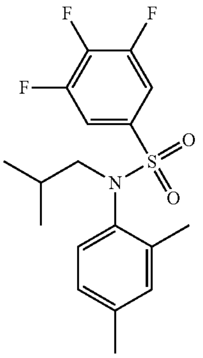 [SMILES: Cc1ccc(N(CC(C)C)S(=O)(=O)c2cc(F)c(F)c(F)c2)c(C)c1] |
| I15 | 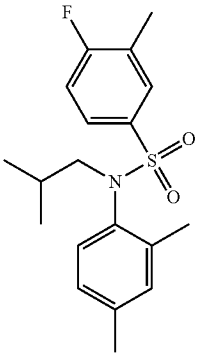 [SMILES: Cc1ccc(N(CC(C)C)S(=O)(=O)c2ccc(F)c(C)c2)c(C)c1] |
| I16 | 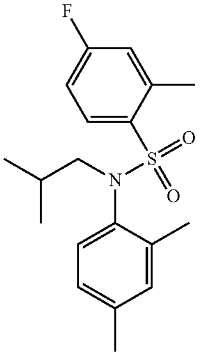 |

TABLE 4-continued
| Intermediate Structures (I3-I24 and I37 to I51) | |
|---|---|
| I17 | 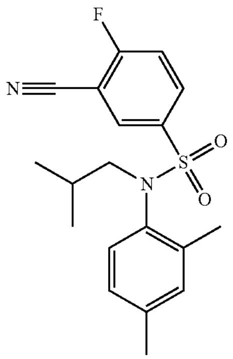 [SMILES: Cc1ccc(N(CC(C)C)S(=O)(=O)c2ccc(F)c(C#N)c2)c(C)c1] |
| I18 | 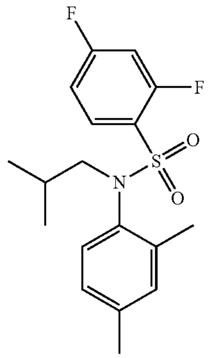 [SMILES: Cc1ccc(N(CC(C)C)S(=O)(=O)c2ccc(F)cc2F)c(C)c1] |
| I19 | 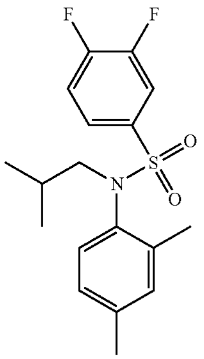 |
| I20 | 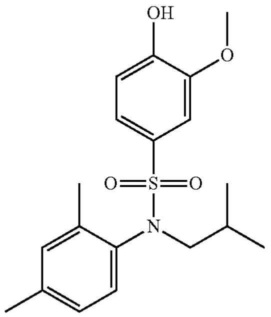 [SMILES: COc1cc(S(=O)(=O)N(CC(C)C)c2ccc(C)cc2C)ccc1O] |
TABLE 4-continued
| Intermediate Structures (I3-I24 and I37 to I51) | |
|---|---|
| I21 | 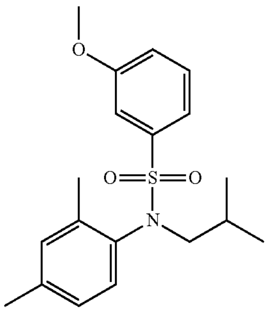 [SMILES: COc1cccc(S(=O)(=O)N(CC(C)C)c2ccc(C)cc2C)c1] |
| I22 | 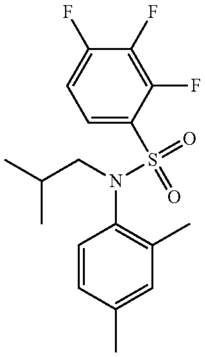 [SMILES: Cc1ccc(N(CC(C)C)S(=O)(=O)c2ccc(F)c(F)c2F)c(C)c1] |
| I23 | 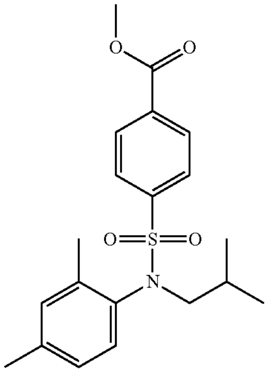 [SMILES: COC(=O)c1ccc(S(=O)(=O)N(CC(C)C)c2ccc(C)cc2C)cc1] |
| I24 | 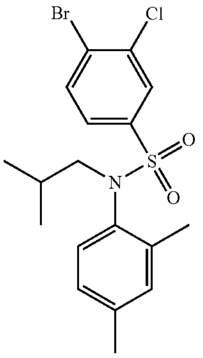 [SMILES: Cc1ccc(N(CC(C)C)S(=O)(=O)c2ccc(Br)c(Cl)c2)c(C)c1] |

TABLE 4-continued
| Intermediate Structures (I3-I24 and I37 to I51) | |
|---|---|
| I37 | 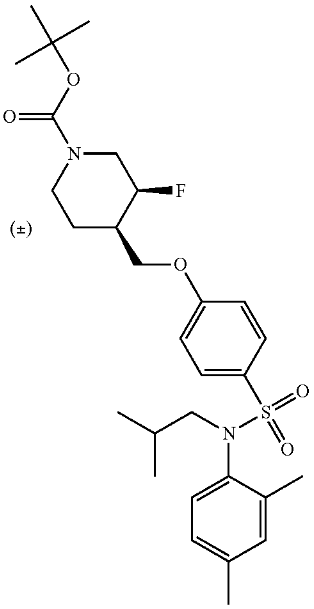 [SMILES: Cc1ccc(N(CC(C)C)S(=O)(=O)c2ccc(OC[C@H]3CCN(C(=O)OC(C)(C)C)C[C@H]3F)cc2)c(C)c1] |
| I38 | 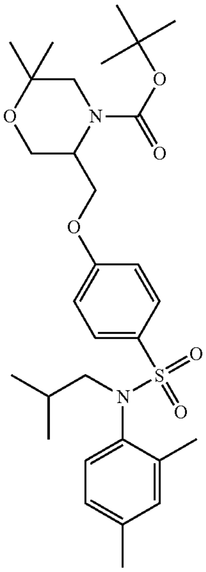 [SMILES: Cc1ccc(N(CC(C)C)S(=O)(=O)c2ccc(OCC3COC(C)(C)CN3C(=O)OC(C)(C)C)cc2)c(C)c1] |
| I39 | 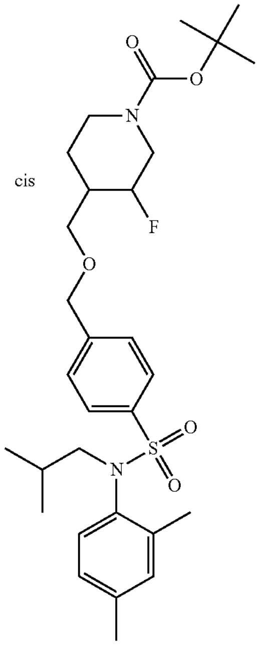 [SMILES: Cc1ccc(N(CC(C)C)S(=O)(=O)c2ccc(COCC3CCN(C(=O)OC(C)(C)C)CC3F)cc2)c(C)c1] |
| I40 | 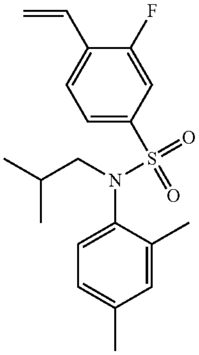 [SMILES: C=Cc1ccc(S(=O)(=O)N(CC(C)C)c2ccc(C)cc2C)cc1F] |
| I41 | 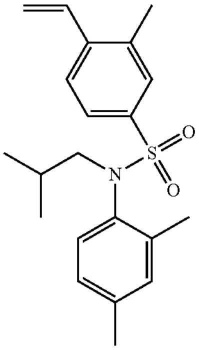 [SMILES: C=Cc1ccc(S(=O)(=O)N(CC(C)C)c2ccc(C)cc2C)cc1C] |

TABLE 4-continued
| Intermediate Structures (I3-I24 and I37 to I51) | |
|---|---|
| I42 | 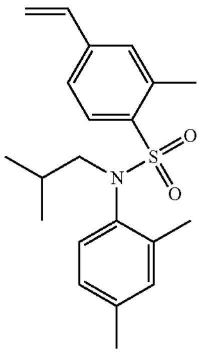 |
| I43 | 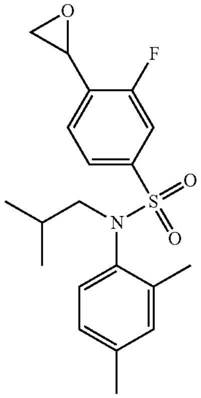 |
| I44 | 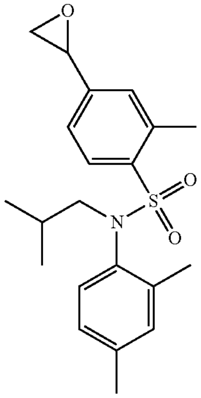 [SMILES: Cc1ccc(N(CC(C)C)S(=O)(=O)c2ccc(C3CO3)cc2C)c(C)c1] |
| I45 | 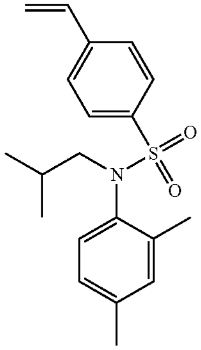 [SMILES: C=Cc1ccc(S(=O)(=O)N(CC(C)C)c2ccc(C)cc2C)cc1] |
TABLE 4-continued
| Intermediate Structures (I3-I24 and I37 to I51) | |
|---|---|
| I46 | 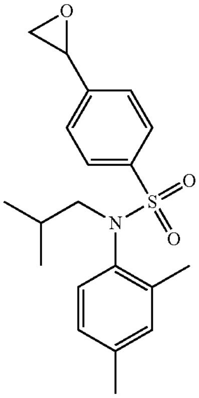 [SMILES: Cc1ccc(N(CC(C)C)S(=O)(=O)c2ccc(C3CO3)cc2)c(C)c1] |
| I47 | 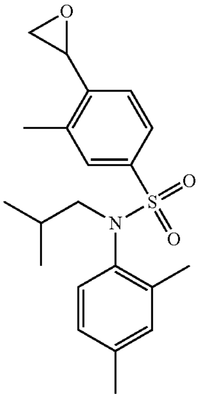 |
| I48 | 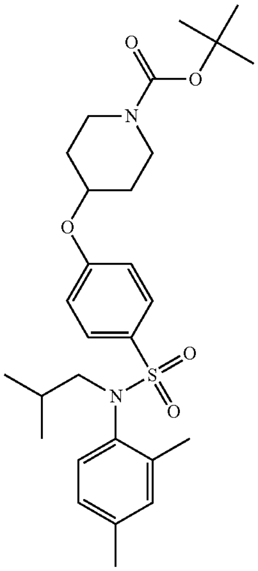 [SMILES: Cc1ccc(N(CC(C)C)S(=O)(=O)c2ccc(OC3CCN(C(=O)OC(C)(C)C)CC3)cc2)c(C)c1] |

TABLE 4-continued
| Intermediate Structures (I3-I24 and I37 to I51) | |
|---|---|
| I49 | 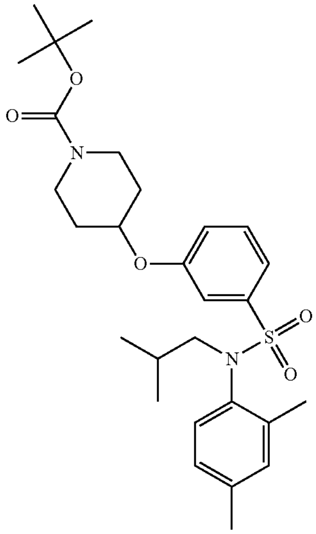 [SMILES: Cc1ccc(N(CC(C)C)S(=O)(=O)c2cccc(OC3CCN(C(=O)OC(C)(C)C)CC3)c2)c(C)c1] |
| I50 | 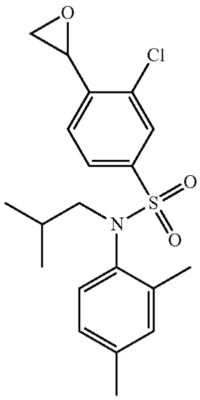 [SMILES: Cc1ccc(N(CC(C)C)S(=O)(=O)c2ccc(C3CO3)c(Cl)c2)c(C)c1] |
| I51 | 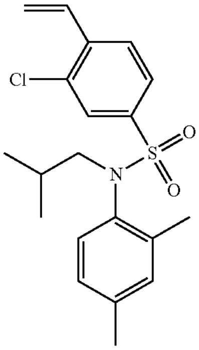 [SMILES: C=Cc1ccc(S(=O)(=O)N(CC(C)C)c2ccc(C)cc2C)cc1Cl] |
TABLE 5
| Starting Materials | |
|---|---|
| S1 | 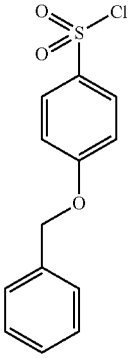 [SMILES: O=S(=O)(Cl)c1ccc(OCc2ccccc2)cc1] |
| S2 | 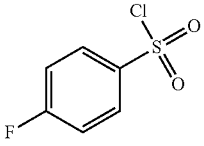 |
| S3 | 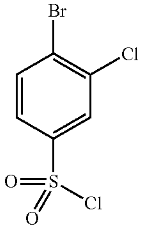 [SMILES: O=S(=O)(Cl)c1ccc(Br)c(Cl)c1] |
| S4 | 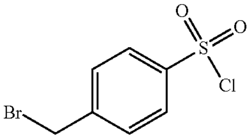 [SMILES: O=S(=O)(Cl)c1ccc(CBr)cc1] |
| S5 | 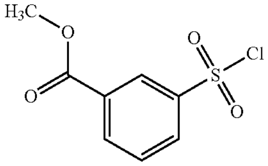 |
| S6 | 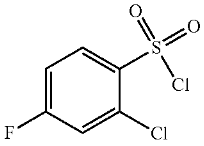 |
| S7 | 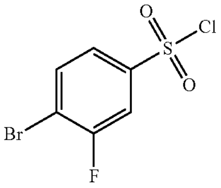 [SMILES: O=S(=O)(Cl)c1ccc(Br)c(F)c1] |

TABLE 5-continued
Starting Materials
S8
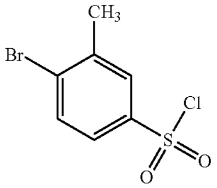
S9
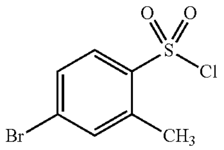
S10
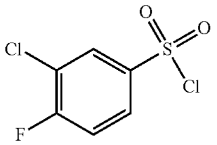 [SMILES: O=S(=O)(Cl)c1ccc(F)c(Cl)c1]
S11
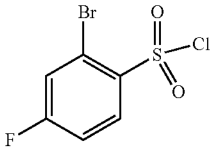
S12
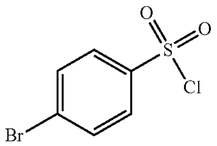 [SMILES: O=S(=O)(Cl)c1ccc(Br)cc1]
S13
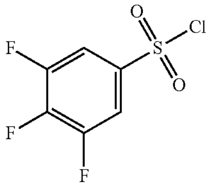 [SMILES: O=S(=O)(Cl)c1cc(F)c(F)c(F)c1]
S14
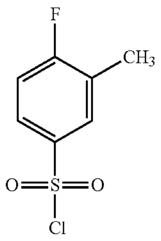
S15
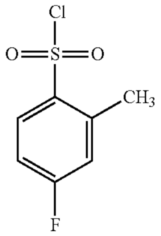
TABLE 5-continued
Starting Materials
S16
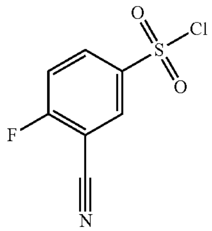 [SMILES: N#Cc1cc(S(=O)(=O)Cl)ccc1F]
S17
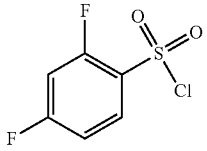
S18
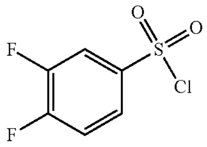
S19
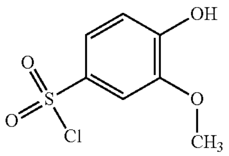
S20
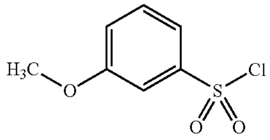
S21
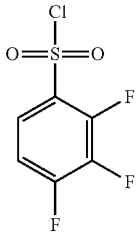 [SMILES: O=S(=O)(Cl)c1ccc(F)c(F)c1F]
S22
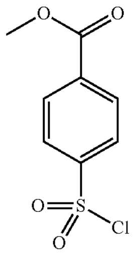

TABLE 5-continued
| Starting Materials | |
|---|---|
| S23 | 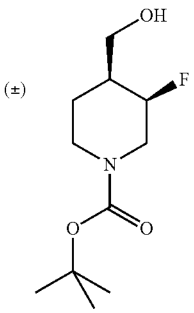 [SMILES: CC(C)(C)OC(=O)N1CC[C@@H](CO)[C@@H](F)C1] |
| S24 | 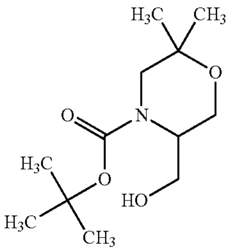 [SMILES: CC(C)(C)OC(=O)N1CC(C)(C)OCC1CO] |
| S25 | 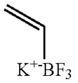 |
| S26 | 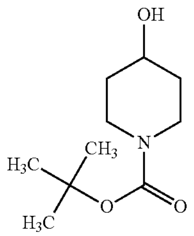 |
| S27 | 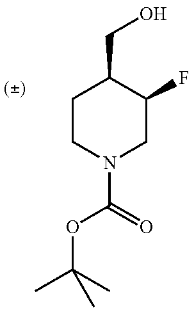 [SMILES: CC(C)(C)OC(=O)N1CC[C@@H](CO)[C@@H](F)C1] |
| S28 | 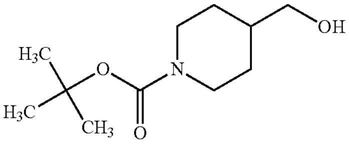 |
| S29 | 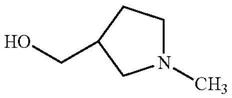 |
TABLE 5-continued
| Starting Materials | |
|---|---|
| S30 | 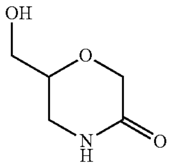 |
| S31 | 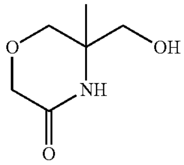 |
| S32 | 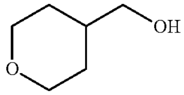 |
| S33 | 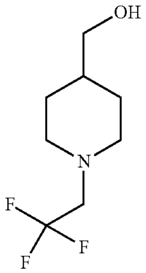 |
| S34 | 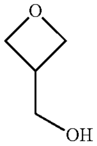 |
| S35 | 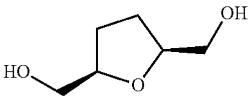 |
| S36 | 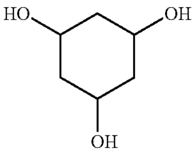 |
| S37 | 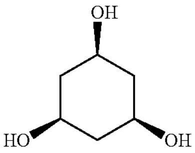 |
| S38 | 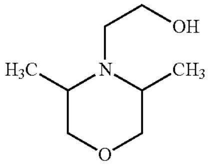 |

TABLE 5-continued
| Starting Materials | |
|---|---|
| S39 | 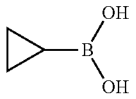 |
| S40 | 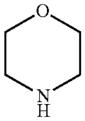 |
| S41 | 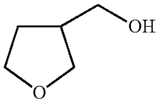 |
| S42 | 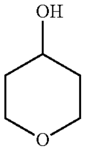 |
| S43 | 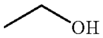 |
| S44 | 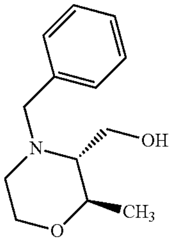 [SMILES: C[C@H]1OCCN(Cc2ccccc2)[C@@H]1CO] |
| S45 | 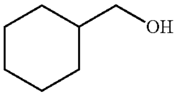 |
| S46 | 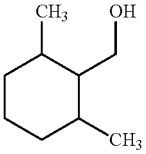 |
| S47 | 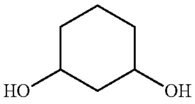 |
| S48 | 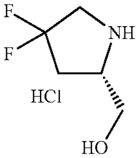 |
| S49 | 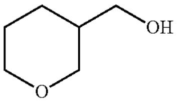 |
TABLE 5-continued
| Starting Materials | |
|---|---|
| S50 | 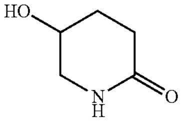 |
| S51 | 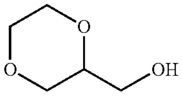 |
| S52 | 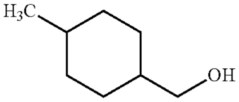 |
| S53 | 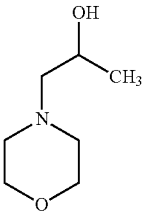 |
| S54 | 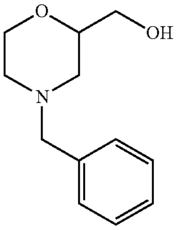 [SMILES: OCC1CN(Cc2ccccc2)CCO1] |
| S55 | 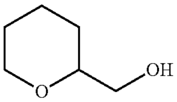 |
| S56 | 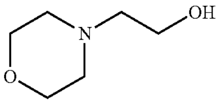 |
| S57 | 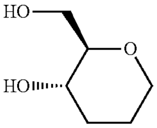 |
| S58 | 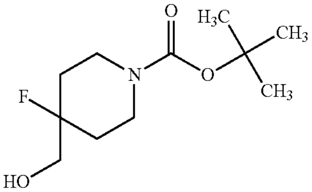 [SMILES: CC(C)(C)OC(=O)N1CCC(F)(CO)CC1] |
| S59 | 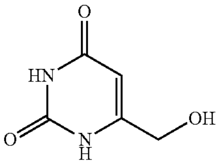 |

TABLE 5-continued
| Starting Materials | |
|---|---|
| S60 | 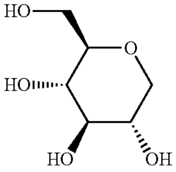 |
| S61 | 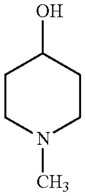 |
| S62 | 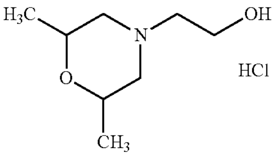 |
| S63 | 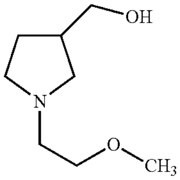 |
| S64 | 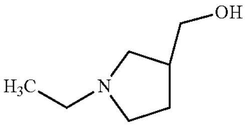 |
| S65 | 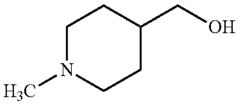 |
| S66 | 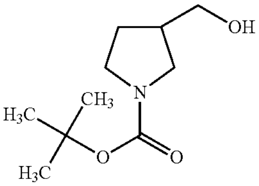 |
| S67 | 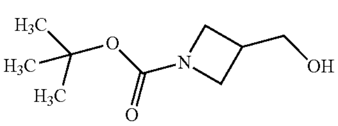 |
| S68 | 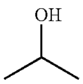 |
| S69 | 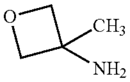 |
| S70 | 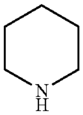 |
| S71 | 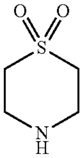 |
| S72 | 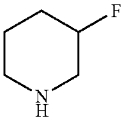 |
| S73 | 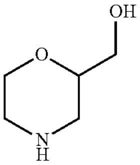 |
| S74 | 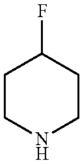 |
| S75 | 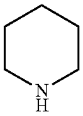 |
| S76 | 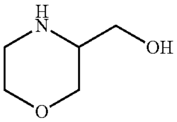 |
| S77 | 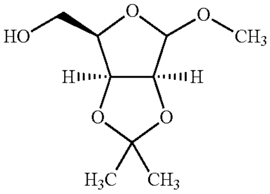 |
| S78 | 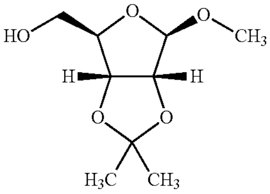 |

TABLE 5-continued
| Starting Materials | |
|---|---|
| S79 | 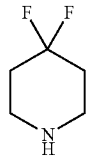 |
| S80 | 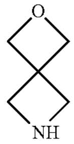 |
| S81 | 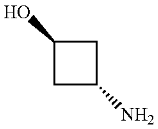 |
| S82 | 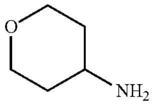 |
| S83 | 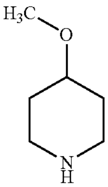 |
| S84 | 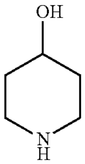 |
| S85 | 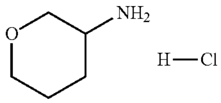 |
TABLE 6
| Example Structures | |
|---|---|
| E1 | 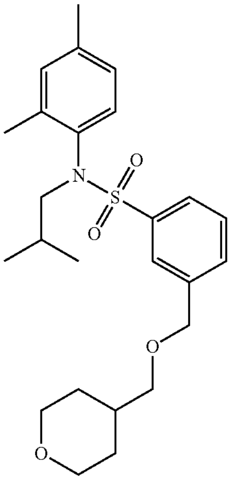 [SMILES: Cc1ccc(N(CC(C)C)S(=O)(=O)c2cccc(COCC3CCOCC3)c2)c(C)c1] |
| E2 | 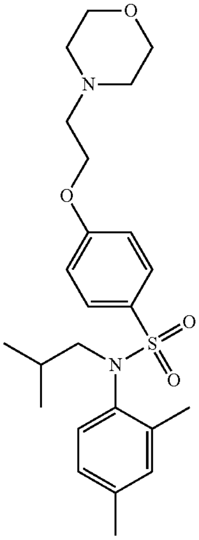 [SMILES: Cc1ccc(N(CC(C)C)S(=O)(=O)c2ccc(OCCN3CCOCC3)cc2)c(C)c1] |
| E3 | 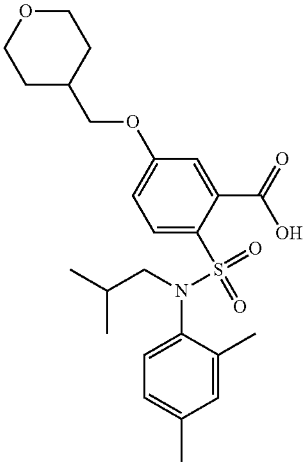 [SMILES: Cc1ccc(N(CC(C)C)S(=O)(=O)c2ccc(OCC3CCOCC3)cc2C(=O)O)c(C)c1] |

TABLE 6-continued
| Example Structures | |
|---|---|
| E4 | 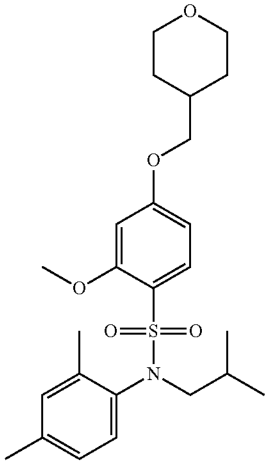 [SMILES: COc1cc(OCC2CCOCC2)ccc1S(=O)(=O)N(CC(C)C)c1ccc(C)cc1C] |
| E5 | 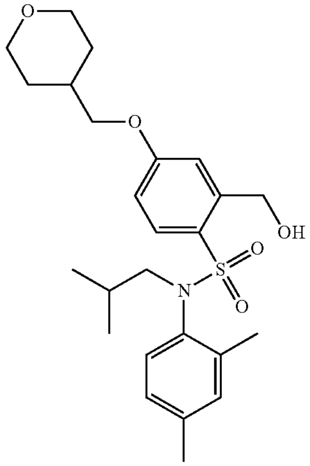 [SMILES: Cc1ccc(N(CC(C)C)S(=O)(=O)c2ccc(OCC3CCOCC3)cc2CO)c(C)c1] |
| E6 | 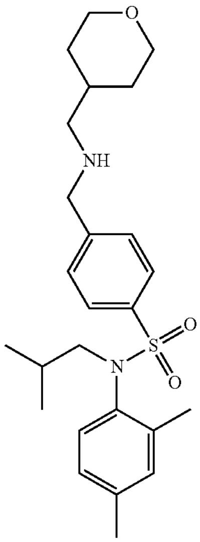 [SMILES: Cc1ccc(N(CC(C)C)S(=O)(=O)c2ccc(CNCC3CCOCC3)cc2)c(C)c1] |
TABLE 6-continued
| Example Structures | |
|---|---|
| E7 | 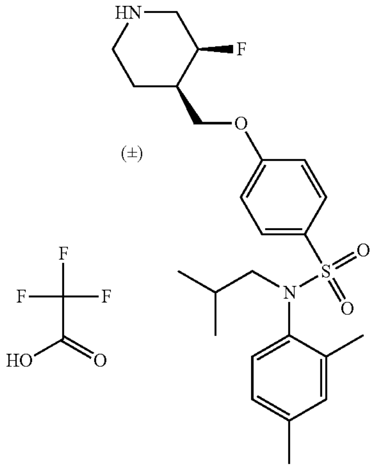 [SMILES: O=C(O)C(F)(F)F ; Cc1ccc(N(CC(C)C)S(=O)(=O)c2ccc(OC[C@H]3CCNC[C@H]3F)cc2)c(C)c1] |
| E8 | 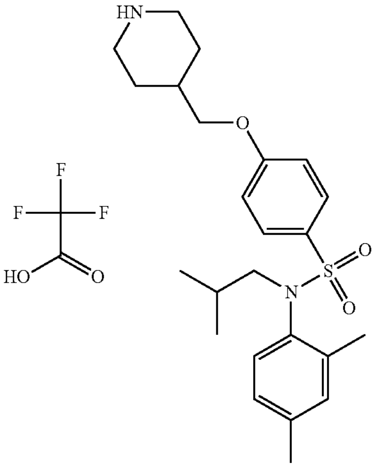 [SMILES: O=C(O)C(F)(F)F ; Cc1ccc(N(CC(C)C)S(=O)(=O)c2ccc(OCC3CCNCC3)cc2)c(C)c1] |
| E9 | 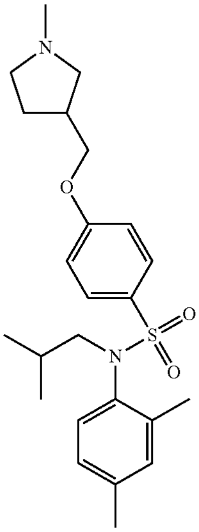 [SMILES: Cc1ccc(N(CC(C)C)S(=O)(=O)c2ccc(OCC3CCN(C)C3)cc2)c(C)c1] |

TABLE 6-continued
| Example Structures | |
|---|---|
| E10 | 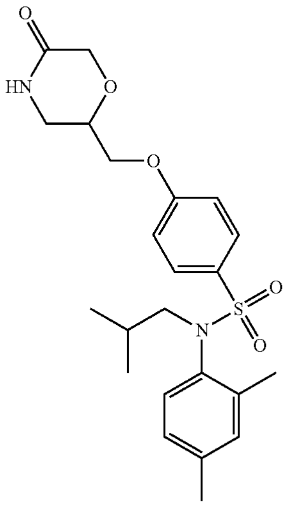 [SMILES: Cc1ccc(N(CC(C)C)S(=O)(=O)c2ccc(OCC3CNC(=O)CO3)cc2)c(C)c1] |
| E11 | 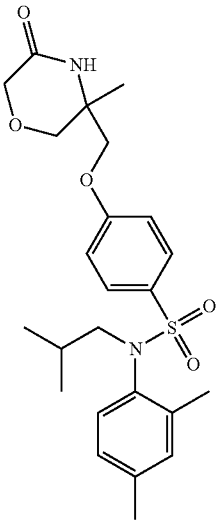 [SMILES: Cc1ccc(N(CC(C)C)S(=O)(=O)c2ccc(OCC3(C)COCC(=O)N3)cc2)c(C)c1] |
| E12 | 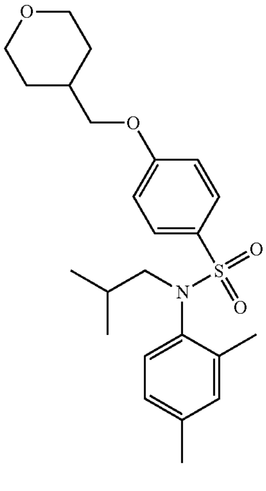 |
TABLE 6-continued
| Example Structures | |
|---|---|
| E13 | 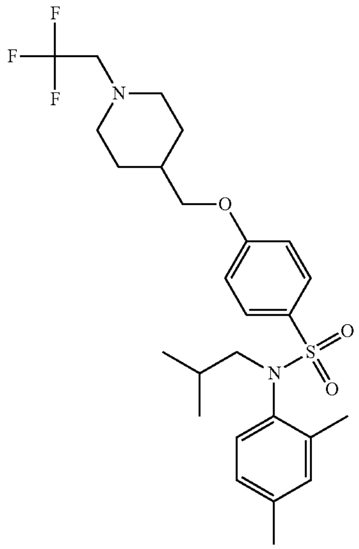 [SMILES: Cc1ccc(N(CC(C)C)S(=O)(=O)c2ccc(OCC3CCN(CC(F)(F)F)CC3)cc2)c(C)c1] |
| E14 | 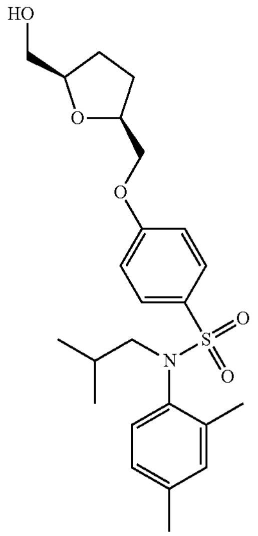 [SMILES: Cc1ccc(N(CC(C)C)S(=O)(=O)c2ccc(OC[C@@H]3CC[C@H](CO)O3)cc2)c(C)c1] |
| E15 | 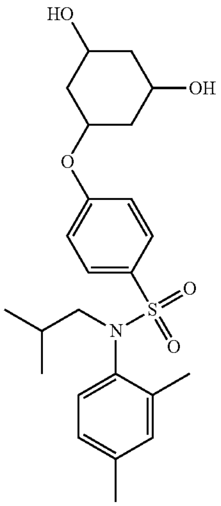 [SMILES: Cc1ccc(N(CC(C)C)S(=O)(=O)c2ccc(OC3CC(O)CC(O)C3)cc2)c(C)c1] |

TABLE 6-continued
| Example Structures | |
|---|---|
| E16 | 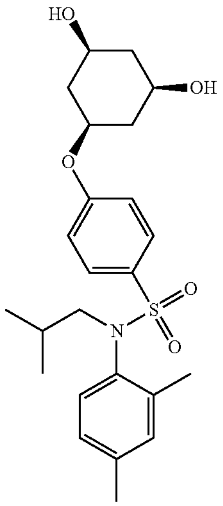 [SMILES: Cc1ccc(N(CC(C)C)S(=O)(=O)c2ccc(O[C@@H]3C[C@H](O)C[C@H](O)C3)cc2)c(C)c1] |
| E17 | 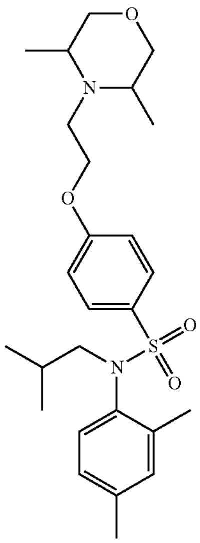 [SMILES: Cc1ccc(N(CC(C)C)S(=O)(=O)c2ccc(OCCN3C(C)COCC3C)cc2)c(C)c1] |
| E18 | 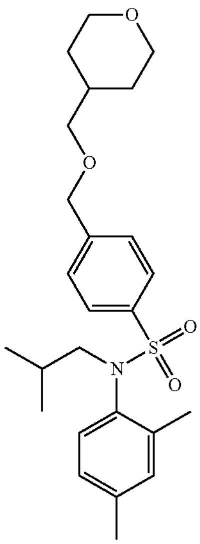 [SMILES: Cc1ccc(N(CC(C)C)S(=O)(=O)c2ccc(COCC3CCOCC3)cc2)c(C)c1] |
TABLE 6-continued
| Example Structures | |
|---|---|
| E19 | 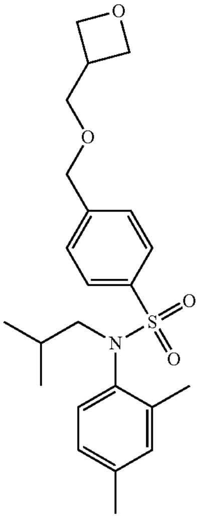 [SMILES: Cc1ccc(N(CC(C)C)S(=O)(=O)c2ccc(COCC3COC3)cc2)c(C)c1] |
| E20 | 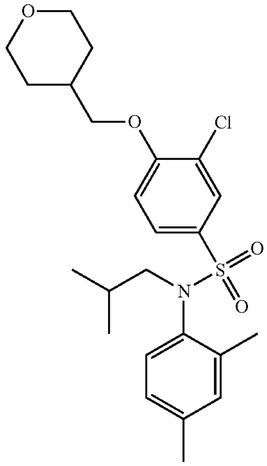 [SMILES: Cc1ccc(N(CC(C)C)S(=O)(=O)c2ccc(OCC3CCOCC3)c(Cl)c2)c(C)c1] |
| E21 | 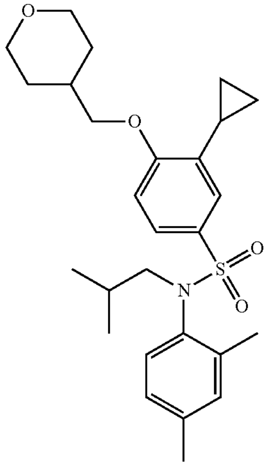 [SMILES: Cc1ccc(N(CC(C)C)S(=O)(=O)c2ccc(OCC3CCOCC3)c(C3CC3)c2)c(C)c1] |

TABLE 6-continued
| Example Structures | |
|---|---|
| E22 | 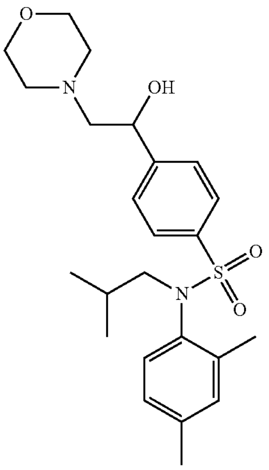 |
| E23 | 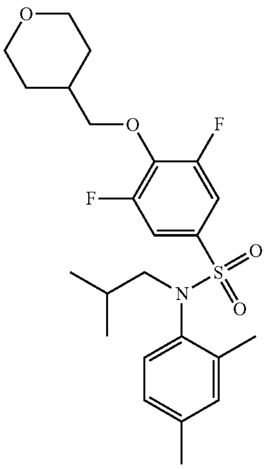 [SMILES: Cc1ccc(N(CC(C)C)S(=O)(=O)c2cc(F)c(OCC3CCOCC3)c(F)c2)c(C)c1] |
| E24 | 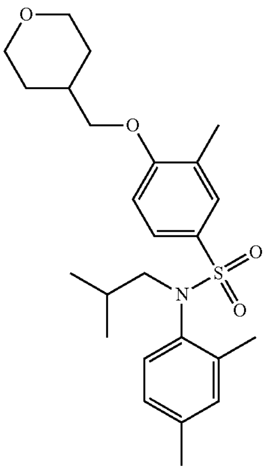 [SMILES: Cc1ccc(N(CC(C)C)S(=O)(=O)c2ccc(OCC3CCOCC3)c(C)c2)c(C)c1] |
| E25 | 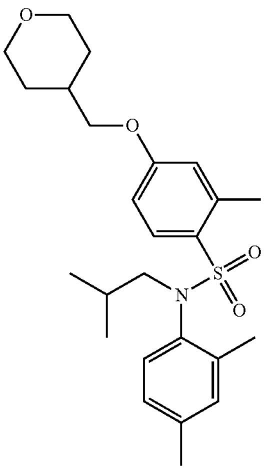 [SMILES: Cc1ccc(N(CC(C)C)S(=O)(=O)c2ccc(OCC3CCOCC3)cc2C)c(C)c1] |
| E26 | 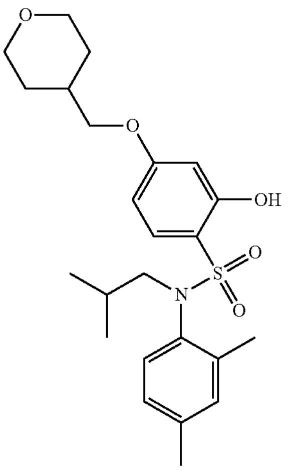 [SMILES: Cc1ccc(N(CC(C)C)S(=O)(=O)c2ccc(OCC3CCOCC3)cc2O)c(C)c1] |
| E27 | 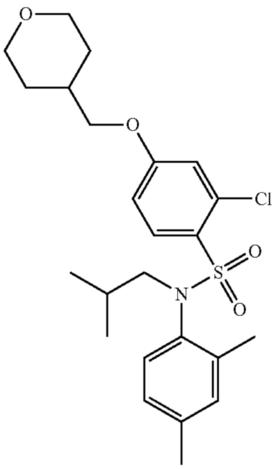 [SMILES: Cc1ccc(N(CC(C)C)S(=O)(=O)c2ccc(OCC3CCOCC3)cc2Cl)c(C)c1] |

TABLE 6-continued
| Example Structures | |
|---|---|
| E28 | 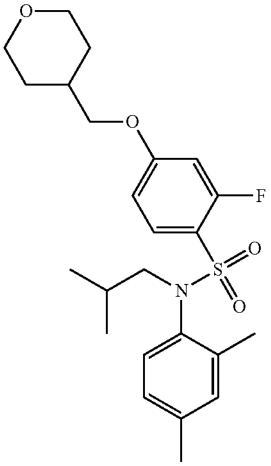 [SMILES: Cc1ccc(N(CC(C)C)S(=O)(=O)c2ccc(OCC3CCOCC3)cc2F)c(C)c1] |
| E29 | 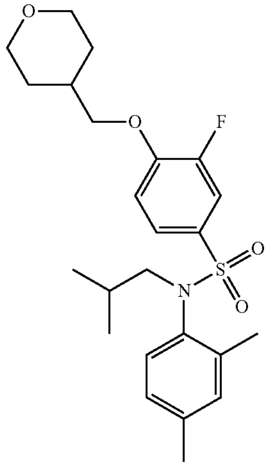 [SMILES: Cc1ccc(N(CC(C)C)S(=O)(=O)c2ccc(OCC3CCOCC3)c(F)c2)c(C)c1] |
| E30 | 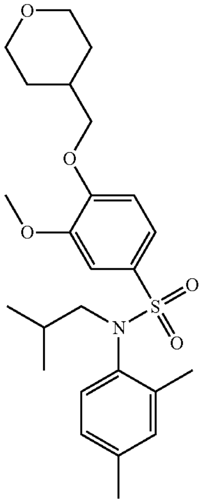 |
TABLE 6-continued
| Example Structures | |
|---|---|
| E31 | 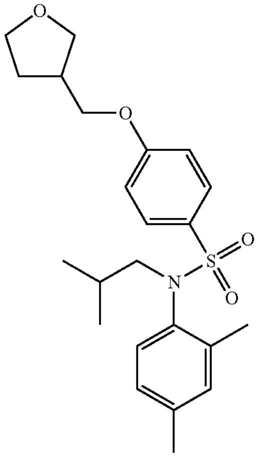 [SMILES: Cc1ccc(N(CC(C)C)S(=O)(=O)c2ccc(OCC3CCOC3)cc2)c(C)c1] |
| E32 | 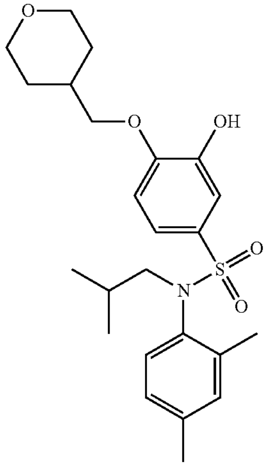 [SMILES: Cc1ccc(N(CC(C)C)S(=O)(=O)c2ccc(OCC3CCOCC3)c(O)c2)c(C)c1] |
| E33 | 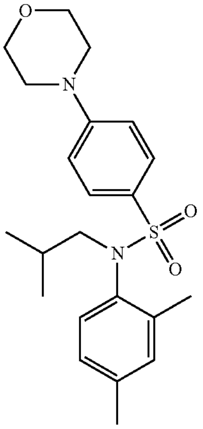 [SMILES: Cc1ccc(N(CC(C)C)S(=O)(=O)c2ccc(N3CCOCC3)cc2)c(C)c1] |

TABLE 6-continued
| Example Structures | |
|---|---|
| E34 | 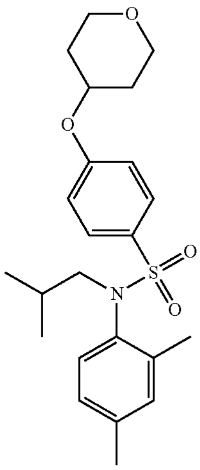 [SMILES: Cc1ccc(N(CC(C)C)S(=O)(=O)c2ccc(OC3CCOCC3)cc2)c(C)c1] |
| E35 | 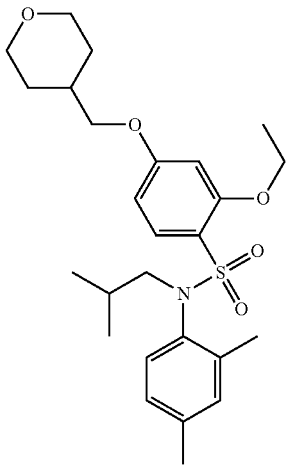 [SMILES: CCOc1cc(OCC2CCOCC2)ccc1S(=O)(=O)N(CC(C)C)c1ccc(C)cc1C] |
| E36 | 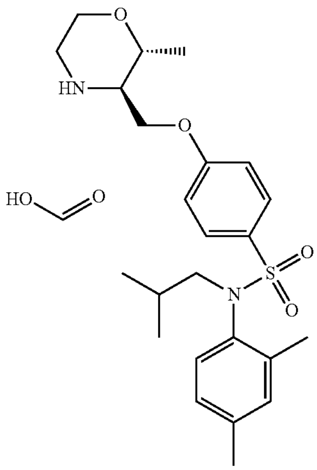 [SMILES: O=CO ; Cc1ccc(N(CC(C)C)S(=O)(=O)c2ccc(OC[C@H]3NCCO[C@@H]3C)cc2)c(C)c1] |
TABLE 6-continued
| Example Structures | |
|---|---|
| E37 | 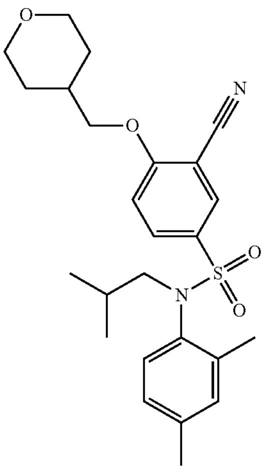 [SMILES: Cc1ccc(N(CC(C)C)S(=O)(=O)c2ccc(OCC3CCOCC3)c(C#N)c2)c(C)c1] |
| E38 | 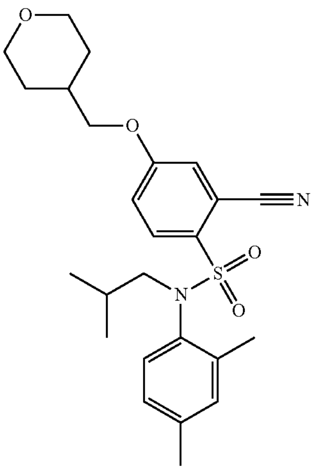 [SMILES: Cc1ccc(N(CC(C)C)S(=O)(=O)c2ccc(OCC3CCOCC3)cc2C#N)c(C)c1] |
| E39 | (±) 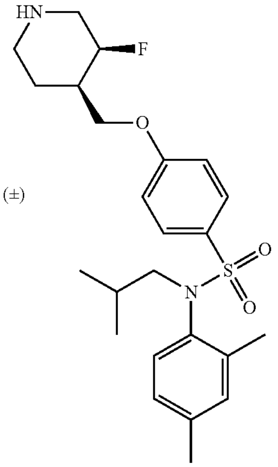 [SMILES: Cc1ccc(N(CC(C)C)S(=O)(=O)c2ccc(OC[C@H]3CCNC[C@H]3F)cc2)c(C)c1] |

TABLE 6-continued
| Example Structures | |
|---|---|
| E40 | 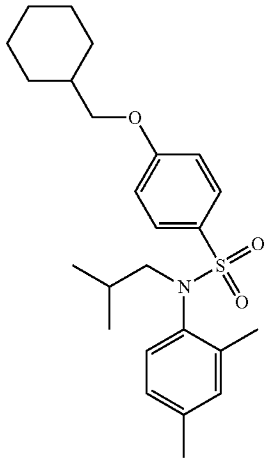 [SMILES: Cc1ccc(N(CC(C)C)S(=O)(=O)c2ccc(OCC3CCCCC3)cc2)c(C)c1] |
| E41 | 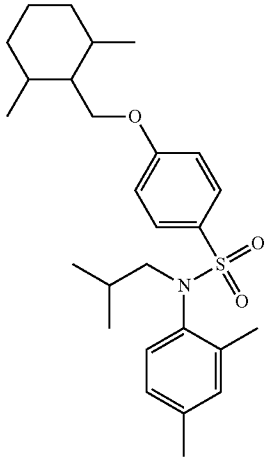 [SMILES: Cc1ccc(N(CC(C)C)S(=O)(=O)c2ccc(OCC3C(C)CCCC3C)cc2)c(C)c1] |
| E42 | 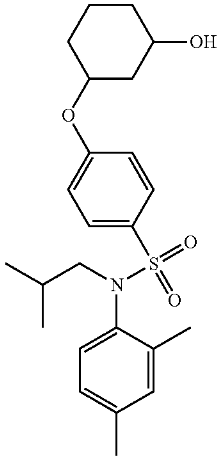 [SMILES: Cc1ccc(N(CC(C)C)S(=O)(=O)c2ccc(OC3CCCC(O)C3)cc2)c(C)c1] |
TABLE 6-continued
| Example Structures | |
|---|---|
| E43 | 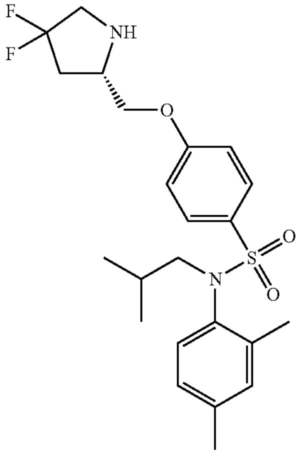 [SMILES: Cc1ccc(N(CC(C)C)S(=O)(=O)c2ccc(OC[C@@H]3CC(F)(F)CN3)cc2)c(C)c1] |
| E44 | 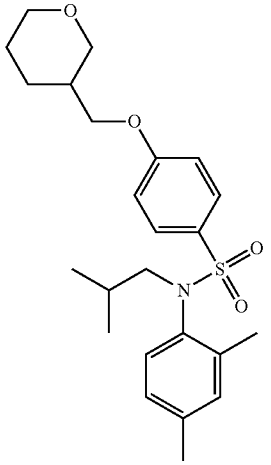 [SMILES: Cc1ccc(N(CC(C)C)S(=O)(=O)c2ccc(OCC3CCCOC3)cc2)c(C)c1] |
| E45 | 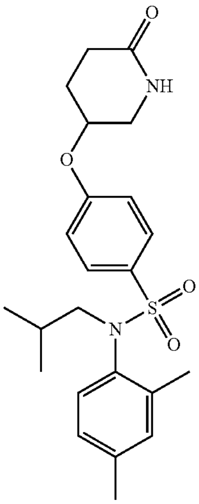 [SMILES: Cc1ccc(N(CC(C)C)S(=O)(=O)c2ccc(OC3CCC(=O)NC3)cc2)c(C)c1] |

TABLE 6-continued
| Example Structures | |
|---|---|
| E46 | 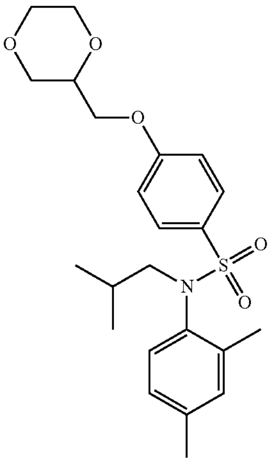 [SMILES: Cc1ccc(N(CC(C)C)S(=O)(=O)c2ccc(OCC3COCCO3)cc2)c(C)c1] |
| E47 | 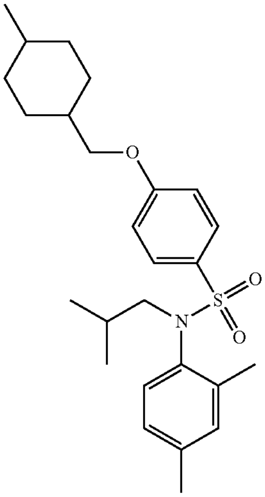 [SMILES: Cc1ccc(N(CC(C)C)S(=O)(=O)c2ccc(OCC3CCC(C)CC3)cc2)c(C)c1] |
| E48 | 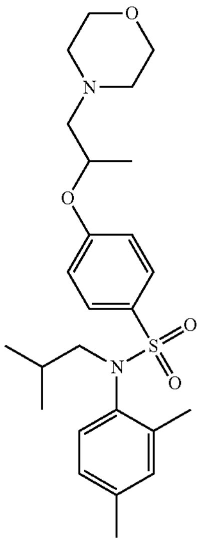 [SMILES: Cc1ccc(N(CC(C)C)S(=O)(=O)c2ccc(OC(C)CN3CCOCC3)cc2)c(C)c1] |
| E49 | 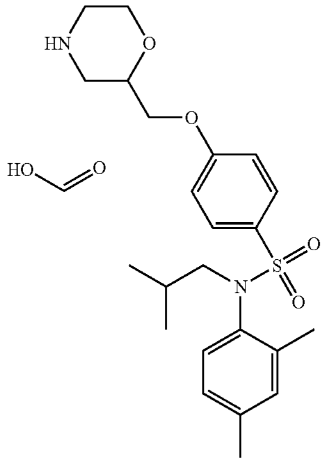 [SMILES: O=CO ; Cc1ccc(N(CC(C)C)S(=O)(=O)c2ccc(OCC3CNCCO3)cc2)c(C)c1] |
| E50 | 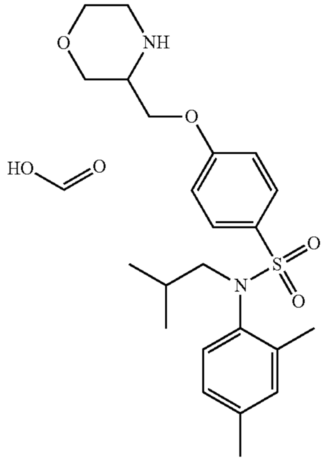 [SMILES: O=CO ; Cc1ccc(N(CC(C)C)S(=O)(=O)c2ccc(OCC3COCCN3)cc2)c(C)c1] |
| E51 | 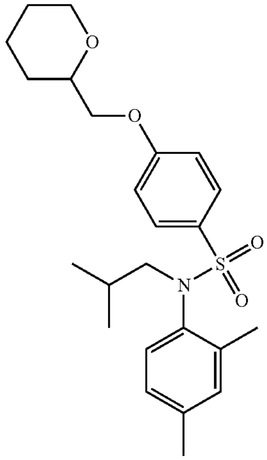 [SMILES: Cc1ccc(N(CC(C)C)S(=O)(=O)c2ccc(OCC3CCCCO3)cc2)c(C)c1] |

TABLE 6-continued
| Example Structures | |
|---|---|
| E52 | 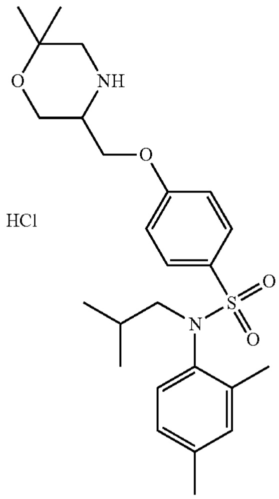 [SMILES: Cl ; Cc1ccc(N(CC(C)C)S(=O)(=O)c2ccc(OCC3COC(C)(C)CN3)cc2)c(C)c1] |
| E53 | 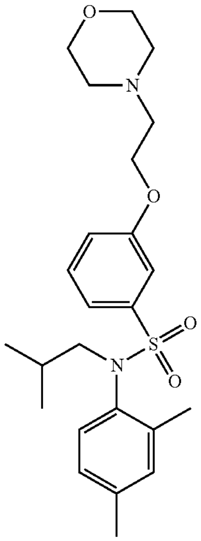 [SMILES: Cc1ccc(N(CC(C)C)S(=O)(=O)c2cccc(OCCN3CCOCC3)c2)c(C)c1] |
| E54 | 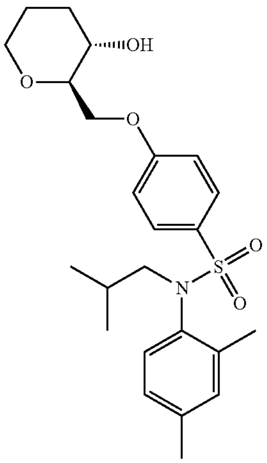 [SMILES: Cc1ccc(N(CC(C)C)S(=O)(=O)c2ccc(OC[C@H]3OCCC[C@@H]3O)cc2)c(C)c1] |
| E55 | 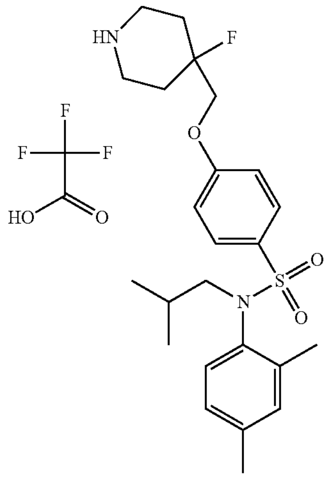 [SMILES: O=C(O)C(F)(F)F ; Cc1ccc(N(CC(C)C)S(=O)(=O)c2ccc(OCC3(F)CCNCC3)cc2)c(C)c1] |
| E56 | 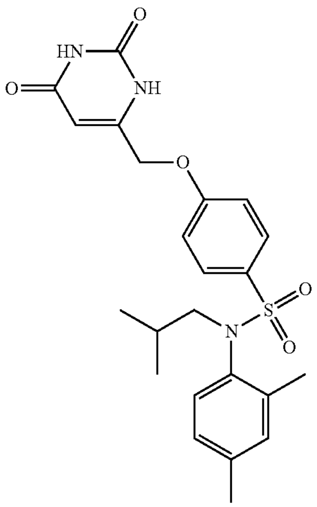 [SMILES: Cc1ccc(N(CC(C)C)S(=O)(=O)c2ccc(OCc3cc(=O)[nH]c(=O)[nH]3)cc2)c(C)c1] |
| E57 | 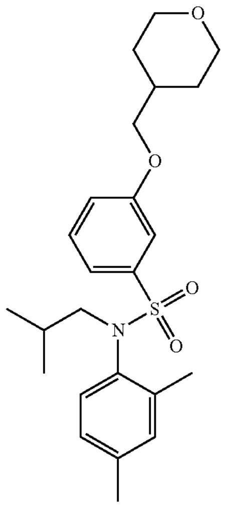 [SMILES: Cc1ccc(N(CC(C)C)S(=O)(=O)c2cccc(OCC3CCOCC3)c2)c(C)c1] |

TABLE 6-continued
| Example Structures | |
|---|---|
| E58 | 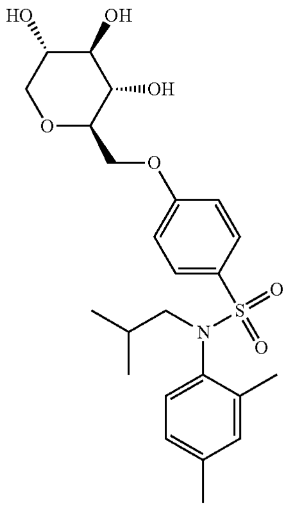 [SMILES: Cc1ccc(N(CC(C)C)S(=O)(=O)c2ccc(OC[C@H]3OC[C@H](O)[C@@H](O)[C@@H]3O)cc2)c(C)c1] |
| E59 | 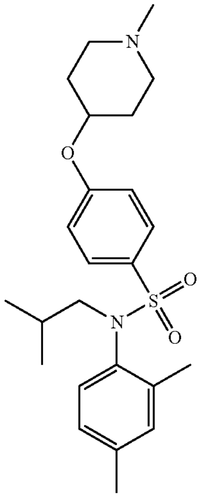 [SMILES: Cc1ccc(N(CC(C)C)S(=O)(=O)c2ccc(OC3CCN(C)CC3)cc2)c(C)c1] |
| E60 | 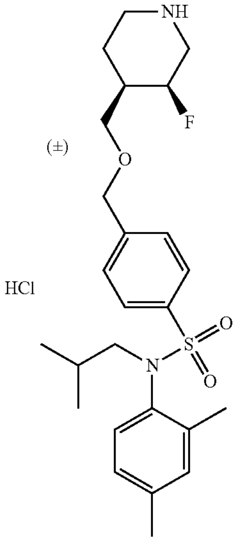 |
TABLE 6-continued
| Example Structures | |
|---|---|
| E61 | 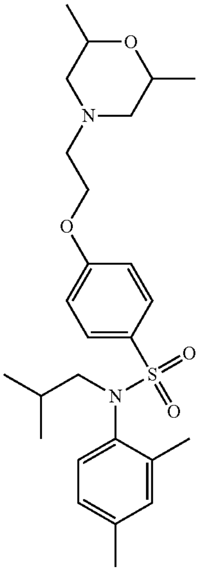 [SMILES: Cc1ccc(N(CC(C)C)S(=O)(=O)c2ccc(OCCN3CC(C)OC(C)C3)cc2)c(C)c1] |
| E62 | 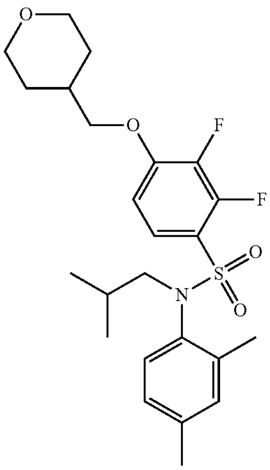 [SMILES: Cc1ccc(N(CC(C)C)S(=O)(=O)c2ccc(OCC3CCOCC3)c(F)c2F)c(C)c1] |

TABLE 6-continued
| Example Structures |
|---|
| E63 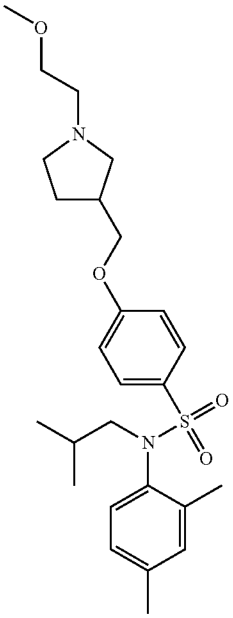 |
| E64 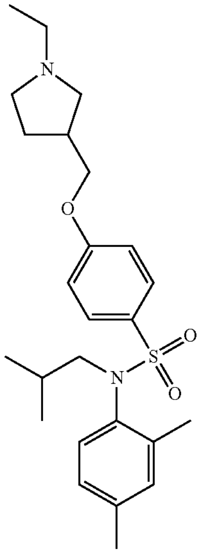 |
TABLE 6-continued
| Example Structures |
|---|
| E65 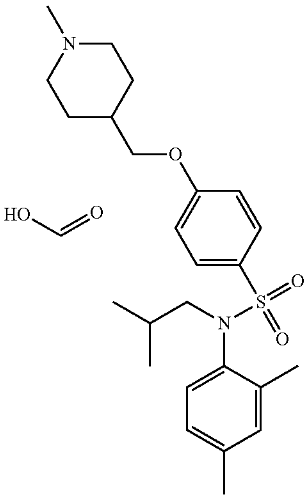 |
| E66 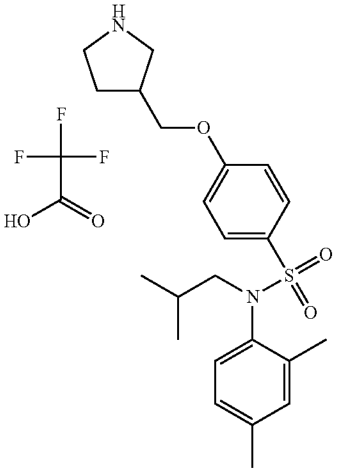 |
| E67 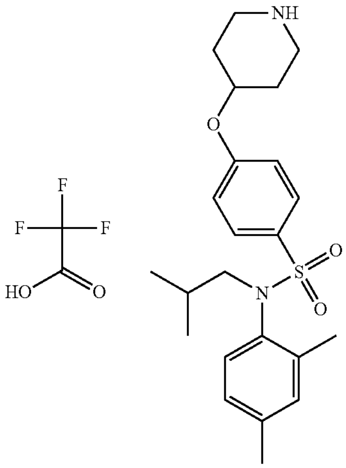 |

TABLE 6-continued
| Example Structures | |
|---|---|
| E68 | 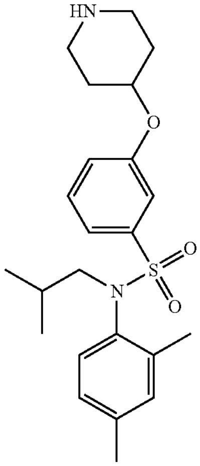 [SMILES: Cc1ccc(N(CC(C)C)S(=O)(=O)c2cccc(OC3CCNCC3)c2)c(C)c1] |
| E69 | 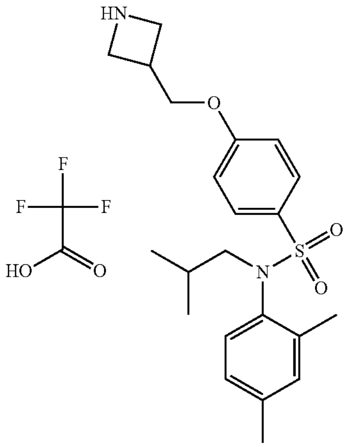 |
| E70 | 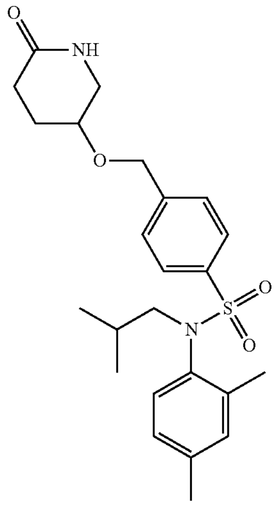 [SMILES: Cc1ccc(N(CC(C)C)S(=O)(=O)c2ccc(COC3CCC(=O)NC3)cc2)c(C)c1] |
TABLE 6-continued
| Example Structures | |
|---|---|
| E71 | 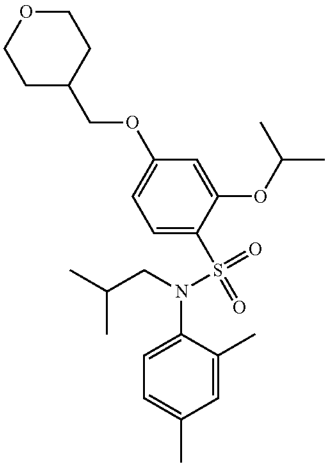 [SMILES: Cc1ccc(N(CC(C)C)S(=O)(=O)c2ccc(OCC3CCOCC3)cc2OC(C)C)c(C)c1] |
| E72 | 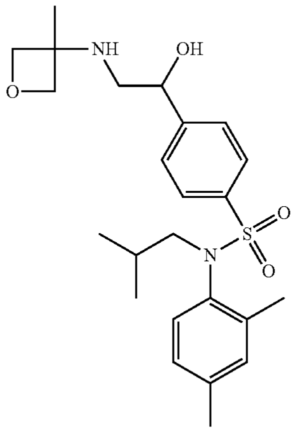 [SMILES: Cc1ccc(N(CC(C)C)S(=O)(=O)c2ccc(C(O)CNC3(C)COC3)cc2)c(C)c1] |
| E73 | 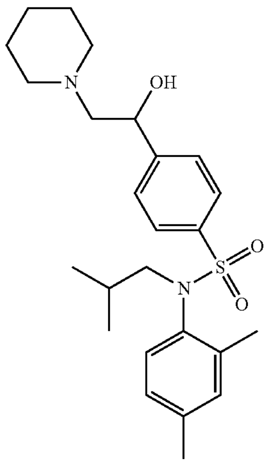 [SMILES: Cc1ccc(N(CC(C)C)S(=O)(=O)c2ccc(C(O)CN3CCCCC3)cc2)c(C)c1]

TABLE 6-continued
| Example Structures | |
|---|---|
| E74 | 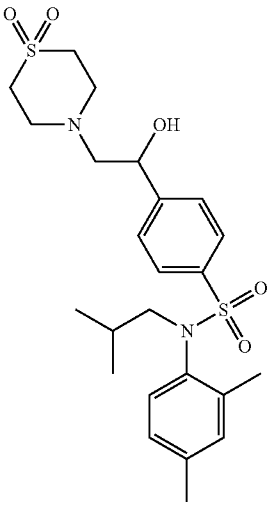 [SMILES: Cc1ccc(N(CC(C)C)S(=O)(=O)c2ccc(C(O)CN3CCS(=O)(=O)CC3)cc2)c(C)c1] |
| E75 | 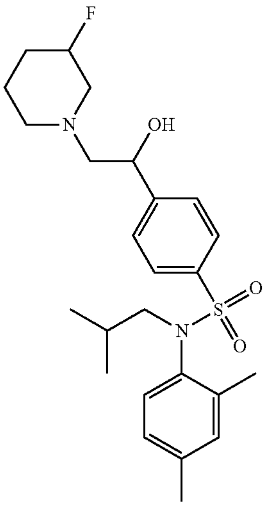 [SMILES: Cc1ccc(N(CC(C)C)S(=O)(=O)c2ccc(C(O)CN3CCCC(F)C3)cc2)c(C)c1] |
| E76 | 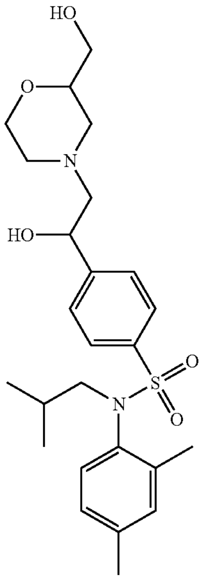 [SMILES: Cc1ccc(N(CC(C)C)S(=O)(=O)c2ccc(C(O)CN3CCOC(CO)C3)cc2)c(C)c1] |
TABLE 6-continued
| Example Structures | |
|---|---|
| E77 | 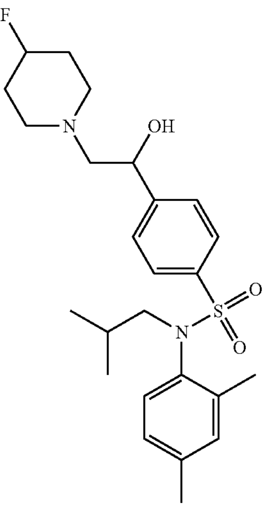 [SMILES: Cc1ccc(N(CC(C)C)S(=O)(=O)c2ccc(C(O)CN3CCC(F)CC3)cc2)c(C)c1] |
| E78 | 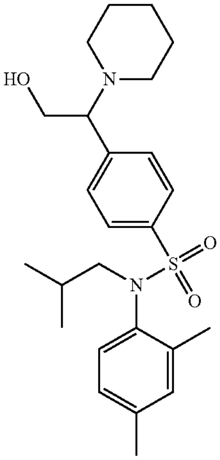 [SMILES: Cc1ccc(N(CC(C)C)S(=O)(=O)c2ccc(C(CO)N3CCCCC3)cc2)c(C)c1] |
| E79 | 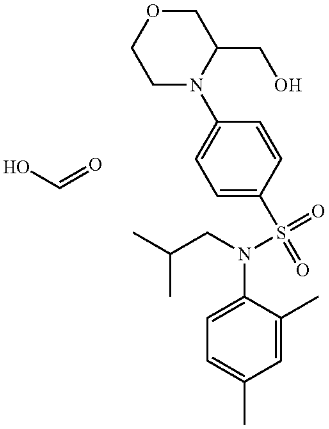 [SMILES: O=CO ; Cc1ccc(N(CC(C)C)S(=O)(=O)c2ccc(N3CCOCC3CO)cc2)c(C)c1] |

TABLE 6-continued
| Example Structures | |
|---|---|
| E80 | 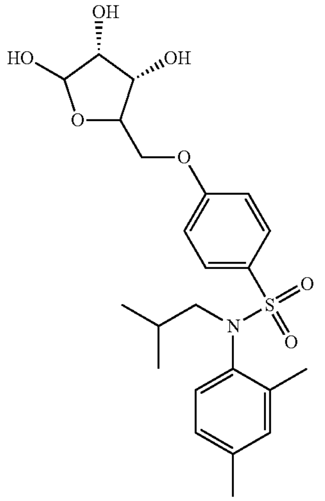 [SMILES: Cc1ccc(N(CC(C)C)S(=O)(=O)c2ccc(OCC3OC(O)[C@H](O)[C@@H]3O)cc2)c(C)c1] |
| E81 | 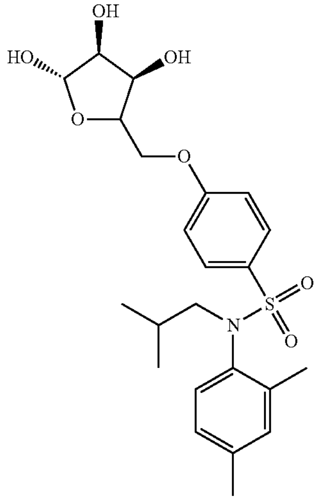 [SMILES: Cc1ccc(N(CC(C)C)S(=O)(=O)c2ccc(OCC3O[C@H](O)[C@@H](O)[C@H]3O)cc2)c(C)c1] |
| E82 | 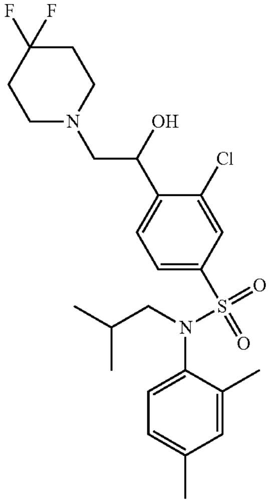 [SMILES: Cc1ccc(N(CC(C)C)S(=O)(=O)c2ccc(C(O)CN3CCC(F)(F)CC3)c(Cl)c2)c(C)c1] |
TABLE 6-continued
| Example Structures | |
|---|---|
| E83 | 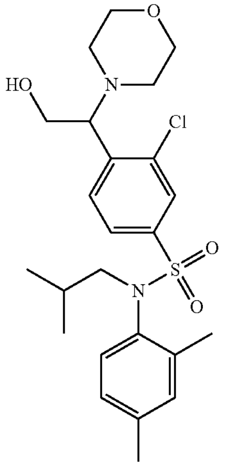 [SMILES: Cc1ccc(N(CC(C)C)S(=O)(=O)c2ccc(C(CO)N3CCOCC3)c(Cl)c2)c(C)c1] |
| E84 | 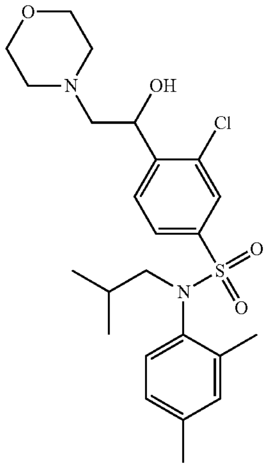 [SMILES: Cc1ccc(N(CC(C)C)S(=O)(=O)c2ccc(C(O)CN3CCOCC3)c(Cl)c2)c(C)c1] |
| E85 | 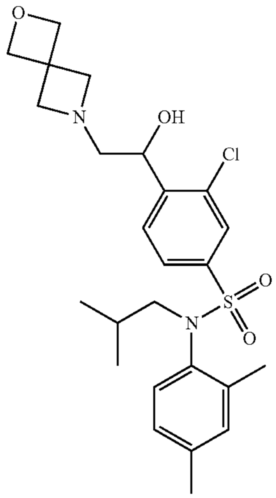 [SMILES: Cc1ccc(N(CC(C)C)S(=O)(=O)c2ccc(C(O)CN3CC4(COC4)C3)c(Cl)c2)c(C)c1] |

TABLE 6-continued
| Example Structures | |
|---|---|
| E86 | 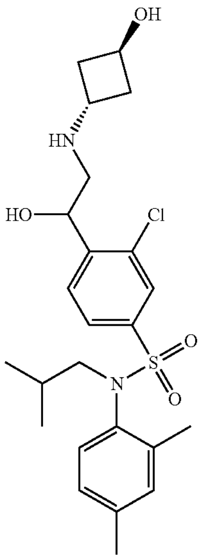 [SMILES: Cc1ccc(N(CC(C)C)S(=O)(=O)c2ccc(C(O)CN[C@H]3C[C@H](O)C3)c(Cl)c2)c(C)c1] |
| E87 | 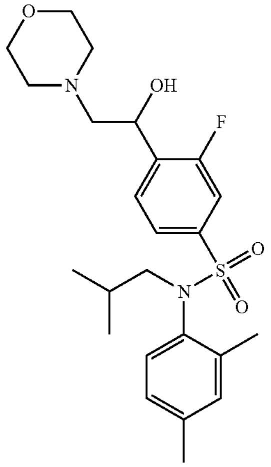 [SMILES: Cc1ccc(N(CC(C)C)S(=O)(=O)c2ccc(C(O)CN3CCOCC3)c(F)c2)c(C)c1] |
| E88 | 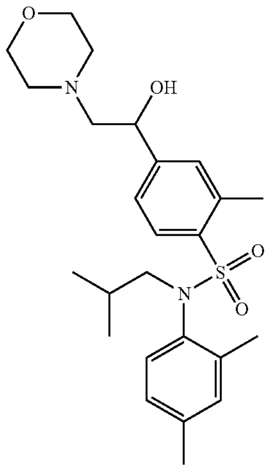 [SMILES: Cc1ccc(N(CC(C)C)S(=O)(=O)c2ccc(C(O)CN3CCOCC3)cc2C)c(C)c1] |
TABLE 6-continued
| Example Structures | |
|---|---|
| E89 | 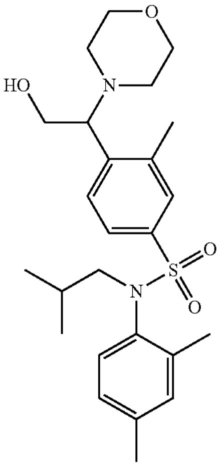 [SMILES: Cc1ccc(N(CC(C)C)S(=O)(=O)c2ccc(C(CO)N3CCOCC3)c(C)c2)c(C)c1] |
| E90 | 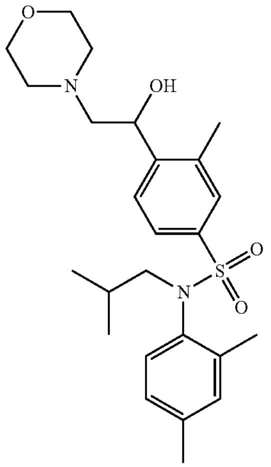 [SMILES: Cc1ccc(N(CC(C)C)S(=O)(=O)c2ccc(C(O)CN3CCOCC3)c(C)c2)c(C)c1] |
| E91 | 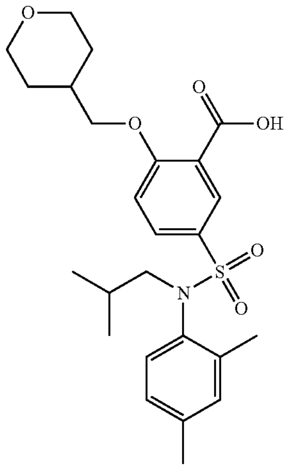 [SMILES: Cc1ccc(N(CC(C)C)S(=O)(=O)c2ccc(OCC3CCOCC3)c(C(=O)O)c2)c(C)c1] |

TABLE 6-continued
| Example Structures | |
|---|---|
| E92 | 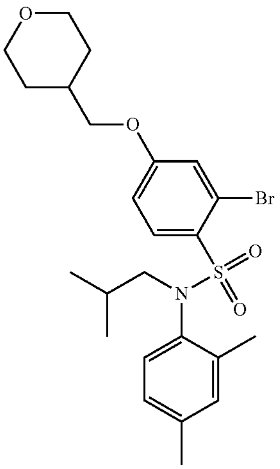 [SMILES: Cc1ccc(N(CC(C)C)S(=O)(=O)c2ccc(OCC3CCOCC3)cc2Br)c(C)c1] |
| E93 | 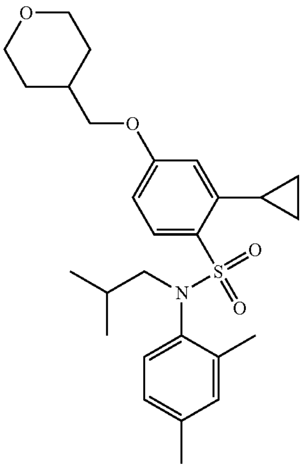 [SMILES: Cc1ccc(N(CC(C)C)S(=O)(=O)c2ccc(OCC3CCOCC3)cc2C2CC2)c(C)c1] |
| E94 | 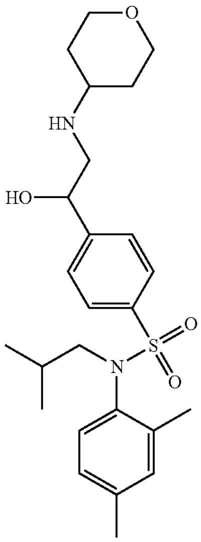 [SMILES: Cc1ccc(N(CC(C)C)S(=O)(=O)c2ccc(C(O)CNC3CCOCC3)cc2)c(C)c1] |
TABLE 6-continued
| Example Structures | |
|---|---|
| E95 | 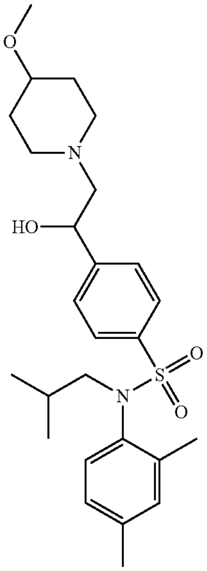 [SMILES: COC1CCN(CC(O)c2ccc(S(=O)(=O)N(CC(C)C)c3ccc(C)cc3C)cc2)CC1] |
| E96 | 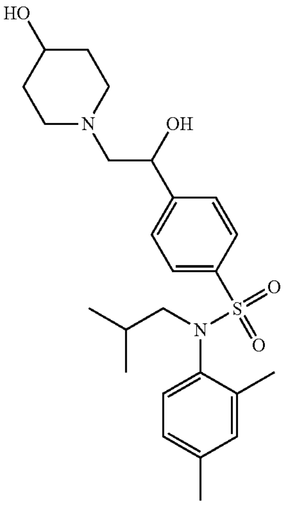 [SMILES: Cc1ccc(N(CC(C)C)S(=O)(=O)c2ccc(C(O)CN3CCC(O)CC3)cc2)c(C)c1] |
| E97 | 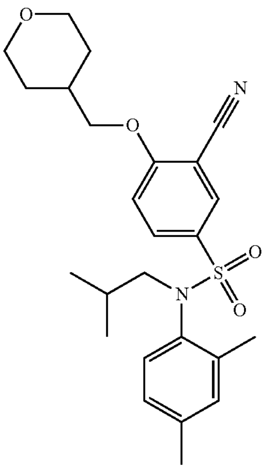 [SMILES: Cc1ccc(N(CC(C)C)S(=O)(=O)c2ccc(OCC3CCOCC3)c(C#N)c2)c(C)c1] |

TABLE 6-continued
| Example Structures | |
|---|---|
| E98 | 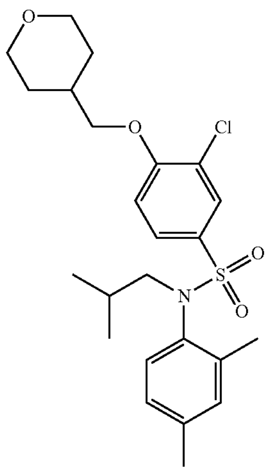 [SMILES: Cc1ccc(N(CC(C)C)S(=O)(=O)c2ccc(OCC3CCOCC3)c(Cl)c2)c(C)c1] |
| E99 | 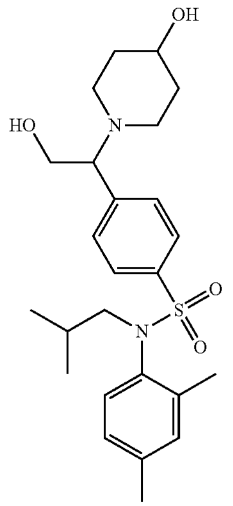 [SMILES: Cc1ccc(N(CC(C)C)S(=O)(=O)c2ccc(C(CO)N3CCC(O)CC3)cc2)c(C)c1] |
| E100 | 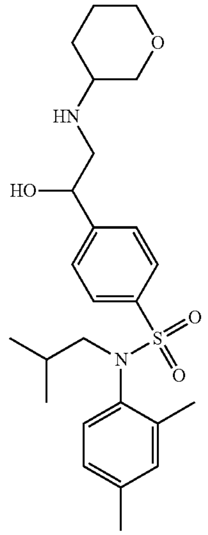 [SMILES: Cc1ccc(N(CC(C)C)S(=O)(=O)c2ccc(C(O)CNC3CCCOC3)cc2)c(C)c1] |
TABLE 6-continued
| Example Structures | |
|---|---|
| E101 | 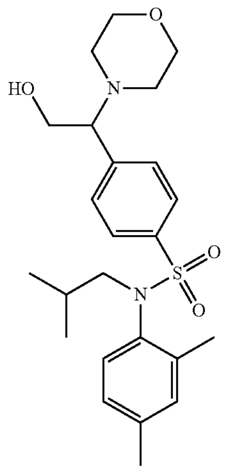 [SMILES: Cc1ccc(N(CC(C)C)S(=O)(=O)c2ccc(C(CO)N3CCOCC3)cc2)c(C)c1] |
| E102 | 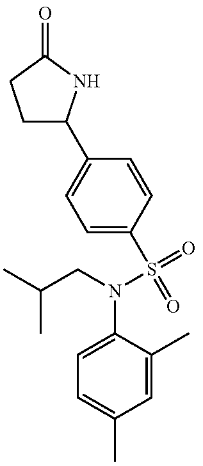 [SMILES: Cc1ccc(N(CC(C)C)S(=O)(=O)c2ccc(C3CCC(=O)N3)cc2)c(C)c1] |
| E103 | 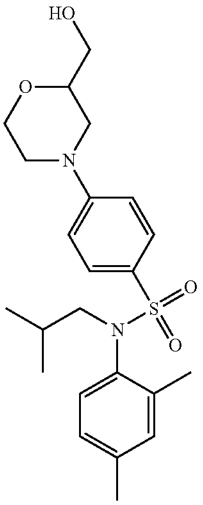 [SMILES: Cc1ccc(N(CC(C)C)S(=O)(=O)c2ccc(N3CCOC(CO)C3)cc2)c(C)c1] |

TABLE 6-continued
| Example Structures | |
|---|---|
| E104 | 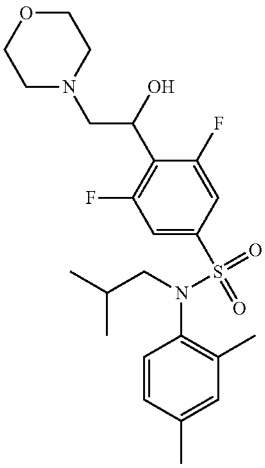 [SMILES: Cc1ccc(N(CC(C)C)S(=O)(=O)c2cc(F)c(C(O)CN3CCOCC3)c(F)c2)c(C)c1] |
| E105 | 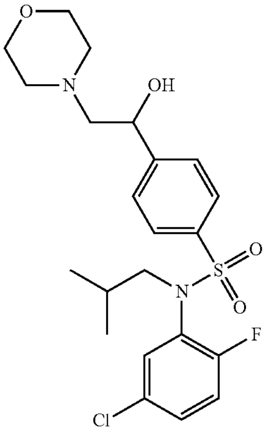 [SMILES: CC(C)CN(c1cc(Cl)ccc1F)S(=O)(=O)c1ccc(C(O)CN2CCOCC2)cc1] |
| E106 | 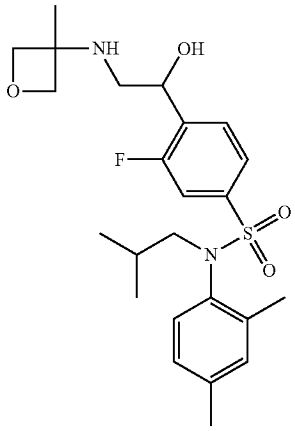 [SMILES: Cc1ccc(N(CC(C)C)S(=O)(=O)c2ccc(C(O)CNC3(C)COC3)c(F)c2)c(C)c1] |
TABLE 6-continued
| Example Structures | |
|---|---|
| E107 | 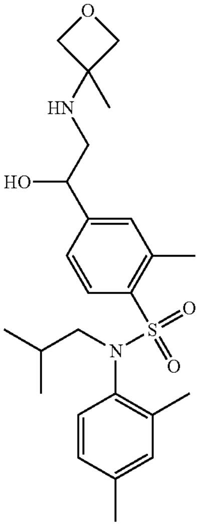 [SMILES: Cc1ccc(N(CC(C)C)S(=O)(=O)c2ccc(C(O)CNC3(C)COC3)cc2C)c(C)c1] |
| E108 | 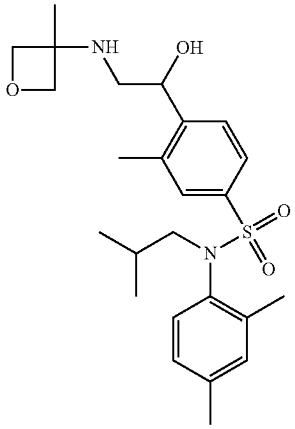 [SMILES: Cc1ccc(N(CC(C)C)S(=O)(=O)c2ccc(C(O)CNC3(C)COC3)c(C)c2)c(C)c1] |
| E109 | 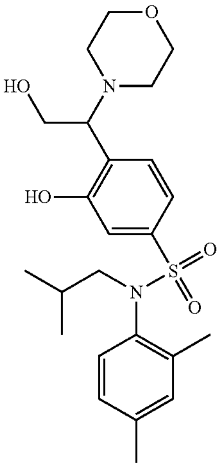 [SMILES: Cc1ccc(N(CC(C)C)S(=O)(=O)c2ccc(C(CO)N3CCOCC3)c(O)c2)c(C)c1] |

TABLE 6-continued
| Example Structures | |
|---|---|
| E110 | 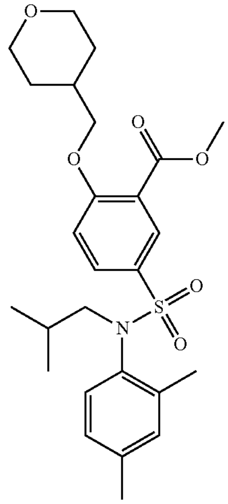 [SMILES: COC(=O)c1cc(S(=O)(=O)N(CC(C)C)c2ccc(C)cc2C)ccc1OCC1CCOCC1] |
| E111 | 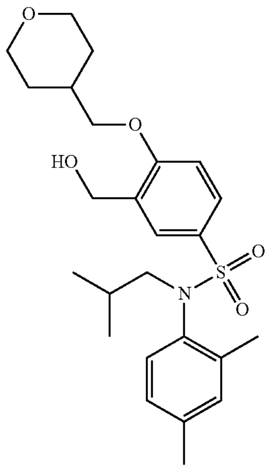 [SMILES: Cc1ccc(N(CC(C)C)S(=O)(=O)c2ccc(OCC3CCOCC3)c(CO)c2)c(C)c1] |
| E112 | 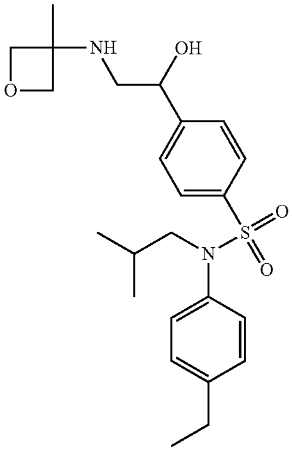 [SMILES: CCc1ccc(N(CC(C)C)S(=O)(=O)c2ccc(C(O)CNC3(C)COC3)cc2)cc1] |
TABLE 6-continued
| Example Structures | |
|---|---|
| E113 | 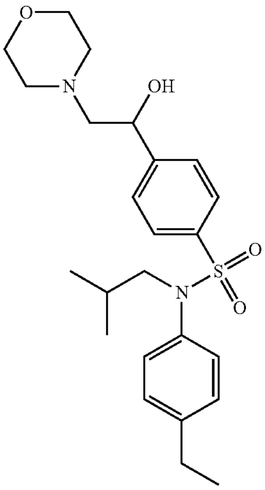 [SMILES: CCc1ccc(N(CC(C)C)S(=O)(=O)c2ccc(C(O)CN3CCOCC3)cc2)cc1] |
| E114 | 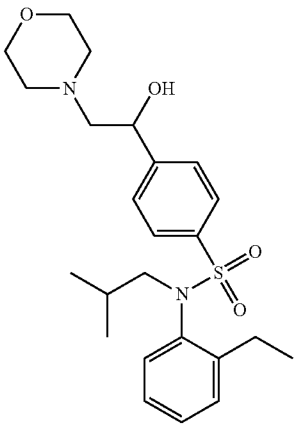 [SMILES: CCc1ccccc1N(CC(C)C)S(=O)(=O)c1ccc(C(O)CN2CCOCC2)cc1] |
| E115 | 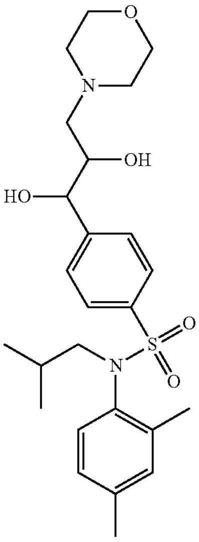<br>α-enantiomer |

TABLE 6-continued
| Example Structures |
|---|
E116
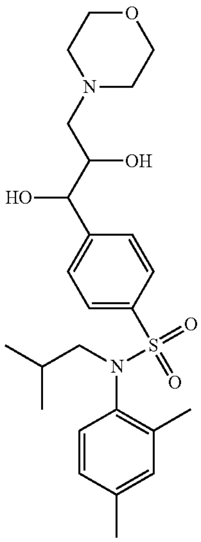
β-enantiomer
E117
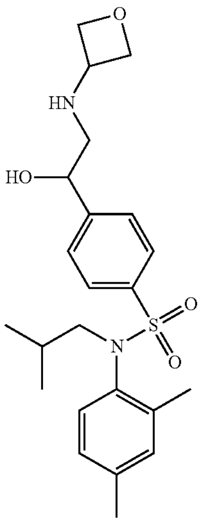 [SMILES: Cc1ccc(N(CC(C)C)S(=O)(=O)c2ccc(C(O)CNC3COC3)cc2)c(C)c1]
TABLE 6-continued
| Example Structures |
|---|
E118
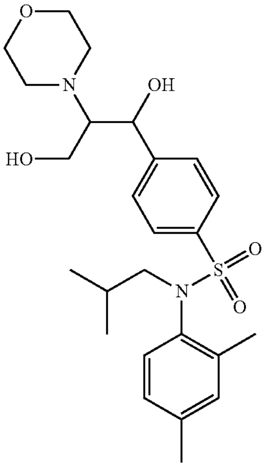
diastereoisomer1
E119
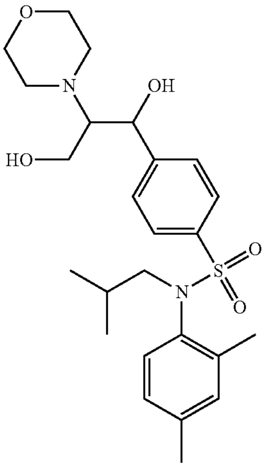
diastereoisomer2
E120
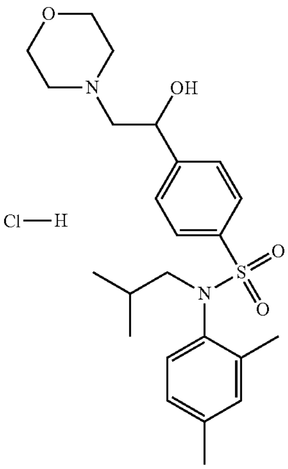 [SMILES: Cl ; Cc1ccc(N(CC(C)C)S(=O)(=O)c2ccc(C(O)CN3CCOCC3)cc2)c(C)c1]

TABLE 6-continued

| Example Structures | |
|---|---|
| E121 | 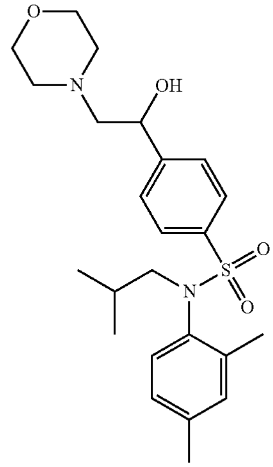<br>enantiomer1 |
| E122 | 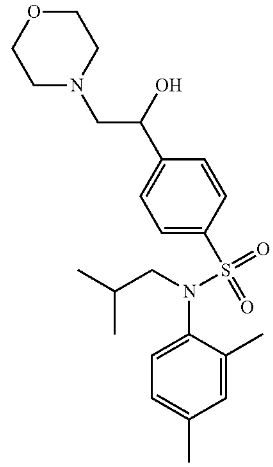<br>enantiomer2 |
| E123 | 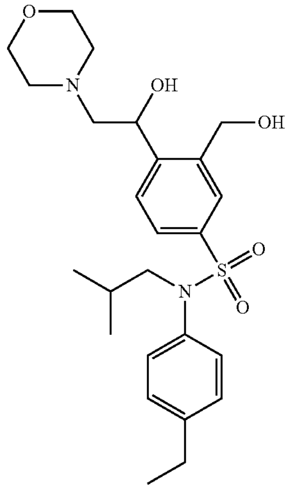 [SMILES: CCc1ccc(N(CC(C)C)S(=O)(=O)c2ccc(C(O)CN3CCOCC3)c(CO)c2)cc1] |

TABLE 6-continued

| Example Structures | |
|---|---|
| E124 | 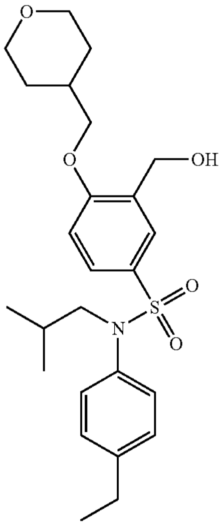 [SMILES: CCc1ccc(N(CC(C)C)S(=O)(=O)c2ccc(OCC3CCOCC3)c(CO)c2)cc1] |
| E125 | 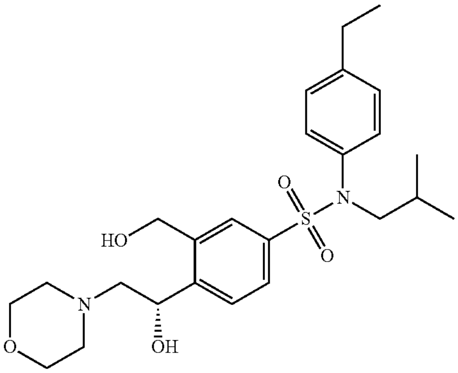 [SMILES: CCc1ccc(N(CC(C)C)S(=O)(=O)c2ccc([C@H](O)CN3CCOCC3)c(CO)c2)cc1] |
| E126 | 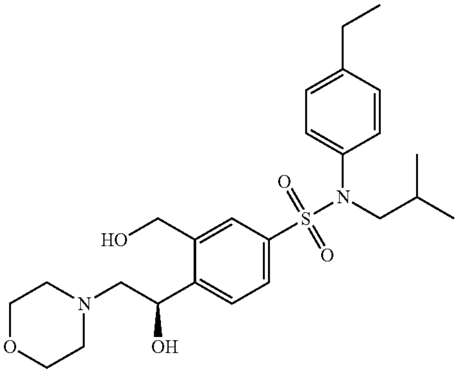 [SMILES: CCc1ccc(N(CC(C)C)S(=O)(=O)c2ccc([C@@H](O)CN3CCOCC3)c(CO)c2)cc1] |

Analytical Methodology

Outlined below are general methods for work-up and purification.

Work-Up

Reactions were worked up in a number of ways which may be combined for example by solid-phase extraction (SPE) using either sulfonic acid (SCX) or aminopropyl ($NH_2$) cartridges eluting with methanol and then 2M methanolic ammonia (Method S); quench with water, isopropanol or methanol (Method Q); solid-phase extraction using fluorous cartridges eluting with methanol:water (Method FL); evaporation either in vacuo or by blowing nitrogen across sample (Method E); and aqueous work up where the sample is diluted with water or dilute acid or dilute base and then extracted with a suitable organic solvent, for example ethyl acetate or dichloromethane (Method A); or filtration of sample through a filter tube (Method F).

Evaporation

Samples were concentrated using Radley's nitrogen blow down unit, rotary evaporator or Biotage V10 evaporator to give crude residue.

Purification

Purification was by a range of methods including: mass-directed autoprep (MDAP) using either low or high pH modifiers see below for column details; automated normal phase chromatography on for example a Biotage Flashmaster II or a ISCO companion, using silica or aminopropyl column and a range of solvents, which included, for example, ethyl acetate/cyclohexane/dichloromethane and methanol; or recrystallisation from suitable solvent.

TABLE 4

Purification Methods

| Purification | Key (as used in Tables 1 to 3) |
|---|---|
| MDAP | F |
| MDAP | A |
| MDAP | T |
| MDAP | N |
| MDAP | O |
| MDAP | R |
| MDAP | M |
| Normal Phase Chromatography: Silica: EtOAc— cyclohexane 0-100% | E1 |
| Normal Phase Chromatography: Silica 0-50% ethyl acetate-cyclohexane | E2 |
| Normal Phase Chromatography: Silica EtOAc— cyclohexane 0-25% | E3 |
| Normal Phase Chromatography: Silica 0-100% DCM in cycohexane | D2 |
| Normal Phase Chromatography Silica 0-50% DCM in cyclohexane | D3 |
| Re-crystallisation from Methanol | R |

MDAP Purification

MDAP: Method F

The HPLC purification was conducted on a Sunfire C18 column (150 mm×30 mm i.d. 5 μm packing diameter) at ambient temperature.

The solvents employed were:

A=0.1% v/v solution of Formic Acid in Water.

B=0.1% v/v solution of Formic Acid in Acetonitrile.

Flow rate 40 mL/min.

The gradient was selected according to the analytical retention time.

The UV detection was an averaged signal from wavelength of 210 nm to 350 nm and mass spectra were recorded on a mass spectrometer using alternate-scan positive and negative mode electrospray ionization.

MDAP: Method A

The HPLC purification was conducted on a Waters XBridge C18 column (100 mm×30 mm i.d. 5 μm packing diameter) at ambient temperature.

The solvents employed were:

A=10 mM Ammonium Bicarbonate in water adjusted to pH 10 with Ammonia solution.

B=Acetonitrile.

Flow rate 40 mL/min.

The gradient was selected according to the analytical retention time.

The UV detection was an averaged signal from wavelength of 210 nm to 350 nm and mass spectra were recorded on a mass spectrometer using alternate-scan positive and negative mode electrospray ionization.

MDAP: Method T

The HPLC purification was conducted on a Sunfire C18 column (150 mm×30 mm i.d. 5 μm packing diameter) at ambient temperature.

The solvents employed were:

A=0.1% v/v solution of trifluoroacetic acid in water.

B=0.1% v/v solution of trifluoroacetic acid in acetonitrile.

The gradient was selected according to the analytical retention time.

The UV detection was an averaged signal from wavelength of 210 nm to 350 nm and mass spectra were recorded on a mass spectrometer using positive electrospray ionisation.

MDAP: Method N

The HPLC purification was conducted on a Waters XBridge C18 column (100 mm×19 mm i.d. 5 μm packing diameter) at ambient temperature.

The solvents employed were:

A=10 mM Ammonium Bicarbonate in water adjusted to pH 10 with Ammonia solution.

B=Methanol.

Flow rate 20 mL/min.

The gradient was selected according to the analytical retention time.

The UV detection was an averaged signal from wavelength of 210 nm to 400 nm and mass spectra were recorded on a mass spectrometer using alternate-scan positive and negative mode electrospray ionization.

MDAP: Method O

The HPLC purification was conducted on a Waters Atlantis dC18 column (100 mm×19 mm i.d. 5 μm packing diameter) at ambient temperature.

The solvents employed were:

A=0.1% v/v solution of Formic Acid in Water.

B=Acetonitrile.

Flow rate 20 mL/min.

The gradient was selected according to the analytical retention time.

The UV detection was an averaged signal from wavelength of 210 nm to 400 nm and mass spectra were recorded on a mass spectrometer using alternate-scan positive and negative mode electrospray ionization.

MDAP: Method R

The HPLC purification was conducted on a Sunfire C18 column (100 mm×19 mm i.d. 5 μm packing diameter) at ambient temperature.

The solvents employed were:

A=0.1% v/v solution of trifluoroacetic acid in water.

B=1:1 acetonitrile:methanol.

Flow rate 20 mL/min.

The gradient was selected according to the analytical retention time.

The UV detection was an averaged signal from wavelength of 210 nm to 400 nm and mass spectra were recorded on a mass spectrometer using positive electrospray ionisation.

MDAP: Method M

The HPLC purification was conducted on a Waters XBridge C18 column (100 mm×19 mm i.d. 5 μm packing diameter) at ambient temperature.

The solvents employed were:

A=10 mM Ammonium Bicarbonate in water adjusted to pH 10 with Ammonia solution.

B=Acetonitrile.

Flow rate 20 mL/min.

The gradient was selected according to the analytical retention time.

The UV detection was an averaged signal from wavelength of 210 nm to 400 nm and mass spectra were recorded on a mass spectrometer using alternate-scan positive and negative mode electrospray ionization.

LCMS Analytical Conditions

LCMS1

UPLC analysis was conducted on an Acquity UPLC BEH C18 column (2.1 mm×50 mm i.d. 1.7 μm packing diameter) at 40° C.

The solvents employed were:

A=0.1% v/v solution of formic acid in water.

B=0.1% v/v solution of formic acid in acetonitrile.

The gradient employed was:

| Time (min) | Flow Rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

LCMS2

UPLC analysis was conducted on an Acquity UPLC BEH C18 column (50 mm×2.1 mm i.d. 1.7 μm packing diameter) at 40° C.

The solvents employed were:

A=10 mM ammonium bicarbonate in water adjusted to pH 10 with ammonia solution.

B=Acetonitrile.

The gradient employed was:

| Time (min) | Flow Rate (mL/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 99 | 1 |

The UV detection was a summed signal from wavelength of 210 nm to 350 nm and mass spectra were recorded on a mass spectrometer, such as a Waters ZQ, using alternate-scan positive and negative mode electrospray ionization.

LCMS3

UPLC analysis was conducted on an Acquity C18 column (2 mm×50 mm, 1.7 μm)

The solvents employed were:

A: Water 10 mM Ammonium Acetate 0.1% formic acid

B: 95% acetonitrile/water 0.05% formic acid

| Time (min) | Flow Rate (mL/min) | % A | % B | Curve |
|---|---|---|---|---|
| 0 | 1 | 97.0 | 3.0 | 6 |
| 0.1 | 1 | 97.0 | 3.0 | 6 |
| 1.4 | 1 | 0.0 | 100.0 | 6 |
| 1.9 | 1 | 0.0 | 100.0 | 6 |
| 2.0 | 1 | 97.0 | 3.0 | 6 |

The UV detection was a summed signal from wavelength of 220 nm to 330 nm and mass spectra were recorded on a mass spectrometer using alternate-scan positive and negative mode electrospray ionization.

LCMS4

The HPLC analysis was conducted on a Sunfire C18 column (30 mm×4.6 mm i.d. 3.5 μm packing diameter) at 30° C.

The solvents employed were:

A=0.1% v/v solution of formic acid in water.

B=0.1% v/v solution of formic acid in acetonitrile.

The gradient employed was:

| Time (min) | Flow Rate (mL/min) | % A | % B |
|---|---|---|---|
| 0 | 3 | 97.0 | 3.0 |
| 0.1 | 3 | 97.0 | 3.0 |
| 4.2 | 3 | 0.0 | 100.0 |
| 4.8 | 3 | 0.0 | 100.0 |
| 4.9 | 3 | 97.0 | 3.0 |
| 5.0 | 3 | 97.0 | 3.0 |

The UV detection was a summed signal from wavelength of 210 nm to 350 nm and mass spectra were recorded on a mass spectrometer using alternate-scan positive and negative mode electrospray ionization.

Chiral HPLC

HPLC1a

Chiral HPLC analysis was conducted using a Chiralcel OJ column (25 cm×4.6 mm i.d.).

Isocratic solvent system was employed: 10% ethanol/heptane

Flow rate=1.0 mL/min

UV detection wavelength 230 nm

Method: Approximately 0.5 mg material was dissolved in 50% ethanol/heptane (1 mL) and 20 uL injected on column.

HPLC1p

Chiral preparative HPLC was conducted using a Chiralcel OJ column (25 cm×2 cm).

Isocratic solvent system was employed: 10% ethanol/heptane

Flow rate=14 mL/min

UV detection wavelength 215 nm

Method: Material was dissolved in 50% ethanol/heptane (2 mL total) and 2 mL injected on column.

HPLC2a

Chiral HPLC analysis was conducted using a Chiralcel OJ column (25 cm×4.6 mm i.d.).

Isocratic solvent system was employed: 20% ethanol/n-hexane

Flow rate=1.0 mL/min

UV detection wavelength 300 nm

HPLC2p

Chiral preparative HPLC was conducted using a Chiralcel OJ-H column (25 cm×3 cm).

Isocratic solvent system was employed: 20% ethanol/n-hexane

Flow rate=45 mL/min

UV detection wavelength 300 nm

Method: Material was dissolved in warm ethanol (1.7 mL) and purification carried out in 0.5 mL injections on column.

Biological Evaluation

The compounds of formula (I) and pharmaceutically acceptable salts thereof are RORγ modulators, and hence have utility in the treatment of inflammatory, metabolic and autoimmune diseases mediated by RORγ. The biological activities of exemplified compounds of formula (I) were assessed in the following disclosed assays.

Dual Fluorescence Energy Transfer (FRET) Assay

This assay is based on the knowledge that nuclear receptors interact with cofactors (transcription factors) in a ligand dependent manner. RORγ is a typical nuclear receptor in that it has an AF2 domain in the ligand binding domain (LBD) which interacts with co-activators. The sites of interaction have been mapped to the LXXLL (SEQ ID NO:1) motifs in the co-activator SRC1(2) sequences. Short peptide sequences containing the LXXLL (SEQ ID NO: 1) motif mimic the behavior of full-length co-activator.

This assay measures ligand-mediated interaction of the co-activator peptide with the purified bacterial-expressed RORγ ligand binding domain (RORγ-LBD) to indirectly assess ligand binding. RORγ has a basal level of interaction with the co-activator SRC1(2) in the absence of ligand, thus, it is possible to find ligands that inhibit or enhance the RORγ/SRC1(2) interaction.

Materials

Generation of RORγ-LBD Bacterial Expression Plasmid

Human RORγ Ligand Binding Domain (RORγ-LBD) was expressed in *E. coli* strain BL21(DE3) as an amino-terminal polyhistidine tagged fusion protein. DNA encoding this recombinant protein was sub-cloned into a modified pET21a expression vector (Novagen). A modified polyhistidine tag (MKKHHHHHHLVPRGS) (SEQ ID NO:2) was fused in frame to residues 263-518 of the human RORγ sequence.

Protein Purification

Approximately 50 g *E. coli* cell pellet was resuspended in 300 mL of lysis buffer (30 mM imidazole pH 7.0 and 150 mM NaCl). Cells were lysed by sonication and cell debris was removed by centrifugation for 30 minutes at 20,000 g at 4° C. The cleared supernatant was filtered through a 0.45 uM cellulose acetate membrane filter. The clarified lysate was loaded onto a column (XK-26) packed with ProBond Nickel Chelating resin (InVitrogen), pre-equilibrated with 30 mM imidazole pH 7.0 and 150 mM NaCl. After washing to baseline absorbance with the equilibration buffer, the column was developed with a gradient from 30 to 500 mM imidazole pH 7.0. Column fractions containing the RORγ-LBD protein were pooled and concentrated to a volume of 5 mLs. The concentrated protein was loaded onto a Superdex 200 column pre-equilibrated with 20 mM Tris-Cl pH 7.2 and 200 mM NaCl. The fractions containing the desired RORγ-LBD protein were pooled together.

Protein Biotinylation

Purified RORγ-LBD was buffer exchanged by exhaustive dialysis [3 changes of at least 20 volumes (>8000×)] against PBS [100 mM NaPhosphate, pH 8 and 150 mM NaCl]. The concentration of RORγ-LBD was approximately 30 uM in PBS. Five-fold molar excess of NHS-LC-Biotin (Pierce) was added in a minimal volume of PBS. This solution was incubated with occasional gentle mixing for 60 minutes at ambient room temperature. The modified RORγ-LBD was dialyzed against 2 buffer changes—TBS pH 8.0 containing 5 mM DTT, 2 mM EDTA and 2% sucrose—each at least 20 times of the volume. The modified protein was distributed into aliquots, frozen on dry ice and stored at −80° C. The biotinylated RORγ-LBD was subjected to mass spectrometric analysis to reveal the extent of modification by the biotinylation reagent. In general, approximately 95% of the protein had at least a single site of biotinylation and the overall extent of biotinylation followed a normal distribution of multiple sites ranged from one to five.

A biotinylated peptide corresponding to amino acid 676 to 700 (CPSSHSSLTERHKILHRLLQEGSPS) (SEQ ID NO:3) of the co-activator steroid receptor coactivator SRC1 (2) was generated using similar method.

Assay

Protocol Step 1: Preparation of Europium Labeled SRC1(2) Peptide

Biotinylated SRC1(2) solution was prepared by adding an appropriate amount of biotinylated SRC1(2) from the 100 uM stock solution to a buffer containing 10 mM of freshly added DTT from solid to give a final concentration of 40 nM. An appropriate amount of Europium labeled Streptavidin was then added to the biotinylated SRC1(2) solution in a tube to give a final concentration of 10 nM. The tube was inverted gently and incubated for 15 minutes at room temperature. Twenty-fold excess biotin from the 10 mM stock solution was added and the tube was inverted gently and incubated for 10 minutes at room temperature.

Protocol Step 2: Preparation of APC Labeled RORγ-LBD

Biotinylated RORγ-LBD solution was prepared by adding an appropriate amount of biotinylated RORγ-LBD from the stock solution to a buffer containing 10 mM of freshly added DTT from solid to give a final concentration of 40 nM. An appropriate amount of APC labeled Streptavidin was then added to the biotinylated RORγ-LBD solution in a tube to give a final concentration of 20 nM. The tube was inverted gently and incubated for 15 minutes at room temperature. Twenty-fold excess biotin from the 10 mM stock solution was then added and the tube was inverted gently and incubated for 10 minutes at room temperature.

Protocol Step 3: Testing

Equal volumes of the above-described Europium labeled SRC1(2) peptide and the APC labeled RORγ-LBD were gently mixed together to give 20 nM RORγ-LBD, 10 nM APC-Strepavidin, 20 nM SRC1(2) and 5 nM Europium-Streptavidin. The reaction mixtures were incubated for 5 minutes. Using a Thermo Combi Multidrop 384 stacker unit, 25 uL of the reaction mixtures per well was added to the 384-well assay plates containing 1 uL of test compound per well in 100% DMSO. The plates were incubated for 1 hour and then read on ViewLux in Lance mode for EU/APC.

Results

The exemplified compounds of formula (I) were tested in the dual FRET assay described above. All exemplified compounds of formula (I), with the exception of E3, E6, E70, E92 and E102 that were not tested, were found to have a mean pIC50 between 5.0 and 8.0. The exemplified compounds of formula (I) E12, E20, E21, E23, E24, E25, E26 and E98 were found to have a mean pIC50 value of ≥7.8. E123, E124, E125 and E126 were found to have mean pIC50 values of 7.5, 7.7, 7.5 and 7.2, respectively.

Peripheral Blood Mononucleocvte Cell Assay (PBMC Assay—IL-17)

RORs (Retinoic Acid Related Orphan Receptors) are members of the class 1 nuclear receptor family. RORs regulate gene transcription by binding to specific DNA response element (RORE) as a monomer and have critical roles of in development, immunity, circadian rhythm, and cellular metabolism (recently reviewed by A. Jetten, *Nuclear Receptor Signaling* 2009, 7, 1-32). One member of this nuclear receptor family, RORγt, has been identified as a regulator of differentiation and development of IL-17 expressing human and mouse CD4+ T cells, so called Th17 cells which play a role in both host defense and inflammatory disorders. RORγt is also required for transcription of the genes encoding IL-17A and IL-17F in iNKT, NKT (*Mucosal Immunol* 2009, 2(5), 383-392; *J. Immunol.* 2008, 180, 5167-5171), γδT cells (*Am. J. Respir. Crit. Care Med.* 2010, 182, 464-476), $CD8^+$ T cells (*J. Leukocyte Biol.* 2007, 82, 354-360) and finally $CD4^-CD8^-TCR\alpha\beta^+$ T cells (*J. Immunol.* 2008, 181, 8761-8766). Additional immune cells such as eosinophils, neutrophils and macrophages can also be a source of IL-17A in allergic inflammation related to asthma (*J. Allergy Clin. Immunol.* 2001, 108, 430-438; *J. Immunol.* 2008, 181, 6117-6124; *Immunity* 2004, 21, 467-476), however, the link with RORγt has not yet been confirmed in the literature.

This assay is designed to measure levels of IL-17A secreted from antiCD3/CD28 stimulated frozen Peripheral Blood Mononuclear cells (PBMC) isolated from human blood with the aim of identifying inhibitors of IL-17A release.

Assay Solutions

Assay Media Components:

RPMI 1640 (as supplied, for example, by Gibco)—90%

FCS (as supplied, for example, by Invitrogen) (endotoxin tested)—10%

Penicillin/Streptomycin solution ×1

Preparation: 50 mL Heat Inactivated Australian FBS, 5 mL Glutamax and 5 mL

Penicillin/Streptomycin are aseptically added to 500 mL RPMI in a biosafety cabinet. The Penicillin/Streptomycin 100× stock is supplied by, for example, Gibco (10,000 Units/mL Penicillin, 10,000 ug/mL Streptomycin). Stock L-glutamine 100× (as supplied, for example, by Invitrogen)

Note: To be kept in a fridge (4° C.) for 4 weeks. Warm up in a water bath set at 37° C. prior to use.

Anti-Human IL-17 Detection Antibody Components:

IL-17 detection antibody and Blocking buffer B (supplied, for example, by Mesoscale Discovery) Dulbecco's PBS without $Ca^{2+}$ and $Mg^{2+}$ (supplied, for example, by Gibco)

Note: Prepare detection anti body at final concentration of 1 ug/mL. Solution to be kept refrigerated.

MSD Read Buffer T×2 Components:

Water and MSD Read Buffer T×4 (as supplied, for example, by MSD)

Note: Dilute MSD Read Buffer T×4 in half with water. To be kept at room temperature.

Assay Capacity: 384

Equipment and Materials

MSD Sector Imager 6000 supplied by MesoScale Discovery (MSD)

Multidrop 384 supplied by Thermo Scientific

CyBi-Well, model 7518-00 supplied by CyBio AG

Microplates 384 clear supplied by Greiner

Assay

Protocol Step 1: Assay Plates Preparation Before Adding Cell Suspension

1. Ensure no external endotoxin is present in media and reagents used in the assay.

2. The compounds for screening are dispensed into a master plate at 10 mM top concentration which are serially diluted 1:3 across 11 points in DMSO, then 500 nL is transferred into a 384-well flat-bottomed Greiner plate to which 50 uL of cell suspension is added: for the single shot screening the highest concentration of compound is $10^{-5}$M; for 11 point full curve dose response studies the highest concentration is $10^{-4}$ M.

Controls:

As a low control, DMSO (as supplied, for example, by VWR) (final concentration 1%) in column 6 (16 points).

As a high control, 5-(4-fluorophenyl)-2-ureidothiophene-3-carboxamide (obtainable from, for example, Sigma) at a final concentration of $10^{-4}$ M in DMSO should be used in column 18 (16 points).

If the compounds dispensed earlier than the day of the assay, they should be kept at −20° C.

Protocol Step 2: Day 1: Thawing and Handing of PBMC

1. Thaw PBMC in the vial using water bath (37° C.). Ensure that water does not cover the vial (the level should be lower than the screw cup of the vial)

2. Transfer the contents of the vial into 50 mL Falcon tube.

3. Add 10 mL of Assay Media drop by drop to decrease the concentration of DMSO (as supplied, for example, by VWR) in the freezing media gradually.

4. Spin down the cells in a centrifuge (1000 rpm-5 mins).

5. Decant the supernatant.

6. Re-suspend the cells in 10 mL of Assay Media.

7. Transfer of 0.1 mL of suspension into Cedex counting tube.

8. Add 0.9 mL of media to achieve volume of the suspension for counting up to 1 mL. Count the cells on Cedex using 1:10 dilution factor settings.

9. Make the cell suspension at the concentration $8\times10^5$ cells/mL to give a final number of 40,000 cells/well.

Protocol Step 3: Day 1: Stimulation of PBMC with CD3/CD28 Beads

1. Add well mixed CD3/CD28 Dynabeads (as supplied, for example, by Dynal) to achieve ratio bead:cell=2:1 (ie. a dilution of 1 in 20). Mix thoroughly.

2. Dispense the suspension into the 384 Assay Plates using Multidrop (50 uL per well). If the volume of cell suspension is large, mix the suspension after dispensing into every other plate.

3. Cover the plates with the lids and place them to the humidified incubator (37° C., 5% $CO_2$) for 48 hours.

Protocol Step 4: Day 2: MSD Plates Preparation

1. Block cytokine capture Mesoscale Discovery MSD plates with 0.1% Block buffer B (provided by Mesoscale Dsicovery) in D-PBS solution using 40 uL per well.

2. Leave the plates covered with lids in the fridge over night.

3 Plates are washed manually using PBS and a multidrop combi. Blocker B buffer is flicked out into a waste pot and 40 uL of PBS is dispensed into the plate using a combi. This is then flicked out manually and the plates tapped on to blue roll to remove as much residual liquid as possible before transferring the cell supernatant.

4 Tap the plates over a paper towel.

Protocol Step 5: Day 3: IL-17 Detection on MSD Plates

1. Transfer 10 uL of supernatants from assay plates to the MSD plates using Cybiwell. Ensure that all wells are covered with the solution. Tap the plate gently, if some of the wells are not covered with the supernatant.

2. Cover the plates with adhesive foil (brown stickers) and leave them for 1 hour of incubation on shaker at room temperature (RT).

3. Add 10 uL of MSD IL-17 detecting antibody using multidrop (1 ug/mL in D-PBS without $Ca^{2+}$ and $Mg^{2+}$ (supplied, for example, by Gibco)).

4. Cover the plates with adhesive foil and incubated with shaking for 3 hours at room temperature 5. Plates are washed manually twice using PBS and a multidrop combi as before.

6. Tap the plates over a paper towel.

7. Add 35 uL of MSD Read Buffer T×2 using multidrop.

8. Read plates on MSD MA6000 reader using the 384 well plate protocol as per manufacturer's instructions.

Results

The exemplified compounds of formula (I) were tested in the PBMC assay described above. All exemplified compounds of formula (I), with the exception of E3, E5, E6, E13, E15-17, E34, E35, E39, E52, E55, E57, E60-62, E67-69, E71, E73, E76, E80, E81, E83, E91-96, E99, E100, E102, E105 and E117-119 that were not tested and E47 which had a mean pIC50 of <4, were found to have a mean pIC50 between 4.5 and 8.0. The exemplified compounds of formula (I) E8, E12, E21, E33, E36, E84, E87-90, E107, E108, E11, E113, E120, E122 to E126 were found to have a mean pIC50 value of >6.0. E123, E124, E125 and E126 were found to have mean pIC50 values of 6.5, 7.2, 6.5 and 6.1, respectively.

Ex-Vivo Human Skin Model

Fresh ex vivo human skin from healthy bariatric patients, that underwent abdominoplasty skin removal, was de-fatted and dermatomed at 750 μm. Dermatomed skin was incubated twice for 5-10 minutes at room temperature in PBS containing a antibiotic/antimycotic solution: Fungizone (Invitrogen #15290018), PSG (Fisher #BW17718R) and Gentamicin (Invitrogen #15750060). Skin was treated aseptically from this point on. Individual skin samples were obtained by 10 mm punch biopsy and placed in a 0.4 μm PCF membrane transwell (Millicell #PIHP01250) containing 30 μl of a 64% bovine collagen solution. After a 30 minute incubation at 37° C., which allows the collagen solution time to set, skin samples on transwells were transferred to 6-well plates (1 sample per well) and the lower chamber filled with 1 ml complete media (Cornification Media)+hydrocortisone (final concentration of 0.4 μg/ml) with or without test compounds at 10 μM (day −3) and allowed to rest overnight (16-18 h) at 37° C. Next, media was aspirated from the lower chamber, replaced with 1 ml complete media without hydrocortisone and incubated at 37° C. for 1 h. This constituted a 'wash' step. Following the hydrocortisone washout, media was again aspirated from the lower chamber and replaced with 1.0 ml complete media without hydrocortisone with or without GSK compounds at 10 μM (day −2). Cultures were incubated at 37° C. in a humidified chamber and media was refreshed one more day (day-1). The following day (day-0), cultures were stimulated for 24 h with a freshly made Th17 cytokine cocktail (CD3, 1 μg/ml, CD28, 2 μg/ml, IL-1b, 10 ng/ml, IL-6, 5 ng/ml, TGFb, 1 ng/ml, IL-21, 10 ng/ml, anti-IL-4, 1 μg/ml and anti-INFg, 1 μg/ml) with or without test compounds at 10 μM. Upon harvest (day +1), skin samples were minced with a razor blade and transferred to 1.5 ml RNAse-free tubes with 1 ml RNAlater solution until later analysis by RT-PCR (stored at −80 C).

RNA Isolation

Total RNA was isolated from about 30-40 mg of tissue using Qiagen's (Cat #74106) Mini RNA Isolation kit. Briefly, tissue was homogenized in the Precellys-24 machine using 300 μL of RLT buffer supplemented with 1% 2-Beta-Mercapto-Ethanol at 6300 rpm for 30 seconds for 6 cycles with a 2-minute ice break. 600 μL of water containing Proteinase K was added to the homogenate and digested at 55 C for 15 minutes. Digested tissue was spun down for 3 minutes at 10,000×g and the supernantant was used for RNA isolation using Qiagen's RNeasy mini columns according to manufacturer's protocol. 100 ng of RNA was used as template in a 20 μL PCR volume using Applied Biosciences RNA-to-CT 1 Step kit (AB Catalog #4392938) as well as the specific TaqMan probe for each gene to be quantified. Life Technologies FAM labeled Probes Catalog Numbers are as follows: ACTb=Hs01060665_g1, IL-17A=Hs00174383_m1, IL-17F=Hs00369400_m1, IL-22=Hs01574154_m1. All probes used (except for ACTb) expand an Exon. Applied Biosciences' Master Mix has a ROX dye internal control. OneStepPlus PCR machine was used for both the RT step and the 40 amplification cycles. RNA levels of gene of interest's relative expression were calculated using the Delta Delta CT formula.

$$\frac{X_{test}}{X_{control}} = 2^{\Delta\Delta C_T} = 2^{\Delta C_{T,control} - \Delta C_{T,test}}$$

First delta: Normalized to ACTb gene expression

Second delta: Normalized to sample 13 (Day 0+DMSO) for the gene of interest.

Results

As seen in Table 1, Example E124 inhibited gene transcription of il17a, il17f and il22 using four different donors. Enantiomers of Example E123: E125 and E126 were also tested in the target engagement model using ex-vivo human skin. Both compounds also inhibited gene transcription of il17a, il17f and il22 genes. The suppressive effect was specific and statistically significant in almost all skin donors tested as the effect was seen in all RORγ-dependent cytokines (IL-17A, IL-17F and IL-22) but in IFNg.

TABLE 1

Percentage of inhibition of IL-17A, IL-17F and IL-22 mRNA expression after treatment with Example E123.

| Example E123 | Skin Donor 1 | Skin Donor 2 | Skin Donor 3 | Skin Donor 4 |
|---|---|---|---|---|
| IL-17A | 76% * | 92% * | 73% * | 91% * |
| IL-17F | 55% * | 84% * | 65% * | 87% * |
| IL-22 | 63% * | 57% | 50% | 68% * |

Note:
* p = <0.05 (Statistically significant)

TABLE 2

Percentage of inhibition of IL-17A, IL-17F and IL-22 mRNA expression after treatment with Example E125.

| Example E125 | Skin Donor 1 | Skin Donor 2 | Skin Donor 3 | Skin Donor 4 |
|---|---|---|---|---|
| IL-17A | 65% * | 92% * | 65% * | 93% * |
| IL-17F | 39% | 89% * | 45% | 80% * |
| IL-22 | 52% * | 52% | 20% | 70% * |

Note:
* p = <0.05 (Statistically significant)

TABLE 3

Percentage of inhibition of IL-17A, IL-17F and IL-22 mRNA expression after treatment with Example E126.

| Example E126 | Skin Donor 1 | Skin Donor 2 | Skin Donor 3 | Skin Donor 4 |
|---|---|---|---|---|
| IL-17A | 76% * | 93% * | 60% * | 85% * |
| IL-17F | 67% * | 89% * | 67% * | 74% * |
| IL-22 | 67% * | 58% | 60% | 58% * |

Note:
* p = <0.05 (Statistically significant)

Utility

Compounds of formula (I), and pharmaceutically acceptable salts thereof, are modulators of RORγ and can be useful in the treatment of inflammatory, metabolic and autoimmune diseases mediated by RORγ such as asthma, chronic obstructive pulmonary disease (COPD) and bronchitis, allergic diseases, such as allergic rhinitis and atopic dermatitis, cystic fibrosis, lung allograph rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatisis, autoimmune diabetes, autoimmune ocular disease, ulcerative colitis, Crohn's disease, inflammatory bowel disease (IBS), inflammatory bowel syndrome (IBD), Sjorgen's syndrome, optic neuritis, type I diabetes, neuromyelitis optica, Myasthenia Gravis, uveitis, Guillain-Barre syndrome, psoriatic arthritis, Graves' disease and scleritis. The use of RORγ modulators for the treatment of the respiratory diseases listed above, such as asthma and COPD is of particular interest.

In a further aspect, the present invention also provides a compound of formula (I), or a pharmaceutically acceptable salt or solvate thereof, for use in therapy.

In a further aspect, the present invention also provides a compound of formula (I), or a pharmaceutically acceptable salt or solvate thereof, for use in the treatment of inflammatory, metabolic and autoimmune diseases mediated by RORγ.

In a further aspect, the present invention provides a compound of formula (I), or a pharmaceutically acceptable salt thereof, for use in the treatment of asthma or chronic obstructive pulmonary disease.

In a further aspect, the present invention provides a compound of formula (I), or a pharmaceutically acceptable salt thereof, for use in the treatment of psoriasis.

In a further aspect, the present invention is directed to a method of treatment of an inflammatory, metabolic or autoimmune disease mediated by RORγ, which comprises administering to a subject in need thereof, a safe and therapeutically effective amount of a compound of formula (I), or a pharmaceutically acceptable salt thereof.

In yet a further aspect, the present invention is directed to a method of treating chronic obstructive pulmonary disease or asthma, which comprises administering to a subject in need thereof, a safe and therapeutically effective amount of a compound of formula (I), or a pharmaceutically acceptable salt thereof.

In yet a further aspect, the present invention is directed to a method of treating psoriasis, which comprises administering to a subject in need thereof, a safe and therapeutically effective amount of a compound of formula (I), or a pharmaceutically acceptable salt thereof.

In a further aspect, the present invention is directed to the use of a compound of formula (I), or a pharmaceutically acceptable salt thereof, in the manufacture of a medicament for use in the treatment of an inflammatory, metabolic or autoimmune disease mediated by RORγ.

In a yet further aspect, the present invention is directed to the use of a compound of formula (I), or a pharmaceutically acceptable salt thereof, in the manufacture of a medicament for use in the treatment of asthma or chronic obstructive pulmonary disease.

In a yet further aspect, the present invention is directed to the use of a compound of formula (I), or a pharmaceutically acceptable salt thereof, in the manufacture of a medicament for use in the treatment of psoriasis.

As used herein, the term "treatment" refers to prophylaxis of the condition, ameliorating or stabilising the specified condition, reducing or eliminating the symptoms of the condition, slowing or eliminating the progression of the condition, and preventing or delaying reoccurrence of the condition in a previously afflicted patient or subject.

As used herein, the term "therapeutically effective amount" refers to the quantity of a compound of formula (I), or a pharmaceutically acceptable salt thereof, which will elicit the desired biological response in an animal or human body.

As used herein, the term "subject" refers to an animal or human body

Pharmaceutical Development

A compound of formula (I), or a pharmaceutically acceptable salt thereof, will normally, but not necessarily, be formulated into pharmaceutical compositions prior to administration to a patient. Accordingly, in another aspect the invention is directed to pharmaceutical compositions comprising a compound of formula (I), or a pharmaceutically acceptable salt thereof, and one or more pharmaceutically-acceptable excipients.

Pharmaceutical compositions comprising a compound of formula (I), or a pharmaceutically acceptable salt thereof, may be prepared using techniques and methods known to those skilled in the art. Some of the methods commonly used in the art are described in Remington's Pharmaceutical Sciences (Mack Publishing Company).

A pharmaceutical composition of a compound of formula (I), or a pharmaceutically acceptable salt thereof, may be formulated for administration by any appropriate route, for example by the inhaled, nasal, oral (including buccal or sublingual), topical (including buccal, sublingual, transdermal, epicutaneous) or parenteral (subcutaneous, intramuscular, intravenous, intradermal) route. Thus, a pharmaceutical composition of a compound of formula (I), or a pharmaceutically acceptable salt thereof, may be formulated as, for example, a solution or suspension (aqueous or non-aqueous), tablet, capsule, powder, granule, lozenge, lotion, cream, ointment, gel, foam or reconstitutable powder depending on the particular route of administration. Such pharmaceutical compositions may be prepared by any method known in the art of pharmacy, for example by bringing into association the active ingredient with the excipient(s).

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulfate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Pharmaceutical compositions of a compound of formula (I) or a pharmaceutically acceptable salt thereof, for topical administration, may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The compositions may also contain compatible conventional carriers, such as cream or ointment bases and ethanol or oleyl alcohol for lotions. Such carriers may be present as from about 1% up to about 98% of the composition. More usually they will form up to about 80% of the composition.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions for topical administration to the lung may include aerosol compositions and dry powder compositions.

Dry powder compositions for topical delivery to the lungs or nose generally contain a powder mix of a compound of formula (I) or a pharmaceutically acceptable salt thereof and a suitable carrier, such as lactose or starch. Dry powder compositions for topical delivery to the lung or nose may, for example, be presented in capsules and cartridges for use in an inhaler or insufflator of, for example, gelatine. Each capsule or cartridge may generally contain between 20 μg-10 mg of the compound of formula (I), or a pharmaceutically acceptable salt thereof. Alternatively, the compounds of formula (I), or pharmaceutically acceptable salts thereof, may be presented without excipients. Packaging of the pharmaceutical composition may be suitable for unit dose or multi-dose delivery. In the case of multi-dose delivery, the composition can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable composition comprising a compound of formula (I), or a pharmaceutically acceptable salt thereof, preferably combined with a carrier, such as lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of compound of formula (I), or a pharmaceutically acceptable salt thereof, may be size reduced by conventional means eg by micronisation. The desired fraction may be separated out by air classification or sieving. Preferably, the particles will be crystalline, prepared for example by a process which comprises mixing in a continuous flow cell in the presence of ultrasonic radiation a flowing solution of compound of formula (I), or a pharmaceutically acceptable salt thereof, as medicament in a liquid solvent with a flowing liquid antisolvent for said medicament (eg as described in International Patent Application PCT/GB99/04368). Alternatively, the particles may be prepared by a process which comprises admitting a stream of solution of the substance in a liquid solvent and a stream of liquid antisolvent for said substance tangentially into a cylindrical mixing chamber having an axial outlet port such that said streams are thereby intimately mixed through formation of a vortex and precipitation of crystalline particles of the substance is thereby caused (eg as described in International Patent Application PCT/GB00/04237). When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Aerosol compositions may be developed, with the use of a suitable liquefied propellant, for delivery from pressurised packs, such as a metered dose inhaler. Aerosol compositions can be either a suspension or a solution and generally contain the compound of formula (I), or a pharmaceutically acceptable salt thereof, and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants eg oleic acid or lecithin and cosolvents eg ethanol. Aerosol compositions will generally be retained in a pressurised canister (eg an aluminium canister) closed with a valve (eg a metering valve) and fitted into an actuator with a mouthpiece. Aerosol compositions may also include aqueous solutions or suspensions that are delivered to the nose or lungs by nebulisation.

Pharmaceutical compositions for topical administration to the nose may also be developed for delivery by nasal spray or as nasal droplets. Pharmaceutical compositions for nasal administration may be developed in such a way to allow the medicament(s) to be delivered to all appropriate areas of the nasal cavities (the target tissue). Moreover, a pharmaceutical composition may be developed for nasal administration, which permits the medicament(s) to remain in contact with the target tissue for an increased period of time.

A suitable dosing regimen for a pharmaceutical composition administered topically to the nose by use of a nasal spray may be for the patient to inhale slowly through the nose subsequent to the nasal cavity being cleared. During inhalation, the composition may be administered to one nostril while the other is manually compressed. This procedure may then be repeated for the other nostril. Generally, one or two sprays per nostril may be administered by the above procedure up to two or three times each day. Typically, each spray to the nostril may deliver from about 25 to about 100 μL of the pharmaceutical composition.

Pharmaceutical compositions for topical administration to the nose by nasal spray or as nasal drops may be prepared as a solution or suspension. The solution or suspension may be aqueous or non-aqueous based, and may contain one or more pharmaceutically acceptable excipients, such as suspending agents, for example carboxymethylcellulose, methylcellulose, veegum, tragacanth, bentonite and polyethylene glycols; preservatives, for example chelating agents (e.g EDTA), quaternary ammonium compounds (e.g benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid) and other anti-microbial agents such as chlorhexidine, chlorocresol, sorbic acid and its salts (e.g. potassium sorbate), and polymyxin; isotonicity adjusting agents, for example sodium chloride, dextrose, xylitol and calcium chloride; buffering agents, wetting agents, for example fatty alcohols, esters and ethers, such as polyoxyethylene (20) sorbitan monooleate (polysorbate 80); antioxidants, sweetening agents and taste-masking agents.

It should be understood that in addition to the ingredients particularly mentioned above, the pharmaceutical compositions may include other agents conventional in the art having regard to the type of formulation in question.

A compound of formula (I), or a pharmaceutically acceptable salt thereof, may also be used in combination with one or more other therapeutic agents, selected from the group consisting of $\beta_2$-adrenoreceptor agonists, anti-inflammatory agents (e.g. corticosteroids and NSAID's) and anticholinergic agents.

$\beta_2$-adrenoreceptor agonists that may be used in combination with a compound of formula (I), or a pharmaceutically acceptable salt thereof, include, for example, salmeterol, salbutamol, formoterol, and salts thereof, for example the xinafoate salt of salmeterol, the sulfate salt of salbutamol or the fumarate salt of formoterol). Further $\beta_2$-adrenoreceptor agonists include those described in WO03/024439, such as 4-{(1R)-2-[(6- {2-[(2,6-dichlorobenzyl)oxy]ethoxy}hexyl)amino]-1-hydroxyethyl}-2-(hydroxymethyl)phenol and its pharmaceutically acceptable salts, such as triphenylacetate.

Corticosteroids that may be used in combination with a compound of formula (I), or a pharmaceutically acceptable salt thereof, include, for example, fluticasone propionate and 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

Anticholinergic agents may also be used in combination with a compound of formula (I), or a pharmaceutically acceptable salt thereof. Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Antimuscarinic compounds for administration via inhalation include, for example, ipratropium (for example, as the bromide, CAS 22254-24-6, sold under the name Atrovent), tiotropium (for example, as the bromide, CAS 136310-93-5, sold under the name Spiriva), (3-endo)-3-(2-cyano-2,2-diphenylethyl)-8,8-dimethyl-8-azoniabicyclo[3.2.1]octane bromide, and 4-[hydroxy(diphenyl)methyl]-1-{2-[(phenylmethyl)oxy]ethyl}-1-azoniabicyclo[2.2.2]octane bromide.

It will be clear to a person skilled in the art that, where appropriate, the other therapeutic agent(s) may be used in the form of pharmaceutically acceptable salts, or prodrugs, or as esters (e.g lower alkyl esters), or as solvates (e.g. hydrates) to optimise the activity and/or stability and/or physical characteristics (e.g. solubility) of the therapeutic agent. It will be clear also that, where appropriate, the therapeutic agent(s) may be used in optically pure form.

The invention thus provides in a further aspect a combination comprising a compound of formula (I), or a pharmaceutically acceptable salt thereof, and one or more other therapeutic agents.

The invention claimed is:

1. A compound of formula (Ia), or a pharmaceutically acceptable salt thereof:

(Ia)

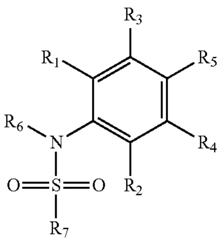

wherein $R_1$ is selected from the group consisting of H, $C_{1-3}$alkyl, $C_{1-3}$alkoxy, $CF_3$, and halo;

$R_2$, $R_3$ and $R_4$ are H;

$R_5$ is $C_{1-3}$alkyl;

$R_6$ is $C_{3-5}$alkyl or $—CH_2C_{3-4}$cycloalkyl;

$R_7$ is selected from the group consisting of:

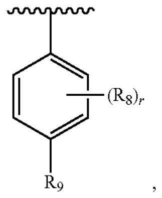

, and

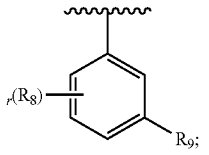

each $R_8$ is independently selected from the group consisting of halo, $C_{1-6}$alkyl, $C_{1-6}$alkoxy, $C_{3-6}$cycloalkyl, CN, OH, C(O)OH, $C(O)OC_{1-3}$alkyl and $CH_2OH$;

$R_9$ is the group $—(CHR_{10})_s—(X)_t—(CHR_{10})_u—R_{11}$;

each $R_{10}$ is independently selected from H, $CH_3$, OH and $CH_2OH$;

X is $CH_2$, NH or O;

$R_{11}$ is a heterocycloalkyl or $C_{3-6}$ cycloalkyl group which may be unsubstituted or substituted with one or more substituents independently selected from the group consisting of $CH_3$, $OCH_3$, OH, $CH_2OH$ and halo;

r is 0, 1 or 2;

s is 0, 1 or 2;

t is 0 or 1;

u is 0, 1 or 2;

with the proviso that no more than two $R_{10}$ groups represent $CH_3$, OH or $CH_2OH$.

2. A compound according to claim 1, or a pharmaceutically acceptable salt thereof, wherein $R_1$ is H.

3. A compound according to claim 1, or a pharmaceutically acceptable salt thereof, wherein $R_6$ is isobutyl.

4. A compound according to claim 1, or a pharmaceutically acceptable salt thereof, wherein $R_7$ is:

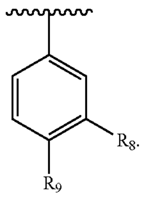

5. A compound according to claim 1, or a pharmaceutically acceptable salt thereof, wherein r is 1.

6. A compound according to claim 1, or a pharmaceutically acceptable salt thereof, wherein $R_8$ is $CH_2OH$.

7. A compound according to claim 1, or a pharmaceutically acceptable salt thereof, wherein s is 0.

8. A compound according to claim 1, or a pharmaceutically acceptable salt thereof, wherein u is 1.

9. A compound according to claim 1, or a pharmaceutically acceptable salt thereof, wherein t is 1 and X is O.

10. A compound according to claim 1, or a pharmaceutically acceptable salt thereof, wherein each $R_{10}$ is H.

11. A compound according to claim 1, or a pharmaceutically acceptable salt thereof, wherein $R_{11}$ is unsubstituted.

12. A compound according to claim 1, or a pharmaceutically acceptable salt thereof, which is selected from the group consisting of:

N-(2,4-dimethylphenyl)-N-(2-methylpropyl)-3-[(oxan-4-ylmethoxy)methyl]benzene-1-sulfonamide;

N-(2,4-dimethylphenyl)-N-(2-methylpropyl)-4-[2-(morpholin-4-yl)ethoxy]benzene-1-sulfonamide;

2-[(2,4-dimethylphenyl)(2-methylpropyl)sulfamoyl]-5-(oxan-4-ylmethoxy)benzoic acid;

N-(2,4-dimethylphenyl)-2-methoxy-N-(2-methylpropyl)-4-(oxan-4-ylmethoxy)benzene-1-sulfonamide;

N-(2,4-dimethylphenyl)-2-(hydroxymethyl)-N-(2-methylpropyl)-4-(oxan-4-ylmethoxy)benzene-1-sulfonamide;

N-(2,4-dimethylphenyl)-N-(2-methylpropyl)-4-{[(oxan-4-ylmethyl)amino]methyl}benzene-1-sulfonamide;

N-(2,4-dimethylphenyl)-4-[(cis-3-fluoropiperidin-4-yl)methoxy]-N-(2-methylpropyl)benzene-1-sulfonamide;
N-(2,4-dimethylphenyl)-N-(2-methylpropyl)-4-(piperidin-4-ylmethoxy)benzene-1-sulfonamide;
N-(2,4-dimethylphenyl)-N-(2-methylpropyl)-4-[(1-methylpyrrolidin-3-yl)methoxy]benzene-1-sulfonamide;
N-(2,4-dimethylphenyl)-N-(2-methylpropyl)-4-[(5-oxomorpholin-2-yl)methoxy]benzene-1-sulfonamide;
N-(2,4-dimethylphenyl)-4-[(3-methyl-5-oxomorpholin-3-yl)methoxy]-N-(2-methylpropyl)benzene-1-sulfonamide;
N-(2,4-dimethylphenyl)-N-(2-methylpropyl)-4-(oxan-4-ylmethoxy)benzene-1-sulfonamide;
N-(2,4-dimethylphenyl)-4-((cis-5-(hydroxymethyl)tetrahydrofuran-2-yl)methoxy)-N-isobutylbenzenesulfonamide;
4-[(3,5-dihydroxycyclohexyl)oxy]-N-(2,4-dimethylphenyl)-N-(2-methylpropyl)benzene-1-sulfonamide;
4-(((1S,3R,5S)-3,5-dihydroxycyclohexyl)oxy)-N-(2,4-dimethylphenyl)-N-isobutylbenzenesulfonamide;
4-[2-(3,5-dimethylmorpholin-4-yl)ethoxy]-N-(2,4-dimethylphenyl)-N-(2-methylpropyl)benzene-1-sulfonamide;
N-(2,4-dimethylphenyl)-N-(2-methylpropyl)-4-[(oxan-4-ylmethoxy)methyl]benzene-1-sulfonamide;
N-(2,4-dimethylphenyl)-N-(2-methylpropyl)-4-[(oxetan-3-ylmethoxy)methyl]benzene-1-sulfonamide;
3-chloro-N-(2,4-dimethylphenyl)-N-(2-methylpropyl)-4-(oxan-4-ylmethoxy)benzene-1-sulfonamide;
3-cyclopropyl-N-(2,4-dimethylphenyl)-N-(2-methylpropyl)-4-(oxan-4-ylmethoxy)benzene-1-sulfonamide;
N-(2,4-dimethylphenyl)-4-[1-hydroxy-2-(morpholin-4-yl)ethyl]-N-(2-methylpropyl)benzene-1-sulfonamide;
N-(2,4-dimethylphenyl)-3,5-difluoro-N-(2-methylpropyl)-4-(oxan-4-ylmethoxy)benzene-1-sulfonamide;
N-(2,4-dimethylphenyl)-3-methyl-N-(2-methylpropyl)-4-(oxan-4-ylmethoxy)benzene-1-sulfonamide;
N-(2,4-dimethylphenyl)-2-methyl-N-(2-methylpropyl)-4-(oxan-4-ylmethoxy)benzene-1-sulfonamide;
N-(2,4-dimethylphenyl)-2-hydroxy-N-(2-methylpropyl)-4-(oxan-4-ylmethoxy)benzene-1-sulfonamide;
2-chloro-N-(2,4-dimethylphenyl)-N-(2-methylpropyl)-4-(oxan-4-ylmethoxy)benzene-1-sulfonamide;
N-(2,4-dimethylphenyl)-2-fluoro-N-(2-methylpropyl)-4-(oxan-4-ylmethoxy)benzene-1-sulfonamide;
N-(2,4-dimethylphenyl)-3-fluoro-N-(2-methylpropyl)-4-(oxan-4-ylmethoxy)benzene-1-sulfonamide;
N-(2,4-dimethylphenyl)-3-methoxy-N-(2-methylpropyl)-4-(oxan-4-ylmethoxy)benzene-1-sulfonamide;
N-(2,4-dimethylphenyl)-N-(2-methylpropyl)-4-(oxolan-3-ylmethoxy)benzene-1-sulfonamide;
N-(2,4-dimethylphenyl)-3-hydroxy-N-(2-methylpropyl)-4-(oxan-4-ylmethoxy)benzene-1-sulfonamide;
N-(2,4-dimethylphenyl)-N-(2-methylpropyl)-4-(morpholin-4-yl)benzene-1-sulfonamide;
N-(2,4-dimethylphenyl)-N-(2-methylpropyl)-4-(oxan-4-yloxy)benzene-1-sulfonamide;
N-(2,4-dimethylphenyl)-2-ethoxy-N-(2-methylpropyl)-4-(oxan-4-ylmethoxy)benzene-1-sulfonamide;
N-(2,4-dimethylphenyl)-N-isobutyl-4-(((2R,3R)-2-methylmorpholin-3-yl)methoxy)benzenesulfonamide;
3-cyano-N-(2,4-dimethylphenyl)-N-(2-methylpropyl)-4-(oxan-4-ylmethoxy)benzene-1-sulfonamide;
2-cyano-N-(2,4-dimethylphenyl)-N-(2-methylpropyl)-4-(oxan-4-ylmethoxy)benzene-1-sulfonamide;
4-(cyclohexylmethoxy)-N-(2,4-dimethylphenyl)-N-(2-methylpropyl)benzene-1-sulfonamide;

4-[(2,6-dimethylcyclohexyl)methoxy]-N-(2,4-dimethylphenyl)-N-(2-methylpropyl)benzene-1-sulfonamide;
N-(2,4-dimethylphenyl)-4-[(3-hydroxycyclohexyl)oxy]-N-(2-methylpropyl)benzene-1-sulfonamide;
4-{[(2S)-4,4-difluoropyrrolidin-2-yl]methoxy}-N-(2,4-dimethylphenyl)-N-(2-methylpropyl)benzene-1-sulfonamide;
N-(2,4-dimethylphenyl)-N-(2-methylpropyl)-4-(oxan-3-ylmethoxy)benzene-1-sulfonamide;
N-(2,4-dimethylphenyl)-N-(2-methylpropyl)-4-[(6-oxopiperidin-3-yl)oxy]benzene-1-sulfonamide;
N-(2,4-dimethylphenyl)-4-(1,4-dioxan-2-ylmethoxy)-N-(2-methylpropyl)benzene-1-sulfonamide;
N-(2,4-dimethylphenyl)-4-[(4-methylcyclohexyl)methoxy]-N-(2-methylpropyl)benzene-1-sulfonamide;
N-(2,4-dimethylphenyl)-N-(2-methylpropyl)-4-{[1-(morpholin-4-yl)propan-2-yl]oxy}benzene-1-sulfonamide;
N-(2,4-dimethylphenyl)-N-(2-methylpropyl)-4-(morpholin-2-ylmethoxy)benzene-1-sulfonamide;
N-(2,4-dimethylphenyl)-N-(2-methylpropyl)-4-(morpholin-3-ylmethoxy)benzene-1-sulfonamide;
N-(2,4-dimethylphenyl)-N-(2-methylpropyl)-4-(oxan-2-ylmethoxy)benzene-1-sulfonamide;
4-[(6,6-dimethylmorpholin-3-yl)methoxy]-N-(2,4-dimethylphenyl)-N-(2-methylpropyl)benzene-1-sulfonamide;
N-(2,4-dimethylphenyl)-N-(2-methylpropyl)-3-[2-(morpholin-4-yl)ethoxy]benzene-1-sulfonamide;
N-(2,4-dimethylphenyl)-4-{[(2R,3S)-3-hydroxyoxan-2-yl]methoxy}-N-(2-methylpropyl)benzene-1-sulfonamide;
N-(2,4-dimethylphenyl)-4-[(4-fluoropiperidin-4-yl)methoxy]-N-(2-methylpropyl)benzene-1-sulfonamide;
N-(2,4-dimethylphenyl)-4-[(2,6-dioxo-1,2,3,6-tetrahydropyrimidin-4-yl)methoxy]-N-(2-methylpropyl)benzene-1-sulfonamide;
N-(2,4-dimethylphenyl)-N-(2-methylpropyl)-3-(oxan-4-ylmethoxy)benzene-1-sulfonamide;
N-(2,4-dimethylphenyl)-N-(2-methylpropyl)-4-{[(2R,3S,4R,5S)-3,4,5-trihydroxyoxan-2-yl]methoxy}benzene-1-sulfonamide;
N-(2,4-dimethylphenyl)-4-[(1-methylpiperidin-4-yl)oxy]-N-(2-methylpropyl)benzene-1-sulfonamide;
N-(2,4-dimethylphenyl)-4-{[(cis-3-fluoropiperidin-4-yl)methoxy]methyl}-N-(2-methylpropyl)benzene-1-sulfonamide;
4-[2-(2,6-dimethylmorpholin-4-yl)ethoxy]-N-(2,4-dimethylphenyl)-N-(2-methylpropyl)benzene-1-sulfonamide;
N-(2,4-dimethylphenyl)-2,3-difluoro-N-(2-methylpropyl)-4-(oxan-4-ylmethoxy)benzene-1-sulfonamide;
N-(2,4-dimethylphenyl)-4-[(1-methylpiperidin-4-yl)methoxy]-N-(2-methylpropyl)benzene-1-sulfonamide;
N-(2,4-dimethylphenyl)-N-(2-methylpropyl)-4-(pyrrolidin-3-ylmethoxy)benzene-1-sulfonamide;
N-(2,4-dimethylphenyl)-N-(2-methylpropyl)-4-(piperidin-4-yloxy)benzene-1-sulfonamide;
N-(2,4-dimethylphenyl)-N-(2-methylpropyl)-3-(piperidin-4-yloxy)benzene-1-sulfonamide;
4-(azetidin-3-ylmethoxy)-N-(2,4-dimethylphenyl)-N-(2-methylpropyl)benzene-1-sulfonamide;
N-(2,4-dimethylphenyl)-N-(2-methylpropyl)-4-{[(6-oxopiperidin-3-yl)oxy]methyl}benzene-1-sulfonamide;
N-(2,4-dimethylphenyl)-N-(2-methylpropyl)-4-(oxan-4-ylmethoxy)-2-(propan-2-yloxy)benzene-1-sulfonamide;

N-(2,4-dimethylphenyl)-4-{1-hydroxy-2-[(3-methyloxetan-3-yl)amino]ethyl}-N-(2-methylpropyl)benzene-1-sulfonamide;

N-(2,4-dimethylphenyl)-4-[1-hydroxy-2-(piperidin-1-yl)ethyl]-N-(2-methylpropyl)benzene-1-sulfonamide;

N-(2,4-dimethylphenyl)-4-(2-(1,1-dioxidothiomorpholino)-1-hydroxyethyl)-N-isobutylbenzenesulfonamide;

N-(2,4-dimethylphenyl)-4-[2-(3-fluoropiperidin-1-yl)-1-hydroxyethyl]-N-(2-methylpropyl)benzene-1-sulfonamide;

N-(2,4-dimethylphenyl)-4-{1-hydroxy-2-[2-(hydroxymethyl)morpholin-4-yl]ethyl}-N-(2-methylpropyl)benzene-1-sulfonamide;

N-(2,4-dimethylphenyl)-4-[2-(4-fluoropiperidin-1-yl)-1-hydroxyethyl]-N-(2-methylpropyl)benzene-1-sulfonamide;

N-(2,4-dimethylphenyl)-4-[2-hydroxy-1-(piperidin-1-yl)ethyl]-N-(2-methylpropyl)benzene-1-sulfonamide;

N-(2,4-dimethylphenyl)-4-[3-(hydroxymethyl)morpholin-4-yl]-N-(2-methylpropyl)benzene-1-sulfonamide;

N-(2,4-dimethylphenyl)-N-(2-methylpropyl)-4-{[(3S, 4R)-3,4,5-trihydroxyoxolan-2-yl]methoxy}benzene-1-sulfonamide;

N-(2,4-dimethylphenyl)-N-(2-methylpropyl)-4-{[(3R, 4S,5 S)-3,4,5-trihydroxyoxolan-2-yl]methoxy}benzene-1-sulfonamide;

3-chloro-4-[2-(4,4-difluoropiperidin-1-yl)-1-hydroxyethyl]-N-(2,4-dimethylphenyl)-N-(2-methylpropyl)benzene-1-sulfonamide;

3-chloro-N-(2,4-dimethylphenyl)-4-[2-hydroxy-1-(morpholin-4-yl)ethyl]-N-(2-methylpropyl)benzene-1-sulfonamide;

3-chloro-N-(2,4-dimethylphenyl)-4-[1-hydroxy-2-(morpholin-4-yl)ethyl]-N-(2-methylpropyl)benzene-1-sulfonamide;

3-chloro-N-(2,4-dimethylphenyl)-4-(1-hydroxy-2-{2-oxa-6-azaspiro[3.3]heptan-6-yl}ethyl)-N-(2-methylpropyl)benzene-1-sulfonamide;

3-chloro-N-(2,4-dimethylphenyl)-4-{1-hydroxy-2-[trans-(3-hydroxycyclobutyl)amino]ethyl}-N-(2-methylpropyl)benzene-1-sulfonamide;

N-(2,4-dimethylphenyl)-3-fluoro-4-[1-hydroxy-2-(morpholin-4-yl)ethyl]-N-(2-methylpropyl)benzene-1-sulfonamide;

N-(2,4-dimethylphenyl)-4-[1-hydroxy-2-(morpholin-4-yl)ethyl]-2-methyl-N-(2-methylpropyl)benzene-1-sulfonamide;

N-(2,4-dimethylphenyl)-4-[2-hydroxy-1-(morpholin-4-yl)ethyl]-3-methyl-N-(2-methylpropyl)benzene-1-sulfonamide;

N-(2,4-dimethylphenyl)-4-[1-hydroxy-2-(morpholin-4-yl)ethyl]-3-methyl-N-(2-methylpropyl)benzene-1-sulfonamide;

5-[(2,4-dimethylphenyl)(2-methylpropyl)sulfamoyl]-2-(oxan-4-ylmethoxy)benzoic acid;

2-bromo-N-(2,4-dimethylphenyl)-N-(2-methylpropyl)-4-(oxan-4-ylmethoxy)benzene-1-sulfonamide;

2-cyclopropyl-N-(2,4-dimethylphenyl)-N-(2-methylpropyl)-4-(oxan-4-ylmethoxy)benzene-1-sulfonamide;

N-(2,4-dimethylphenyl)-4-{1-hydroxy-2-[(oxan-4-yl)amino]ethyl}-N-(2-methylpropyl)benzene-1-sulfonamide;

N-(2,4-dimethylphenyl)-4-[1-hydroxy-2-(4-methoxypiperidin-1-yl)ethyl]-N-(2-methylpropyl)benzene-1-sulfonamide;

N-(2,4-dimethylphenyl)-4-[1-hydroxy-2-(4-hydroxypiperidin-1-yl)ethyl]-N-(2-methylpropyl)benzene-1-sulfonamide;

3-cyano-N-(2,4-dimethylphenyl)-N-(2-methylpropyl)-4-(oxan-4-ylmethoxy)benzene-1-sulfonamide;

3-chloro-N-(2,4-dimethylphenyl)-N-(2-methylpropyl)-4-(oxan-4-ylmethoxy)benzene-1-sulfonamide;

N-(2,4-dimethylphenyl)-4-[2-hydroxy-1-(4-hydroxypiperidin-1-yl)ethyl]-N-(2-methylpropyl)benzene-1-sulfonamide;

N-(2,4-dimethylphenyl)-4-{1-hydroxy-2-[(oxan-3-yl)amino]ethyl}-N-(2-methylpropyl)benzene-1-sulfonamide;

N-(2,4-dimethylphenyl)-4-[2-hydroxy-1-(morpholin-4-yl)ethyl]-N-(2-methylpropyl)benzene-1-sulfonamide;

N-(2,4-dimethylphenyl)-N-(2-methylpropyl)-4-(5-oxopyrrolidin-2-yl)benzene-1-sulfonamide;

N-(2,4-dimethylphenyl)-4-[2-(hydroxymethyl)morpholin-4-yl]-N-(2-methylpropyl)benzene-1-sulfonamide;

N-(2,4-dimethylphenyl)-3,5-difluoro-4-[1-hydroxy-2-(morpholin-4-yl)ethyl]-N-(2-methylpropyl)benzene-1-sulfonamide;

N-(2,4-dimethylphenyl)-3-fluoro-4-{1-hydroxy-2-[(3-methyloxetan-3-yl)amino]ethyl}-N-(2-methylpropyl)benzene-1-sulfonamide;

N-(2,4-dimethylphenyl)-4-{1-hydroxy-2-[(3-methyloxetan-3-yl)amino]ethyl}-2-methyl-N-(2-methylpropyl)benzene-1-sulfonamide;

N-(2,4-dimethylphenyl)-4-{1-hydroxy-2-[(3-methyloxetan-3-yl)amino]ethyl}-3-methyl-N-(2-methylpropyl)benzene-1-sulfonamide;

N-(2,4-dimethylphenyl)-3-hydroxy-4-[2-hydroxy-1-(morpholin-4-yl)ethyl]-N-(2-methylpropyl)benzene-1-sulfonamide;

methyl 5-[(2,4-dimethylphenyl)(2-methylpropyl)sulfamoyl]-2-(oxan-4-ylmethoxy)benzoate;

N-(2,4-dimethylphenyl)-3-(hydroxymethyl)-N-(2-methylpropyl)-4-(oxan-4-ylmethoxy)benzene-1-sulfonamide;

N-(4-ethylphenyl)-4-{1-hydroxy-2-[(3-methyloxetan-3-yl)amino]ethyl}-N-(2-methylpropyl)benzene-1-sulfonamide;

N-(4-ethylphenyl)-4-[1-hydroxy-2-(morpholin-4-yl)ethyl]-N-(2-methylpropyl)benzene-1-sulfonamide;

4-[1,2-dihydroxy-3-(morpholin-4-yl)propyl]-N-(2,4-dimethylphenyl)-N-(2-methylpropyl)benzene-1-sulfonamide;

N-(2,4-dimethylphenyl)-4-{1-hydroxy-2-[(oxetan-3-yl)amino]ethyl}-N-(2-methylpropyl)benzene-1-sulfonamide;

4-[1,3-dihydroxy-2-(morpholin-4-yl)propyl]-N-(2,4-dimethylphenyl)-N-(2-methylpropyl)benzene-1-sulfonamide;

N-(4-ethylphenyl)-4-(1-hydroxy-2-morpholinoethyl)-3-(hydroxymethyl)-N-isobutylbenzenesulfonamide;

N-(4-ethylphenyl)-3-(hydroxymethyl)-N-isobutyl-4-((tetrahydro-2H-pyran-4-yl)methoxy)benzenesulfonamide;

(S)—N-(4-ethylphenyl)-4-(1-hydroxy-2-morpholinoethyl)-3-(hydroxymethyl)-N-isobutylbenzenesulfonamide; and (R)—N-(4-ethylphenyl)-4-(1-hydroxy-2-morpholinoethyl)-3-(hydroxymethyl)-N-isobutylbenzenesulfonamide.

13. A compound which is

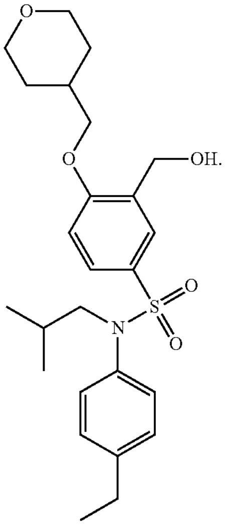 [SMILES: CCc1ccc(N(CC(C)C)S(=O)(=O)c2ccc(OCC3CCOCC3)c(CO)c2)cc1]

14. A pharmaceutical composition comprising a compound according to claim 1, or a pharmaceutically acceptable salt thereof, and one or more pharmaceutically acceptable excipients.

15. A method of treating a disease in a subject in need thereof, comprising administering to said subject an effective amount of a compound according to claim 1, or a pharmaceutically acceptable salt thereof, wherein the disease is selected from asthma, chronic obstructive pulmonary disease, bronchitis, allergic rhinitis, atopic dermatitis, psoriasis, ulcerative colitis, Crohn's disease, inflammatory bowel disease, and inflammatory bowel syndrome.

16. A method of treating a disease in a subject in need thereof, comprising administering to said subject an effective amount of a compound according to claim 13, wherein the disease is selected from asthma, chronic obstructive pulmonary disease, bronchitis, allergic rhinitis, atopic dermatitis, psoriasis, ulcerative colitis, Crohn's disease, inflammatory bowel disease, and inflammatory bowel syndrome.

17. A method of treatment according to claim 15, wherein the disease is atopic dermatitis or psoriasis.

18. A method of treatment according to claim 16, wherein the disease is psoriasis.

19. A pharmaceutical composition comprising a compound according to claim 12, or a pharmaceutically acceptable salt thereof, and one or more pharmaceutically acceptable excipients.

20. A pharmaceutical composition comprising a compound according to claim 13, and one or more pharmaceutically acceptable excipients.

21. A method of treatment according to claim 16, wherein the disease is atopic dermatitis.

22. A compound according to claim 1, or a pharmaceutically acceptable salt thereof, wherein $R_{11}$ is a heterocycloalkyl group.

23. A compound according to claim 22, or a pharmaceutically acceptable salt thereof, wherein the heterocycloalkyl group is selected from oxirane, oxetane, tetrahydrofuran, tetrahydro-2H-pyran, pyrrolidine, piperidine, morpholine, morpholin-3-one, thiomorpholine and thiomorpholine 1,1-dioxide.

24. A compound according to claim 22, or a pharmaceutically acceptable salt thereof, wherein $R_{11}$ is a heterocycloalkyl selected from tetrahydro-2H-pyran and morpholine.

25. A compound according to claim 22, or a pharmaceutically acceptable salt thereof, wherein $R_{11}$ is tetrahydro-2H-pyran.

26. A compound according to claim 22, or a pharmaceutically acceptable salt thereof, wherein $R_{11}$ is morpholine.

27. A compound according to claim 1, or a pharmaceutically acceptable salt thereof, wherein r is 0 or 1, t is 1, and u is 1.

28. A compound according to claim 27, or a pharmaceutically acceptable salt thereof, wherein $R_7$ is:

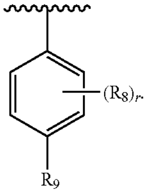

29. A compound according to claim 27, or a pharmaceutically acceptable salt thereof, wherein $R_6$ is $C_{3-5}$alkyl, $R_1$ is H, and s is 0.

30. A compound according to claim 29, or a pharmaceutically acceptable salt thereof, wherein $R_7$ is:

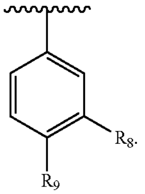

31. A compound according to claim 28, or a pharmaceutically acceptable salt thereof, wherein $R_6$ is isobutyl and X is O.

32. A compound according to claim 28, or a pharmaceutically acceptable salt thereof, wherein each $R_{10}$ is H, and $R_8$ is $CH_2OH$.

33. A compound according to claim 28, or a pharmaceutically acceptable salt thereof, wherein $R_5$ is methyl or ethyl.

34. A compound according to claim 28, or a pharmaceutically acceptable salt thereof, wherein $R_{11}$ is unsubstituted.

35. A compound according to claim 30, or a pharmaceutically acceptable salt thereof, wherein $R_{11}$ is tetrahydro-2H-pyran.

36. A compound according to claim 1, or a pharmaceutically acceptable salt thereof, wherein $R_5$ is methyl or ethyl.

37. A compound according to claim 1, or a pharmaceutically acceptable salt thereof, wherein $R_5$ is ethyl.

38. A compound, or a pharmaceutically acceptable salt thereof, which is selected from the group consisting of:

N-(2,4-dimethylphenyl)-2-(hydroxymethyl)-N-(2-methylpropyl)-4-(oxan-4-ylmethoxy)benzene-1-sulfonamide;

N-(2,4-dimethylphenyl)-N-(2-methylpropyl)-4-(piperidin-4-ylmethoxy)benzene-1-sulfonamide;

N-(2,4-dimethylphenyl)-3-methyl-N-(2-methylpropyl)-4-(oxan-4-ylmethoxy)benzene-1-sulfonamide;

N-(2,4-dimethylphenyl)-2-methyl-N-(2-methylpropyl)-4-(oxan-4-ylmethoxy)benzene-1-sulfonamide;

N-(2,4-dimethylphenyl)-3-fluoro-N-(2-methylpropyl)-4-(oxan-4-ylmethoxy)benzene-1-sulfonamide;

N-(2,4-dimethylphenyl)-N-(2-methylpropyl)-4-(oxolan-3-ylmethoxy)benzene-1-sulfonamide;

N-(2,4-dimethylphenyl)-N-(2-methylpropyl)-4-(morpholin-4-yl)benzene-1-sulfonamide;

N-(4-ethylphenyl)-4-{1-hydroxy-2-[(3-methyloxetan-3-yl)amino]ethyl}-N-(2-methylpropyl)benzene-1-sulfonamide; and N-(4-ethylphenyl)-4-(1-hydroxy-2-morpholinoethyl)-3-(hydroxymethyl)-N-isobutylbenzenesulfonamide.

39. A pharmaceutical composition comprising a compound according to claim 38, or a pharmaceutically acceptable salt thereof, and one or more pharmaceutically acceptable excipients.

* * * * *

```
SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 2, 3
<223> OTHER INFORMATION: Xaa = Any Amino Acid

<400> SEQUENCE: 1

Leu Xaa Xaa Leu Leu
 1               5


<210> SEQ ID NO 2
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 2

Met Lys Lys His His His His His His Leu Val Pro Arg Gly Ser
 1               5                  10                  15
```

-continued

<210> SEQ ID NO 3
<211> LENGTH: 25
<212> TYPE: PRT
<213> ORGANISM: Artificial Sequence
<220> FEATURE:
<223> OTHER INFORMATION: Amino acid sequence identified using molecular biology techniques.

<400> SEQUENCE: 3

```
Cys Pro Ser Ser His Ser Ser Leu Thr Glu Arg His Lys Ile Leu His
 1               5                  10                  15

Arg Leu Leu Gln Glu Gly Ser Pro Ser
            20                  25
```